(12) United States Patent
Smith et al.

(10) Patent No.: US 10,647,689 B2
(45) Date of Patent: May 12, 2020

(54) APELIN RECEPTOR AGONISTS AND METHODS OF USE THEREOF

(71) Applicant: Sanford Burnham Prebys Medical Discovery Institute, La Jolla, CA (US)

(72) Inventors: Layton H. Smith, La Jolla, CA (US); Anthony B. Pinkerton, La Jolla, CA (US); Paul Hershberger, La Jolla, CA (US); Patrick Maloney, La Jolla, CA (US); Danielle McAnally, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 15/568,208

(22) PCT Filed: Apr. 28, 2016

(86) PCT No.: PCT/US2016/029823
§ 371 (c)(1),
(2) Date: Oct. 20, 2017

(87) PCT Pub. No.: WO2016/176473
PCT Pub. Date: Nov. 3, 2016

(65) Prior Publication Data
US 2018/0118698 A1    May 3, 2018

Related U.S. Application Data

(60) Provisional application No. 62/154,025, filed on Apr. 28, 2015.

(51) Int. Cl.
| | | |
|---|---|---|
| *C07D 235/04* | (2006.01) | |
| *C07D 277/82* | (2006.01) | |
| *C07D 263/58* | (2006.01) | |
| *C07D 513/04* | (2006.01) | |
| *A61P 3/00* | (2006.01) | |
| *A61P 9/00* | (2006.01) | |

(52) U.S. Cl.
CPC .............. *C07D 277/82* (2013.01); *A61P 3/00* (2018.01); *A61P 9/00* (2018.01); *C07D 263/58* (2013.01); *C07D 513/04* (2013.01)

(58) Field of Classification Search
CPC .. C07D 277/82; C07D 263/58; C07D 513/04; C07D 235/04; C07D 401/12; C07D 413/12; C07D 417/12; A61P 3/00; A61P 9/00
See application file for complete search history.

(56) References Cited

U.S. PATENT DOCUMENTS

| | | | |
|---|---|---|---|
| 8,541,453 | B2 | 9/2013 | Hadida-Ruah et al. |
| 9,156,796 | B2 | 10/2015 | Hachtel et al. |
| 2011/0306637 | A1 | 12/2011 | Hadida-Ruah et al. |
| 2014/0005181 | A1 | 1/2014 | Smith |
| 2014/0094450 | A1 | 4/2014 | Hachtel et al. |

FOREIGN PATENT DOCUMENTS

| | | | | |
|---|---|---|---|---|
| WO | WO-03074515 A1 | * | 9/2003 | ........... C07D 401/14 |
| WO | WO-2008104994 A2 | * | 9/2008 | ........... C07D 213/40 |

OTHER PUBLICATIONS

T. Ogawa et al., 37 Chemical & Pharmaceutical Bulletin, 1609-1611 (1989).*
CAS Abstract of T. Ogawa et al., 37 Chemical & Pharmaceutical Bulletin, 1609-1611 (1989).*
D. Fajkusova et al., 20 Bioorganic & Medicinal Chemistry, 7059-7068 (2012).*
Compound Registry Nos. Indexed by CAS (2007).*
CAS Abstract and Indexed Compounds WO 03/074515 (2003) (Year: 2003).*
CAS Registry Nos. 1371128-01-6 and 1370885-90-7 (2012) (Year: 2012).*
CAS Registry No. 303195-00-8 (2012) (Year: 2012).*
CAS Registry Nos. Indexed by CAS (2011) (Year: 2011).*
CAS Registry Nos. Indexed by CAS (2010) (Year: 2010).*
PubChem, Open Chemistry Database, PubChem CID: 16838063, Create Date: Nov. 13, 2007, 1-10.
PubChem, Open Chemistry Database, PubChem CID: 18587085, Create Date: Dec. 4, 2007, 1-9.

* cited by examiner

*Primary Examiner* — Alexander R Pagano
(74) *Attorney, Agent, or Firm* — Wilson Sonsini Goodrich & Rosati

(57) ABSTRACT

Provided herein are agonists of the apelin receptor for the treatment of disease. The compounds disclosed herein are useful for the treatment of a range of cardiovascular, renal and metabolic conditions.

10 Claims, No Drawings

APELIN RECEPTOR AGONISTS AND METHODS OF USE THEREOF

CROSS-REFERENCE TO RELATED APPLICATIONS

This application is a 35 USC § 371 National Stage application of International Application No. PCT/US2016/029823 filed Apr. 28, 2016; which claims the benefit under 35 USC § 119(e) to U.S. Application Ser. No. 62/154,025 filed Apr. 28, 2015, now expired. The disclosure of each of the prior applications is considered part of and is incorporated by reference in the disclosure of this application.

FIELD OF THE APPLICATION

This invention relates generally to small molecule agonists of the apelin receptor (APJ) and, more specifically, to small molecule compounds for the treatment of apelin receptor-mediated diseases and disorders.

BACKGROUND INFORMATION

G protein-coupled receptors (GPCRs) are activated by a plethora of molecules including neuropeptides, polypeptide hormones and non-peptides such as biogenic amines, lipids, nucleotides and ions. They are classically composed of seven membrane-spanning domains and constitute one of the largest and most diverse gene families in the mammalian genome. Some novel GPCRs do not have obvious endogenous ligands and are termed orphan receptors, a number of which appear to be constitutively active. The cognate ligands for some of these orphan GPCRs have been identified, often based on the cellular and tissue distributions of the orphan GPCRs and occasionally using 'reverse pharmacology' where orphan GPCRs have been used to isolate novel endogenous substances. The human apelin receptor (APJ, gene symbol APLNR) first identified in 1993 is one such GPCR whose endogenous ligand, apelin, has been described.

Both APJ and apelin have been implicated as the key mediators of physiological responses to multiple homeostatic perturbations, including cardiovascular control, water balance, hypothalamic-pituitary-adrenal (HPA) axis regulation and metabolic homeostasis. Homeostatic stability is critical in mammalian organisms, and knowledge as to how this vital function is regulated and how this mechanism can go wrong in pathological conditions is still limited.

APJ was first identified as an orphan GPCR, with closest identity to the angiotensin II (Ang II) receptor, type $AT_{1a}$. APJ remained an orphan receptor until 1998 when a 36-amino acid peptide termed apelin, for APJ endogenous ligand was identified. In the ensuing years, the receptor was deorphanised when its cognate ligand, apelin, was isolated from bovine stomach extracts. Recently, the apelinergic system has been shown to be critically involved in multiple homeostatic processes.

The protein structure of APJ is typical of a GPCR, containing seven hydrophobic transmembrane domains, with consensus sites for phosphorylation by protein kinase A (PKA), palmitoylation and glycosylation. The N-terminal glycosylation of GPCRs has been implicated in receptor expression, stability, correct folding of the nascent protein and ligand binding. Furthermore, the palmitoylation of the C-terminal tail has been reported to play a role in membrane association and, combined with receptor phosphorylation, these fatty acid modifications can influence the internalization, dimerization and ligand binding of a GPCR. Structural studies on APJ have determined that amino acids in both the N-terminal (e.g., $Asp^{23}$ and $Glu^{20}$) and C-terminal portions of the receptor are required for internalization.

The gene encoding human apelin, termed APLN, is located on chromosome Xq25-26.1 and possesses one intron within its open reading frame of ~6 kb. In rat and mouse, the genes are termed Apln and are located at chromosomal locations Xq35 and XA3.2 respectively. The core promoter regions of these genes have been identified as −207/−1 and −100/+74 bp in rats and humans respectively. Similar to APJ, a CAAT box, but no TATA box, sequence is present in the rat and human promoter regions. Furthermore, rat and human preproapelin cDNAs do not have a classical Kozak consensus sequence surrounding the initiating methionine codon.

Human and bovine APLN cDNA sequences encode a 77-amino acid preproprotein (preproapelin) containing a hydrophobic rich N-terminal region, likely to be a secretory signal sequence. Bovine, human, rat and mouse preproapelin precursors have 76-95% homology and appear to exist endogenously as a dimeric protein, as a consequence of disulfide bridges formed between cysteine residues.

There are several mature forms of the apelin peptide. As the sequence of the purified peptide corresponded to the 36 C-terminal amino acids of the preproapelin protein, it was predicted that apelin-36 would constitute a mature form of the peptide. Additionally, as the C-terminal portion of preproapelin also contained lysine (Lys, K) and arginine (Arg, R) residues, and given their potential as sites for proteolytic cleavage, the existence of apelin-17 and apelin-13 peptides was predicted, along with a pyroglutamylated form of apelin-13 (($Pyr^1$)apelin-13). These mature forms of apelin lack cysteine residues and are probably only present in monomeric form. The likely secondary structures of apelin-36 and apelin-13 have been determined in aqueous solution, indicating that both possess an unordered structure. The amino acid sequence homology of the mature apelin-36 peptide is more conserved between species than that of preproapelin, with 86-100% homology between bovine, human, rat and mouse amino acid sequences, while the 23 C-terminal amino acids have 100% homology between species, suggesting an important physiological role.

Although APJ does not bind Ang II, apelin-13 shares a limited homology (four amino acids) with the vasoconstrictive peptide. Moreover, Ang I-converting enzyme 2 (ACE2), which catalyzes the C-terminal dipeptide cleavage of Ang I to Ang II, or Ang II to Ang 1-7, also acts on apelin-13 with a high catalytic efficiency, removing the C-terminal phenylalanine (Phe, F) residue. However, this cleavage may not inactivate the peptide, as the apelin isoform K16P, which lacks the terminal Phe, while ineffective at inducing receptor internalization or regulating blood pressure (BP) (effects associated with the full peptide), still binds to APJ and inhibits forskolin-stimulated cAMP production.

Although it is clear that APJ and apelin mRNAs and proteins are widely distributed in the CNS and peripheral tissues, whether the levels of mRNAs present in most of the regions of the brain and tissues are functionally relevant is not yet known.

Early studies of the expression of APJ mRNA by northern blot and quantitative PCR (qPCR) analyses have revealed strongest signals in the human caudate nucleus, corpus callosum, hippocampus, substantia nigra, subthalamic nucleus, medulla and spinal cord. Recently, the expression of APJ mRNA has also been demonstrated in the human cortex and hippocampus using a sensitive GPCR gene array profiling method—interestingly, APJ transcripts have also been detected in human bone marrow stromal cell lines. Transcriptomic analysis of multiple brain regions of human donors has revealed a widespread central expression of APJ mRNA with high levels in samples including the hippocampus (e.g., CA4 region), habenular nuclei, paraventricular nucleus (PVN) of the thalamus, supraoptic nucleus (SON) of the hypothalamus and various hindbrain structures. The salient feature of these studies is that APJ has been reported to have a widespread central distribution; although the function of APJ in the majority of brain regions is unknown, foremost among those regions probably important from a functional perspective include the PVN and SON of the hypothalamus.

In the periphery, the expression of human APJ mRNA was originally reported to be strongest in the spleen, with less expression being reported for the small intestine, colonic mucosa and ovary. A broader qPCR study has also reported strongest expression in the spleen, with high levels also being reported to be present in the placenta and weaker levels in the lung, stomach and intestine. (Pyr$^1$)apelin-13-binding sites can be found within the media and intimal layers of muscular arteries and large elastic arteries and veins, while in the lung, apelin-binding sites have a predominantly vascular localization. Furthermore, APJ distribution in cardiovascular tissues, as demonstrated by immunohistochemistry (IHC), indicates APJ to be present in ventricular cardiomyocytes, vascular smooth muscle cells (VSMCs) and intramyocardial endothelial cells.

APJ binds numerous apelin isoforms and signals through various G proteins to a variety of signaling pathways to culminate in different patterns of activation and desensitization that may be tissue- and cell type-specific. Recently, APJ has also been reported to heterodimerize with other GPCRs and to signal in the absence of an endogenous ligand.

The C-terminal region of the apelin peptide may be responsible for its overall biological activity. N-terminal deletions of apelin-17 reveal that the 12 C-terminal amino acids may be the core requirements for the internalization and biological potency of APJ. Apelin-17 induces the internalization of APJ, which decreases with every N-terminal deletion to apelin-12, while the deletion of the terminal F amino acid results in a peptide that no longer internalizes APJ or affects arterial BP. The N-terminal residues within the RPRL motif (residues 2-5) of apelin-13 are critical for functional potency, and the C-terminal sequence KGPM (residues 8-11) is important for binding activity and for internalization. In contrast, the five N-terminal and two C-terminal amino acids of apelin-17 are not required for binding of the peptide to APJ or activation of receptor signaling (e.g., cAMP production). Although this may indicate a possible dissociation between the conformational states of the receptor responsible for receptor signaling and internalization, it is also possible that different ligand isoforms may induce differential receptor trafficking and signaling. These studies provide information on the structural importance of key apelin residues critical for efficient binding, activity and internalization, which have proved significant in the design and synthesis of apelin analogs.

Although progress has been made in recent years in clarifying the physiological significance of apelin/APJ, much remains to be discovered about the expression of the apelinergic system and precisely how it affects numerous physiological functions. Since the discovery of the apelin ligand, both apelin and APJ have been implicated as key regulators of central and peripheral responses to multiple homeostatic perturbations. These include playing pivotal roles in the regulation of cardiovascular function, angiogenesis, fluid homeostasis and energy metabolism and acting as neuroendocrine modulators of the HPA axis responses to stress. It is becoming apparent that the apelinergic system may play a pathophysiological role within many of these regulatory systems.

The central mRNA expression of preproapelin in regions of the hippocampus, hypothalamus, thalamus and midbrain shares a distribution pattern, as shown by ISHH, similar to that of angiotensinogen (Ang II precursor). Ang 1 is part of the rennin-angiotensin system (RAS), which controls extracellular fluid volume and arterial vasoconstriction, thereby regulating mean arterial blood pressure (MABP). The central actions of the RAS include the regulation of drinking behavior, salt appetite and VP secretion. Importantly, the RAS plays a critical role in the pathogenesis of heart failure. Interestingly, apelin exerts many physiological effects that appear to oppose those exerted by Ang II. More recently, apelin has been shown to block many Ang 1-initiated processes, perhaps partly by dimerization between APJ and $AT_1$.

It is clear that apelin has both peripheral and central cardiovascular effects. However, experiments carried out in animal models have yielded conflicting results about the role of peripheral apelin in the regulation of vascular tone, with both pressor and depressor responses being described. In anaesthetized intact rats, the overall effect of peripherally administered apelin is the reduction of MABP. This hypotensive action is blocked by the NOS inhibitor L-NAME, indicating a nitric oxide-mediated pathway. In conscious rats, the effect is even less clear, with both increases and decreases in MABP being reported. Discrepancies among these reports may reflect the conscious state of the animal or the different apelin isoforms used in these studies; it is unknown which specific apelin peptide may be responsible for the (patho)-physiological roles of apelin. Further evidence that APJ plays a role in the regulation of BP comes from a study on mice with a global deletion of APJ, where a transient decrease in systolic BP observed in conscious wild-type (WT) mice following i.p. injection of (Pyr$^1$) apelin-13 is abolished in APJ KO mice. However, while peripheral apelin is a vasodilator in the human saphenous vein, in vessels denuded of endothelium, apelin acts as a vasoconstrictor. Therefore, peripheral apelin may act as an antihypertensive factor, and sensitivity to the peripheral administration of apelin might be altered in hypertensive disease.

Additionally, the apelinergic system has an important role in cardiac function. In the isolated rat heart, infusion of apelin-16 induces a potent dose-dependent positive inotropic effect, with an $EC_{50}$ of 40-125 pM in humans and ~33 pM in rats, an effect also observed in the failing heart. In mice, administration of apelin increases myocardial contraction while reducing cardiac preload and afterload, without causing hypertrophy. Furthermore, apelin increases the shortening of sarcomeres in cardiomyocytes, an effect that is impaired in isolated ventricular myocytes from apelin and APJ KO mice. Apelin KO mice have an impaired response to cardiac pressure overload, thus suggesting a role for apelin/APJ in the sustainability and amplification of the cardiac response to stress. There is also evidence for a role in essential hypertension (EHT) as circulating levels of apelin-12 are decreased in patients with EHT. Functionally, the apelinergic system plays a role in the Cripto signaling pathway (which stimulates signaling by the transforming growth factor Nodal or growth/differentiation factors 1 and 3, via activin type IB and type IIB receptors) in mammalian cardiac myogenesis.

Cardiovascular development defects have been reported in APJ KO mice, where a loss of homozygous mutants has been described, but not in apelin KO mice, indicating possible ligand-independent effects of the receptor. This effect may perhaps be explained by the recent report that APJ signals independently of apelin in response to cardiac mechanical stretch. APJ KO embryos at E10.5, when lethality begins, have poorly developed vasculature of the yolk sac, delayed formation of the atrioventricular cushion and unusually formed cardinal veins and dorsal aorta. APJ KOs that survive do not reveal any apparent morphological differences; however, they have decreased vascular smooth muscle layer recruitment and myocardial defects including thinning of the myocardium, enlarged right ventricles and ventricular septal defects, suggesting an involvement of apelin/APJ signaling in cardiovascular development.

Apelin appears to have a role to play in the pathophysiology of the cardiovascular system—it has been implicated in vascular diseases, heart failure, and ischemia and subsequent reperfusion. In vascular diseases, the expression of apelin is up-regulated in the atherosclerosis of human coronary artery. Yet its role is undetermined, as conflicting evidence has been found in KO studies, indicating both antagonistic and inducing roles for apelin in atherosclerotic formation. During heart failure, plasma apelin levels rise in the early stages of disease and stabilize or lower as the condition develops. However, APJ mRNA is decreased in the weakened and enlarged heart of humans with idiopathic dilated cardiomyopath. Apelin may have a cardioprotective role in hypoxia and ischemia, where the cardiac levels of apelin and APJ respectively are increased. Apelin may also play a protective a role in ischemia/reperfusion injury, although the method of signaling appears to be independent of the characteristic myocardial kinase cascade, termed the reperfusion injury salvage kinase pathway. Post-infarct treatment with $(Pyr^1)$apelin-13 reduces infarct size and increases HR, with a long-term antioxidant cardioprotective action.

Apelin is an angiogenic factor and mitogen of endothelial cells. Significantly, apelin is required for the normal development of frog heart and formation of murine blood vessels. Additionally, the development of the retinal vasculature is stunted in apelin KO mice, and apelin is necessary for hypoxia-induced retinal angiogenesis, and is also involved in non-neovascular remodeling of the retina.

The apelinergic system has been implicated in tumor neoangiogenesis. In brain tumors, the expression of apelin and APJ is up-regulated in microvascular proliferations, while tumor cell lines overexpressing apelin show increased growth. The pathophysiological effects of apelin in angiogenesis have also been reported for the liver, where the apelinergic system is a factor in portosystemic collaterization and splanchnic neovascularization in portal hypotensive rats as well as in neovascularization during liver cirrhosis. However, apelin may have therapeutic effects in ischemia recovery due to vessel regeneration and endothelial proliferation and blood vessel diameter regulation. These findings indicate that apelin is a crucial factor for angiogenesis and that there may be therapeutic potential in both the disruption of its signaling (e.g., tumors) and the stimulation of APJ expression (e.g., ischemia recovery).

The detection of APJ mRNA expression in areas of the brain critical for the control of fluid homeostasis led to the hypothesis that apelin may play a role in the regulation of body fluid balance. VP, along with OT, is synthesized primarily in the neurones of the mPVN and SON, which project to the posterior pituitary and release the peptides into the systemic circulation. The predominant endocrine function of VP from this source is to increase water permeability in the renal collecting duct cells, thereby allowing the retention of water.

The regulatory actions of apelin on thirst and drinking behavior have been reported. In water-replete animals, a significant increase in water intake is observed following i.p. or i.c.v. injection of apelin, whereas in other studies apelin has been reported to reduce water intake post i.c.v. injection or to have no effect. Additionally, in water-deprived rats, an inhibitory effect or lack of any effect of apelin on drinking behavior is observed, while in apelin KO mice, the dehydration-induced drinking response is comparable to that observed in WT mice. The expression of apelin and APJ mRNAs, and labelling of apelin-immunoreactive magnocellular cells, are increased by dehydration, while the labelling of VP-immunoreactive cells decreases, implying the differential regulation of these peptides in response to dehydration. Recently, however, abnormal fluid homeostasis has been demonstrated in APJ KO mice, manifested by a decrease in drinking behavior and an inability to concentrate urine to levels observed in controls during water deprivation, suggesting an antidiuretic effect of apelin in vivo. However, in lactating rats, apelin induces diuresis and has direct effects on renal vasculature. APJ is also necessary in dehydration-induced signaling in the subfornical organ, implicating the apelinergic pathway in responses to hyperosmotic stimuli.

A number of studies have pointed out an emerging involvement of apelin in energy metabolism and a role for adipocyte-derived apelin in the (patho)-physiology of obesity has been reported. Both apelin and APJ mRNAs are present in mouse, human and rat adipose tissue, and their levels increase in adipose tissue and plasma with obesity. This highlights APJ as an intriguing therapeutic target for metabolic disorders. However, the expression of plasma apelin is increased only in obese humans and in mouse models of obesity associated with hyperinsulinemia, indicating that obesity or high-fat feeding may not be the main cause for the rise in the expression of apelin, and implying a close relationship between apelin and insulin both in vivo and in vitro. Insulin directly acts on adipocytes in vitro to stimulate the production of apelin, and the expression of apelin mRNA is down-regulated in the adipocytes of mice treated with the β-cell toxin streptozotocin, which leads to a fall in plasma insulin levels. In mice, nutritional status influences apelin levels in vivo—fasting inhibits plasma levels, which are then restored by re-feeding—thus strengthening the implication that insulin regulates apelin gene expression and secretion. Additionally, apelin, perhaps through APJ expressed in pancreatic islet β-cells, regulates the secretion of insulin—apelin inhibits glucose-stimulated insulin secretion in vivo in mice and in isolated islets of Langerhans in vitro. Interestingly, in a recent study, apelin has been shown to alleviate diabetes-induced reduction of pancreatic islet mass and to improve the insulin content of pancreatic islets in type 1 diabetic mice.

Apelin may have a positive effect in the metabolic syndrome (a combination of risk factors that when occurring together increase the risk of coronary artery disease, stroke and type 2 diabetes (T2D)). Apelin KO mice have reduced insulin sensitivity, are glucose intolerant and are hyperinsulinemic. The peripheral administration of apelin reduces peak plasma glucose concentrations by increasing glucose uptake in skeletal muscle and adipose tissue and improves insulin sensitivity in both apelin KO and obese high-fat diet fed mice, with the insulin-sensitizing effects continuing for up to 4 weeks, with no tolerance to the actions of apelin. Apelin increases glucose uptake, both in vitro and in vivo, through both insulin-dependent and -independent pathways. Apelin may also decrease body adiposity, independently of altered food intake, by increasing energy expenditure through the activation of mitochondrial uncoupling proteins 1 and 3. Clinical studies have shown a promising therapeutic value for apelin, as apelin displays beneficial glucose-lowering effects in human adipose tissue and plasma apelin levels correlate with glucose and HbA1c levels. Apelin is linked to the pathogenesis of T2D—plasma apelin concentrations are increased in insulin-resistant patients, in type T2D patients and in morbidly obese T2D individuals, perhaps indicating a compensatory role of apelin in the reduction of insulin resistance. However, conversely, plasma apelin levels are reduced in newly diagnosed T2D patients and increased in T2D patients and obese non-diabetic individuals. The increased expression of apelin in plasma and adipose tissue of obese individuals can, however, be reversed by a hypocaloric diet. As a result of such studies, similarities between the function of apelin and that of insulin, and a link between this adipokine and glucose homeostasis, have been hypothesized.

As has been noted previously, APJ is localized in the hypothalamic pPVN and the anterior pituitary gland, key areas involved in the stress response. Apelin mRNA is also present in these areas, co-localizing with VP in the mPVN, SON and pituitary. Additionally, apelin immunostaining of cell bodies and fibers is highest in the hypothalamus, with large numbers of apelin-positive cell bodies present in the PVN and SON. The presence of APJ and apelin in VP- and CRH-containing hypothalamic nuclei, which are pivotal to the HPA axis responses to stress, suggests a role for apelin/APJ in neuroadenohypophysial hormone release.

A role for apelin in the regulation of the HPA axis responses to stress is supported by studies showing that central administration of (Pyr$^1$)apelin-13 increases the expression of c-fos, an indicator of neuronal activity, in the PVN. Furthermore, administration of apelin-13 stimulates the release of CRH and VP from hypothalamic extracts in vitro, effects consistent with stimulation of the stress axis. APJ mRNA levels increase in the PVN in response to acute and chronic stress and following adrenalectomy, implying negative regulation of the expression of APJ mRNA by glucocorticoids. Additionally, dexamethasone, a glucocorticoid agonist, decreases apelin mRNA levels in 3T3-L1 mouse adipocytes.

Apelin may potentially stimulate the secretion of ACTH either directly at the level of the pituitary corticotroph or via an indirect action on the hypothalamus involving the release of both VP and CRH. Consistent with the expression of apelin and APJ in anterior pituitary corticotrophs, administration of apelin-17 directly increases the release of ACTH, while also augmenting K$^+$-stimulated ACTH release, in an ex vivo perfusion system of anterior pituitary glands, suggesting possible autocrine or paracrine functions for apelin in this tissue. Central administration of (Pyr$^1$)apelin-13 in rats also increases plasma ACTH and CORT levels while decreasing prolactin, luteinizing hormone and follicle-stimulating hormone levels. However, increases in plasma ACTH and CORT levels observed after i.c.v. administration of (Pyr$^1$)apelin-13 in mice are reduced to control levels by pre-treatment with the CRH receptor antagonist α-helical CRH$_{9-41}$, while (Pyr$^1$)apelin-13-mediated increases in plasma ACTH levels are abolished in VP V1b receptor KO mice, indicating that apelin also modulates the release of ACTH via an indirect action on the hypothalamus involving both CRH- and VP-dependent mechanisms. Recently, using APJ KO mice, APJ has been shown to play a regulatory role in the modulation of the HPA axis responses to some acute stressors including LPS challenge (an immune stressor), insulin-induced hypoglycemia (a metabolic stressor) and forced swim (a physical/psychological stressor). These studies suggest that other peptides cannot compensate for the loss of APJ to directly, or indirectly, induce the release of ACTH in response to stress. Thus, the integration of neurobehavioral responses to stress may be more complicated than previously envisioned, with apelin/APJ exerting a pivotal neuroregulatory role.

Apelin was first isolated from stomach extracts, and studies on the actions of apelin in the gastrointestinal system have found functional, and possible cell survival, roles. In the gastrointestinal system, apelin/APJ may be regulators of hormone and gastric acid secretion. Apelin/APJ may also have a direct effect on vascular smooth muscle, including vasoconstriction, which may affect renal glomerular hemodynamic function in the rat kidney. Some studies have also proposed an immunological role for apelin as it reduces the production of cytokines in mouse spleen cells, suggesting that apelin may modulate neonatal immune responses through rodent and bovine colostrum and milk. APJ is also a co-receptor of HIV entry into target cells, an action that is blocked by apelin. APJ may contribute to HIV-1 infection and pathogenesis in CNS-based cells as viral envelope proteins can mediate fusion with APJ-positive, cluster of differentiation 4 (CD4)-negative cells, provided that CD4 is added in trans, and HIV can infect APJ-expressing cells despite their CD4 status. Other possible roles for apelin and APJ in the rodent CNS include antinociception, enhancement of depressive behavior, and facilitation of passive avoidance learning. Apelin may also have a role in neuroprotection, as apelin pre-treatment protects hippocampal neurones against N-methyl-D-aspartate (NMDA) receptor-mediated excitotoxic injury, possibly via the phosphorylation of Akt and ERK1/2, and prevents apoptosis in cultured mouse cortical neurones.

Furthermore, apelin and APJ are expressed in osteoblasts where they may induce cell proliferation and promote survival; however, an increase in bone mass can be observed in apelin KO mice. Recently, apelin has been reported to have a potential role in the pathophysiology of osteoarthritis (OA), as apelin is present in synovial fluid, and OA patients have elevated plasma apelin concentrations. Blood plasma levels of apelin are reduced in patients with polycystic ovary syndrome, consistent with the role played by apelin/APJ in metabolic disturbances such as insulin resistance.

Elevated levels of apelin have been detected in many pathological states or disease processes, such as heart disease, atherosclerosis, tumor angiogenesis and diabetes. However, in many systems, apelin has been shown to have positive effects, for example in the cardiovascular system, where it has a cardioprotective effect. This has led to speculation that apelin and APJ could be beneficial targets for therapeutic strategies for a number of diseases and disorders.

To date, there are few reports of selective small molecule apelin receptor agonists, and thus far none of the reported agonists have favorable pharmacokinetic profiles. There is a need, therefore, for potent compounds that target and exhibit dose dependent agonism of the apelin receptor.

SUMMARY OF THE INVENTION

The present invention is based on the seminal discovery of a series of potent small molecule apelin receptor agonists, which are useful for the treatment of diseases including heart failure, chronic kidney disease, hypertension, and metabolic disorders such as insulin resistance/diabetes and obesity. The compounds disclosed herein are highly specific for the apelin receptor versus the angiotensin II receptor (AT1).

Provided herein are compounds of structural Formula I, or a pharmaceutically acceptable salt, polymorph, solvate, tautomer, or N-oxide thereof:

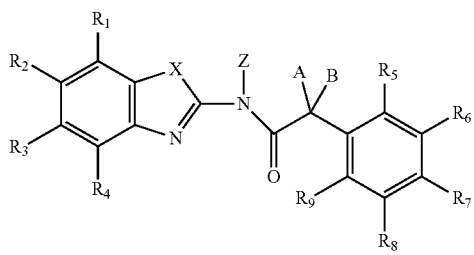

(I)

wherein:

X is selected from the group consisting of S, O, and $NR^9$;

A and B are independently selected from the group consisting of H, optionally substituted alkyl, aryl, alkoxy, phenoxy, amino, aniline, and optionally substituted 5- or 6-membered heteroaryl or heteroaryl-oxy. A and B can be combined to form a fused ring such as cyclopropyl, cyclopentyl and cyclohexyl;

each $R^1$-$R^9$ is independently selected from the group consisting of hydrogen, halogen, —CN, —C(O)—N($R^{10}$)—$R^{11}$, —C(O)—O—$R^2$, —SO2$R^{13}$ optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

each $R^{10}$-$R^{13}$ is independently selected from the group consisting of optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl; and Z is selected from the group consisting of hydrogen, optionally substituted alkyl, optionally substituted cycloalkyl, and optionally substituted heterocycloalkyl.

Provided herein are compounds of structural Formula II, or a pharmaceutically acceptable salt, polymorph, solvate, tautomer, or N-oxide thereof:

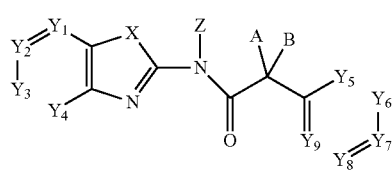

(II)

wherein:

X is selected from the group consisting of S, O and $NR^9$;

A and B are each independently selected from the group consisting of H, optionally substituted alkyl, aryl, alkoxy, phenoxy, amino, aniline, and optionally substituted 5- or 6-membered heteroaryl or heteroaryl-oxy or A and B can be taken together and joined to form a carbocyclic, heterocyclic, aryl or heteroaryl fused ring system;

each $Y^1$-$Y^9$ are independently selected from the group consisting of N and $CR^{14}$;

$R^{14}$ is selected from the group consisting of hydrogen, halogen, —CN, —C(O)—N($R^{15}$)—$R^6$, —C(O)—O—$R^7$, —SO2$R^{18}$ optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

each $R^{15}$-$R^{18}$ is independently selected from the group consisting of optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl; and Z is selected from the group consisting of hydrogen, optionally substituted alkyl, optionally substituted cycloalkyl, and optionally substituted heterocycloalkyl.

In certain aspects, A and B are taken together and joined to form cyclopropyl, cyclopentyl or cyclohexyl.

Provided herein are compounds of structural Formula III, or a pharmaceutically acceptable salt, polymorph, solvate, tautomer, or N-oxide thereof:

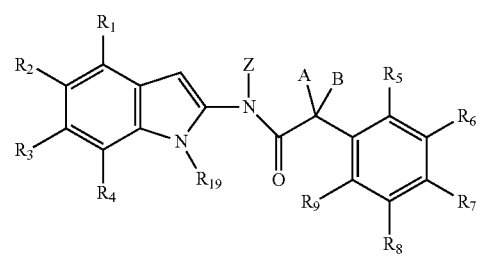

(III)

wherein:

A and B are independently selected from the group consisting of H, optionally substituted alkyl, aryl, alkoxy, phenoxy, amino, aniline, and optionally substituted 5- or 6-membered heteroaryl or heteroaryl-oxy. A and B can be combined to form a fused ring such as cyclopropyl, cyclopentyl and cyclohexyl;

each $R^1$-$R^9$ is independently selected from the group consisting of hydrogen, halogen, —CN, —C(O)—N($R^{10}$)—$R^{11}$, —C(O)—O—$R^2$, —SO2$R^{13}$ optionally substituted alkyl, optionally substituted cycloalkyl, optionally substituted heterocycloalkyl, optionally substituted alkoxy, haloalkyl, haloalkoxy, optionally substituted phenyl, optionally substituted amino, and optionally substituted 5- or 6-membered heteroaryl;

each $R^{10}$-$R^{13}$ is independently selected from the group consisting of hydrogen, optionally substituted alkyl, optionally substituted cycloalkyl, optionally substituted heterocycloalkyl, optionally substituted alkoxy, haloalkyl, haloalkoxy, optionally substituted phenyl, optionally substituted amino, and optionally substituted 5- or 6-membered heteroaryl; and Z and $R^{19}$ are independently selected from the group consisting of hydrogen, optionally substituted alkyl, optionally substituted cycloalkyl, and optionally substituted heterocycloalkyl.

In other aspects, the compounds provided herein are methyl 4-{[N-(5,6-dimethoxybenzothiazol-2-yl)carbamoyl]methyl}benzoate, methyl 3-{[N-(5,6-dimethoxybenzothiazol-2-yl)carbamoyl]methyl}benzoate, 3-{[N-(5,6-dimethoxybenzothiazol-2-yl)carbamoyl]methyl}benzoic acid, 4-{[N-(5,6-dimethoxybenzothiazol-2-yl)carbamoyl]methyl}benzoic acid, 2-{[N-(5,6-dimethoxybenzothiazol-2-yl)carbamoyl]methyl}benzoic acid, N-(5,6-dimethoxybenzothiazol-2-yl)-2-[4-(ethylsulfonyl)phenyl]propanamide, N-(5,6-dimethoxybenzothiazol-2-yl)-2-[4-(ethylsulfonyl)phenyl]butanamide, N-(5,6-dimethoxybenzothiazol-2-yl)-2-[4-(ethylsulfonyl)phenyl]-3-methylbutanamide, N-(5,6-dimethoxybenzothiazol-2-yl)-2-[4-(ethylsulfonyl)phenyl]-2-(4-methoxyphenoxy)acetamide, N-(5,6-dimethoxybenzothiazol-2-yl)-2-[3-(N,N-dimethylcarbamoyl)phenyl]acetamide, N-(5,6-dimethoxybenzothiazol-2-yl)-2-[4-(N,N-dimethylcarbamoyl)phenyl]acetamide, N-(5,6-dimethoxybenzothiazol-2-yl)-2-{4-[(dimethylamino)sulfonyl]phenyl}acetamide, N-(5,6-dimethoxybenzothiazol-2-yl)-2-[4-(ethylsulfonyl)phenyl]-4-methoxybutanamide, N-(5,6-dimethoxybenzothiazol-2-yl)-3-cyclopropyl-2-[4-(ethylsulfonyl)phenyl]propanamide, N-(5,6-dimethoxybenzothiazol-2-yl)-2-[4-(ethylsulfonyl)phenyl]-3-phenylpropanamide, N-(5,6-dimethoxybenzothiazol-2-yl)-2-[2-(N,N-dimethylcarbamoyl)phenyl]acetamide, N-(5,6-dimethoxybenzothiazol-2-yl)-2-[3-(ethylsulfonyl)phenyl]acetamide, N-(2H-1,3-dioxolano[4,5-e]benzothiazol-7-yl)-2-[4-(ethylsulfonyl)phenyl]acetamide, N-(5,6-dimethoxybenzothiazol-2-yl){[4-(ethylsulfonyl)phenyl]cyclopropyl}carboxamide, N-(5,6-dimethoxybenzothiazol-2-yl)-2-cyclopentyl-2-[4-(ethylsulfonyl)phenyl]acetamide, N-(7H,8H-1,4-dioxano[5,6-e]benzothiazol-2-yl)-2-[4-(ethylsulfonyl)phenyl]acetamide, N-[5-(diethylamino)benzothiazol-2-yl]-2-[4-(ethylsulfonyl)phenyl]acetamide, N-(5,6-dimethoxybenzothiazol-2-yl)-2-{3-[(4-fluorophenyl)sulfonyl]phenyl}acetamide, N-(5,6-dimethoxybenzothiazol-2-yl)-2-{4-[(cyclopropylmethyl)sulfonyl]phenyl}acetamide, N-(5,6-dimethoxybenzothiazol-2-yl)-2-{4-[(methylethyl)sulfonyl]phenyl}acetamide, N-(5,6-dimethoxybenzothiazol-2-yl)-2-[4-(cyclopentylsulfonyl)phenyl]acetamide, N-(5,6-dimethoxybenzothiazol-2-yl)-2-[4-(ethylsulfonyl)phenyl]-2-methoxyacetamide, N-(5,6-dimethoxybenzimidazol-2-yl)-2-[4-(ethylsulfonyl)phenyl]acetamide, N-(5,6-dimethoxybenzothiazol-2-yl)-2-(dimethylamino)-2-[4-(ethylsulfonyl)phenyl]acetamide, N-(5,6-dimethoxybenzothiazol-2-yl)-2-[4-(ethylsulfonyl)phenyl]-2-piperidylacetamide, N-(5,6-dimethoxybenzothiazol-2-yl)-2-[4-(ethylsulfonyl)phenyl]-2-morpholin-4-yl acetamide, N-(5,6-dimethoxybenzoxazol-2-yl)-2-[4-(ethylsulfonyl)phenyl]acetamide, N-(5,6-dimethoxybenzothiazol-2-yl)-2-{4-[(2-methoxyethyl)sulfonyl]phenyl}acetamide, N-(5,6-dimethoxybenzothiazol-2-yl)-2-{3-[(methylethyl)sulfonyl]phenyl}acetamide, N-(5,6-dimethoxybenzothiazol-2-yl)-2-{3-[(cyclopropylmethyl)sulfonyl]phenyl}acetamide, N-(5,6-dimethoxybenzothiazol-2-yl)-2-[3-(cyclopentyl sulfonyl)phenyl]acetamide, N-(5,6-dimethoxybenzothiazol-2-yl)-2-[4-(ethylsulfonyl)phenyl]-2-(2-methoxyphenoxy)acetamide, N-(5,6-dimethoxybenzothiazol-2-yl)-2-[4-(ethylsulfonyl)phenyl]-2-(3-methoxyphenoxy)acetamide, N-(5,6-dimethoxybenzothiazol-2-yl)-2-[4-(ethylsulfonyl)phenyl]-2-[4-(trifluoromethyl)phenoxy]acetamide, N-(5,6-dimethoxybenzothiazol-2-yl)-2-(4-cyanophenoxy)-2-[4-(ethylsulfonyl)phenyl]acetamide, N-(5,6-dimethoxybenzothiazol-2-yl)-2-[4-(ethylsulfonyl)phenyl]-2-(methylethoxy)acetamide, N-(5,6-dimethoxybenzothiazol-2-yl)-2-[4-(ethylsulfonyl)phenyl]-2-propoxyacetamide, N-(5,6-dimethoxybenzothiazol-2-yl)-2-cyclopentyloxy-2-[4-(ethylsulfonyl)phenyl]acetamide, N-(5,6-dimethoxybenzothiazol-2-yl)-2-cyclohexyloxy-2-[4-(ethylsulfonyl)phenyl]acetamide, N-(5,6-dimethoxybenzothiazol-2-yl)-2-[4-(ethylsulfonyl)phenyl]-2-(3-methylbutoxy)acetamide, 2-[4-(ethylsulfonyl)phenyl]-N-[6-(4-methylpiperazinyl)benzothiazol-2-yl]acetamide, 2-[4-(ethylsulfonyl)phenyl]-2-(4-methoxyphenoxy)-N-[6-(4-methylpiperazinyl)benzothiazol-2-yl]acetamide, N-(5,6-dimethoxybenzothiazol-2-yl)-2-{2-[(4-fluorophenyl)sulfonyl]phenyl}-2-(4-methoxyphenoxy)acetamide, N-(5,6-dimethoxybenzothiazol-2-yl)-2-[3-(ethylsulfonyl)phenyl]-2-(4-methoxyphenoxy)acetamide, N-(5,6-dimethoxybenzothiazol-2-yl)-2-[4-(ethylsulfonyl)phenyl]-2-(4-methylphenoxy)acetamide, N-(5,6-dimethoxybenzothiazol-2-yl)-2-(4-chlorophenoxy)-2-[4-(ethylsulfonyl)phenyl]acetamide, N-(5,6-dimethoxybenzothiazol-2-yl)-2-[4-(ethylsulfonyl)phenyl]-2-(2-methylphenoxy)acetamide, N-(5,6-dimethoxybenzothiazol-2-yl)-2-(2-chlorophenoxy)-2-[4-(ethylsulfonyl)phenyl]acetamide, N-(5,6-dimethoxybenzothiazol-2-yl)-2-[4-(ethylsulfonyl)phenyl]-2-(phenylmethoxy)acetamide, N-(5,6-dimethoxybenzothiazol-2-yl)-2-[4-(ethylsulfonyl)phenyl]-2-(2-methylpropoxy)acetamide, N-(5,6-dimethoxybenzothiazol-2-yl)-2-[4-(ethylsulfonyl)phenyl]-2-(3-methylbut-2-enyloxy)acetamide, 2-(2H-3,4,5,6-tetrahydropyran-4-yloxy)-N-(5,6-dimethoxybenzothiazol-2-yl)-2-[4-(ethylsulfonyl)phenyl]acetamide, N-(7H,8H-1,4-dioxano[5,6-g]benzothiazol-2-yl)-2-[4-(ethylsulfonyl)phenyl]-2-(4-methoxyphenoxy)acetamide, N-(7H,8H-1,4-dioxano[5,6-g]benzothiazol-2-yl)-2-(4-cyanophenoxy)-2-[4-(ethylsulfonyl)phenyl]acetamide, 2-[4-(ethylsulfonyl)phenyl]-N-(6-methoxybenzothiazol-2-yl)-2-(4-methoxyphenoxy)acetamide, 2-(4-cyanophenoxy)-2-[4-(ethylsulfonyl)phenyl]-N-(6-methoxybenzothiazol-2-yl)acetamide, N-(5,6-dimethoxybenzothiazol-2-yl)-2-(4-cyanophenoxy)-2-{2-[(4-fluorophenyl)sulfonyl]phenyl}acetamide, N-(5,6-dimethoxybenzothiazol-2-yl)-2-(4-methoxyphenoxy)-2-{2-[(4-methoxyphenyl)sulfonyl]phenyl}acetamide, N-(5,6-dimethoxybenzothiazol-2-yl)-2-(4-cyanophenoxy)-2-{2-[(4-methoxyphenyl)sulfonyl]phenyl}acetamide, N-(5,6-dimethoxybenzothiazol-2-yl)-2-{3-[(4-fluorophenyl)sulfonyl]phenyl}-2-(4-methoxyphenoxy)acetamide, N-(5,6-dimethoxybenzothiazol-2-yl)-2-(3-chlorophenoxy)-2-[4-(ethylsulfonyl)phenyl]acetamide, N-(5,6-dimethoxybenzothiazol-2-yl)-2-[4-(ethylsulfonyl)phenyl]-2-(3-methylphenoxy)acetamide, N-(5,6-dimethoxybenzothiazol-2-yl)-2-[4-(ethylsulfonyl)phenyl]-2-phenoxyacetamide, N-(5,6-dimethoxybenzothiazol-2-yl)-2-(4-cyano-3-fluorophenoxy)-2-[4-(ethylsulfonyl)phenyl]acetamide, N-(5,6-dimethoxybenzothiazol-2-yl)-2-[4-(ethylsulfonyl)phenyl]-2-(2-methoxyethoxy)acetamide, N-(2H-1,3-dioxolano[4,5-g]benzothiazol-7-yl)-2-[4-(ethylsulfonyl)phenyl]-2-(4-methoxyphenoxy)acetamide, N-(2H-1,3-dioxolano[4,5-g]benzothiazol-7-yl)-2-(4-cyanophenoxy)-2-[4-(ethylsulfonyl)phenyl]acetamide, 2-(4-cyanophenoxy)-2-[4-(ethylsulfonyl)phenyl]-N-(5-methoxybenzothiazol-2-yl)acetamide, N-(4,7-dimethoxybenzothiazol-2-yl)-2-(4-cyanophenoxy)-2-[4-(ethylsulfonyl)phenyl]acetamide, N-(2H-1,3-dioxoleno[4,5- f]benzothiazol-6-yl)-2-[4-(ethylsulfonyl)phenyl]-2-(4-methoxyphenoxy)acetamide, N-(4,7-dimethoxybenzothiazol-2-yl)-2-[4-(ethylsulfonyl)phenyl]-2-(4-methoxyphenoxy)acetamide, 2-(4-cyanophenoxy)-2-[4-(ethylsulfonyl)phenyl]-N-[6-(4-methylpiperazinyl)benzothiazol-2-yl] acetamide, N-(5,6-dimethoxybenzothiazol-2-yl)-2-(4-cyanophenoxy)-2-{2-[benzylsulfonyl]phenyl}acetamide, N-(5,6-dimethoxybenzothiazol-2-yl)-2-(4-cyanophenoxy)-2-[2-(ethylsulfonyl)phenyl]acetamide, N-(5,6-dimethoxybenzothiazol-2-yl)-2-(4-cyanophenoxy)-2-f 3-[(4-fluorophenyl)sulfonyl]phenyl)acetamide, N-(5,6-dimethoxybenzothiazol-2-yl)-2-(4-cyanophenoxy)-2-{3-[benzylsulfonyl]phenyl}acetamide, N-[4-(3,4-dimethoxyphenyl)(1,3-thiazol-2-yl)]-2-(4-cyanophenoxy)-2-[4-(ethylsulfonyl)phenyl]acetamide, 2-(4-cyanophenoxy)-2-[4-(ethylsulfonyl)phenyl]-N-[4-(3-methoxyphenyl)(1,3-thiazol-2-yl)]acetamide, 2-(4-cyanophenoxy)-2-[4-(ethylsulfonyl)phenyl]-N-(4-phenyl(1,3-thiazol-2-yl)) acetamide, methyl 2-(2-{2-(4-cyanophenoxy)-2-[4-(ethylsulfonyl)phenyl]acetylamino}-1,3-thiazol-4-yl) acetate, 4-{1-[4-(ethylsulfonyl)phenyl]-2-(4-hydroxypiperidyl)-2-oxoethoxy}benzenecarbonitrile, 4-{1-[4-(ethylsulfonyl)phenyl]-2-oxo-2-(4-oxopiperidyl) ethoxy}benzenecarbonitrile, 2-(4-cyanophenoxy)-2-[4-(ethylsulfonyl)phenyl]-N-(4-hydroxycyclohexyl)acetamide, 2-(4-cyanophenoxy)-2-[4-(ethylsulfonyl)phenyl]-N-(3-methoxypropyl)acetamide or 2-(4-cyanophenoxy)-2-[4-(ethylsulfonyl)phenyl]-N-(2-morpholin-4-ylethyl)acetamide.

In other aspects, the compounds provided herein are N-(5,6-Dimethoxy-benzothiazol-2-yl)-2-(4-ethanesulfonyl-phenyl)-acetamide, N-(6,7-Dihydro-5,8-dioxa-1-thia-3-aza-cyclopenta[b]naphthalen-2-yl)-2-(4-ethanesulfonyl-phenyl)-acetamide, N-[1,3]Dioxolo[4',5':4,5]benzo[1,2-d]thiazol-6-yl-2-(4-ethanesulfonyl-phenyl)-acetamide, N-[1,3]Dioxolo[4',5':3,4]benzo[2,1-d]thiazol-7-yl-2-(4-ethanesulfonyl-phenyl)-acetamide, N-(7,8-Dihydro-6,9-dioxa-3-thia-1-aza-cyclopenta[a]naphthalen-2-yl)-2-(4-ethanesulfonyl-phenyl)-acetamide, N-(4,7-Dimethoxy-benzothiazol-2-yl)-2-(4-ethanesulfonyl-phenyl)-acetamide, N-(5-Dimethylamino-benzothiazol-2-yl)-2-(4-ethanesulfonyl-phenyl)-acetamide, N-(5-Diethylamino-benzothiazol-2-yl)-2-(4-ethanesulfonyl-phenyl)-acetamide, 2-(4-Ethanesulfonyl-phenyl)-N-[6-(4-methyl-piperazin-11-yl)-benzothiazol-2-yl]-acetamide, N-(5,6-Dimethoxy-1H-benzoimidazol-2-yl)-2-(4-ethanesulfonyl-phenyl)-acetamide, N-(5,6-dimethoxy-benzooxazol-2-yl)-2-(4-ethanesulfonyl-phenyl)-acetamide, 2-(4-Cyclopropylmethanesulfonyl-phenyl)-N-(5,6-dimethoxy-benzothiazol-2-yl)-acetamide, N-(5,6-Dimethoxy-benzothiazol-2-yl)-2-[4-(propane-2-sulfonyl)-phenyl]-acetamide, 2-(4-Cyclopentanesulfonyl-phenyl)-N-(5,6-dimethoxy-benzothiazol-2-yl)-acetamide, N-(5,6-Dimethoxy-benzothiazol-2-yl)-2-[4-(2-methoxy-ethanesulfonyl)-phenyl]-acetamide, N-(5,6-Dimethoxy-benzothiazol-2-yl)-2-(3-ethanesulfonyl-phenyl)-acetamide, 2-(3-Cyclopropylmethanesulfonyl-phenyl)-N-(5,6-dimethoxy-benzothiazol-2-yl)-acetamide, N-(5,6-Dimethoxy-benzothiazol-2-yl)-2-[3-(propane-2-sulfonyl)-phenyl]-acetamide, 2-(3-Cyclopentanesulfonyl-phenyl)-N-(5,6-dimethoxy-benzothiazol-2-yl)-acetamide, N-(5,6-Dimethoxy-benzothiazol-2-yl)-2-(3-ethanesulfonyl-phenyl)-acetamide, N-(5,6-Dimethoxy-benzothiazol-2-yl)-2-(4-dimethylsulfamoyl-phenyl)-acetamide, 2-[(5,6-Dimethoxy-benzothiazol-2-ylcarbamoyl)-methyl]-benzoic acid, 3-[(5,6-Dimethoxy-benzothiazol-2-ylcarbamoyl)-methyl]-benzoic acid, 4-[(5,6-Dimethoxy-benzothiazol-2-ylcarbamoyl)-methyl]-benzoic acid, 3-[(5,6-Dimethoxy-benzothiazol-2-ylcarbamoyl)-methyl]-benzoic acid methyl ester, 4-[(5,6-Dimethoxy-benzothiazol-2-ylcarbamoyl)-methyl]-benzoic acid methyl ester, 2-[(5,6-Dimethoxy-benzothiazol-2-ylcarbamoyl)-methyl]-N,N-dimethyl-benzamide, 3-[(5,6-Dimethoxy-benzothiazol-2-ylcarbamoyl)-methyl]-N,N-dimethyl-benzamide, 4-[(5,6-Dimethoxy-benzothiazol-2-ylcarbamoyl)-methyl]-N,N-dimethyl-benzamide, N-(5,6-Dimethoxy-benzothiazol-2-yl)-2-(4-ethanesulfonyl-phenyl)-propionamide, N-(5,6-Dimethoxy-benzothiazol-2-yl)-2-(4-ethanesulfonyl-phenyl)-butyramide, N-(5,6-Dimethoxy-benzothiazol-2-yl)-2-(4-ethanesulfonyl-phenyl)-3-methyl-butyramide, N-(5,6-Dimethoxy-benzothiazol-2-yl)-2-(4-ethanesulfonyl-phenyl)-4-methoxy-butyramide, 3-Cyclopropyl-N-(5,6-dimethoxy-benzothiazol-2-yl)-2-(4-ethanesulfonyl-phenyl)-propionamide, N-(5,6-Dimethoxy-benzothiazol-2-yl)-2-(4-ethanesulfonyl-phenyl)-3-phenyl-propionamide, 2-Cyclopentyl-N-(5,6-dimethoxy-benzothiazol-2-yl)-2-(4-ethanesulfonyl-phenyl)-acetamide, 1-(4-Ethanesulfonyl-phenyl)-cyclopropanecarboxylic acid (5,6-dimethoxy-benzothiazol-2-yl)-amide, N-(5,6-Dimethoxy-benzothiazol-2-yl)-2-(4-ethanesulfonyl-phenyl)-2-isopropoxy-acetamide, N-(5,6-Dimethoxy-benzothiazol-2-yl)-2-(4-ethanesulfonyl-phenyl)-2-methoxy-acetamide, N-(5,6-Dimethoxy-benzothiazol-2-yl)-2-(4-ethanesulfonyl-phenyl)-2-propoxy-acetamide, 2-Cyclopentyloxy-N-(5,6-dimethoxy-benzothiazol-2-yl)-2-(4-ethanesulfonyl-phenyl)-acetamide, 2-Cyclohexyloxy-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(3-methyl-butoxy)-acetamide, 2-Benzyloxy-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-isobutoxy-acetamide, N-(5,6-Dimethoxy-benzothiazol-2-yl)-2-(4-ethanesulfonyl-phenyl)-2-(3-methyl-but-2-enyloxy)-acetamide, N-(5,6-Dimethoxy-benzothiazol-2-yl)-2-(4-ethanesulfonyl-phenyl)-2-(tetrahydro-pyran-4-yloxy)-acetamide, N-(5,6-Dimethoxy-benzothiazol-2-yl)-2-(4-ethanesulfonyl-phenyl)-2-(2-methoxy-ethoxy)-acetamide, 2-Cyclohexylmethoxy-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(tetrahydro-pyran-4-ylmethoxy)-acetamide, N-(5,6-Dimethoxy-benzothiazol-2-yl)-2-(4-ethanesulfonyl-phenyl)-2-(3-methoxy-propoxy)-acetamide, N-(5,6-Dimethoxy-benzothiazol-2-yl)-2-(4-ethanesulfonyl-phenyl)-2-phenethyloxy-acetamide, 2-(4-Cyano-benzyloxy)-N-(5,6-dimethoxy-benzothiazol-2-yl)-2-(4-ethanesulfonyl-phenyl)-acetamide, 2-(4-Cyano-phenoxy)-N-(5,6-dimethoxy-benzothiazol-2-yl)-2-(4-ethanesulfonyl-phenyl)-acetamide (SBI-0662457), 2-(4-Cyano-phenoxy)-N-(5,6-dimethoxy-benzothiazol-2-yl)-2-(4-ethanesulfonyl-phenyl)-acetamide, 2-(4-Cyano-phenoxy)-N-(5,6-dimethoxy-benzothiazol-2-yl)-2-(4-ethanesulfonyl-phenyl)-acetamide, 2-(4-Cyano-phenoxy)-N-(5,6-dimethoxy-benzothiazol-2-yl)-2-(4-ethanesulfonyl-phenyl)-N-methyl-acetamide, 2-(3-Cyano-phenoxy)-N-(5,6-dimethoxy-benzothiazol-2-yl)-2-(4-ethanesulfonyl-phenyl)-acetamide, 2-(4-Cyano-2-trifluoromethyl-phenoxy)-N-(5,6-dimethoxy-benzothiazol-2-yl)-2-(4-ethanesulfonyl-phenyl)-acetamide, 2-(2-Chloro-4-cyano-phenoxy)-N-(5,6-dimethoxy-benzothiazol-2-yl)-2-(4-ethanesulfonyl-phenyl)-acetamide, 2-(3-Chloro-4-cyano-phenoxy)-N-(5,6-dimethoxy-benzothiazol-2-yl)-2-(4-ethanesulfonyl-phenyl)-acetamide, 2-(4-Cyano-2-fluoro-phenoxy)-N-(5,6-dimethoxy-benzothiazol-2-yl)-2-

(4-ethanesulfonyl-phenyl)-acetamide, 2-(4-Cyano-3-fluoro-phenoxy)-N-(5,6-dimethoxy-benzothiazol-2-yl)-2-(4-ethanesulfonyl-phenyl)-acetamide, 2-(4-Cyano-2-methyl-phenoxy)-N-(5,6-dimethoxy-benzothiazol-2-yl)-2-(4-ethanesulfonyl-phenyl)-acetamide, 2-(4-Cyano-3-methyl-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(naphthalen-1-yloxy)-acetamide, N-(5,6-Dimethoxy-benzothiazol-2-yl)-2-(4-ethanesulfonyl-phenyl)-2-(naphthalen-2-yloxy)-acetamide, N-(5,6-Dimethoxy-benzothiazol-2-yl)-2-(4-ethanesulfonyl-phenyl)-2-phenoxy-acetamide, 2-(4-Chloro-phenoxy)-N-(5,6-dimethoxy-benzothiazol-2-yl)-2-(4-ethanesulfonyl-phenyl)-acetamide, 2-(2-Chloro-phenoxy)-N-(5,6-dimethoxy-benzothiazol-2-yl)-2-(4-ethanesulfonyl-phenyl)-acetamide, 2-(3-Chloro-phenoxy)-N-(5,6-dimethoxy-benzothiazol-2-yl)-2-(4-ethanesulfonyl-phenyl)-acetamide, 2-(4-Bromo-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(4-iodo-phenoxy)-acetamide, N-(5,6-Dimethoxy-benzothiazol-2-yl)-2-(4-ethanesulfonyl-phenyl)-2-(4-ethynyl-phenoxy)-acetamide, N-(5,6-Dimethoxy-benzothiazol-2-yl)-2-(4-ethanesulfonyl-phenyl)-2-(2-iodo-phenoxy)-acetamide, N-(5,6-Dimethoxy-benzothiazol-2-yl)-2-(4-ethanesulfonyl-phenyl)-2-(4-fluoro-phenoxy)-acetamide, N-(5,6-Dimethoxy-benzothiazol-2-yl)-2-(4-ethanesulfonyl-phenyl)-2-(4-trifluoromethyl-phenoxy)-acetamide, N-(5,6-Dimethoxy-benzothiazol-2-yl)-2-(4-ethanesulfonyl-phenyl)-2-p-tolyloxy-acetamide, N-(5,6-Dimethoxy-benzothiazol-2-yl)-2-(4-ethanesulfonyl-phenyl)-2-o-tolyloxy-acetamide, N-(5,6-Dimethoxy-benzothiazol-2-yl)-2-(4-ethanesulfonyl-phenyl)-2-m-tolyloxy-acetamide, N-(5,6-Dimethoxy-benzothiazol-2-yl)-2-(4-ethanesulfonyl-phenyl)-2-(4-ethyl-phenoxy)-acetamide, N-(5,6-Dimethoxy-benzothiazol-2-yl)-2-(4-ethanesulfonyl-phenyl)-2-(4-propyl-phenoxy)-acetamide, N-(5,6-Dimethoxy-benzothiazol-2-yl)-2-(4-ethanesulfonyl-phenyl)-2-(4-isopropyl-phenoxy)-acetamide, 2-(4-Butyl-phenoxy)-N-(5,6-dimethoxy-benzothiazol-2-yl)-2-(4-ethanesulfonyl-phenyl)-acetamide, 2-(4-Cyclopentyl-phenoxy)-N-(5,6-dimethoxy-benzothiazol-2-yl)-2-(4-ethanesulfonyl-phenyl)-acetamide, 2-(4-Cyclohexyl-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(4-trifluoromethoxy-phenoxy)-acetamide, N-(5,6-Dimethoxy-benzothiazol-2-yl)-2-(4-ethanesulfonyl-phenyl)-2-(4-methoxy-phenoxy)-acetamide, N-(5,6-Dimethoxy-benzothiazol-2-yl)-2-(4-ethanesulfonyl-phenyl)-2-(2-methoxy-phenoxy)-acetamide, N-(5,6-Dimethoxy-benzothiazol-2-yl)-2-(4-ethanesulfonyl-phenyl)-2-(3-methoxy-phenoxy)-acetamide, N-(5,6-Dimethoxy-benzothiazol-2-yl)-2-(4-ethanesulfonyl-phenyl)-2-(4-ethoxy-phenoxy)-acetamide, N-(5,6-Dimethoxy-benzothiazol-2-yl)-2-(4-ethanesulfonyl-phenyl)-2-(4-propoxy-phenoxy)-acetamide, 2-(4-Butoxy-phenoxy)-N-(5,6-dimethoxy-benzothiazol-2-yl)-2-(4-ethanesulfonyl-phenyl)-acetamide, 2-(4-Benzyloxy-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(4-nitro-phenoxy)-acetamide, N-(5,6-Dimethoxy-benzothiazol-2-yl)-2-(4-dimethyl amino-phenoxy)-2-(4-ethanesulfonyl-phenyl)-acetamide, 4-[(5,6-Dimethoxy-benzothiazol-2-ylcarbamoyl)-(4-ethane-sulfonyl-phenyl)-methoxy]-benzoic acid methyl ester, 4-[(5,6-Dimethoxy-benzothiazol-2-ylcarbamoyl)-(4-ethanesulfo-nyl-phenyl)-methoxy]-benzoic acid, 4-[(5,6-Dimethoxy-benzothiazol-2-ylcarbamoyl)-(4-ethanesulfonyl-phenyl)-methoxy]-N,N-dimethyl-benzamide, N-(5,6-Dimethoxy-benzothiazol-2-yl)-2-(4-ethanesulfonyl-phenyl)-2-(4-methoxy-phenylamino)-acetamide, N-(5,6-Dimethoxy-benzothiazol-2-yl)-2-(4-ethanesulfonyl-phenyl)-2-(3-methoxy-phenylamino)-acetamide, N-(5,6-Dimethoxy-benzothiazol-2-yl)-2-(4-ethanesulfonyl-phenyl)-2-(2-methoxy-phenylamino)-acetamide, N-(5,6-Dimethoxy-benzothiazol-2-yl)-2-(4-ethanesulfonyl-phenyl)-2-p-tolylamino-acetamide, N-(5,6-Dimethoxy-benzothiazol-2-yl)-2-(4-ethanesulfonyl-phenyl)-2-m-tolylamino-acetamide, N-(5,6-Dimethoxy-benzothiazol-2-yl)-2-(4-ethanesulfonyl-phenyl)-2-o-tolylamino-acetamide, 2-(4-Cyano-phenylamino)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-isobutylamino-acetamide, 2-Cyclopentylamino-N-(5,6-dimethoxy-benzothiazol-2-yl)-2-(4-ethanesulfonyl-phenyl)-acetamide, N-(5,6-Dimethoxy-benzothiazol-2-yl)-2-dimethylamino-2-(4-ethanesulfonyl-phenyl)-acetamide, N-(5,6-Dimethoxy-benzothiazol-2-yl)-2-(4-ethanesulfonyl-phenyl)-2-piperidin-1-yl-acetamide, N-(5,6-Dimethoxy-benzothiazol-2-yl)-2-(4-ethanesulfonyl-phenyl)-2-morpho-lin-4-yl-acetamide, 2-(4-Cyano-phenoxy)-N-(5,6-dimethoxy-benzothiazol-2-yl)-2-(4-phenylmethanesulfonyl-phenyl)-acetamide, 2-(4-Cyano-phenoxy)-N-(5,6-dimethoxy-benzothiazol-2-yl)-2-[4-(propane-2-sulfonyl)-phenyl]-acetamide, 2-[4-(Butane-1-sulfonyl)-phenyl]-2-(4-cyano-phenoxy)-N-(5,6-dimethoxy-benzothiazol-2-yl)-acetamide, 2-(4-Cyano-phenoxy)-2-(4-cyclopropylmethanesulfonyl-phenyl)-N-(5,6-dimethoxy-benzothiazol-2-yl)-acetamide, 2-(4-Cyano-phenoxy)-N-(5,6-dimethoxy-benzothiazol-2-yl)-2-[4-(2-methoxy-ethanesulfonyl)-phenyl]-acetamide, 2-(4-Cyano-phenoxy)-N-(5,6-dimethoxy-benzothiazol-2-yl)-2-(2-phenylmethanesulfonyl-phenyl)-acetamide, 2-(4-Cyano-phenoxy)-N-(5,6-dimethoxy-benzothiazol-2-yl)-2-(2-ethanesulfonyl-phenyl)-acetamide, 2-(4-Cyano-phenoxy)-N-(5,6-dimethoxy-benzothiazol-2-yl)-2-[2-(propane-2-sulfonyl)-phenyl]-acetamide, 2-[2-(Butane-1-sulfonyl)-phenyl]-2-(4-cyano-phenoxy)-N-(5,6-dimethoxy-benzothiazol-2-yl)-acetamide, N-(5,6-Dimethoxy-benzothiazol-2-yl)-2-[2-(4-fluoro-benzenesulfonyl)-phenyl]-2-(4-methoxy-phenoxy)-acetamide, 2-(4-Cyano-phenoxy)-N-(5,6-dimethoxy-benzothiazol-2-yl)-2-[2-(4-fluoro-benzenesulfonyl)-phenyl]1-acetamide, N-(5,6-Dimethoxy-benzothiazol-2-yl)-2-[2-(4-methoxy-benzenesulfonyl)-phenyl]-2-(4-methoxy-phenoxy)-acetamide, 2-(4-Cyano-phenoxy)-N-(5,6-di methoxy-benzothiazol-2-yl)-2-[2-(4-methoxy-benzenesulfonyl)-phenyl]-acetamide, 2-(4-Cyano-phenoxy)-N-(5,6-dimethoxy-benzothiazol-2-yl)-2-(3-phenylmethanesulfonyl-phenyl)-acetamide, 2-(4-Cyano-phenoxy)-N-(5,6-dimethoxy-benzothiazol-2-yl)-2-(3-ethanesulfonyl-phenyl)-acetamide, 2-(4-Cyano-phenoxy)-N-(5,6-dimethoxy-benzothiazol-2-yl)-2-[3-(propane-2-sulfonyl)-phenyl]-acetamide, 2-[3-(Butane-1-sulfonyl)-phenyl]-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-[3-(2-methyl-propane-2-sulfonyl)-phenyl]-acetamide, 2-(4-Cyano-phenoxy)-N-(5,6-dimethoxy-benzothiazol-2-yl)-2-[3-(4-fluoro-benzenesulfonyl)-phenyl]-acetamide, 2-(4-Cyano-phenoxy)-N-(5,6-dimethoxy-benzothiazol-2-yl)-2-[3-(4-methoxy-benzenesulfonyl)-phenyl]-acetamide, 2-(4-Cyano-phenoxy)-N-(5,6-dimethoxy-benzothiazol-2-yl)-2-[4-(4- fluoro-benzenesulfonyl)-phenyl]-acetamide, 2-(4-Cyano-phenoxy)-N-(5,6-dimethoxy-benzothiazol-2-yl)-2-[4-(4-methoxy-benzenesulfonyl)-phenyl]-acetamide, 2-[3-(4-Chloro-benzenesulfonyl)-phenyl]-2-(4-cyano-phenoxy)-N-(5,6-dimethoxy-benzothiazol-2-yl)-acetamide, 2-[4-(4-Chloro-benzenesulfonyl)-phenyl]-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-[4-(4-trifluoromethyl-benzenesulfonyl)-phenyl]-acetamide, N-(5,6-Dimethoxy-benzothiazol-2-yl)-2-(3-ethanesulfonyl-phenyl)-2-(4-methoxy-phenoxy)-acetamide, N-(5,6-Dimethoxy-benzothiazol-2-yl)-2-[3-(4-fluoro-benzenesulfonyl)-phenyl]-2-(4-methoxy-phenoxy)-acetamide, 2-(4-Cyano-phenoxy)-N-(5,6-dimethoxy-benzothiazol-2-yl)-2-(4-dimethylsulfamoyl-phenyl)-acetamide, 2-(4-Cyano-phenoxy)-N-(5,6-dimethoxy-benzothiazol-2-yl)-2-[4-(2-methoxy-ethylsulfamoyl)-phenyl]-acetamide, 2-(4-Cyano-phenoxy)-N-(5,6-dimethoxy-benzothiazol-2-yl)-2-[4-(2-dimethylamino-ethylsulfamoyl)-phenyl]-acetamide, 4-[(4-Cyano-phenoxy)-(5,6-dimethoxy-benzothiazol-2-ylcarbamoyl)-methyl]-benzoic acid methyl ester, 4-[(4-Cyano-phenoxy)-(5,6-dimethoxy-benzothiazol-2-ylcarbamoyl)-methyl]-benzoic acid, 4-[(4-Cyano-phenoxy)-(5,6-dimethoxy-benzothiazol-2-ylcarbamoyl)-methyl]-N,N-dimethyl-benzamide, 4-[(4-Cyano-phenoxy)-(5,6-dimethoxy-benzothiazol-2-ylcarbamoyl)-methyl]-N-(2-methoxy-ethyl)-benzamide, 4-[(4-Cyano-phenoxy)-(5,6-dimethoxy-benzothiazol-2-ylcarbamoyl)-methyl]-N-(2-dimethylamino-ethyl)-benzamide, 4-[(4-Cyano-phenoxy)-(5,6-dimethoxy-benzothiazol-2-ylcarbamoyl)-methyl]-N-(2-morpholin-4-yl-ethyl)-benzamide, 4-[(4-Cyano-phenoxy)-(5,6-dimethoxy-benzothiazol-2-ylcarbamoyl)-methyl]-N-(2-hydroxy-ethyl)-benzamide, 4-[(4-Cyano-phenoxy)-(5,6-dimethoxy-benzothiazol-2-ylcarbamoyl)-methyl]-N-(2-piperidin-1-yl-ethyl)-benzamide, 4-[(4-Cyano-phenoxy)-(5,6-dimethoxy-benzothiazol-2-ylcarbamoyl)-methyl]-N-(2-pyrrolidin-1-yl-ethyl)-benzamide, 2-(4-Cyano-phenoxy)-N-(5,6-dimethoxy-benzothiazol-2-yl)-2-[4-(4-methyl-piperazine-1-carbonyl)-phenyl]-acetamide, 2-(4-Cyano-phenoxy)-N-(5,6-dimethoxy-benzothiazol-2-yl)-2-[4-(piperazine-1-carbonyl)-phenyl]-acetamide, 2-(4-Cyano-phenoxy)-N-(5,6-dimethoxy-benzothiazol-2-yl)-2-(4-trifluoromethyl-phenyl)-acetamide, 2-(3-Bromo-phenyl)-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-p-tolyl-acetamide, 2-(4-Chloro-phenyl)-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-(4-fluoro-phenyl)-acetamide, 2-(4-Cyano-phenoxy)-N-(5,6-dimethoxy-benzothiazol-2-yl)-2-phenyl-acetamide, 2-(4-Cyano-phenoxy)-N-(5,6-dimethoxy-benzothiazol-2-yl)-2-(4-nitro-phenyl)-acetamide, 2-(4-Cyano-phenoxy)-N-(5,6-dimethoxy-benzothiazol-2-yl)-2-(4-methoxy-phenyl)-acetamide, 2-(4-Cyano-phenoxy)-N-(5,6-dimethoxy-benzothiazol-2-yl)-2-(4-ethoxy-phenyl)-acetamide, 2-(4-Cyano-phenoxy)-N-(5,6-dimethoxy-benzothiazol-2-yl)-2-[4-(2-methoxy-ethoxy)-phenyl]-acetamide, 2-(4-Cyano-phenoxy)-N-(5,6-dimethoxy-benzothiazol-2-yl)-2-(4-isopropoxy-phenyl)-acetamide, 2-(4-cyano-phenoxy)-N-(5,6-dimethoxy-benzothiazol-2-yl)-2-[4-(2-morpholin-4-yl-ethoxy)-phenyl]-acetamide, 2-(4-cyano-phenoxy)-N-(5,6-dimethoxy-benzothiazol-2-yl)-2-[4-(2-piperidin-1-yl-ethoxy)-phenyl]-acetamide, 2-(4-Cyano-phenoxy)-N-(5,6-dimethoxy-benzothiazol-2-yl)-2-[4-(2-dimethylamino-ethoxy)-phenyl]-acetamide, 2-(4-Cyano-phenoxy)-N-(5,6-dimethoxy-benzothiazol-2-yl)-2-[4-(2-pyrrolidin-1-yl-ethoxy)-phenyl]-acetamide, 2-(4-Cyano-phenoxy)-N-(5,6-dimethoxy-benzothiazol-2-yl)-2-[4-(1H-tetrazol-5-yl)-phenyl]-acetamide, 2-(4-Cyano-phenoxy)-2-(4-cyano-phenyl)-N-(5,6-dimethoxy-benzothiazol-2-yl)-acetamide, 2-(4-Cyano-phenyl)-N-(5,6-dimethoxy-benzothiazol-2-yl)-2-phenoxy-acetamide, 4-[(4-Cyano-phenyl)-(5,6-dimethoxy-benzothiazol-2-ylcarbamoyl)-methoxy]-benzoic acid methyl ester, 4-[(4-Cyano-phenyl)-(5,6-dimethoxy-benzothiazol-2-ylcarbamoyl)-methoxy]-benzoic acid, 4-[(4-Cyano-phenyl)-(5,6-dimethoxy-benzothiazol-2-ylcarbamoyl)-methoxy]-N-(2-methoxy-ethyl)-benzamide, 4-[(4-Cyano-phenyl)-(5,6-dimethoxy-benzothiazol-2-ylcarbamoyl)-methoxy]-N-(2-morpholin-4-yl-ethyl)-benzamide, 4-[(4-Cyano-phenyl)-(5,6-dimethoxy-benzothiazol-2-ylcarbamoyl)-methoxy]-N-(2-hydroxy-ethyl)-benzamide, 4-[(4-Cyano-phenyl)-(5,6-dimethoxy-benzothiazol-2-ylcarbamoyl)-methoxy]-N-(2-pyrrolidin-1-yl-ethyl)-benzamide, 2-(4-Cyano-phenyl)-N-(5,6-dimethoxy-benzothiazol-2-yl)-2-[4-(4-methyl-piperazine-1-carbonyl)-phenoxy]-acetamide, 4-[(4-Cyano-phenyl)-(5,6-dimethoxy-benzothiazol-2-ylcarbamoyl)-methoxy]-N-(2-dimethylamino-ethyl)-benzamide, 4-[(4-Cyano-phenyl)-(5,6-dimethoxy-benzothiazol-2-ylcarbamoyl)-methoxy]-N-(2-piperidin-1-yl-ethyl)-benzamide, 4-[(4-Cyano-phenyl)-(5,6-dimethoxy-benzothiazol-2-ylcarbamoyl)-methoxy]-N,N-dimethyl-benzamide, 2-(4-Cyano-phenyl)-N-(5,6-dimethoxy-benzothiazol-2-yl)-2-[4-(piperazine-1-carbonyl)-phenoxy]-acetamide, 2-(4-Cyano-phenyl)-N-(5,6-dimethoxy-benzothiazol-2-yl)-2-(4-methoxy-phenoxy)-acetamide, 2-(4-Cyano-phenyl)-N-(5,6-dimethoxy-benzothiazol-2-yl)-2-(4-hydroxy-phenoxy)-acetamide, 2-(4-Cyano-phenyl)-N-(5,6-dimethoxy-benzothiazol-2-yl)-2-[4-(2-methoxy-ethoxy)-phenoxy]-acetamide, 2-(4-Cyano-phenyl)-N-(5,6-dimethoxy-benzothiazol-2-yl)-2-[4-(2-piperidin-1-yl-ethoxy)-phenoxy]-acetamide, 2-(4-Cyano-phenyl)-N-(5,6-dimethoxy-benzothiazol-2-yl)-2-[4-(2-pyrrolidin-1-yl-ethoxy)-phenoxy]-acetamide, 2-(4-Cyano-phenyl)-N-(5,6-dimethoxy-benzothiazol-2-yl)-2-[4-(2-morpholin-4-yl-ethoxy)-phenoxy]-acetamide, 2-(4-Cyano-phenyl)-N-(5,6-dimethoxy-benzothiazol-2-yl)-2-[4-(2-dimethylamino-ethoxy)-phenoxy]-acetamide, 2-(4-Cyano-phenyl)-N-(5,6-dimethoxy-benzothiazol-2-yl)-2-[4-(2-hydroxy-ethoxy)-phenoxy]-acetamide, 2-(4-Cyano-phenyl)-N-(5,6-dimethoxy-benzothiazol-2-yl)-2-[4-(1H-tetrazol-5-yl)-phenoxy]-acetamide, 2-(4-Cyano-phenoxy)-2-(4-ethanesulfonyl-phenyl)-N-(5-methoxy-benzothiazol-2-yl)-acetamide, 2-(4-Cyano-phenoxy)-N-(5-diethylamino-benzothiazol-2-yl)-2-(4-ethanesulfonyl-phenyl)-acetamide, 2-(4-Cyano-phenoxy)-2-(4-ethanesulfonyl-phenyl)-N-(6-methoxy-benzothiazol-2-yl)-acetamide, 2-(4-Ethanesulfonyl-phenyl)-N-(6-methoxy-benzothiazol-2-yl)-2-(4-methoxy-phenoxy)-acetamide, 2-(4-Cyano-phenoxy)-2-(4-ethanesulfonyl-phenyl)-N-[6-(4-methyl-piperazin-1-yl)-benzothiazol-2-yl]-acetamide, 2-(4-Ethanesulfonyl-phenyl)-2-(4-methoxy-phenoxy)-N-[6-(4-methyl-piperazin-1-yl)-benzothiazol-2-yl]-acetamide, 2-(4-Cyano-phenoxy)-2-(4-ethanesulfonyl-phenyl)-N-(6-morpholin-4-yl-benzothiazol-2-yl)-acetamide, 2-(4-Cyano-phenoxy)-N-(4,7-dimethoxy-benzothiazol-2-yl)-2-(4-ethanesulfonyl-phenyl)-acetamide, N-(4,7-Dimethoxy-benzothiazol-2-yl)-2-(4-ethanesulfonyl-phenyl)-2-(4-methoxy-phenoxy)-acetamide, 2-(4-Cyano-phenoxy)-N-[1,3]dioxolo[4',5':4,5]benzo[1,2-d]thiazol-6-yl-2-(4-ethanesulfonyl-phenyl)-acetamide, N-[1,3]Dioxolo[4',5':4,5]benzo[1,2-d]thiazol-6-yl-2-(4-ethanesulfonyl-phenyl)-2-(4-methoxy-phenoxy)-acetamide, 2-(4-cyano-phenoxy)-N-(6,7-dihydro-5,8-dioxa-1-thia-3-aza-cyclopenta[b]naphthalen-2-yl)-2-(4-ethanesulfonylphenyl)-acetamide, 2-(4-Cyano-phenoxy)-N-[1,3]dioxolo[4',5':3,4]benzo[2,1-d]thiazol-7-yl-2-(4-ethanesulfonyl-phenyl)-acetamide, 2-(4-Cyano-phenoxy)-N-(7,8-dihydro-6,9-dioxa-3-thia-1-aza-cyclopenta[a]naphthalen-2-yl)-2-(4-ethanesulfonyl-phenyl)-acetamide, 2-(4-Cyano-phenoxy)-2-(4-ethanesulfonyl-phenyl)-N-[6-(2-methoxy-ethoxy)-benzothiazol-2-yl]-acetamide, 2-(4-Cyano-phenoxy)-2-(4-ethanesulfonyl-phenyl)-N-[6-(2-morpholin-4-yl-ethoxy)-benzothiazol-2-yl]-acetamide, 2-(4-Cyano-phenoxy)-2-(4-ethanesulfonyl-phenyl)-N-[6-(2-hydroxy-ethoxy)-benzothiazol-2-yl]-acetamide, 2-(4-Cyano-phenoxy)-2-(4-ethanesulfonyl-phenyl)-N-{6-[2-(4-methyl-piperazin-1-yl)-ethoxy]-benzothiazol-2-yl}-acetamide, 2-(4-Cyano-phenoxy)-N-(7,8-dihydro-6,9-dioxa-1-thia-3-aza-cyclopenta[a]naphthalen-2-yl)-2-(4-ethanesulfonyl-phenyl)-acetamide, N-(7,8-Dihydro-6,9-dioxa-1-thia-3-aza-cyclopenta[a]naphthalen-2-yl)-2-(4-ethanesulfonyl-phenyl)-2-(4-methoxy-phenoxy)-acetamide, 2-(4-Cyano-phenoxy)-N-(1,3-dioxa-8-thia-6-aza-as-indacen-7-yl)-2-(4-ethanesulfonyl-phenyl)-acetamide, N-(1,3-Dioxa-8-thia-6-aza-as-indacen-7-yl)-2-(4-ethanesulfonyl-phenyl)-2-(4-methoxy-phenoxy)-acetamide 2-(4-Cyano-phenoxy)-N-(6,7-dimethoxy-benzothiazol-2-yl)-2-(4-ethanesulfonyl-phenyl)-acetamide, 2-(4-Cyano-phenoxy)-2-(4-ethanesulfonyl-phenyl)-N-(7-ethoxy-6-methoxy-benzothiazol-2-yl)-acetamide, 2-(4-Cyano-phenoxy)-2-(4-ethanesulfonyl-phenyl)-N-(7-isopropoxy-6-methoxy-benzothiazol-2-yl)-acetamide, 2-(4-Cyano-phenoxy)-2-(4-ethanesulfonyl-phenyl)-N-(7-methoxy-6-methyl-benzothiazol-2-yl)-acetamide, 2-(4-Cyano-phenoxy)-2-(4-ethanesulfonyl-phenyl)-N-(6-fluoro-7-methoxy-benzothiazol-2-yl)-acetamide, 2-(4-Cyano-phenoxy)-2-(4-ethanesulfonyl-phenyl)-N-(6-methoxy-5-methyl-benzothiazol-2-yl)-acetamide, N-(5-Chloro-6-methoxy-benzothiazol-2-yl)-2-(4-cyano-phenoxy)-2-(4-ethanesulfonyl-phenyl)-acetamide, 2-(4-Cyano-phenoxy)-2-(4-ethanesulfonyl-phenyl)-N-(5-fluoro-6-methoxy-benzothiazol-2-yl)-acetamide, N-(6-Chloro-5-methoxy-benzothiazol-2-yl)-2-(4-cyano-phenoxy)-2-(4-ethanesulfonyl-phenyl)-acetamide, 2-(4-Cyano-phenoxy)-2-(4-ethanesulfonyl-phenyl)-N-(5-methoxy-6-methyl-benzothiazol-2-yl)-acetamide, N-(5-Benzyloxy-6-methoxy-benzothiazol-2-yl)-2-(4-cyano-phenoxy)-2-(4-ethanesulfonyl-phenyl)-acetamide, 2-(4-Cyano-phenoxy)-2-(4-ethanesulfonyl-phenyl)-N-(5-isopropoxy-6-methoxy-benzothiazol-2-yl)-acetamide, 2-(4-Cyano-phenoxy)-2-(4-ethanesulfonyl-phenyl)-N-(5-ethoxy-6-methoxy-benzothiazol-2-yl)-acetamide, 2-(4-Cyano-phenoxy)-2-(4-ethanesulfonyl-phenyl)-N-[6-methoxy-5-(2-methoxy-ethoxy)-benzothiazol-2-yl]-acetamide, 2-(4-Cyano-phenoxy)-2-(4-ethanesulfonyl-phenyl)-N-[5-(2-hydroxy-ethoxy)-6-methoxy-benzothiazol-2-yl]-acetamide, 2-(4-Cyano-phenoxy)-N-(5-cyclopropylmethoxy-6-methoxy-benzothiazol-2-yl)-2-(4-ethanesulfonyl-phenyl)-acetamide, 2-(4-Cyano-phenoxy)-N-[5-(2-dimethylamino-ethoxy)-6-methoxy-benzothiazol-2-yl]-2-(4-ethanesulfonyl-phenyl)-acetamide, 2-(4-Cyano-phenoxy)-2-(4-ethanesulfonyl-phenyl)-N-[6-methoxy-5-(2-morpholin-4-yl-ethoxy)-benzothiazol-2-yl]-acetamide, 2-(4-Cyano-phenoxy)-2-(4-ethanesulfonyl-phenyl)-N-[5-(2-fluoro-ethoxy)-6-methoxy-benzothiazol-2-yl]-acetamide, 2-(4-Cyano-phenoxy)-2-(4-ethanesulfonyl-phenyl)-N-(6-methoxy-thiazolo[4,5-b]pyridin-2-yl)-acetamide, 2-(4-Cyano-phenoxy)-2-(4-ethanesulfonyl-phenyl)-N-(6-methoxy-thiazolo[4,5-b]pyridin-2-yl)-acetamide, 2-(4-Cyano-phenoxy)-N-(5,6-dimethoxy-benzooxazol-2-yl)-2-(4-ethanesulfonyl-phenyl)-acetamide, N-Benzooxazol-2-yl-2-(4-cyano-phenoxy)-2-(4-ethanesulfonyl-phenyl)-acetamide, 4-[(4-Cyano-phenoxy)-(5,6-dimethoxy-benzooxazol-2-ylcarbamoyl)-methyl]-N-(2-piperidin-1-yl-ethyl)-benzamide, 2-(4-Cyano-phenoxy)-N-(5,6-dimethoxy-benzooxazol-2-yl)-2-[4-(2-methoxy-ethoxy)-phenyl]-acetamide, 4-[(4-Cyano-phenoxy)-(5,6-dimethoxy-benzooxazol-2-ylcarbamoyl)-methyl]-N,N-dimethyl-benzamide, 2-(4-Cyano-phenoxy)-N-(5,6-dimethoxy-benzooxazol-2-yl)-2-[4-(4-methyl-piperazine-1-carbonyl)-phenyl]-acetamide, 4-[(4-Cyano-phenoxy)-(5,6-dimethoxy-benzooxazol-2-ylcarbamoyl)-methyl]-N-(2-morpholin-4-yl-ethyl)-benzamide, 4-[(4-Cyano-phenoxy)-(5,6-dimethoxy-benzooxazol-2-ylcarbamoyl)-methyl]-N-(2-methoxy-ethyl)-benzamide, 2-(4-Cyano-phenoxy)-N-(5,6-dimethoxy-1-methyl-1H-benzoimidazol-2-yl)-2-(4-ethanesulfonyl-phenyl)-acetamide, 2-(4-Cyano-phenoxy)-N-(5,6-dimethoxy-1H-indol-2-yl)-2-(4-ethanesulfonyl-phenyl)-acetamide, 2-(4-Cyano-phenoxy)-2-(4-ethanesulfonyl-phenyl)-N-(1H-indol-2-yl)-acetamide, 2-(4-Chloro-phenyl)-2-(4-cyano-phenoxy)-N-(5,6-dimethoxy-benzothiazol-2-yl)-acetamide, 2-(4-Cyano-phenyl)-N-(5,6-dimethoxy-benzothiazol-2-yl)-2-[4-(2-dimethylamino-ethoxy)-phenoxy]-acetamide, N-(5,6-dimethoxy-benzooxazol-2-yl)-2-(4-ethanesulfonyl-phenyl)-acetamide, or 4-[(4-Cyano-phenoxy)-(5,6-dimethoxy-benzothiazol-2-ylcarbamoyl)-methyl]-N-(2-methoxy-ethyl)-benzamide.

Provided herein are compounds having a structural formula as disclosed in Table 1.

TABLE 1

| Structure | Name |
|---|---|
| 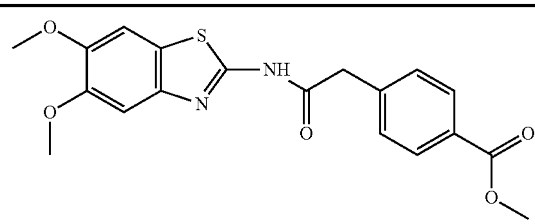 | methyl 4-{[N-(5,6-dimethoxybenzothiazol-2-yl)carbamoyl]methyl}benzoate |
| 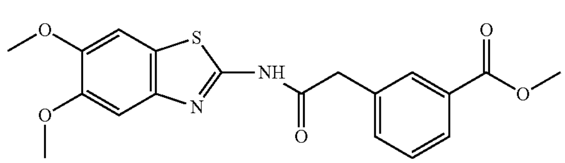 | methyl 3-{[N-(5,6-dimethoxybenzothiazol-2-yl)carbamoyl]methyl}benzoate |

TABLE 1-continued

| Structure | Name |
|---|---|
| 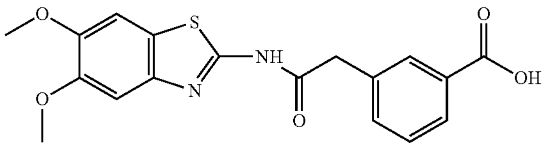 [SMILES: COc1cc2nc(NC(=O)Cc3cccc(C(=O)O)c3)sc2cc1OC] | 3-{[N-(5,6-dimethoxybenzothiazol-2-yl)carbamoyl]methyl}benzoic acid |
| 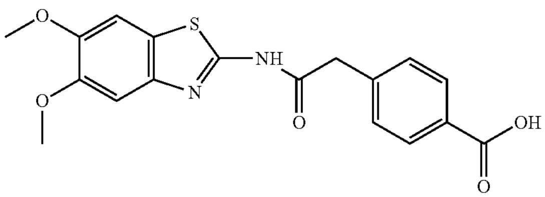 [SMILES: COc1cc2nc(NC(=O)Cc3ccc(C(=O)O)cc3)sc2cc1OC] | 4-{[N-(5,6-dimethoxybenzothiazol-2-yl)carbamoyl]methyl}benzoic acid |
| 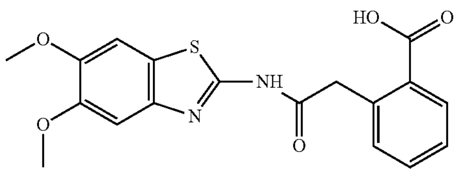 [SMILES: COc1cc2nc(NC(=O)Cc3ccccc3C(=O)O)sc2cc1OC] | 2-{[N-(5,6-dimethoxybenzothiazol-2-yl)carbamoyl]methyl}benzoic acid |
| 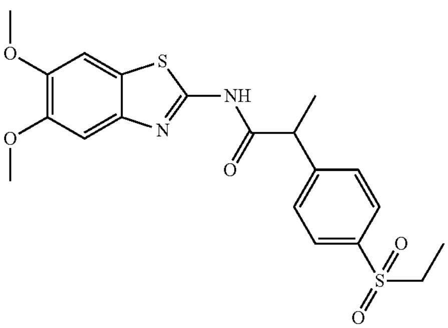 [SMILES: CCS(=O)(=O)c1ccc(C(C)C(=O)Nc2nc3cc(OC)c(OC)cc3s2)cc1] | N-(5,6-dimethoxybenzothiazol-2-yl)-2-[4-(ethylsulfonyl)phenyl]propanamide |
| 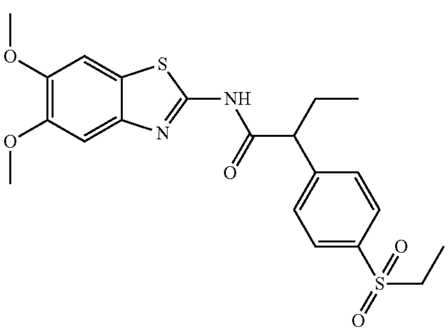 [SMILES: CCC(C(=O)Nc1nc2cc(OC)c(OC)cc2s1)c1ccc(S(=O)(=O)CC)cc1] | N-(5,6-dimethoxybenzothiazol-2-yl)-2-[4-(ethylsulfonyl)phenyl]butanamide |
| 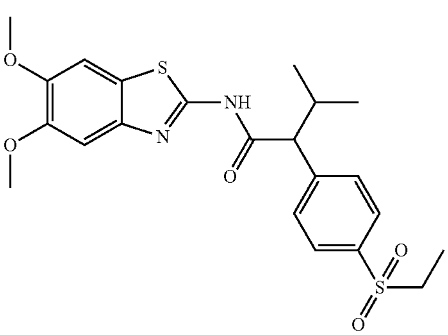 [SMILES: CCS(=O)(=O)c1ccc(C(C(=O)Nc2nc3cc(OC)c(OC)cc3s2)C(C)C)cc1] | N-(5,6-dimethoxybenzothiazol-2-yl)-2-[4-(ethylsulfonyl)phenyl]-3-methylbutanamide |

TABLE 1-continued

| Structure | Name |
|---|---|
| 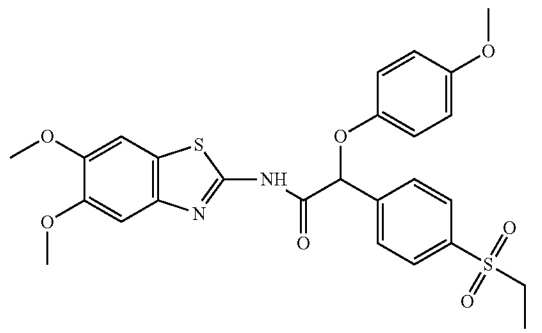 [SMILES: CCS(=O)(=O)c1ccc(C(Oc2ccc(OC)cc2)C(=O)Nc2nc3cc(OC)c(OC)cc3s2)cc1] | N-(5,6-dimethoxybenzothiazol-2-yl)-2-[4-(ethylsulfonyl)phenyl]-2-(4-methoxyphenoxy)acetamide |
| 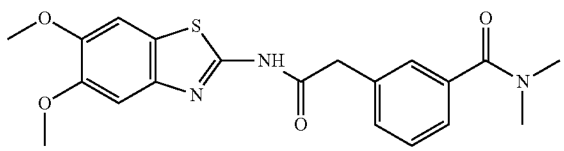 | N-(5,6-dimethoxybenzothiazol-2-yl)-2-[3-(N,N-dimethylcarbamoyl)phenyl]acetamide |
| 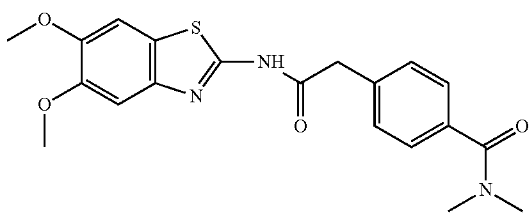 [SMILES: COc1cc2nc(NC(=O)Cc3ccc(C(=O)N(C)C)cc3)sc2cc1OC] | N-(5,6-dimethoxybenzothiazol-2-yl)-2-[4-(N,N-dimethylcarbamoyl)phenyl]acetamide |
| 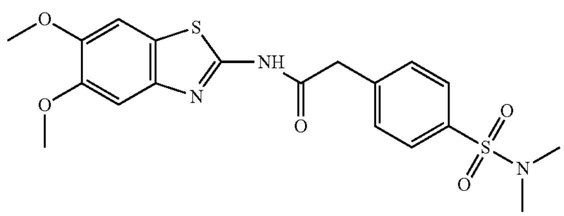 | N-(5,6-dimethoxybenzothiazol-2-yl)-2-{4-[(dimethylamino)sulfonyl]phenyl}acetamide |
| 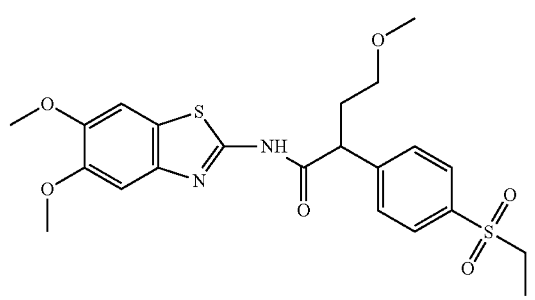 [SMILES: CCS(=O)(=O)c1ccc(C(CCOC)C(=O)Nc2nc3cc(OC)c(OC)cc3s2)cc1] | N-(5,6-dimethoxybenzothiazol-2-yl)-2-[4-(ethylsulfonyl)phenyl]-4-methoxybutanamide |
| 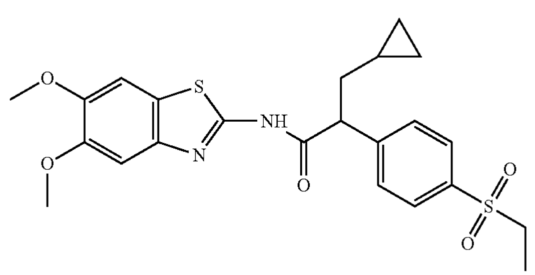 [SMILES: CCS(=O)(=O)c1ccc(C(CC2CC2)C(=O)Nc2nc3cc(OC)c(OC)cc3s2)cc1] | N-(5,6-dimethoxybenzothiazol-2-yl)-3-cyclopropyl-2-[4-(ethylsulfonyl)phenyl]propanamide |

TABLE 1-continued

| Structure | Name |
|---|---|
| 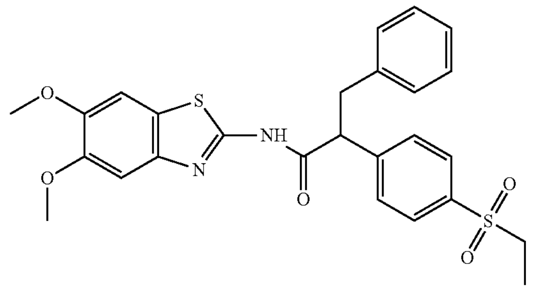 [SMILES: CCS(=O)(=O)c1ccc(C(Cc2ccccc2)C(=O)Nc2nc3cc(OC)c(OC)cc3s2)cc1] | N-(5,6-dimethoxybenzothiazol-2-yl)-2-[4-(ethylsulfonyl)phenyl]-3-phenylpropanamide |
| 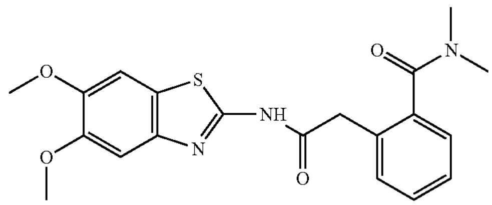 | N-(5,6-dimethoxybenzothiazol-2-yl)-2-[2-(N,N-dimethylcarbamoyl)phenyl]acetamide |
| 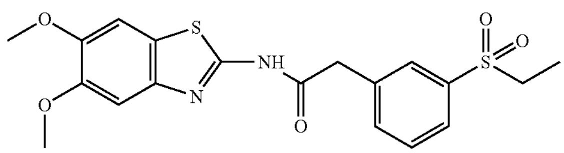 [SMILES: CCS(=O)(=O)c1cccc(CC(=O)Nc2nc3cc(OC)c(OC)cc3s2)c1] | N-(5,6-dimethoxybenzothiazol-2-yl)-2-[3-(ethylsulfonyl)phenyl]acetamide |
| 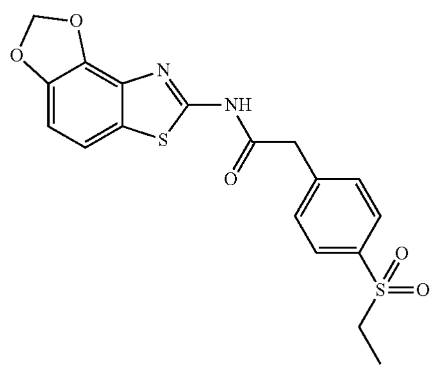 [SMILES: CCS(=O)(=O)c1ccc(CC(=O)Nc2nc3c4c(ccc3s2)OCO4)cc1] | N-(2H-1,3-dioxolano[4,5-e]benzothiazol-7-yl)-2-[4-(ethylsulfonyl)phenyl]acetamide |
| 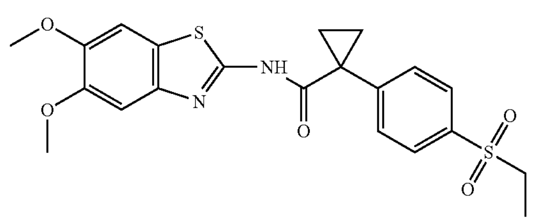 [SMILES: CCS(=O)(=O)c1ccc(C2(C(=O)Nc3nc4cc(OC)c(OC)cc4s3)CC2)cc1] | N-(5,6-dimethoxybenzothiazol-2-yl){[4-(ethylsulfonyl)phenyl]cyclopropyl}carboxamide |
| 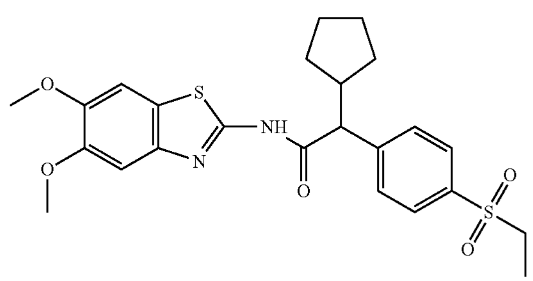 [SMILES: CCS(=O)(=O)c1ccc(C(C(=O)Nc2nc3cc(OC)c(OC)cc3s2)C2CCCC2)cc1] | N-(5,6-dimethoxybenzothiazol-2-yl)-2-cyclopentyl-2-[4-(ethylsulfonyl)phenyl]acetamide |

TABLE 1-continued

| Structure | Name |
|---|---|
| 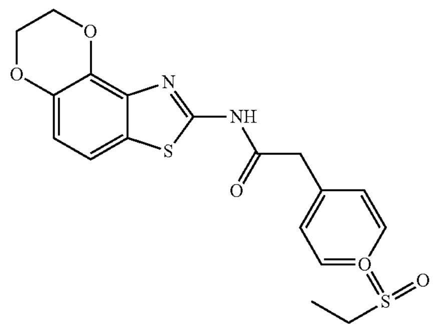 | N-(7H,8H-1,4-dioxano[5,6-e]benzothiazol-2-yl)-2-[4-(ethylsulfonyl)phenyl]acetamide |
| 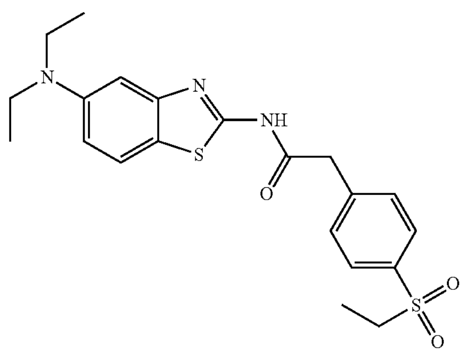 [SMILES: CCN(CC)c1ccc2sc(NC(=O)Cc3ccc(S(=O)(=O)CC)cc3)nc2c1] | N-[5-(diethylamino)benzothiazol-2-yl]-2-[4-(ethylsulfonyl)phenyl]acetamide |
| 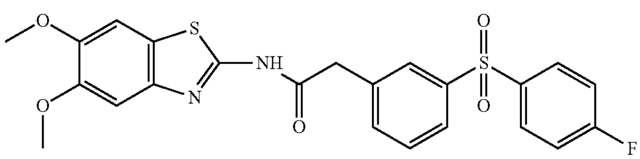 [SMILES: COc1cc2nc(NC(=O)Cc3cccc(S(=O)(=O)c4ccc(F)cc4)c3)sc2cc1OC] | N-(5,6-dimethoxybenzothiazol-2-yl)-2-{3-[(4-fluorophenyl)sulfonyl]phenyl}acetamide |
| 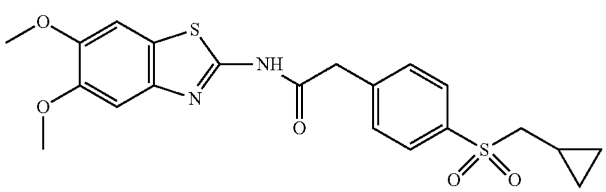 [SMILES: COc1cc2nc(NC(=O)Cc3ccc(S(=O)(=O)CC4CC4)cc3)sc2cc1OC] | N-(5,6-dimethoxybenzothiazol-2-yl)-2-{4-[(cyclopropylmethyl)sulfonyl]phenyl}acetamide |
| 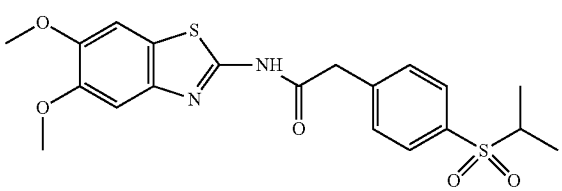 [SMILES: COc1cc2nc(NC(=O)Cc3ccc(S(=O)(=O)C(C)C)cc3)sc2cc1OC] | N-(5,6-dimethoxybenzothiazol-2-yl)-2-{4-[(methylethyl)sulfonyl]phenyl}acetamide |
| 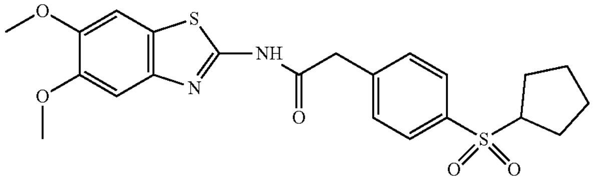 [SMILES: COc1cc2nc(NC(=O)Cc3ccc(S(=O)(=O)C4CCCC4)cc3)sc2cc1OC] | N-(5,6-dimethoxybenzothiazol-2-yl)-2-[4-(cyclopentylsulfonyl)phenyl]acetamide |

TABLE 1-continued

| Structure | Name |
| --- | --- |
| 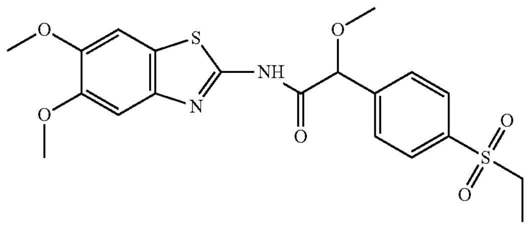 [SMILES: CCS(=O)(=O)c1ccc(C(OC)C(=O)Nc2nc3cc(OC)c(OC)cc3s2)cc1] | N-(5,6-dimethoxybenzothiazol-2-yl)-2-[4-(ethylsulfonyl)phenyl]-2-methoxyacetamide |
| 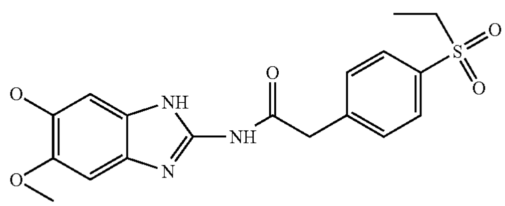 [SMILES: CCS(=O)(=O)c1ccc(CC(=O)Nc2nc3cc(OC)c(O)cc3[nH]2)cc1] | N-(5,6-dimethoxybenzimidazol-2-yl)-2-[4-(ethylsulfonyl)phenyl]acetamide |
| 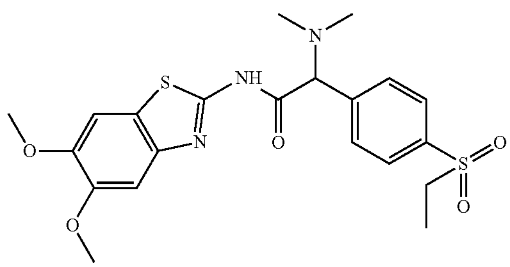 [SMILES: CCS(=O)(=O)c1ccc(C(C(=O)Nc2nc3cc(OC)c(OC)cc3s2)N(C)C)cc1] | N-(5,6-dimethoxybenzothiazol-2-yl)-2-(dimethylamino)-2-[4-(ethylsulfonyl)phenyl]acetamide |
| 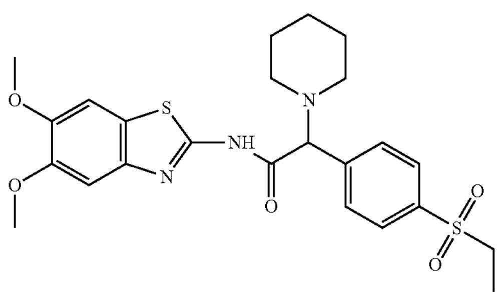 [SMILES: CCS(=O)(=O)c1ccc(C(C(=O)Nc2nc3cc(OC)c(OC)cc3s2)N2CCCCC2)cc1] | N-(5,6-dimethoxybenzothiazol-2-yl)-2-[4-(ethylsulfonyl)phenyl]-2-piperidylacetamide |
| 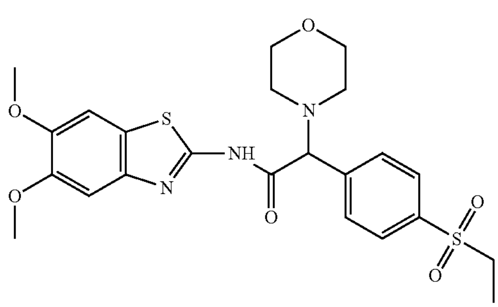 [SMILES: CCS(=O)(=O)c1ccc(C(C(=O)Nc2nc3cc(OC)c(OC)cc3s2)N2CCOCC2)cc1] | N-(5,6-dimethoxybenzothiazol-2-yl)-2-[4-(ethylsulfonyl)phenyl]-2-morpholin-4-ylacetamide |

TABLE 1-continued

| Structure | Name |
|---|---|
| 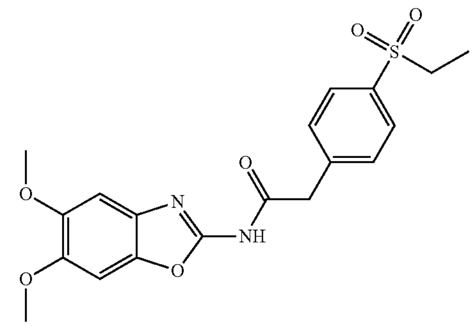 [SMILES: CCS(=O)(=O)c1ccc(CC(=O)Nc2nc3cc(OC)c(OC)cc3o2)cc1] | N-(5,6-dimethoxybenzoxazol-2-yl)-2-[4-(ethylsulfonyl)phenyl]acetamide |
| 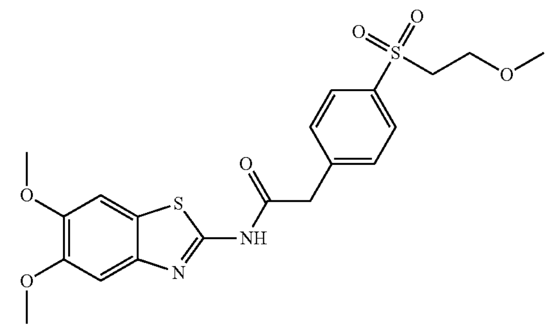 [SMILES: COCCS(=O)(=O)c1ccc(CC(=O)Nc2nc3cc(OC)c(OC)cc3s2)cc1] | N-(5,6-dimethoxybenzothiazol-2-yl)-2-{4-[(2-methoxyethyl)sulfonyl]phenyl}acetamide |
| 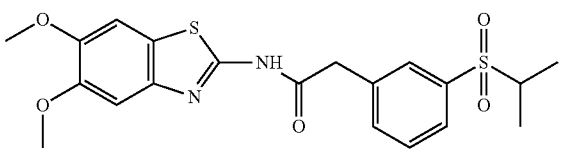 [SMILES: COc1cc2nc(NC(=O)Cc3cccc(S(=O)(=O)C(C)C)c3)sc2cc1OC] | N-(5,6-dimethoxybenzothiazol-2-yl)-2-{3-[(methylethyl)sulfonyl]phenyl}acetamide |
| 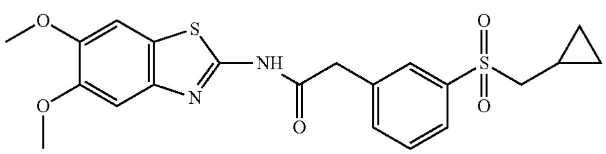 [SMILES: COc1cc2nc(NC(=O)Cc3cccc(S(=O)(=O)CC4CC4)c3)sc2cc1OC] | N-(5,6-dimethoxybenzothiazol-2-yl)-2-{3-[(cyclopropylmethyl)sulfonyl]phenyl}acetamide |
| 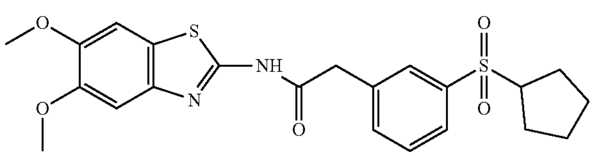 [SMILES: COc1cc2nc(NC(=O)Cc3cccc(S(=O)(=O)C4CCCC4)c3)sc2cc1OC] | N-(5,6-dimethoxybenzothiazol-2-yl)-2-[3-(cyclopentylsulfonyl)phenyl]acetamide |
| 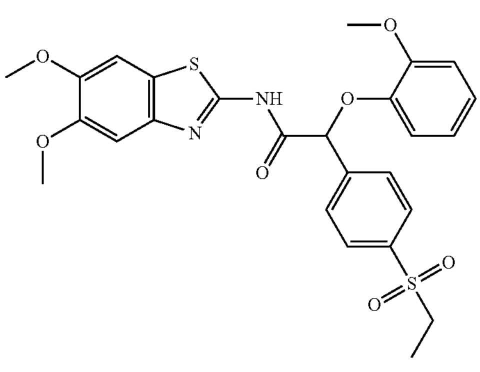 [SMILES: CCS(=O)(=O)c1ccc(C(Oc2ccccc2OC)C(=O)Nc2nc3cc(OC)c(OC)cc3s2)cc1] | N-(5,6-dimethoxybenzothiazol-2-yl)-2-[4-(ethylsulfonyl)phenyl]-2-(2-methoxyphenoxy)acetamide |

TABLE 1-continued

| Structure | Name |
|---|---|
| 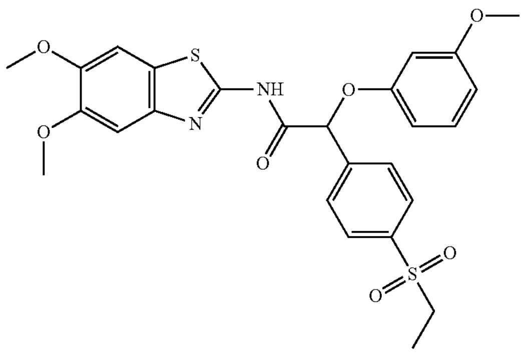 | N-(5,6-dimethoxybenzothiazol-2-yl)-2-[4-(ethylsulfonyl)phenyl]-2-(3-methoxyphenoxy)acetamide |
| 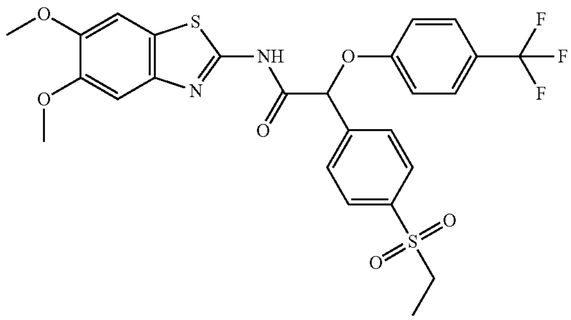 [SMILES: CCS(=O)(=O)c1ccc(C(Oc2ccc(C(F)(F)F)cc2)C(=O)Nc2nc3cc(OC)c(OC)cc3s2)cc1] | N-(5,6-dimethoxybenzothiazol-2-yl)-2-[4-(ethylsulfonyl)phenyl]-2-[4-(trifluoromethyl)phenoxy]acetamide |
| 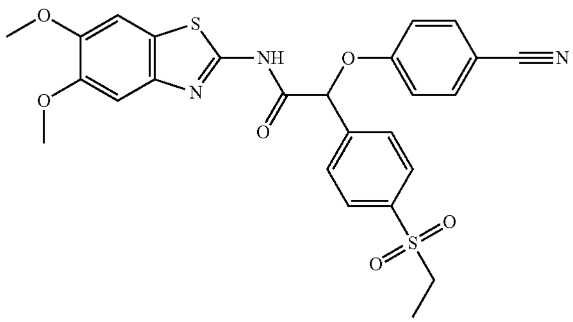 [SMILES: CCS(=O)(=O)c1ccc(C(Oc2ccc(C#N)cc2)C(=O)Nc2nc3cc(OC)c(OC)cc3s2)cc1] | N-(5,6-dimethoxybenzothiazol-2-yl)-2-(4-cyanophenoxy)-2-[4-(ethylsulfonyl)phenyl]acetamide |
| 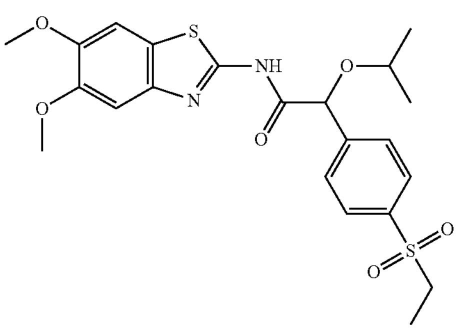 [SMILES: CCS(=O)(=O)c1ccc(C(OC(C)C)C(=O)Nc2nc3cc(OC)c(OC)cc3s2)cc1] | N-(5,6-dimethoxybenzothiazol-2-yl)-2-[4-(ethylsulfonyl)phenyl]-2-(methylethoxy)acetamide |

TABLE 1-continued

| Structure | Name |
|---|---|
| 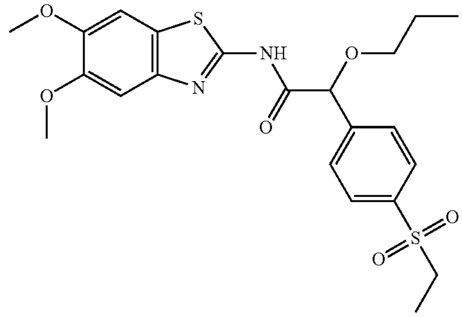 [SMILES: CCCOC(C(=O)Nc1nc2cc(OC)c(OC)cc2s1)c1ccc(S(=O)(=O)CC)cc1] | N-(5,6-dimethoxybenzothiazol-2-yl)-2-[4-(ethylsulfonyl)phenyl]-2-propoxyacetamide |
| | N-(5,6-dimethoxybenzothiazol-2-yl)-2-cyclopentyloxy-2-[4-(ethylsulfonyl)phenyl]acetamide |
| | N-(5,6-dimethoxybenzothiazol-2-yl)-2-cyclopentyloxy-2-[4-(ethylsulfonyl)phenyl]acetamide |
| 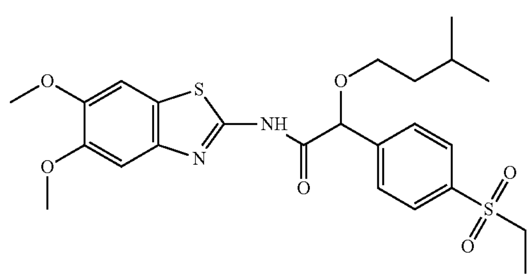 [SMILES: CCS(=O)(=O)c1ccc(C(OCCC(C)C)C(=O)Nc2nc3cc(OC)c(OC)cc3s2)cc1] | N-(5,6-dimethoxybenzothiazol-2-yl)-2-[4-(ethylsulfonyl)phenyl]-2-(3-methylbutoxy)acetamide |
| 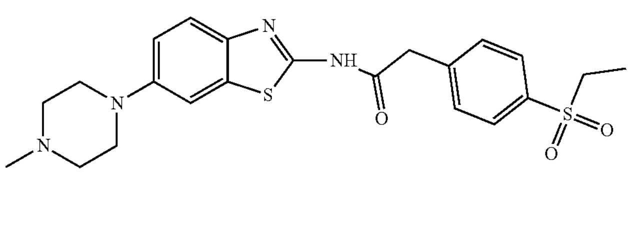 [SMILES: CCS(=O)(=O)c1ccc(CC(=O)Nc2nc3ccc(N4CCN(C)CC4)cc3s2)cc1] | 2-[4-(ethylsulfonyl)phenyl]-N-[6-(4-methylpiperazinyl)benzothiazol-2-yl]acetamide |

TABLE 1-continued

| Structure | Name |
|---|---|
| 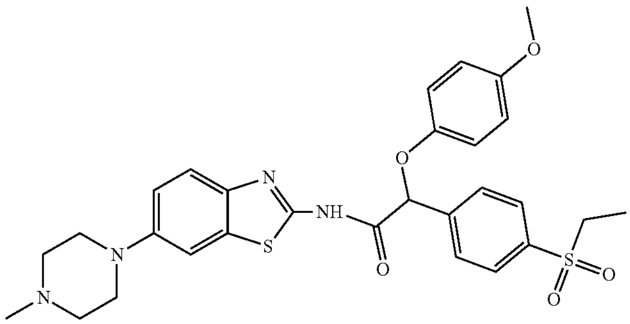 [SMILES: CCS(=O)(=O)c1ccc(C(Oc2ccc(OC)cc2)C(=O)Nc2nc3ccc(N4CCN(C)CC4)cc3s2)cc1] | 2-[4-(ethylsulfonyl)phenyl]-2-(4-methoxyphenoxy)-N-[6-(4-methylpiperazinyl)benzothiazol-2-yl]acetamide |
| 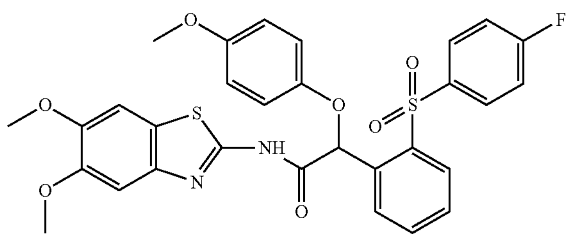 [SMILES: COc1ccc(OC(C(=O)Nc2nc3cc(OC)c(OC)cc3s2)c2ccccc2S(=O)(=O)c2ccc(F)cc2)cc1] | N-(5,6-dimethoxybenzothiazol-2-yl)-2-{2-[(4-fluorophenyl)sulfonyl]phenyl}-2-(4-methoxyphenoxy)acetamide |
| 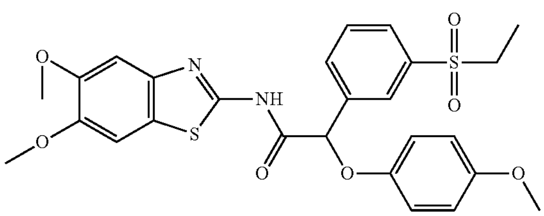 | N-(5,6-dimethoxybenzothiazol-2-yl)-2-[3-(ethylsulfonyl)phenyl]-2-(4-methoxyphenoxy)acetamide |
| 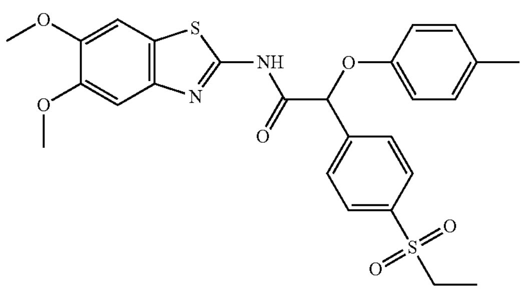 | N-(5,6-dimethoxybenzothiazol-2-yl)-2-[4-(ethylsulfonyl)phenyl]-2-(4-methylphenoxy)acetamide |
| 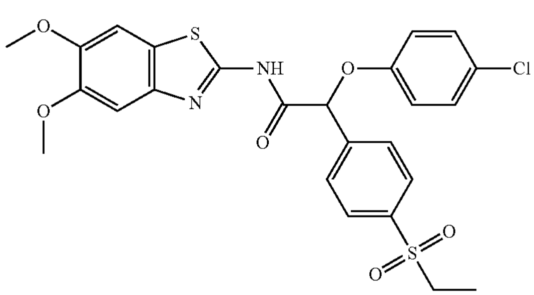 [SMILES: CCS(=O)(=O)c1ccc(C(Oc2ccc(Cl)cc2)C(=O)Nc2nc3cc(OC)c(OC)cc3s2)cc1] | N-(5,6-dimethoxybenzothiazol-2-yl)-2-(4-chlorophenoxy)-2-[4-(ethylsulfonyl)phenyl]acetamide |

TABLE 1-continued

| Structure | Name |
|---|---|
| 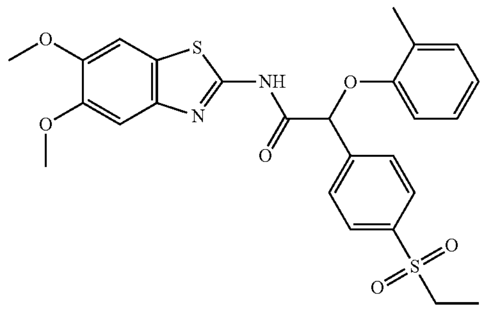 [SMILES: CCS(=O)(=O)c1ccc(C(Oc2ccccc2C)C(=O)Nc2nc3cc(OC)c(OC)cc3s2)cc1] | N-(5,6-dimethoxybenzothiazol-2-yl)-2-[4-(ethylsulfonyl)phenyl]-2-(2-methylphenoxy)acetamide |
| 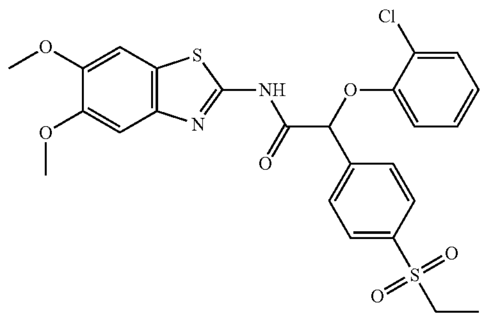 [SMILES: CCS(=O)(=O)c1ccc(C(Oc2ccccc2Cl)C(=O)Nc2nc3cc(OC)c(OC)cc3s2)cc1] | N-(5,6-dimethoxybenzothiazol-2-yl)-2-(2-chlorophenoxy)-2-[4-(ethylsulfonyl)phenyl]acetamide |
| 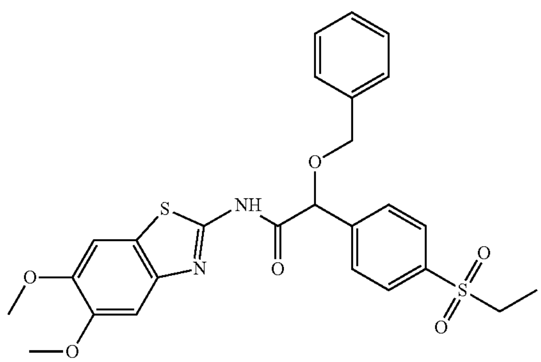 [SMILES: CCS(=O)(=O)c1ccc(C(OCc2ccccc2)C(=O)Nc2nc3cc(OC)c(OC)cc3s2)cc1] | N-(5,6-dimethoxybenzothiazol-2-yl)-2-[4-(ethylsulfonyl)phenyl]-2-(phenylmethoxy)acetamide |
| 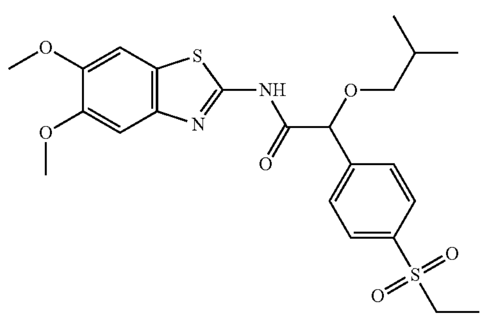 [SMILES: CCS(=O)(=O)c1ccc(C(OCC(C)C)C(=O)Nc2nc3cc(OC)c(OC)cc3s2)cc1] | N-(5,6-dimethoxybenzothiazol-2-yl)-2-[4-(ethylsulfonyl)phenyl]-2-(2-methylpropoxy)acetamide |
| 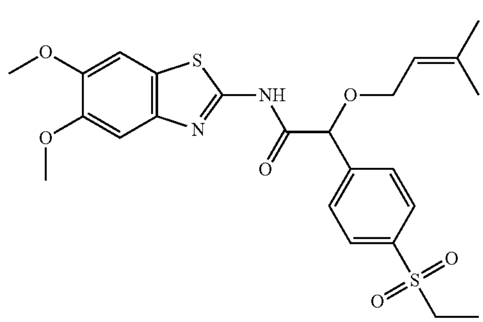 [SMILES: CCS(=O)(=O)c1ccc(C(OCC=C(C)C)C(=O)Nc2nc3cc(OC)c(OC)cc3s2)cc1] | N-(5,6-dimethoxybenzothiazol-2-yl)-2-[4-(ethylsulfonyl)phenyl]-2-(3-methylbut-2-enyloxy)acetamide |

TABLE 1-continued

| Structure | Name |
|---|---|
| 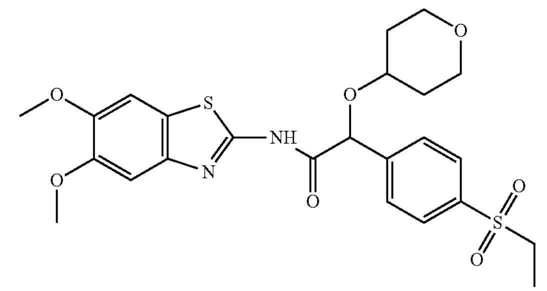 [SMILES: CCS(=O)(=O)c1ccc(C(OC2CCOCC2)C(=O)Nc2nc3cc(OC)c(OC)cc3s2)cc1] | 2-(2H-3,4,5,6-tetrahydropyran-4-yloxy)-N-(5,6-dimethoxybenzothiazol-2-yl)-2-[4-(ethylsulfonyl)phenyl]acetamide |
| 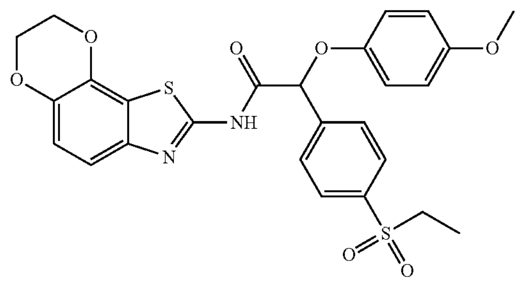 [SMILES: CCS(=O)(=O)c1ccc(C(Oc2ccc(OC)cc2)C(=O)Nc2nc3ccc4c(c3s2)OCCO4)cc1] | N-(7H,8H-1,4-dioxano[5,6-g]benzothiazol-2-yl)-2-(4-(ethylsulfonyl)phenyl]-2-(4-methoxyphenoxy)acetamide |
| 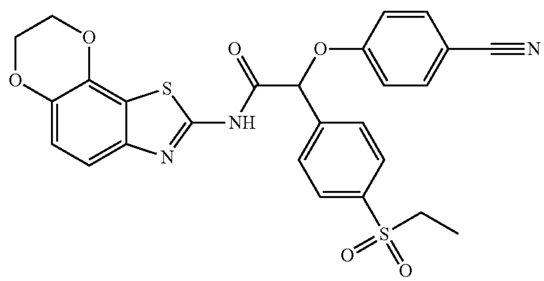 [SMILES: CCS(=O)(=O)c1ccc(C(Oc2ccc(C#N)cc2)C(=O)Nc2nc3ccc4c(c3s2)OCCO4)cc1] | N-(7H,8H-1,4-dioxano[5,6-g]benzothiazol-2-yl)-2-(4-cyanophenoxy)-2-[4-(ethylsulfonyl)phenyl]acetamide |
| 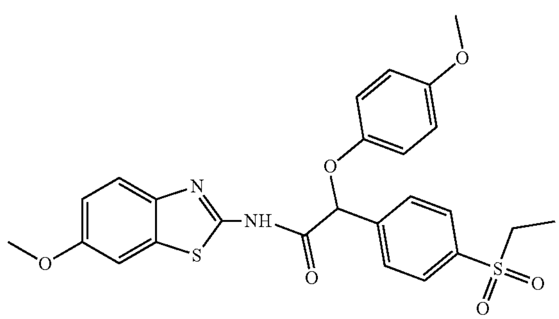 [SMILES: CCS(=O)(=O)c1ccc(C(Oc2ccc(OC)cc2)C(=O)Nc2nc3ccc(OC)cc3s2)cc1] | 2-[4-(ethylsulfonyl)phenyl]-N-(6-methoxybenzothiazol-2-yl)-2-(4-methoxyphenoxy)acetamide |
| 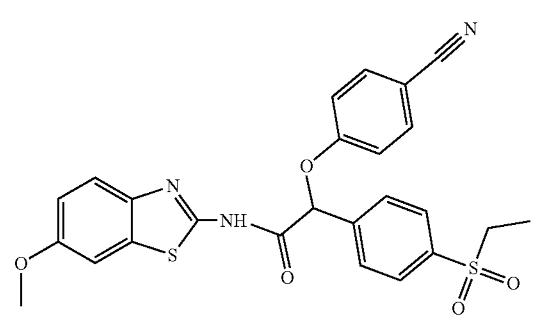 [SMILES: CCS(=O)(=O)c1ccc(C(Oc2ccc(C#N)cc2)C(=O)Nc2nc3ccc(OC)cc3s2)cc1] | 2-(4-cyanophenoxy)-2-[4-(ethylsulfonyl)phenyl]-N-(6-methoxybenzothiazol-2-yl)acetamide |

TABLE 1-continued

| Structure | Name |
|---|---|
| 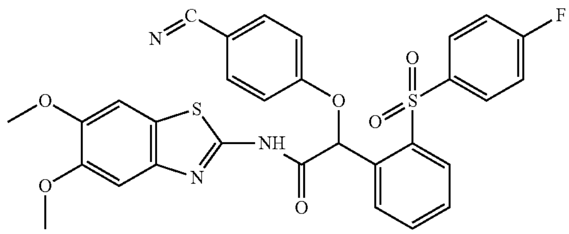 [SMILES: COc1cc2nc(NC(=O)C(Oc3ccc(C=N)cc3)c3ccccc3S(=O)(=O)c3ccc(F)cc3)sc2cc1OC] | N-(5,6-dimethoxybenzothiazol-2-yl)-2-(4-cyanophenoxy)-2-{2-[(4-fluorophenyl)sulfonyl]phenyl}acetamide |
| 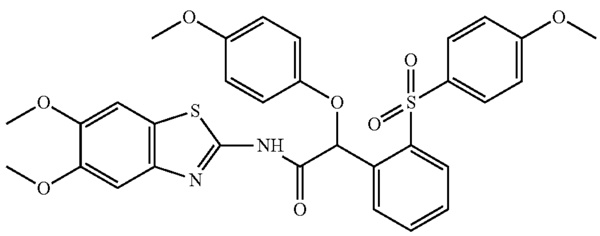 | N-(5,6-dimethoxybenzothiazol-2-yl)-2-(4-methoxyphenoxy)-2-{2-[(4-methoxyphenyl)sulfonyl]phenyl}acetamide |
| 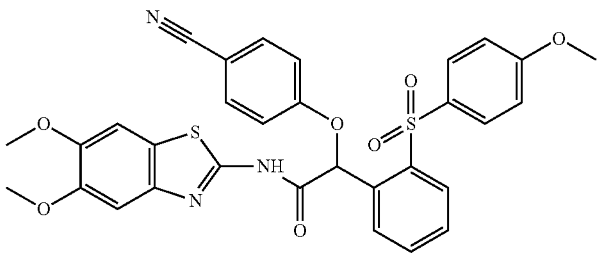 | N-(5,6-dimethoxybenzothiazol-2-yl)-2-(4-cyanophenoxy)-2-{2-[(4-methoxyphenyl)sulfonyl]phenyl}acetamide |
| 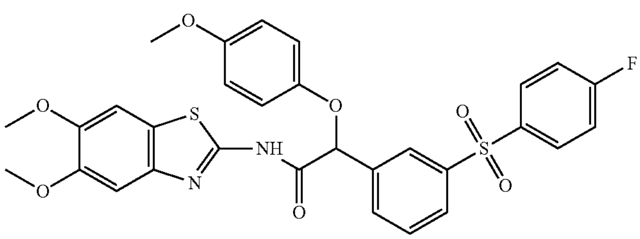 [SMILES: COc1ccc(OC(C(=O)Nc2nc3cc(OC)c(OC)cc3s2)c2cccc(S(=O)(=O)c3ccc(F)cc3)c2)cc1] | N-(5,6-dimethoxybenzothiazol-2-yl)-2-{3-[(4-fluorophenyl)sulfonyl]phenyl}-2-(4-methoxyphenoxy)acetamide |
| 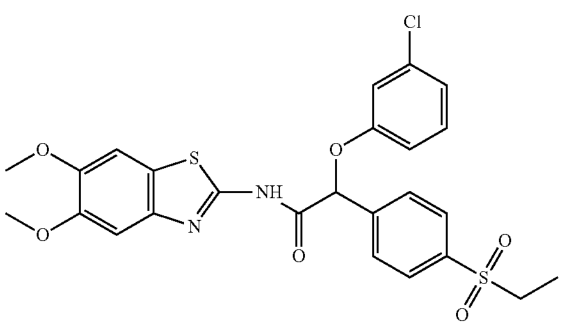 [SMILES: CCS(=O)(=O)c1ccc(C(Oc2cccc(Cl)c2)C(=O)Nc2nc3cc(OC)c(OC)cc3s2)cc1] | N-(5,6-dimethoxybenzothiazol-2-yl)-2-(3-chlorophenoxy)-2-[4-(ethylsulfonyl)phenyl]acetamide |
| 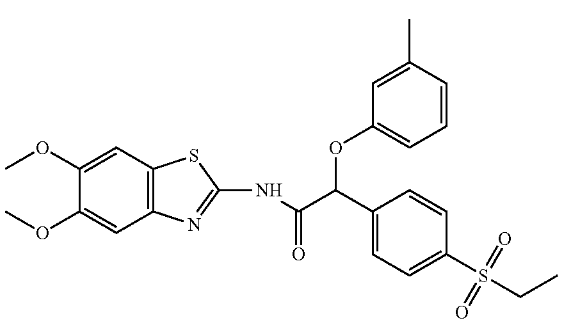 [SMILES: CCS(=O)(=O)c1ccc(C(Oc2cccc(C)c2)C(=O)Nc2nc3cc(OC)c(OC)cc3s2)cc1] | N-(5,6-dimethoxybenzothiazol-2-yl)-2-[4-(ethylsulfonyl)phenyl]-2-(3-methylphenoxy)acetamide |

TABLE 1-continued

| Structure | Name |
|---|---|
| 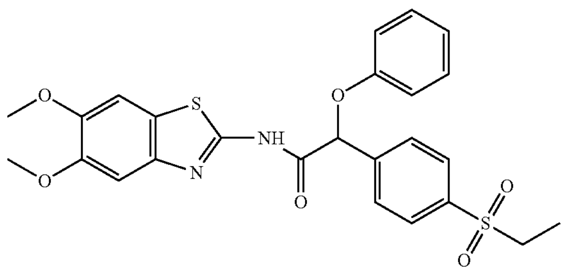 [SMILES: CCS(=O)(=O)c1ccc(C(Oc2ccccc2)C(=O)Nc2nc3cc(OC)c(OC)cc3s2)cc1] | N-(5,6-dimethoxybenzothiazol-2-yl)-2-[4-(ethylsulfonyl)phenyl]-2-phenoxyacetamide |
| 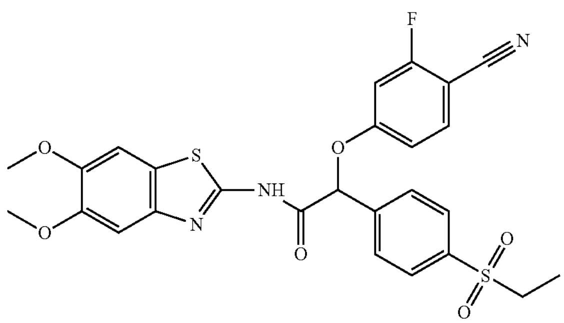 [SMILES: CCS(=O)(=O)c1ccc(C(Oc2ccc(C#N)c(F)c2)C(=O)Nc2nc3cc(OC)c(OC)cc3s2)cc1] | N-(5,6-dimethoxybenzothiazol-2-yl)-2-(4-cyano-3-fluorophenoxy)-2-[4-(ethylsulfonyl)phenyl]acetamide |
| 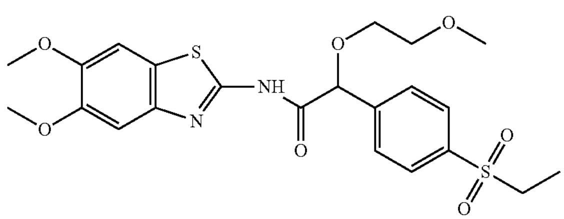 [SMILES: CCS(=O)(=O)c1ccc(C(OCCOC)C(=O)Nc2nc3cc(OC)c(OC)cc3s2)cc1] | N-(5,6-dimethoxybenzothiazol-2-yl)-2-[4-(ethylsulfonyl)phenyl]-2-(2-methoxyethoxy)acetamide |
| 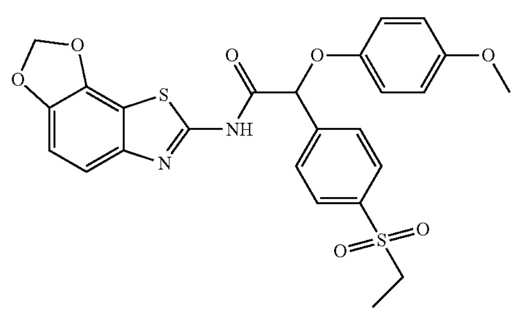 [SMILES: CCS(=O)(=O)c1ccc(C(Oc2ccc(OC)cc2)C(=O)Nc2nc3ccc4c(c3s2)OCO4)cc1] | N-(2H-1,3-dioxolano[4,5-g]benzothiazol-7-yl)-2-[4-(ethylsulfonyl)phenyl]-2-(4-methoxyphenoxy)acetamide |
| 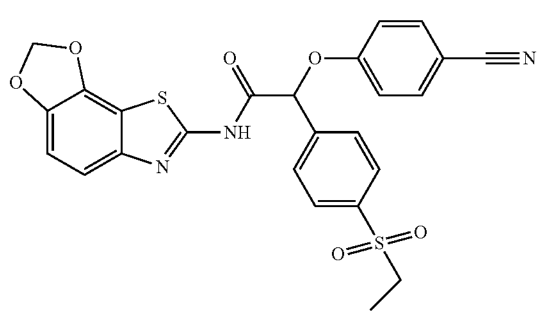 [SMILES: CCS(=O)(=O)c1ccc(C(Oc2ccc(C#N)cc2)C(=O)Nc2nc3ccc4c(c3s2)OCO4)cc1] | N-(2H-1,3-dioxolano[4,5-g]benzothiazol-7-yl)-2-(4-cyanophenoxy)-2-[4-(ethylsulfonyl)phenyl]acetamide |

TABLE 1-continued

| Structure | Name |
|---|---|
| 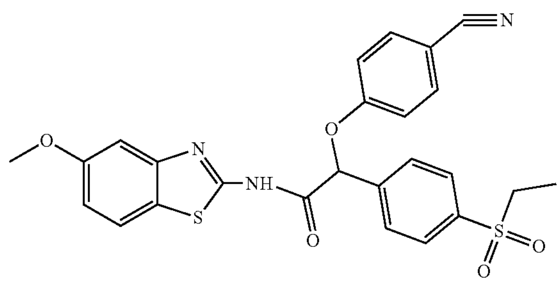 [SMILES: CCS(=O)(=O)c1ccc(C(Oc2ccc(C#N)cc2)C(=O)Nc2nc3cc(OC)ccc3s2)cc1] | 2-(4-cyanophenoxy)-2-[4-(ethylsulfonyl)phenyl]-N-(5-methoxybenzothiazol-2-yl)acetamide |
| 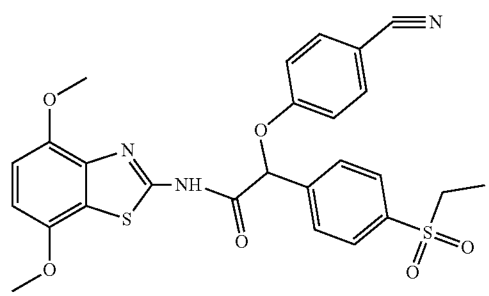 [SMILES: CCS(=O)(=O)c1ccc(C(Oc2ccc(C#N)cc2)C(=O)Nc2nc3c(OC)ccc(OC)c3s2)cc1] | N-(4,7-dimethoxybenzothiazol-2-yl)-2-(4-cyanophenoxy)-2-[4-(ethylsulfonyl)phenyl]acetamide |
| 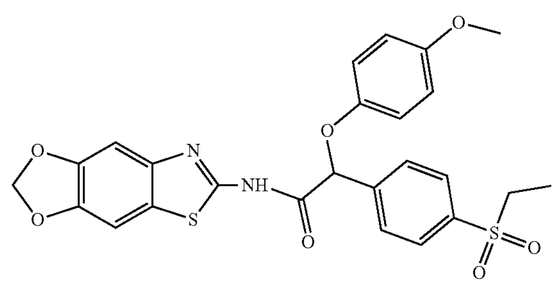 [SMILES: CCS(=O)(=O)c1ccc(C(Oc2ccc(OC)cc2)C(=O)Nc2nc3cc4c(cc3s2)OCO4)cc1] | N-(2H-1,3-dioxoleno[4,5-f]benzothiazol-6-yl)-2-[4-(ethylsulfony)phenyl]-2-(4-methoxyphenoxy)acetamide |
| 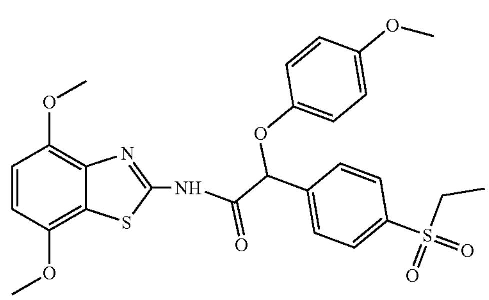 [SMILES: CCS(=O)(=O)c1ccc(C(Oc2ccc(OC)cc2)C(=O)Nc2nc3c(OC)ccc(OC)c3s2)cc1] | N-(4,7-dimethoxybenzothiazol-2-yl)-2-[4-(ethylsulfonyl)phenyl]-2-(4-methoxyphenoxy)acetamide |
| 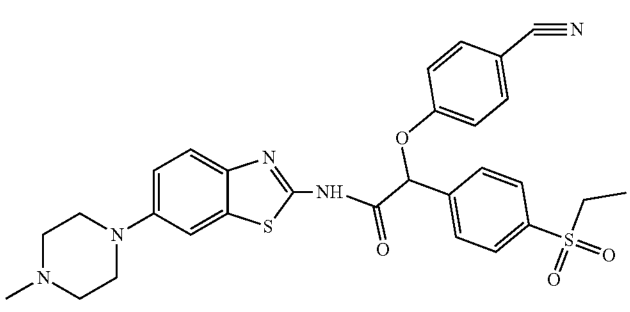 [SMILES: CCS(=O)(=O)c1ccc(C(Oc2ccc(C#N)cc2)C(=O)Nc2nc3ccc(N4CCN(C)CC4)cc3s2)cc1] | 2-(4-cyanophenoxy)-2-[4-(ethylsulfonyl)phenyl]-N-[6-(4-methylpiperazinyl)benzothiazol-2-yl]acetamide |

TABLE 1-continued

| Structure | Name |
|---|---|
| 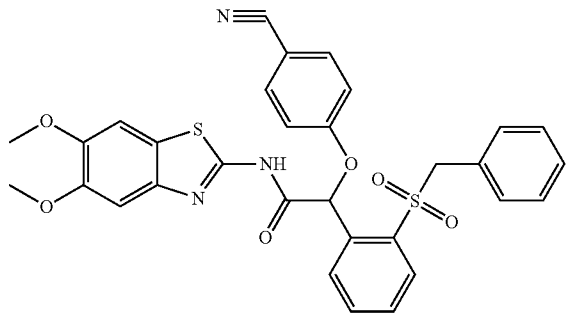 [SMILES: COc1cc2nc(NC(=O)C(Oc3ccc(C#N)cc3)c3ccccc3S(=O)(=O)Cc3ccccc3)sc2cc1OC] | N-(5,6-dimethoxybenzothiazol-2-yl)-2-(4-cyanophenoxy)-2-{2-[benzylsulfonyl]phenyl}acetamide |
| 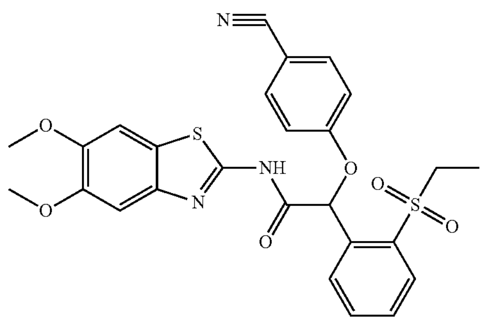 [SMILES: CCS(=O)(=O)c1ccccc1C(Oc1ccc(C#N)cc1)C(=O)Nc1nc2cc(OC)c(OC)cc2s1] | N-(5,6-dimethoxybenzothiazol-2-yl)-2-(4-cyanophenoxy)-2-[2-(ethylsulfonyl)phenyl]acetamide |
| 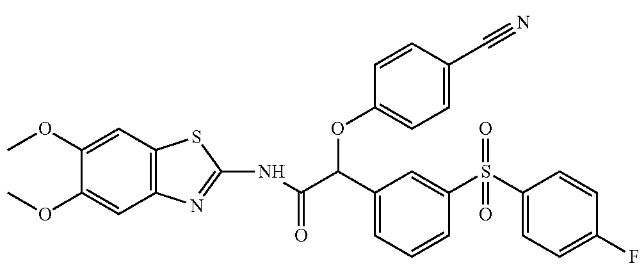 [SMILES: COc1cc2nc(NC(=O)C(Oc3ccc(C#N)cc3)c3cccc(S(=O)(=O)c4ccc(F)cc4)c3)sc2cc1OC] | N-(5,6-dimethoxybenzothiazol-2-yl)-2-(4-cyanophenoxy)-2-{3-[(4-fluorophenyl)sulfonyl]phenyl}acetamide |
| 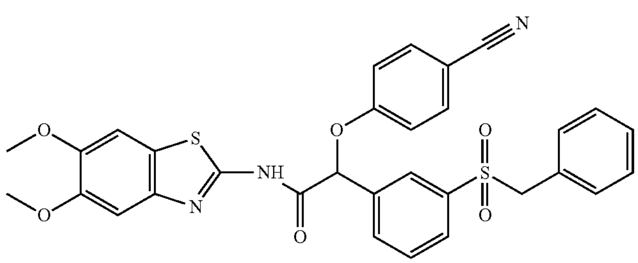 [SMILES: COc1cc2nc(NC(=O)C(Oc3ccc(C#N)cc3)c3cccc(S(=O)(=O)Cc4ccccc4)c3)sc2cc1OC] | N-(5,6-dimethoxybenzothiazol-2-yl)-2-(4-cyanophenoxy)-2-{3-[benzylsulfonyl]phenyl}acetamide |
| 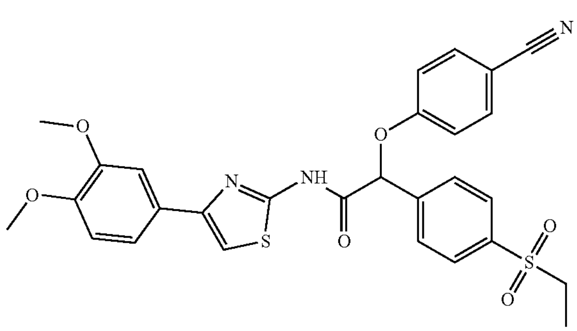 [SMILES: CCS(=O)(=O)c1ccc(C(Oc2ccc(C#N)cc2)C(=O)Nc2nc(-c3ccc(OC)c(OC)c3)cs2)cc1] | N-[4-(3,4-dimethoxyphenyl)(1,3-thiazol-2-yl)]-2-(4-cyanophenoxy)-2-[4-(ethylsulfonyl)phenyl]acetamide |

TABLE 1-continued

| Structure | Name |
|---|---|
| 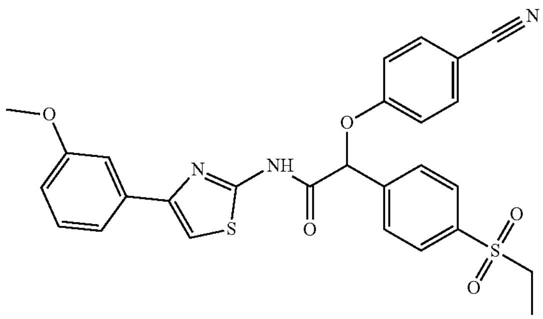 [SMILES: CCS(=O)(=O)c1ccc(C(Oc2ccc(C#N)cc2)C(=O)Nc2nc(-c3cccc(OC)c3)cs2)cc1] | 2-(4-cyanophenoxy)-2-[4-(ethylsulfonyl)phenyl]-N-[4-(3-methoxyphenyl)(1,3-thiazol-2-yl)] acetamide |
| 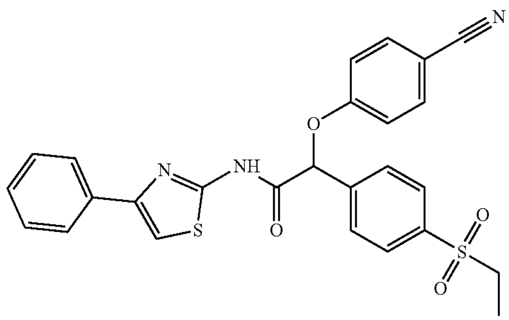 [SMILES: CCS(=O)(=O)c1ccc(C(Oc2ccc(C#N)cc2)C(=O)Nc2nc(-c3ccccc3)cs2)cc1] | 2-(4-cyanophenoxy)-2-[4-(ethylsulfonyl)phenyl]-N-(4-phenyl(1,3-thiazol-2-yl))acetamide |
| 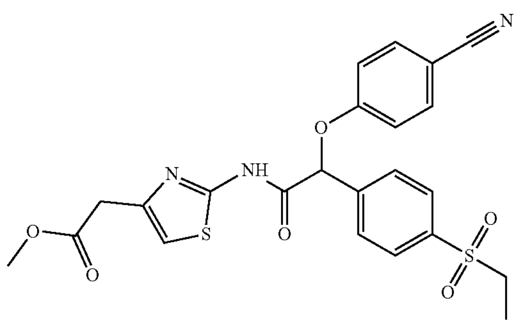 [SMILES: CCS(=O)(=O)c1ccc(C(Oc2ccc(C#N)cc2)C(=O)Nc2nc(CC(=O)OC)cs2)cc1] | methyl 2-(2-{2-(4-cyanophenoxy)-2-[4-(ethylsulfonyl)phenyl]acetylamino}-1,3-thiazol-4-yl)acetate |
| 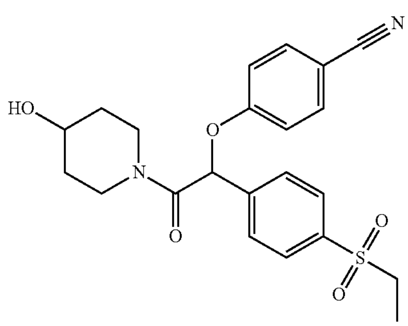 [SMILES: CCS(=O)(=O)c1ccc(C(Oc2ccc(C#N)cc2)C(=O)N2CCC(O)CC2)cc1] | 4-{1-[4-(ethylsulfonyl)phenyl]-2-(4-hydroxypiperidyl)-2-oxoethoxy}benzenecarbonitrile |
| 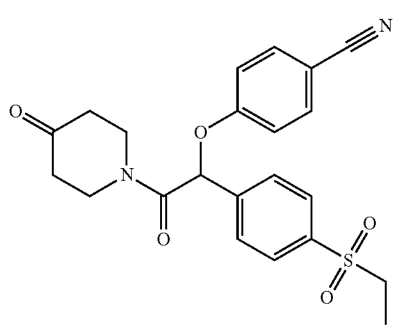 [SMILES: CCS(=O)(=O)c1ccc(C(Oc2ccc(C#N)cc2)C(=O)N2CCC(=O)CC2)cc1] | 4-{1-[4-(ethylsulfonyl)phenyl]-2-oxo-2-(4-oxopiperidyl)ethoxy}benzenecarbonitrile |

TABLE 1-continued

| Structure | Name |
|---|---|
| 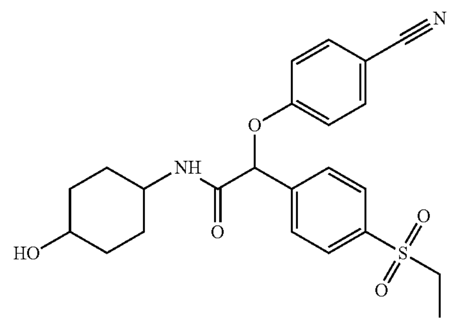 [SMILES: CCS(=O)(=O)c1ccc(C(Oc2ccc(C#N)cc2)C(=O)NC2CCC(O)CC2)cc1] | 2-(4-cyanophenoxy)-2-[4-(ethylsulfonyl)phenyl]-N-(4-hydroxycyclohexyl)acetamide |
| 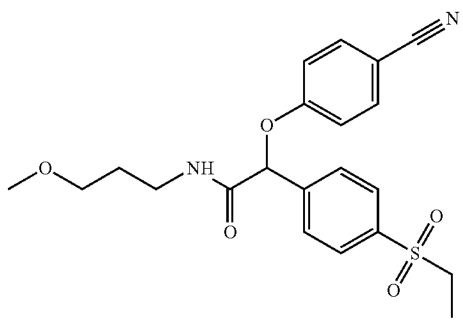 [SMILES: CCS(=O)(=O)c1ccc(C(Oc2ccc(C#N)cc2)C(=O)NCCCOC)cc1] | 2-(4-cyanophenoxy)-2-[4-(ethylsulfonyl)phenyl]-N-(3-methoxypropyl)acetamide |
| 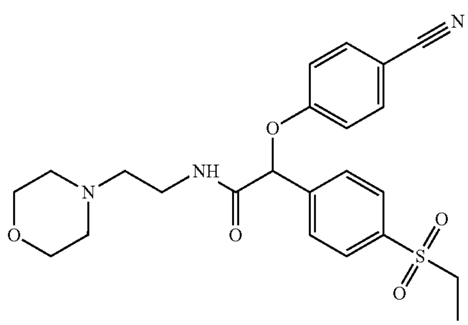 [SMILES: CCS(=O)(=O)c1ccc(C(Oc2ccc(C#N)cc2)C(=O)NCCN2CCOCC2)cc1] | 2-(4-cyanophenoxy)-2-[4-(ethylsulfonyl)phenyl]-N-(2-morpholin-4-ylethyl)acetamide |
| 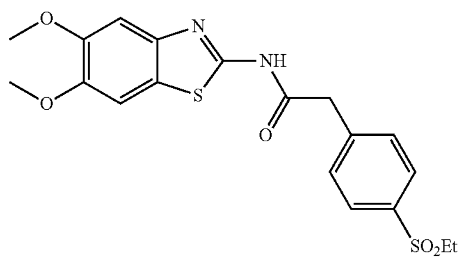 | N-(5,6-Dimethoxy-benzothiazol-2-yl)-2-(4-ethanesulfonyl-phenyl)-acetamide |
| 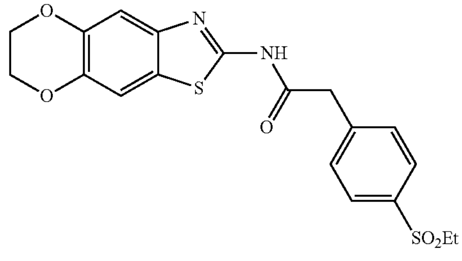 | N-(6,7-Dihydro-5,8-dioxa-1-thia-3-aza-cyclopenta[b]naphthalen-2-yl)-2-(4-ethanesulfonyl-phenyl)-acetamide |

TABLE 1-continued

| Structure | Name |
|---|---|
| 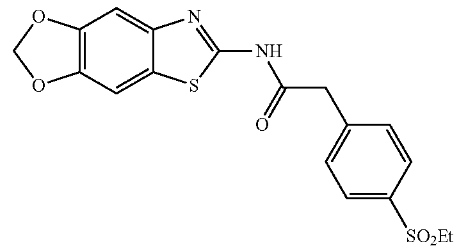 | N-[1,3]Dioxolo[4',5':4,5]benzo[1,2-d]thiazol-6-yl-2-(4-ethanesulfonyl-phenyl)-acetamide |
| 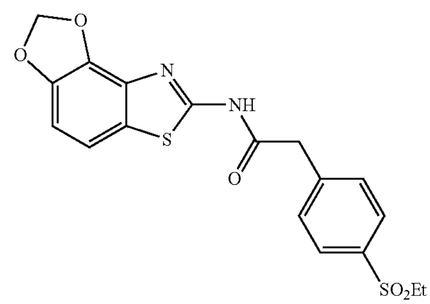 | N-[1,3]Dioxolo[4',5':3,4]benzo[2,1-d]thiazol-7-yl-2-(4-ethanesulfonyl-phenyl)-acetamide |
| 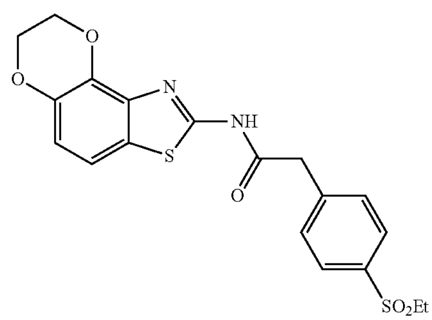 | N-(7,8-Dihydro-6,9-dioxa-3-thia-1-aza-cyclopenta[a]naphthalen-2-yl)-2-(4-ethanesulfonyl-phenyl)-acetamide |
| 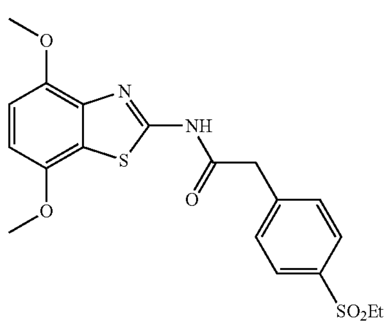 | N-(4,7-Dimethoxy-benzothiazol-2-yl)-2-(4-ethanesulfonyl-phenyl)-acetamide |
| 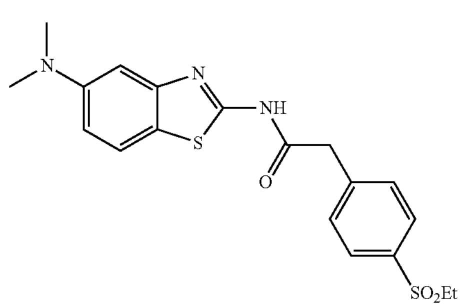 | N-(5-Dimethylamino-benzothiazol-2-yl)-2-(4-ethanesulfonyl-phenyl)-acetamide |

TABLE 1-continued

| Structure | Name |
| --- | --- |
| 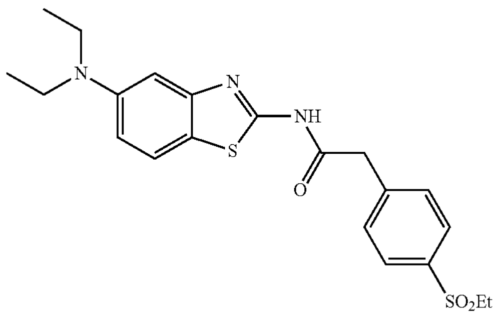 | N-(5-Diethylamino-benzothiazol-2-yl)-2-(4-ethanesulfonyl-phenyl)-acetamide |
| 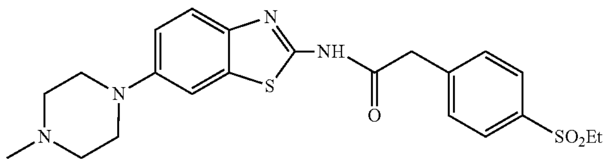 | 2-(4-Ethanesulfonyl-phenyl)-N-[6-(4-methyl-piperazin-1-yl)-benzothiazol-2-yl]-acetamide |
| 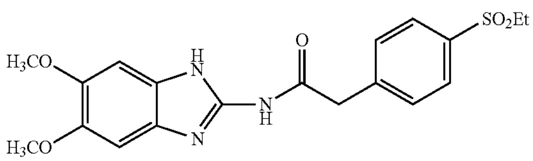 | N-(5,6-Dimethoxy-1H-benzoimidazol-2-yl)-2-(4-ethanesulfonyl-phenyl)-acetamide |
| 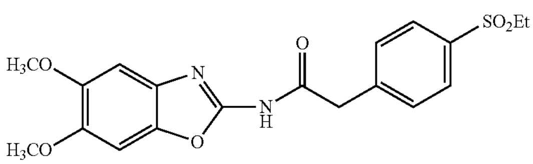 | N-(5,6-dimethoxy-benzooxazol-2-yl)-2-(4-ethanesulfonyl-phenyl)-acetamide |
| 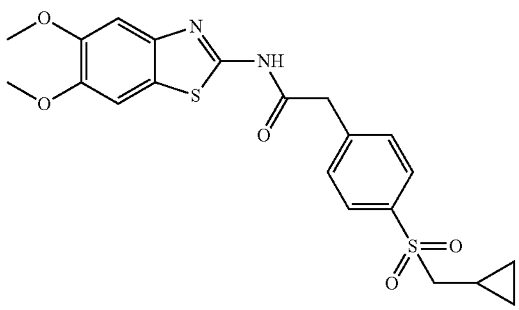 [SMILES: COc1cc2nc(NC(=O)Cc3ccc(S(=O)(=O)CC4CC4)cc3)sc2cc1OC] | 2-(4-Cyclopropylmethanesulfonyl-pheny)-N-(5,6-dimethoxy-benzothiazol-2-yl)-acetamide |
| 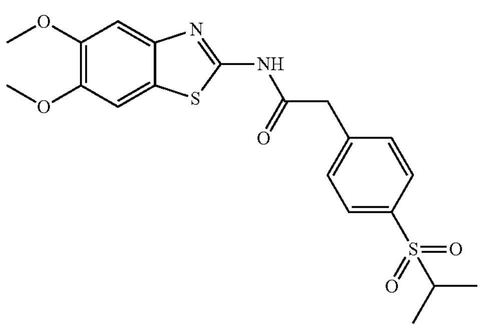 [SMILES: COc1cc2nc(NC(=O)Cc3ccc(S(=O)(=O)C(C)C)cc3)sc2cc1OC] | N-(5,6-Dimethoxy-benzothiazol-2-yl)-2-[4-(propane-2-sulfonyl)-phenyl]-acetamide |

TABLE 1-continued

| Structure | Name |
|---|---|
| 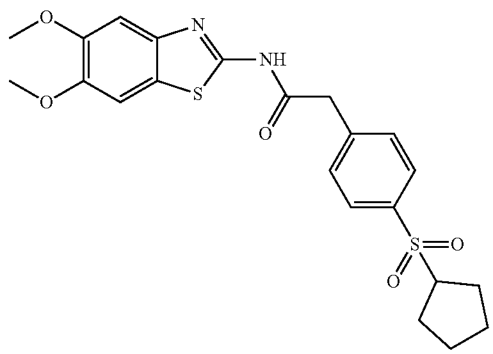 [SMILES: COc1cc2nc(NC(=O)Cc3ccc(S(=O)(=O)C4CCCC4)cc3)sc2cc1OC] | 2-(4-Cyclopentanesulfonyl-phenyl)-N-(5,6-dimethoxy-benzothiazol-2-yl)-acetamide |
| 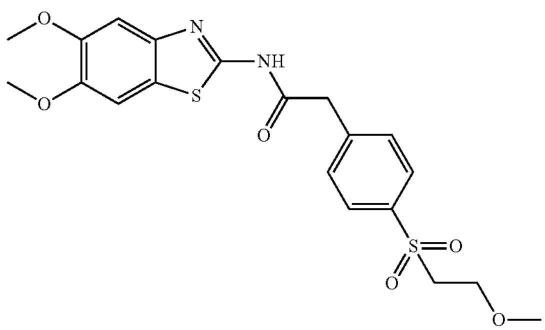 | N-(5,6-Dimethoxy-benzothiazol-2-yl)-2-[4-(2-methoxy-ethanesulfonyl)-phenyl]-acetamide |
| | N-(5,6-Dimethoxy-benzothiazol-2-yl)-2-(3-ethanesulfonyl-phenyl)-acetamide |
| 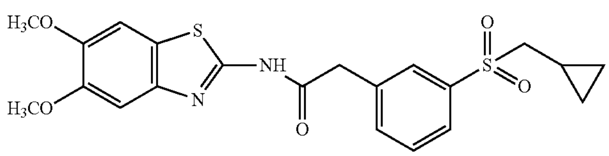 [SMILES: COc1cc2nc(NC(=O)Cc3cccc(S(=O)(=O)CC4CC4)c3)sc2cc1OC] | 2-(3-Cyclopropylmethanesulfonyl-phenyl)-N-(5,6-dimethoxy-benzothiazol-2-yl)-acetamide |
| 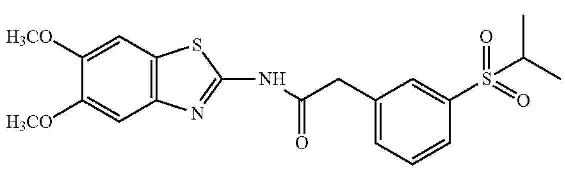 [SMILES: COc1cc2nc(NC(=O)Cc3cccc(S(=O)(=O)C(C)C)c3)sc2cc1OC] | N-(5,6-Dimethoxy-benzothiazol-2-yl)-2-[3-(propane-2-sulfonyl)-phenyl]-acetamide ( |
| 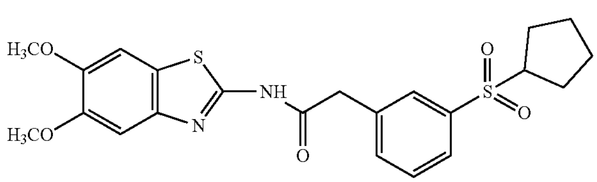 [SMILES: COc1cc2nc(NC(=O)Cc3cccc(S(=O)(=O)C4CCCC4)c3)sc2cc1OC] | 2-(3-Cyclopentanesulfonyl-phenyl)-N-(5,6-dimethoxy-benzothiazol-2-yl)-acetamide |
| | N-(5,6-Dimethoxy-benzothiazol-2-yl)-2-(3-ethanesulfonyl-phenyl)-acetamide |

TABLE 1-continued

| Structure | Name |
|---|---|
| 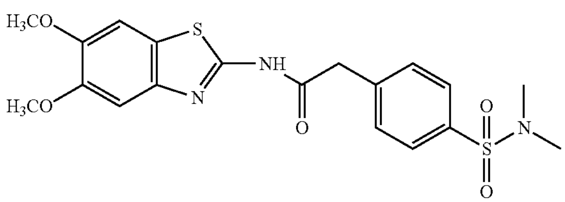 [SMILES: COc1cc2nc(NC(=O)Cc3ccc(S(=O)(=O)N(C)C)cc3)sc2cc1OC] | N-(5,6-Dimethoxy-benzothiazol-2-yl)-2-(4-dimethylsulfonyl-phenyl)-acetamide |
| 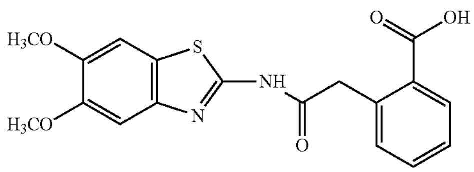 [SMILES: COc1cc2nc(NC(=O)Cc3ccccc3C(=O)O)sc2cc1OC] | 2-[(5,6-Dimethoxy-benzothiazol-2-ylcarbamoyl)-methyl]-benzoic acid |
| 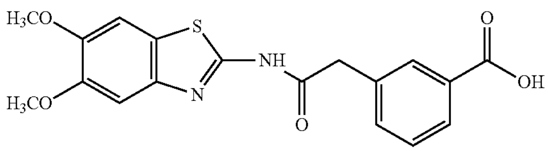 [SMILES: COc1cc2nc(NC(=O)Cc3cccc(C(=O)O)c3)sc2cc1OC] | 3-[(5,6-Dimethoxy-benzothiazol-2-ylcarbamoyl)-methyl]-benzoic acid |
| 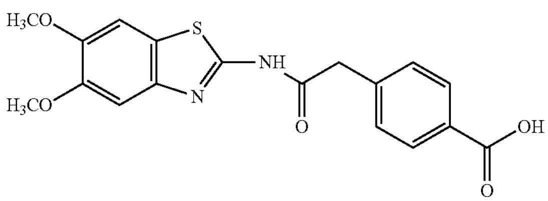 [SMILES: COc1cc2nc(NC(=O)Cc3ccc(C(=O)O)cc3)sc2cc1OC] | 4-[(5,6-Dimethoxy-benzothiazol-2-ylcarbamoyl)-methyl]-benzoic acid |
| 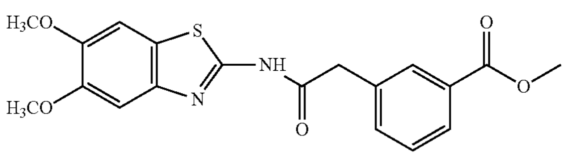 [SMILES: COC(=O)c1cccc(CC(=O)Nc2nc3cc(OC)c(OC)cc3s2)c1] | 3-[(5,6-Dimethoxy-benzothiazol-2-ylcarbamoyl)-methyl]-benzoic acid methyl ester |
| 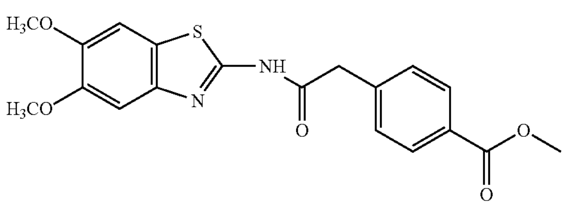 [SMILES: COC(=O)c1ccc(CC(=O)Nc2nc3cc(OC)c(OC)cc3s2)cc1] | 4-[(5,6-Dimethoxy-benzothiazol-2-ylcarbamoyl)-methyl]-benzoic acid methyl ester |
| 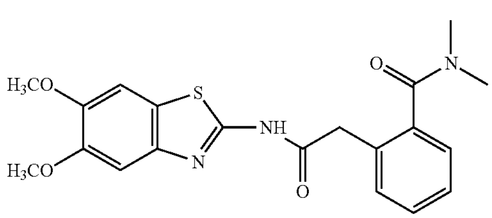 [SMILES: COc1cc2nc(NC(=O)Cc3ccccc3C(=O)N(C)C)sc2cc1OC] | 2-[(5,6-Dimethoxy-benzothiazol-2-ylcarbamoyl)-methyl]-N,N-dimethyl-benzamide |
| 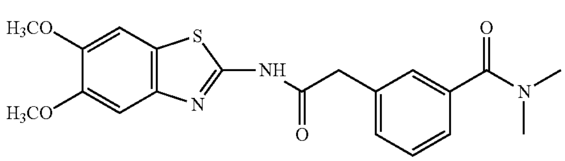 [SMILES: COc1cc2nc(NC(=O)Cc3cccc(C(=O)N(C)C)c3)sc2cc1OC] | 3-[(5,6-Dimethoxy-benzothiazol-2-ylcarbamoyl)-methyl]-N,N-dimethyl-benzamide |

TABLE 1-continued

| Structure | Name |
|---|---|
| 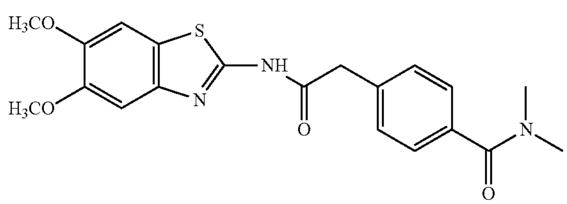 [SMILES: COc1cc2nc(NC(=O)Cc3ccc(C(=O)N(C)C)cc3)sc2cc1OC] | 4-[(5,6-Dimethoxy-benzothiazol-2-ylcarbamoyl)-methyl]-N,N-dimethyl-benzamide |
| 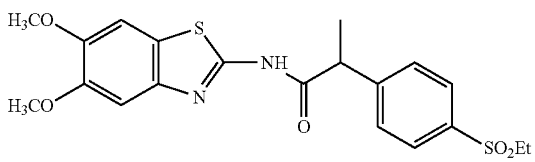 | N-(5,6-Dimethoxy-benzothiazol-2-yl)-2-(4-ethanesulfonyl-phenyl)-propionamide |
| 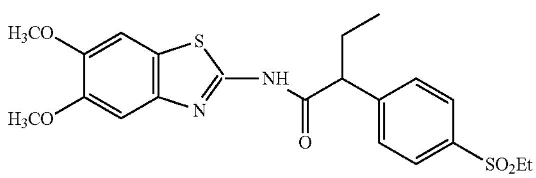 | N-(5,6-Dimethoxy-benzothiazol-2-yl)-2-(4-ethanesulfonyl-phenyl)-butyramide |
| 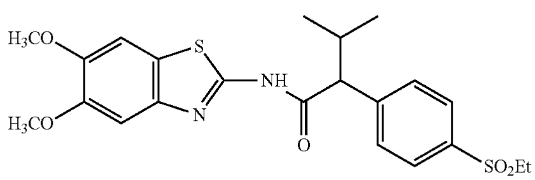 | N-(5,6-Dimethoxy-benzothiazol-2-yl)-2-(4-ethanesulfonyl-phenyl)-3-methyl-butyramide |
| 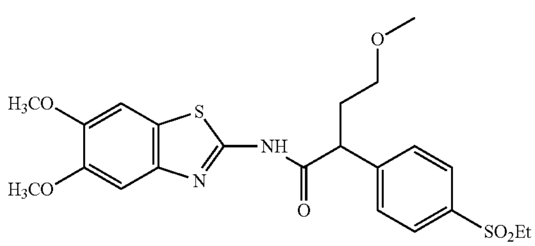 | N-(5,6-Dimethoxy-benzothiazol-2-yl)-2-(4-ethanesulfonyl-phenyl)-4-methyl-butyramide |
| 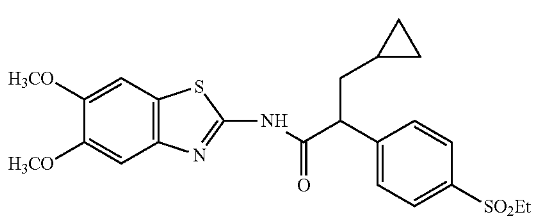 | 3-Cyclopropyl-N-(5,6-dimethoxy-benzothiazol-2-yl)-2-(4-ethanesulfonyl-phenyl)-propionamide |
| 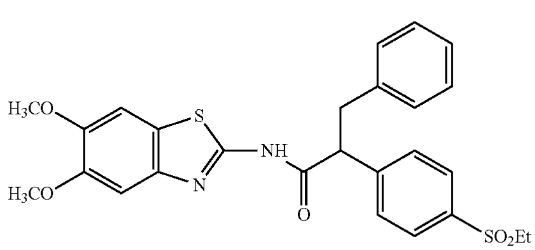 | N-(5,6-Dimethoxy-benzothiazol-2-yl)-2-(4-ethanesulfonyl-phenyl)-3-phenyl-propionamide |

TABLE 1-continued

| Structure | Name |
|---|---|
| 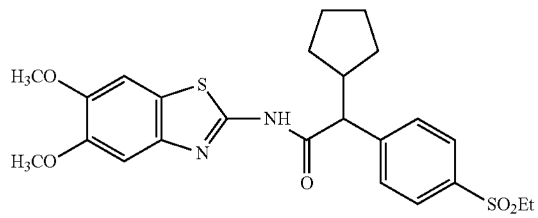 | 2-Cyclopentyl-N-(5,6-dimethoxy-benzothiazol-2-yl)-2-(4-ethanesulfonyl-phenyl)-acetamide |
| 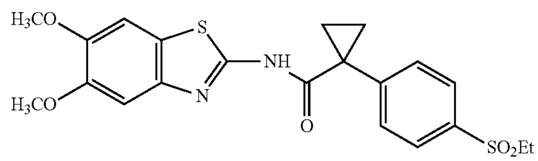 | 1-(4-Ethanesulfonyl-phenyl)-cyclopropanecarboxylic acid (5,6-dimethoxy-benzothiazol-2-yl)-amide |
| 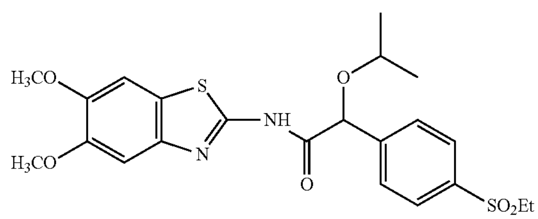 | N-(5,6-Dimethoxy-benzothiazol-2-yl)-2-(4-ethanesulfonyl-phenyl)-2-isopropoxy-acetamide |
| 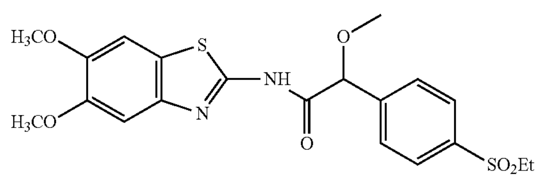 | N-(5,6-Dimethoxy-benzothiazol-2-yl)-2-(4-ethanesulfonyl-phenyl)-2-methoxy-acetamide ( |
| 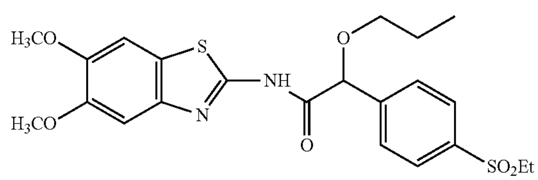 | N-(5,6-Dimethoxy-benzothiazol-2-yl)-2-(4-ethanesulfonyl-phenyl)-2-propoxy-acetamide |
| 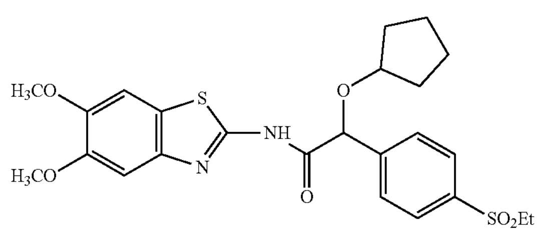 | 2-Cyclopentyloxy-N-(5,6-dimethoxy-benzothiazol-2-yl)-2-(4-ethanesulfonyl-phenyl)-acetamide |
| 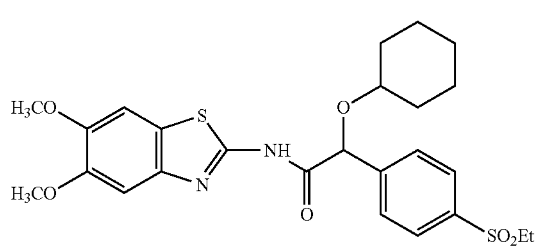 | 2-Cyclohexyloxy-N-(5,6-dimethoxy-benzothiazol-2-yl)-2-(4-ethanesulfonyl-phenyl)-acetamide |

TABLE 1-continued

| Structure | Name |
| --- | --- |
| 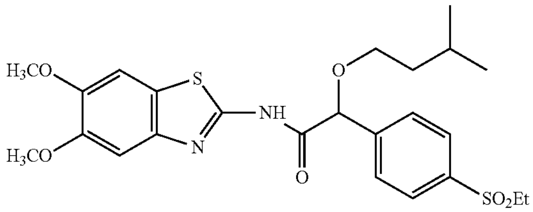 | N-(5,6-Dimethoxy-benzothiazol-2-yl)-2-(4-ethanesulfonyl-phenyl)-2-(3-methyl-butoxy)-acetamide |
| 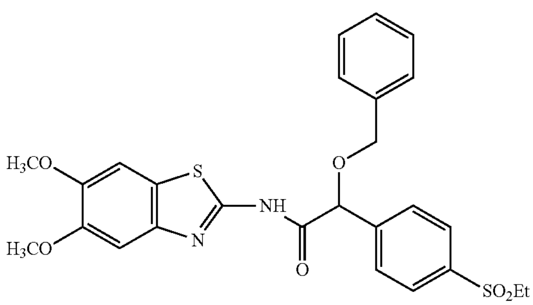 | 2-Benzyloxy-N-(5,6-dimethoxy-benzothiazol-2-yl)-2-(4-ethanesulfonyl-phenyl)-acetamide |
| 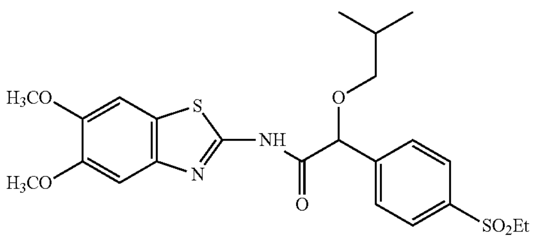 | N-(5,6-Dimethoxy-benzothiazol-2-yl)-2-(4-ethanesulfonyl-phenyl)-2-isobutoxy-acetamide |
| 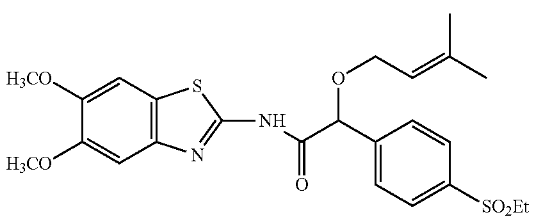 | N-(5,6-Dimethoxy-benzothiazol-2-yl)-2-(4-ethanesulfonyl-phenyl)-2-(3-methyl-but-2-enyloxy)-acetamide |
| 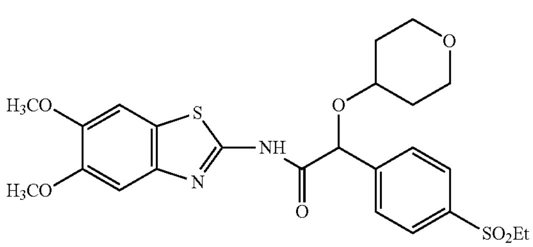 | N-(5,6-Dimethoxy-benzothiazol-2-yl)-2-(4-ethanesulfonyl-phenyl)-2-(tetrahydro-pyran-4-yloxy)-acetamide |
| 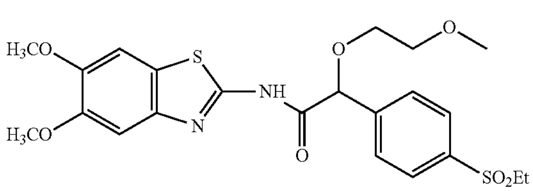 | N-(5,6-Dimethoxy-benzothiazol-2-yl)-2-(4-ethanesulfonyl-phenyl)-2-(2-methoxy-ethoxy)-acetamide |

TABLE 1-continued

| Structure | Name |
| --- | --- |
| 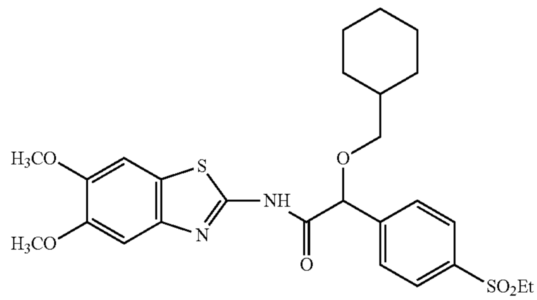 | 2-Cyclopentylmethoxy-N-(5,6-dimethoxy-benzothiazol-2-yl)-2-(4-ethanesulfonyl-phenyl)-acetamide |
| 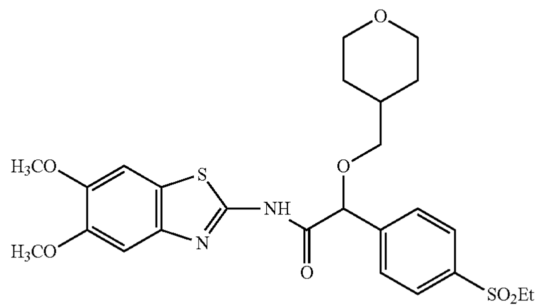 | N-(5,6-Dimethoxy-benzothiazol-2-yl)-2-(4-ethanesulfonyl-phenyl)-2-(tetrahydro-pyran-4-ylmethoxy)-acetamide |
| 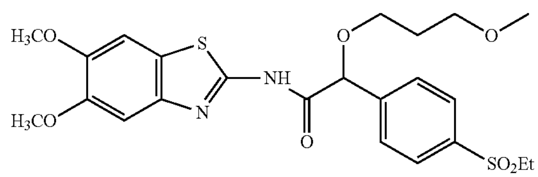 | N-(5,6-Dimethoxy-benzothiazol-2-yl)-2-(4-ethanesulfonyl-phenyl)-2-(3-methoxy-propoxy)-acetamide |
| 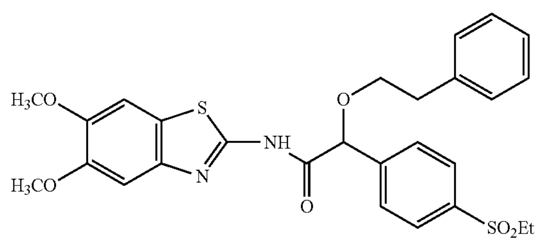 | N-(5,6-Dimethoxy-benzothiazol-2-yl)-2-(4-ethanesulfonyl-phenyl)-2-phenethyloxy-acetamide |
| 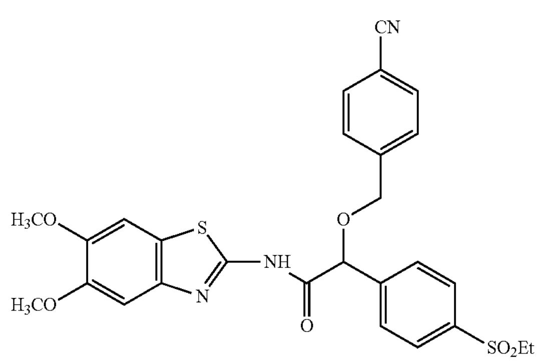 | 2-(4-Cyano-benzyloxy)-N-(5,6-dimethoxy-benzothiazol-2-yl)-2-(4-ethanesulfonyl-phenyl)-acetamide |

TABLE 1-continued

| Structure | Name |
|---|---|
| 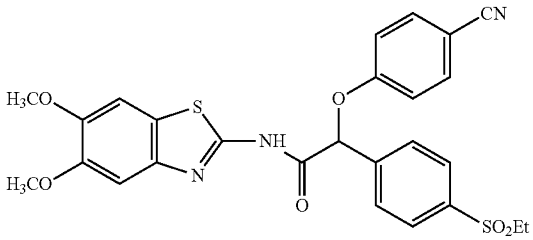 | 2-(4-Cyano-phenoxy)-N-(5,6-dimethoxy-benzothiazol-2-yl)-2-(4-ethanesulfonyl-phenyl)-acetamide |
| 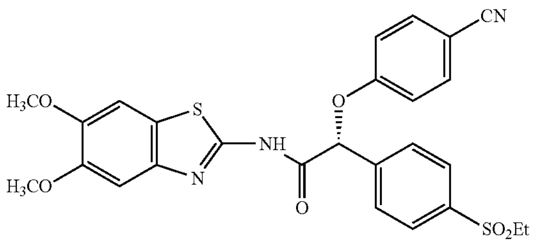 | 2-(4-Cyano-phenoxy)-N-(5,6-dimethoxy-benzothiazol-2-yl)-2-(4-ethanesulfonyl-phenyl)-acetamide (peak 1) |
| 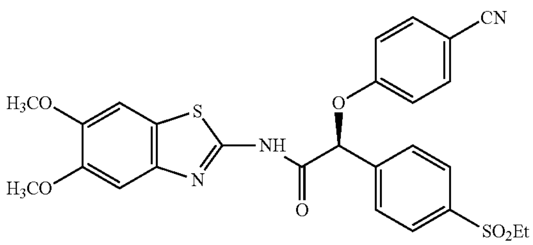 | 2-(4-Cyano-phenoxy)-N-(5,6-dimethoxy-benzothiazol-2-yl)-2-(4-ethanesulfonyl-phenyl)-acetamide (peak 2) |
| 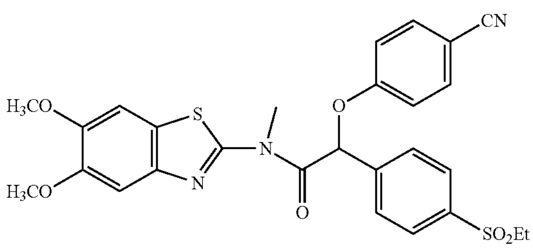 | 2-(4-Cyano-phenoxy)-N-(5,6-dimethoxy-benzothiazol-2-yl)-2-(4-ethanesulfonyl-phenyl)-N-methyl-acetamide |
| 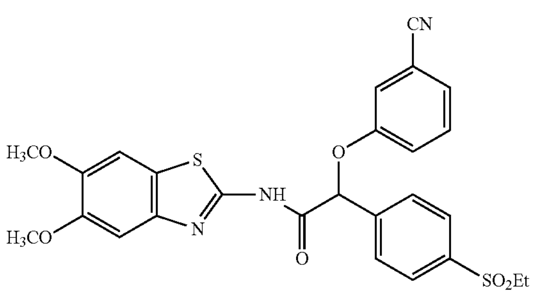 | 2-(3-Cyano-phenoxy)-N-(5,6-dimethoxy-benzothiazol-2-yl)-2-(4-ethanesulfonyl-phenyl)-acetamide |
| 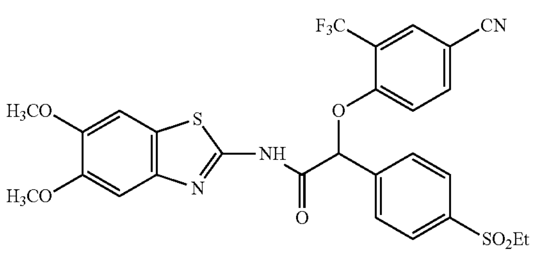 | 2-(4-Cyano-2-trifluoromethyl-phenoxy)-N-(5,6-dimethoxy-benzothiazol-2-yl)-2-(4-ethanesulfonyl-phenyl)-acetamide |

TABLE 1-continued

| Structure | Name |
|---|---|
| 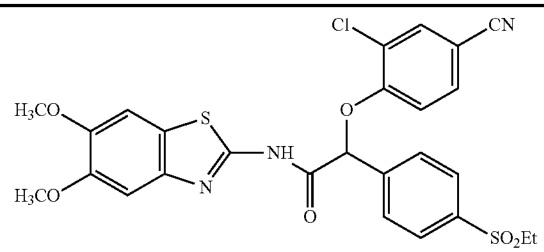 | 2-(2-Chloro-4-cyano-phenoxy)-N-(5,6-dimethoxy-benzothiazol-2-yl)-2-(4-ethanesulfonyl-phenyl)-acetamide |
| 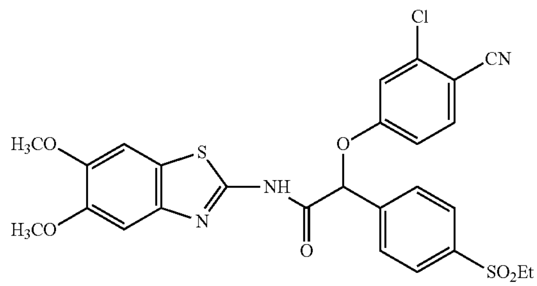 | 2-(3-Chloro-4-cyano-phenoxy)-N-(5,6-dimethoxy-benzothiazol-2-yl)-2-(4-ethanesulfonyl-phenyl)-acetamide |
| 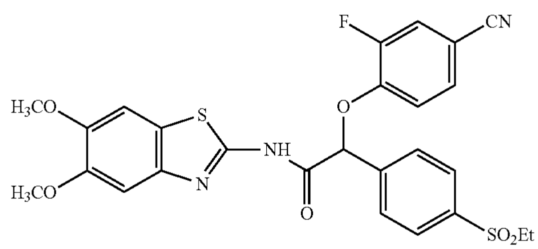 | 2-(4-Cyano-2-fluoro-phenoxy)-N-(5,6-dimethoxy-benzothiazol-2-yl)-2-(4-ethanesulfonyl-phenyl)-acetamide |
| 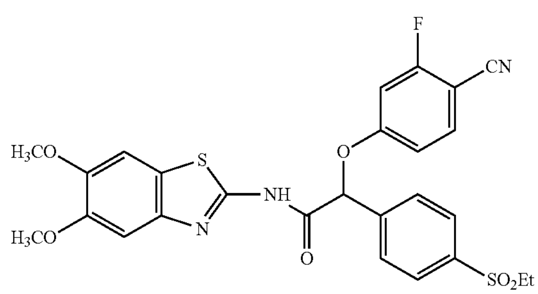 | 2-(4-Cyano-3-fluoro-phenoxy)-N-(5,6-dimethoxy-benzothiazol-2-yl)-2-(4-ethanesulfonyl-phenyl)-acetamide |
| 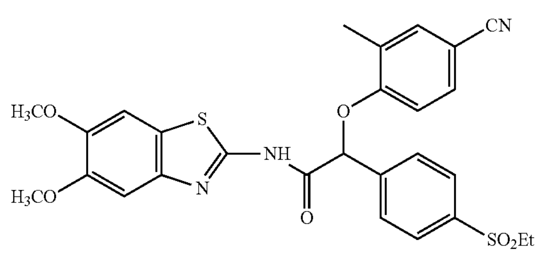 | 2-(4-Cyano-2-methyl-phenoxy)-N-(5,6-dimethoxy-benzothiazol-2-yl)-2-(4-ethanesulfonyl-phenyl)-acetamide |
| 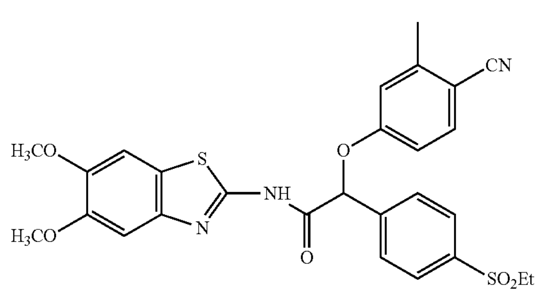 | 2-(4-Cyano-3-methyl-phenoxy)-N-(5,6-dimethoxy-benzothiazol-2-yl)-2-(4-ethanesulfonyl-phenyl)-acetamide |

TABLE 1-continued

| Structure | Name |
|---|---|
| 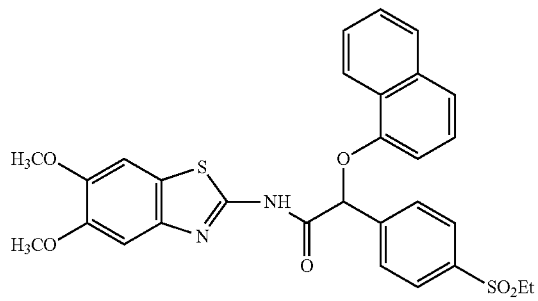 | N-(5,6-Dimethoxy-benzothiazol-2-yl)-2-(4-ethanesulfonyl-phenyl)-2-(naphthalen-1-yloxy)-acetamide |
| 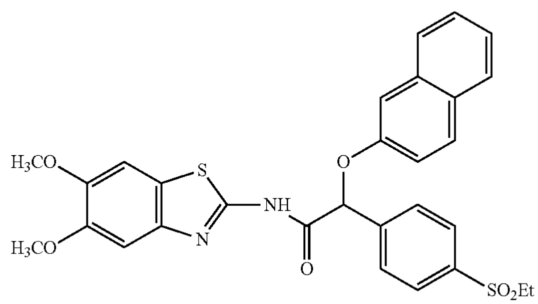 | N-(5,6-Dimethoxy-benzothiazol-2-yl)-2-(4-ethanesulfonyl-phenyl)-2-(naphthalen-2-yloxy)-acetamide |
| 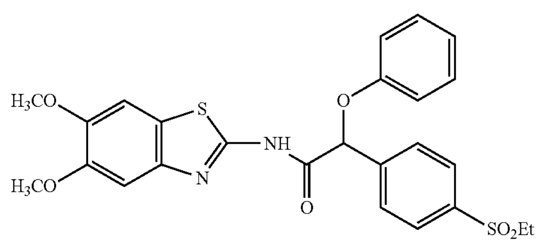 | N-(5,6-Dimethoxy-benzothiazol-2-yl)-2-(4-ethanesulfonyl-phenyl)-2-phenoxy-acetamide |
| 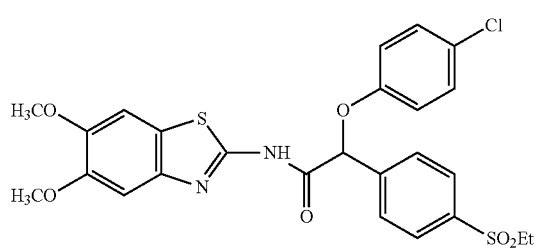 | 2-(4-Chloro-phenoxy)-N-(5,6-dimethoxy-benzothiazol-2-yl)-2-(4-ethanesulfonyl-phenyl)-acetamide |
| 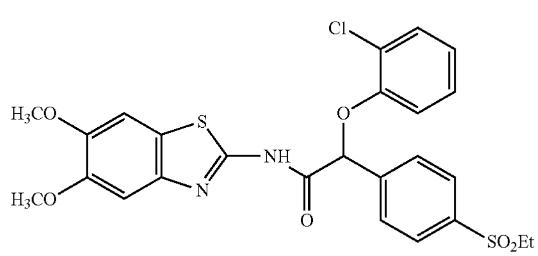 | 2-(2-Chloro-phenoxy)-N-(5,6-dimethoxy-benzothiazol-2-yl)-2-(4-ethanesulfonyl-phenyl)-acetamide |

TABLE 1-continued

| Structure | Name |
|---|---|
| 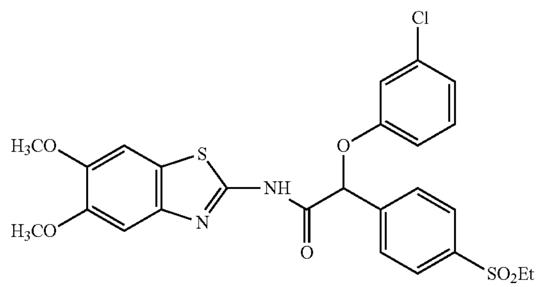 | 2-(3-Chloro-phenoxy)-N-(5,6-dimethoxy-benzothiazol-2-yl)-2-(4-ethanesulfonyl-phenyl)-acetamide |
| 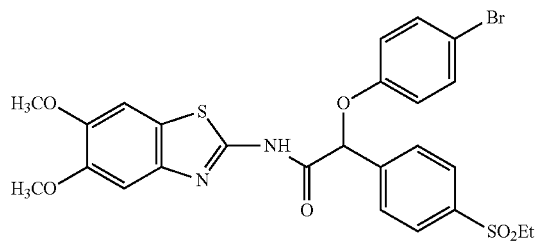 | 2-(4-Bromo-phenoxy)-N-(5,6-dimethoxy-benzothiazol-2-yl)-2-(4-ethanesulfonyl-phenyl)-acetamide |
| 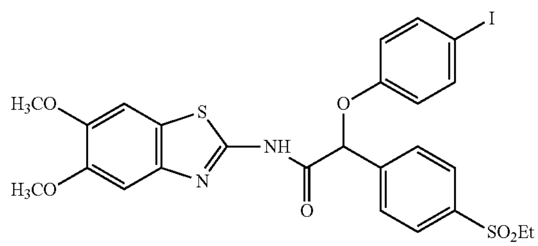 | N-(5,6-Dimethoxy-benzothiazol-2-yl)-2-(4-ethanesulfonyl-phenyl)-2-(4-iodo-phenoxy)-acetamide |
| 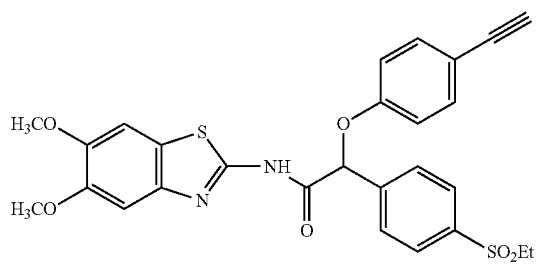 | N-(5,6-Dimethoxy-benzothiazol-2-yl)-2-(4-ethanesulfonyl-phenyl)-2-(4-ethynyl-phenoxy)-acetamide |
| 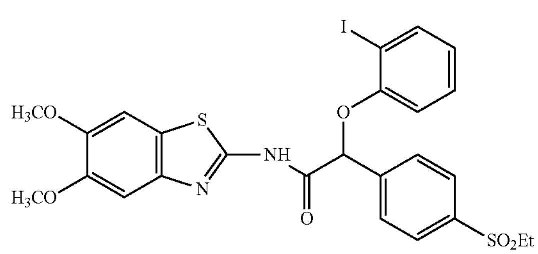 | N-(5,6-Dimethoxy-benzothiazol-2-yl)-2-(4-ethanesulfonyl-phenyl)-2-(2-iodo-phenoxy)-acetamide |
| 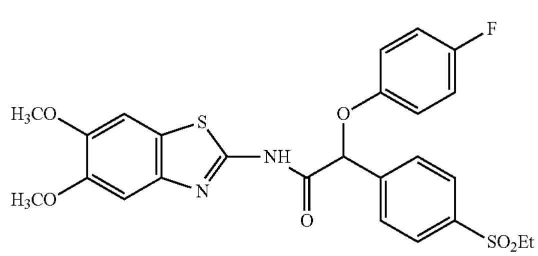 | N-(5,6-Dimethoxy-benzothiazol-2-yl)-2-(4-ethanesulfonyl-phenyl)-2-(4-fluoro-phenoxy)-acetamide |

TABLE 1-continued

| Structure | Name |
|---|---|
| 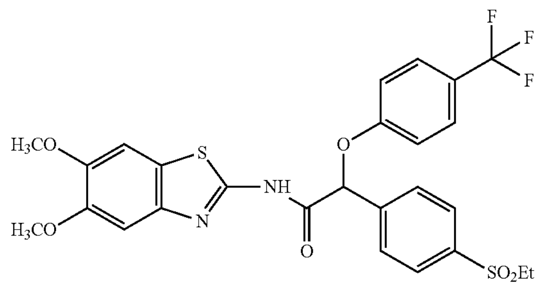 | N-(5,6-Dimethoxy-benzothiazol-2-yl)-2-(4-ethanesulfonyl-phenyl)-2-(4-trifluoromethyl-phenoxy)-acetamide |
| 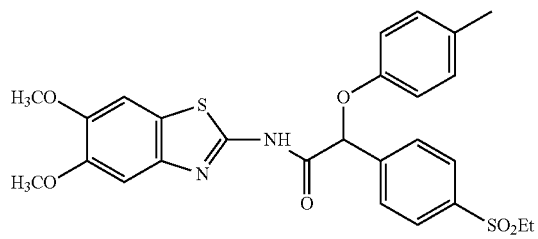 | N-(5,6-Dimethoxy-benzothiazol-2-yl)-2-(4-ethanesulfonyl-phenyl)-2-p-tolyloxy-acetamide |
| 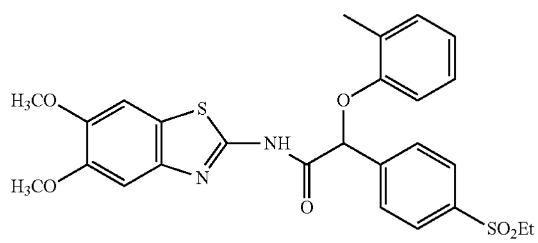 | N-(5,6-Dimethoxy-benzothiazol-2-yl)-2-(4-ethanesulfonyl-phenyl)-2-o-tolyloxy-acetamide |
| 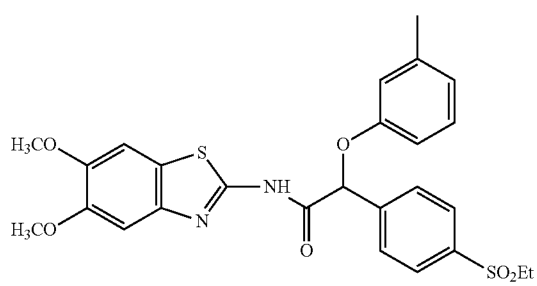 | N-(5,6-Dimethoxy-benzothiazol-2-yl)-2-(4-ethanesulfonyl-phenyl)-2-m-tolyloxy-acetamide |
| 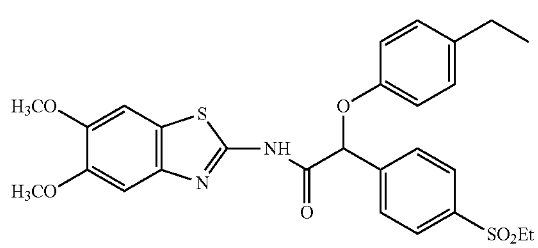 | N-(5,6-Dimethoxy-benzothiazol-2-yl)-2-(4-ethanesulfonyl-phenyl)-2-(4-ethyl-phenoxy)-acetamide |
| 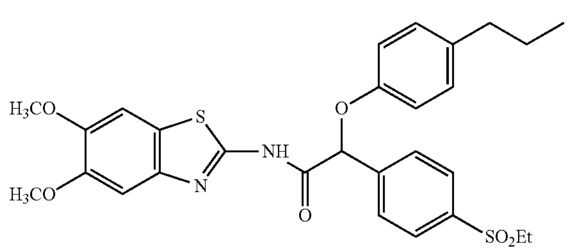 | N-(5,6-Dimethoxy-benzothiazol-2-yl)-2-(4-ethanesulfonyl-phenyl)-2-(4-propyl-phenoxy)-acetamide |

TABLE 1-continued

| Structure | Name |
|---|---|
| 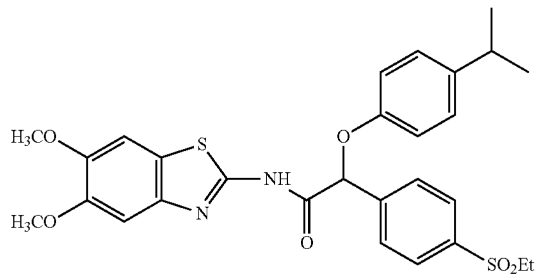 | N-(5,6-Dimethoxy-benzothiazol-2-yl)-2-(4-ethanesulfonyl-phenyl)-2-(4-isopropyl-phenoxy)-acetamide |
| 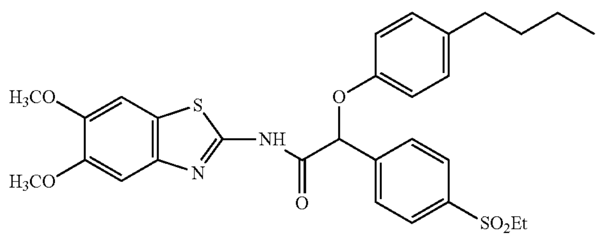 | 2-(4-Butyl-phenoxy)-N-(5,6-dimethoxy-benzothiazol-2-yl)-2-(4-ethanesulfonyl-phenyl)-acetamide |
| 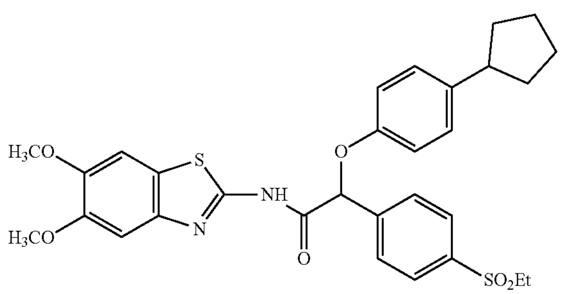 | 2-(4-Cyclopentyl-phenoxy)-N-(5,6-dimethoxy-benzothiazol-2-yl)-2-(4-ethanesulfonyl-phenyl)-acetamide |
| 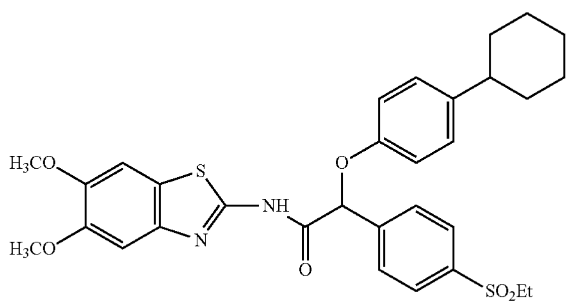 | 2-(4-Cyclohexyl-phenoxy)-N-(5,6-dimethoxy-benzothiazol-2-yl)-2-(4-ethanesulfonyl-phenyl)-acetamide |
| 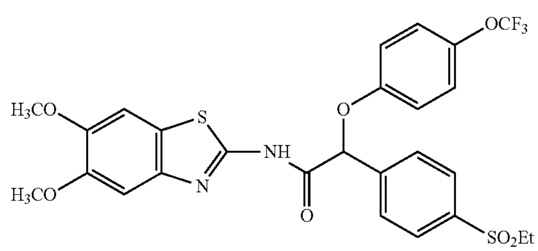 | N-(5,6-Dimethoxy-benzothiazol-2-yl)-2-(4-ethanesulfonyl-phenyl)-2-(4-trifluoromethoxy-phenoxy)-acetamide |
| 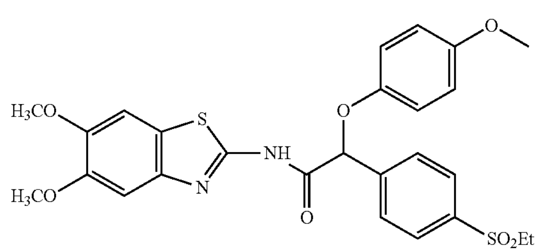 | N-(5,6-Dimethoxy-benzothiazol-2-yl)-2-(4-ethanesulfonyl-phenyl)-2-(4-methoxy-phenoxy)-acetamide |

TABLE 1-continued

| Structure | Name |
|---|---|
| 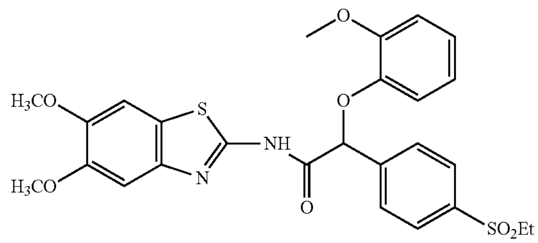 | N-(5,6-Dimethoxy-benzothiazol-2-yl)-2-(4-ethanesulfonyl-phenyl)-2-(2-methoxy-phenoxy)-acetamide |
| 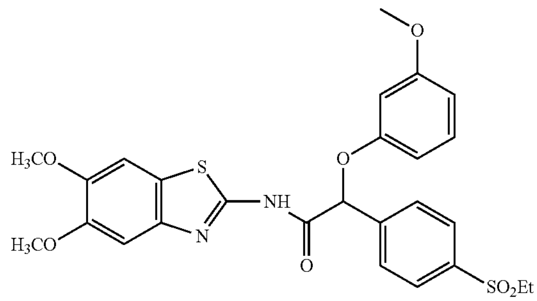 | N-(5,6-Dimethoxy-benzothiazol-2-yl)-2-(4-ethanesulfonyl-phenyl)-2-(3-methoxy-phenoxy)-acetamide |
| 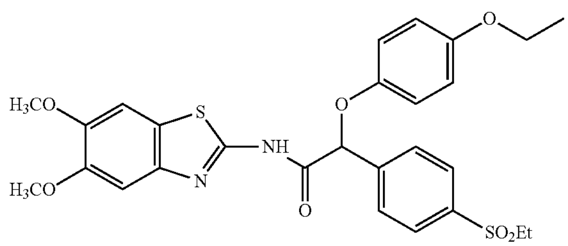 | N-(5,6-Dimethoxy-benzothiazol-2-yl)-2-(4-ethanesulfonyl-phenyl)-2-(4-ethoxy-phenoxy)-acetamide |
| 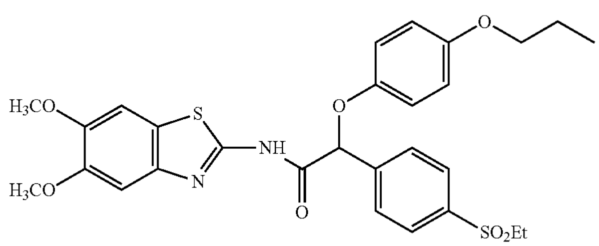 | N-(5,6-Dimethoxy-benzothiazol-2-yl)-2-(4-ethanesulfonyl-phenyl)-2-(4-propoxy-phenoxy)-acetamide |
| 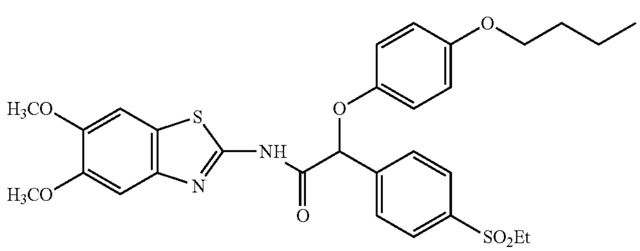 | 2-(4-Butoxy-phenoxy)-N-(5,6-dimethoxy-benzothiazol-2-yl)-2-(4-ethanesulfonyl-phenyl)-acetamide |
| 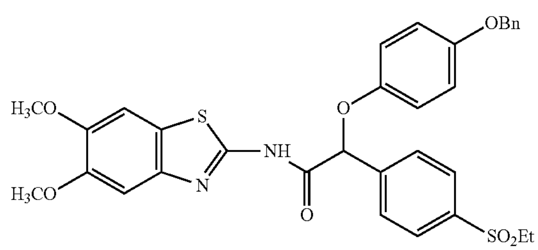 | 2-(4-Benzyloxy-phenoxy)-N-(5,6-dimethoxy-benzothiazol-2-yl)-2-(4-ethanesulfonyl-phenyl)-acetamide |

TABLE 1-continued

| Structure | Name |
|---|---|
| 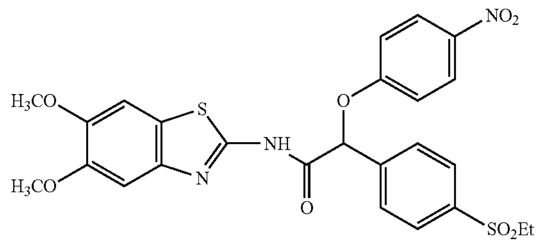 | N-(5,6-Dimethoxy-benzothiazol-2-yl)-2-(4-ethanesulfonyl-phenyl)-2-(4-nitro-phenoxy)-acetamide |
| 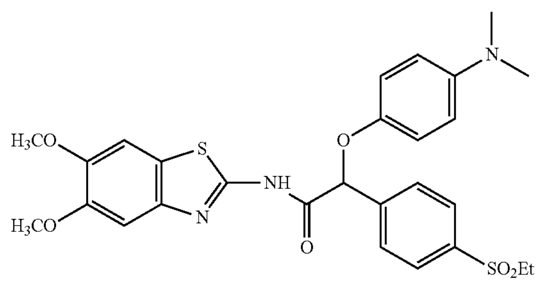 | N-(5,6-Dimethoxy-benzothiazol-2-yl)-2-(4-dimethylamino-phenoxy)-2-(4-ethanesulfonyl-phenyl)-acetamide |
| 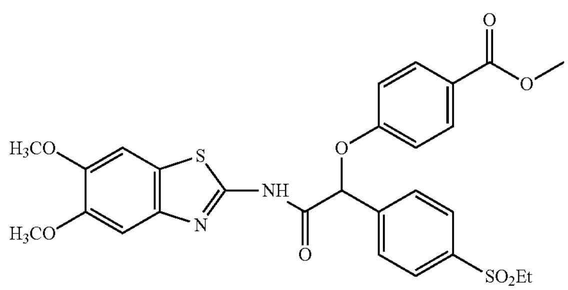 | 4-[(5,6-Dimethoxy-benzothiazol-2-ylcarbamoyl)-(4-ethanesulfonyl-phenyl)-methoxy]-benzoic acid methyl ester |
| 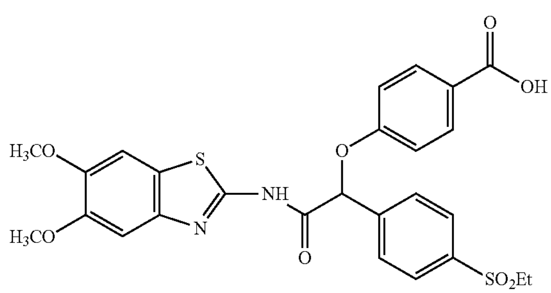 | 4-[(5,6-Dimethoxy-benzothiazol-2-ylcarbamoyl)-(4-ethanesulfonyl-phenyl)-methoxy]-benzoic acid |
| 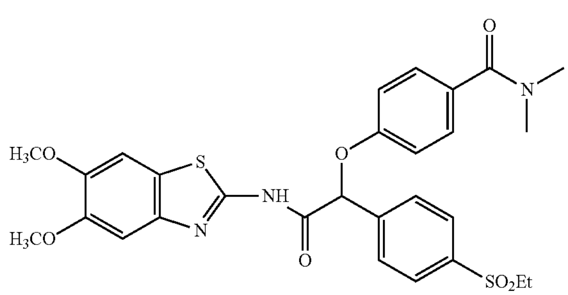 | 4-[(5,6-Dimethoxy-benzothiazol-2-ylcarbamoyl)-(4-ethanesulfonyl-phenyl)-methoxy]-N,N-dimethyl-benzamide |

TABLE 1-continued

| Structure | Name |
|---|---|
| 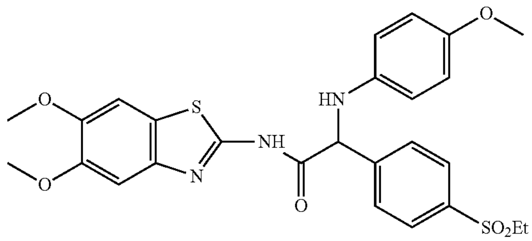 | N-(5,6-Dimethoxy-benzothiazol-2-yl)-2-(4-ethanesulfonyl-phenyl)-2-(4-methoxy-phenylamino)-acetamide |
| 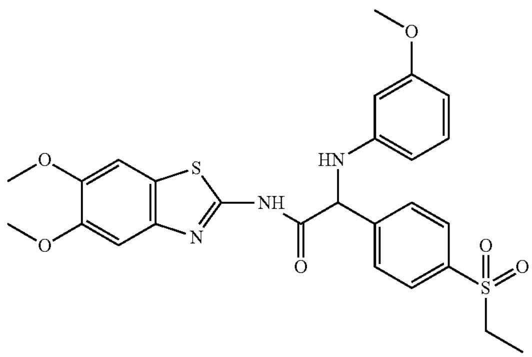 [SMILES: CCS(=O)(=O)c1ccc(C(Nc2cccc(OC)c2)C(=O)Nc2nc3cc(OC)c(OC)cc3s2)cc1] | N-(5,6-Dimethoxy-benzothiazol-2-yl)-2-(4-ethanesulfonyl-phenyl)-2-(3-methoxy-phenylamino)-acetamide |
| 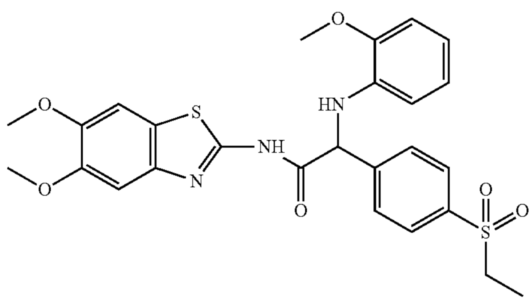 [SMILES: CCS(=O)(=O)c1ccc(C(Nc2ccccc2OC)C(=O)Nc2nc3cc(OC)c(OC)cc3s2)cc1] | N-(5,6-Dimethoxy-benzothiazol-2-yl)-2-(4-ethanesulfonyl-phenyl)-2-(2-methoxy-phenylamino)-acetamide |
| 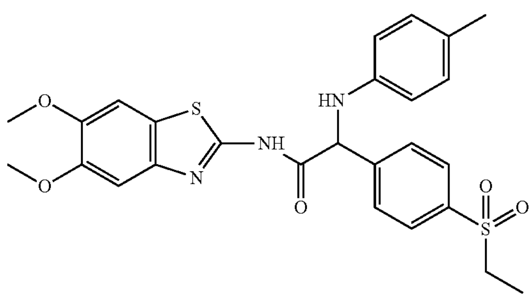 [SMILES: CCS(=O)(=O)c1ccc(C(Nc2ccc(C)cc2)C(=O)Nc2nc3cc(OC)c(OC)cc3s2)cc1] | N-(5,6-Dimethoxy-benzothiazol-2-yl)-2-(4-ethanesulfonyl-phenyl)-2-p-tolylamino-acetamide |
| 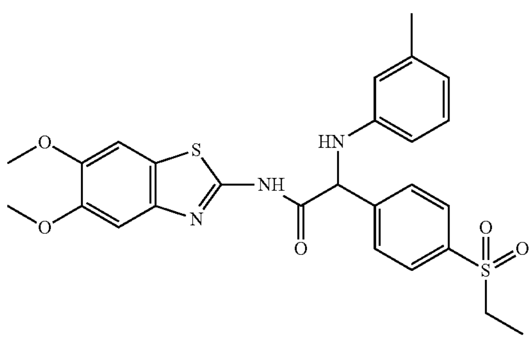 [SMILES: CCS(=O)(=O)c1ccc(C(Nc2cccc(C)c2)C(=O)Nc2nc3cc(OC)c(OC)cc3s2)cc1] | N-(5,6-Dimethoxy-benzothiazol-2-yl)-2-(4-ethanesulfonyl-phenyl)-2-m-tolylamino-acetamide |

TABLE 1-continued

| Structure | Name |
|---|---|
| 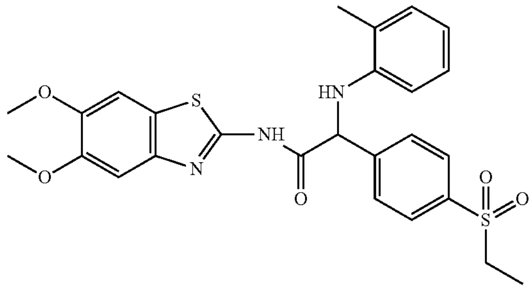 [SMILES: CCS(=O)(=O)c1ccc(C(Nc2ccccc2C)C(=O)Nc2nc3cc(OC)c(OC)cc3s2)cc1] | N-(5,6-Dimethoxy-benzothiazol-2-yl)-2-(4-ethanesulfonyl-phenyl)-2-o-tolylamino-acetamide |
| 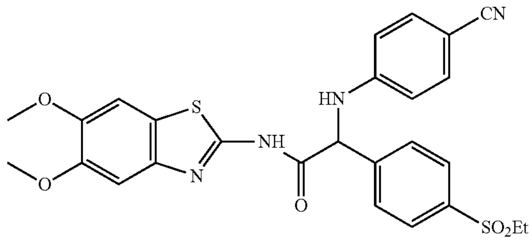 | 2-(4-Cyano-phenylamino)-N-(5,6-dimethoxy-benzothiazol-2-yl)-2-(4-ethanesulfonyl-phenyl)-acetamide |
| 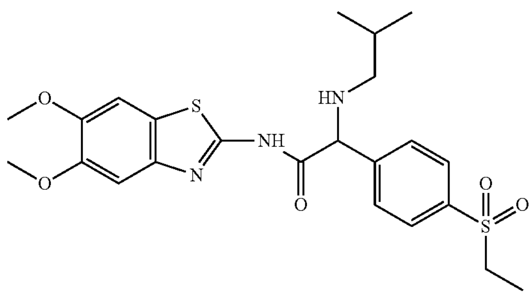 [SMILES: CCS(=O)(=O)c1ccc(C(NCC(C)C)C(=O)Nc2nc3cc(OC)c(OC)cc3s2)cc1] | N-(5,6-Dimethoxy-benzothiazol-2-yl)-2-(4-ethanesulfonyl-phenyl)-2-isobutylamino-acetamide |
| 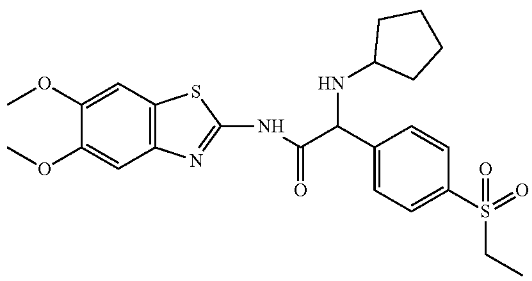 [SMILES: CCS(=O)(=O)c1ccc(C(NC2CCCC2)C(=O)Nc2nc3cc(OC)c(OC)cc3s2)cc1] | 2-Cyclopentylamino-N-(5,6-dimethoxy-benzothiazol-2-yl)-2-(4-ethanesulfonyl-phenyl)-acetamide |
| 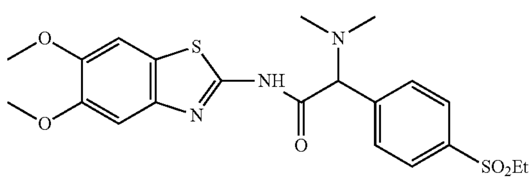 | N-(5,6-Dimethoxy-benzothiazol-2-yl)-2-dimethylamino-2-(4-ethanesulfonyl-phenyl)-acetamide |
| 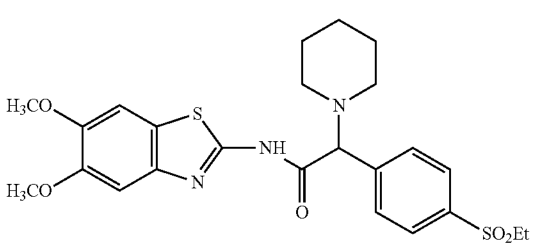 | N-(5,6-Dimethoxy-benzothiazol-2-yl)-2-(4-ethanesulfonyl-phenyl)-2-piperidin-1-yl-acetamide |

| Structure | Name |
|---|---|
| 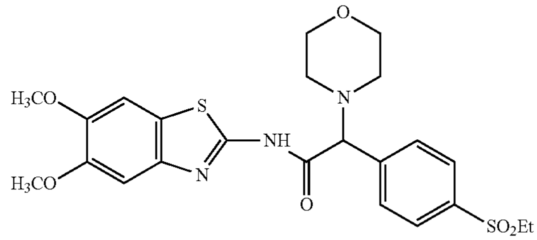 | N-(5,6-Dimethoxy-benzothiazol-2-yl)-2-(4-ethanesulfonyl-phenyl)-2-morpholin-4-yl-acetamide |
| 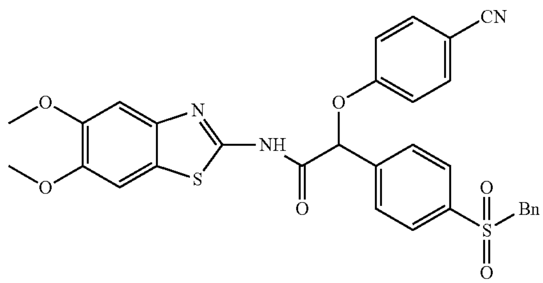 [SMILES: COc1cc2nc(NC(=O)C(Oc3ccc(C#N)cc3)c3ccc(S(=O)(=O)Cc4ccccc4)cc3)sc2cc1OC] | 2-(4-Cyano-phenoxy)-N-(5,6-dimethoxy-benzothiazol-2-yl)-2-(4-phenylmethanesulfonyl-phenyl)-acetamide |
| 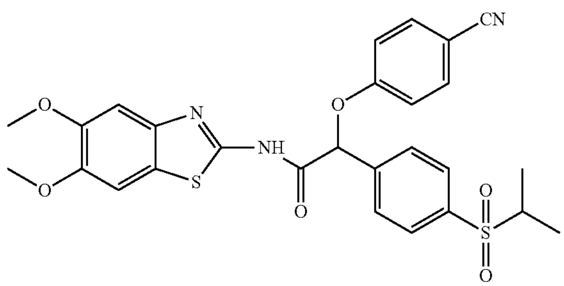 [SMILES: COc1cc2nc(NC(=O)C(Oc3ccc(C#N)cc3)c3ccc(S(=O)(=O)C(C)C)cc3)sc2cc1OC] | 2-(4-Cyano-phenoxy)-N-(5,6-dimethoxy-benzothiazol-2-yl)-2-[4-(propane-2-sulfonyl)-phenyl]-acetamide |
| 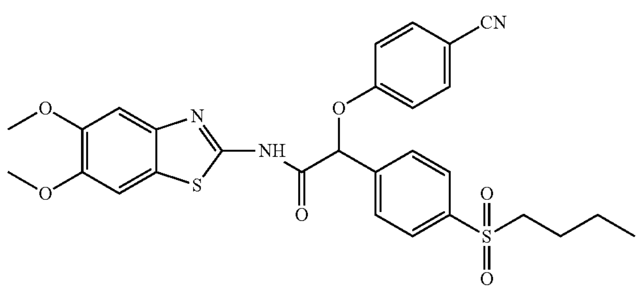 [SMILES: CCCCS(=O)(=O)c1ccc(C(Oc2ccc(C#N)cc2)C(=O)Nc2nc3cc(OC)c(OC)cc3s2)cc1] | 2-[4-(Butane-1-sulfonyl)-phenyl]-2-(4-cyano-phenoxy)-N-(5,6-dimethoxy-benzothiazol-2-yl)-acetamide |
| 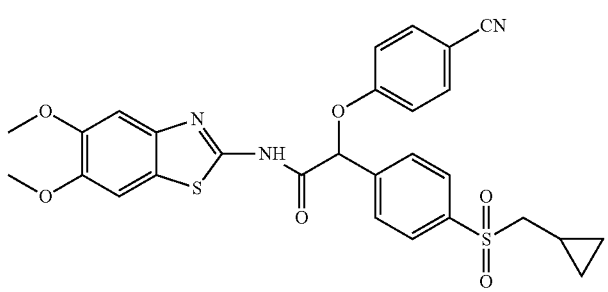 [SMILES: COc1cc2nc(NC(=O)C(Oc3ccc(C#N)cc3)c3ccc(S(=O)(=O)CC4CC4)cc3)sc2cc1OC] | 2-(4-Cyano-phenoxy)-2-(4-cyclopropylmethanesulfonyl-phenyl)-N-(5,6-dimethoxy-benzothiazol-2-yl)-acetamide |

TABLE 1-continued

| Structure | Name |
|---|---|
| 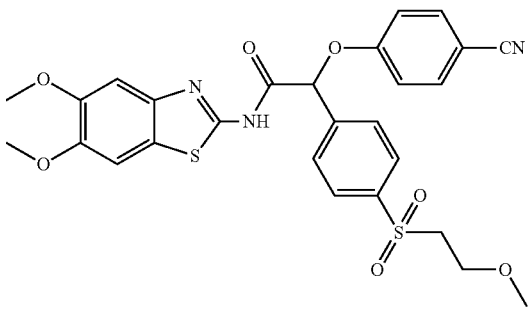 | 2-(4-Cyano-phenoxy)-N-(5,6-dimethoxy-benzothiazol-2-yl)-2-[4-(2-methoxy-ethanesulfonyl)-phenyl]-acetamide |
| 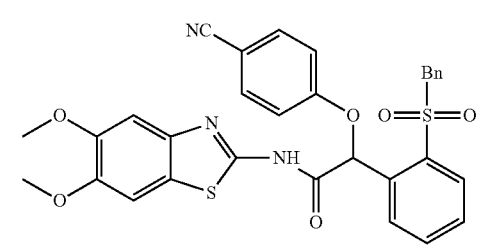 [SMILES: COc1cc2nc(NC(=O)C(Oc3ccc(C#N)cc3)c3ccccc3S(=O)(=O)Cc3ccccc3)sc2cc1OC] | 2-(4-Cyano-phenoxy)-N-(5,6-dimethoxy-benzothiazol-2-yl)-2-(2-phenylmethanesulfonyl-phenyl)-acetamide |
| 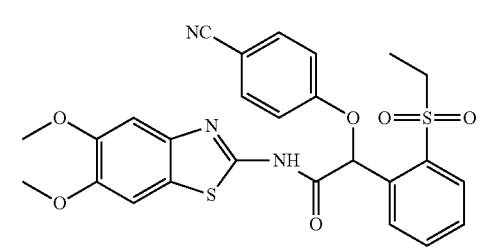 [SMILES: CCS(=O)(=O)c1ccccc1C(Oc1ccc(C#N)cc1)C(=O)Nc1nc2cc(OC)c(OC)cc2s1] | 2-(4-Cyano-phenoxy)-N-(5,6-dimethoxy-benzothiazol-2-yl)-2-(2-ethanesulfonyl-phenyl)-acetamide |
| 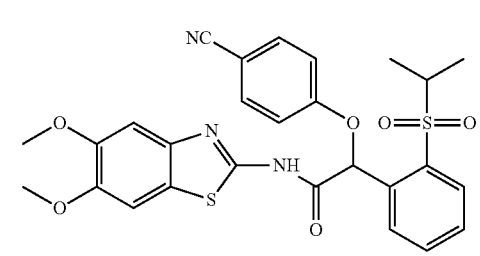 [SMILES: COc1cc2nc(NC(=O)C(Oc3ccc(C#N)cc3)c3ccccc3S(=O)(=O)C(C)C)sc2cc1OC] | 2-(4-Cyano-phenoxy)-N-(5,6-dimethoxy-benzothiazol-2-yl)-2-[2-(propane-2-sulfonyl)-phenyl]-acetamide |
| 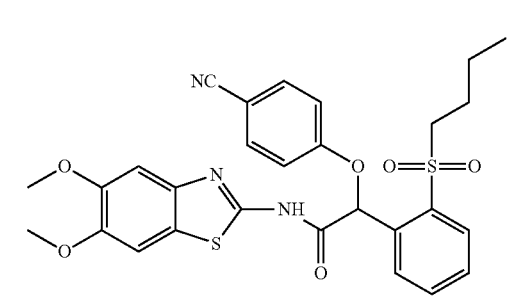 [SMILES: CCCCS(=O)(=O)c1ccccc1C(Oc1ccc(C#N)cc1)C(=O)Nc1nc2cc(OC)c(OC)cc2s1] | 2-[2-(Butane-1-sulfonyl)-phenyl]-2-(4-cyano-phenoxy)-N-(5,6-dimethoxy-benzothiazol-2-yl)-acetamide |
| 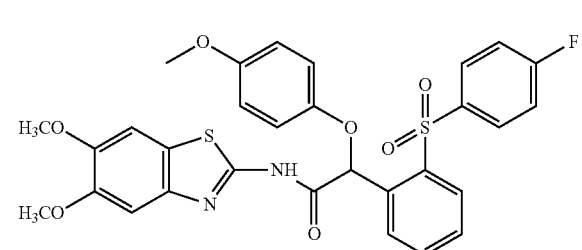 | N-(5,6-Dimethoxy-benzothiazol-2-yl)-2-[2-(4-fluoro-benzenesulfonyl)-phenyl]-2-(4-methoxy-phenoxy)-acetamide |

TABLE 1-continued

| Structure | Name |
|---|---|
| 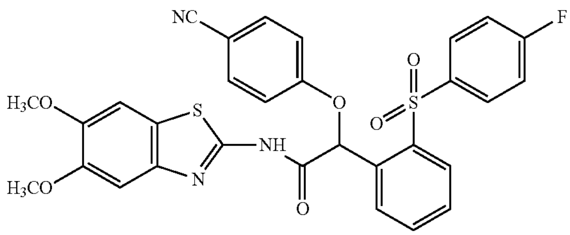 [SMILES: COc1cc2nc(NC(=O)C(Oc3ccc(C#N)cc3)c3ccccc3S(=O)(=O)c3ccc(F)cc3)sc2cc1OC] | 2-(4-Cyano-phenoxy)-N-(5,6-dimethoxy-benzothiazol-2-yl)-2-[2-(4-fluoro-benzenesulfonyl)-phenyl]-acetamide |
| 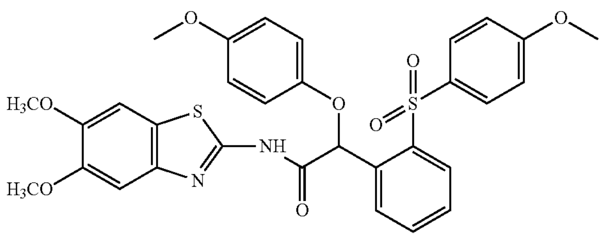 [SMILES: COc1ccc(OC(C(=O)Nc2nc3cc(OC)c(OC)cc3s2)c2ccccc2S(=O)(=O)c2ccc(OC)cc2)cc1] | N-(5,6-Dimethoxy-benzothiazol-2-yl)-2-[2-(4-methoxy-benzenesulfonyl)-phenyl]-2-(4-methoxy-phenoxy)-acetamide |
| 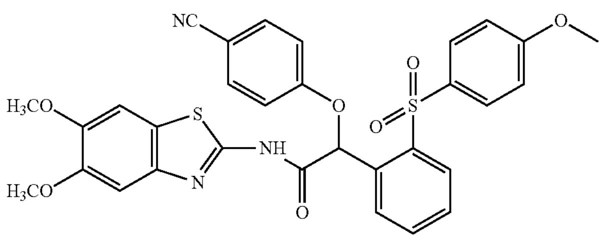 [SMILES: COc1ccc(S(=O)(=O)c2ccccc2C(Oc2ccc(C#N)cc2)C(=O)Nc2nc3cc(OC)c(OC)cc3s2)cc1] | 2-(4-Cyano-phenoxy)-N-(5,6-dimethoxy-benzothiazol-2-yl)-2-[2-(4-methoxy benzenesulfonyl)-phenyl]-acetamide |
| 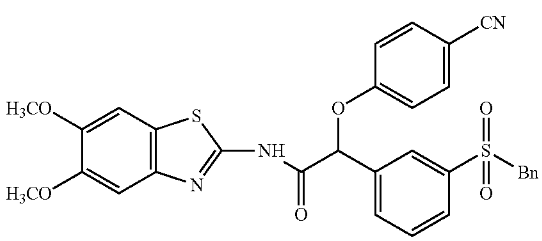 [SMILES: COc1cc2nc(NC(=O)C(Oc3ccc(C#N)cc3)c3cccc(S(=O)(=O)Cc4ccccc4)c3)sc2cc1OC] | 2-(4-Cyano-phenoxy)-N-(5,6-dimethoxy-benzothiazol-2-yl)-2-(3-phenylmethanesulfonyl-phenyl)-acetamide |
| 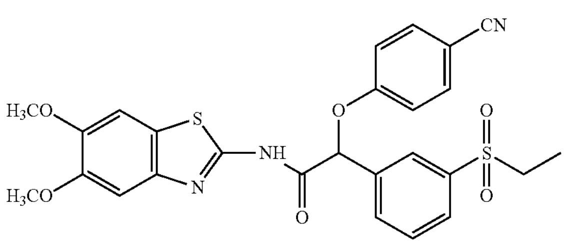 [SMILES: CCS(=O)(=O)c1cccc(C(Oc2ccc(C#N)cc2)C(=O)Nc2nc3cc(OC)c(OC)cc3s2)c1] | 2-(4-Cyano-phenoxy)-N-(5,6-dimethoxy-benzothiazol-2-yl)-2-(3-ethanesulfonyl-phenyl)-acetamide |
| 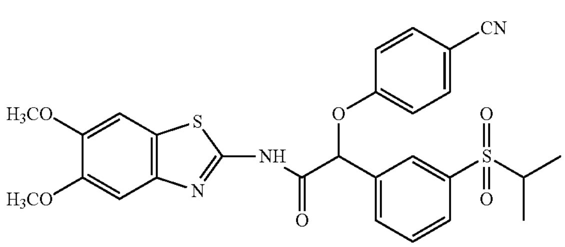 [SMILES: COc1cc2nc(NC(=O)C(Oc3ccc(C#N)cc3)c3cccc(S(=O)(=O)C(C)C)c3)sc2cc1OC] | 2-(4-Cyano-phenoxy)-N-(5,6-dimethoxy-benzothiazol-2-yl)-2-[3-(propane-2-sulfonyl)-phenyl]-acetamide |

TABLE 1-continued

| Structure | Name |
|---|---|
| 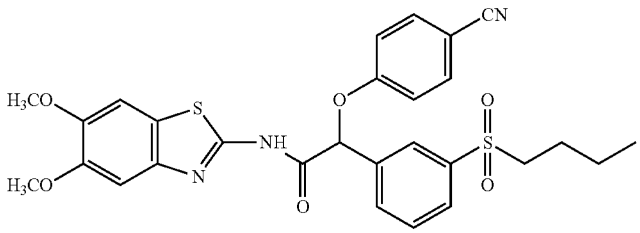 [SMILES: CCCCS(=O)(=O)c1cccc(C(Oc2ccc(C#N)cc2)C(=O)Nc2nc3cc(OC)c(OC)cc3s2)c1] | 2-[3-(Butane-1-sulfonyl)-phenyl]-2-(4-cyano-phenoxy)-N-(5,6-dimethoxy-benzothiazol-2-yl)-acetamide |
| 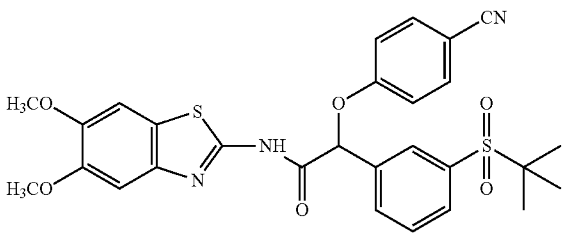 [SMILES: COc1cc2nc(NC(=O)C(Oc3ccc(C#N)cc3)c3cccc(S(=O)(=O)C(C)(C)C)c3)sc2cc1OC] | 2-(4-Cyano-phenoxy)-N-(5,6-dimethoxy-benzothiazol-2-yl)-2-[3-(2-methyl-propane-2-sulfonyl)-phenyl]-acetamide |
| 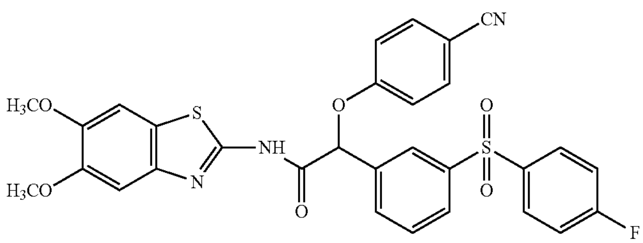 [SMILES: COc1cc2nc(NC(=O)C(Oc3ccc(C#N)cc3)c3cccc(S(=O)(=O)c4ccc(F)cc4)c3)sc2cc1OC] | 2-(4-Cyano-phenoxy)-N-(5,6-dimethoxy-benzothiazol-2-yl)-2-[3-(4-fluoro-benzenesulfonyl)-phenyl]-acetamide |
| 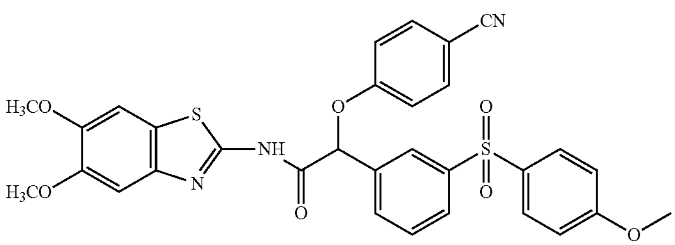 [SMILES: COc1ccc(S(=O)(=O)c2cccc(C(Oc3ccc(C#N)cc3)C(=O)Nc3nc4cc(OC)c(OC)cc4s3)c2)cc1] | 2-(4-Cyano-phenoxy)-N-(5,6-dimethoxy-benzothiazol-2-yl)-2-[3-(4-methoxy-benzenesulfonyl)-phenyl]-acetamide |
| 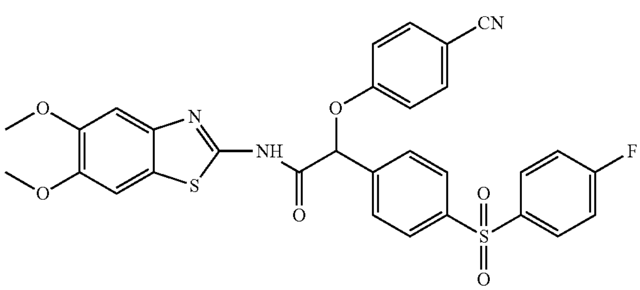 [SMILES: COc1cc2nc(NC(=O)C(Oc3ccc(C#N)cc3)c3ccc(S(=O)(=O)c4ccc(F)cc4)cc3)sc2cc1OC] | 2-(4-Cyano-phenoxy)-N-(5,6-dimethoxy-benzothiazol-2-yl)-2-[4-(4-fluoro-benzenesulfonyl)-phenyl]-acetamide |
| 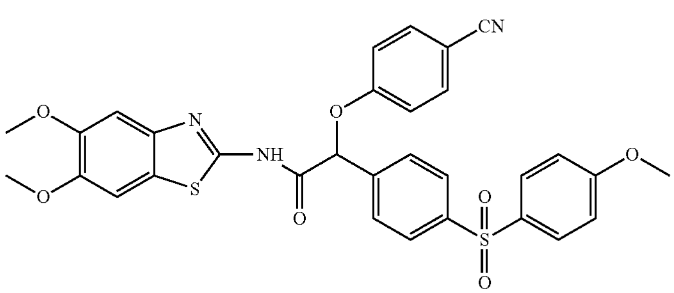 | 2-(4-Cyano-phenoxy)-N-(5,6-dimethoxy-benzothiazol-2-yl)-2-[4-(4-methoxy-benzenesulfonyl)-phenyl]-acetamide |

TABLE 1-continued

| Structure | Name |
|---|---|
| 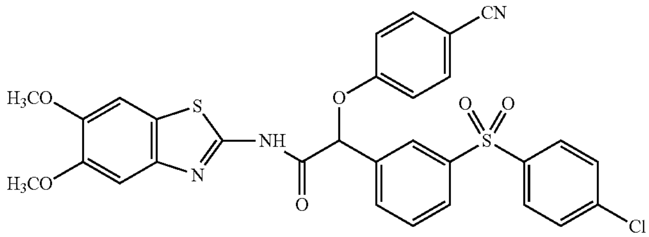 [SMILES: COc1cc2nc(NC(=O)C(Oc3ccc(C#N)cc3)c3cccc(S(=O)(=O)c4ccc(Cl)cc4)c3)sc2cc1OC] | 2-[3-(4-Chloro-benzenesulfonyl)-phenyl]-2-(4-cyano-phenoxy)-N-(5,6-dimethoxy-benzothiazol-2-yl)-acetamide |
| 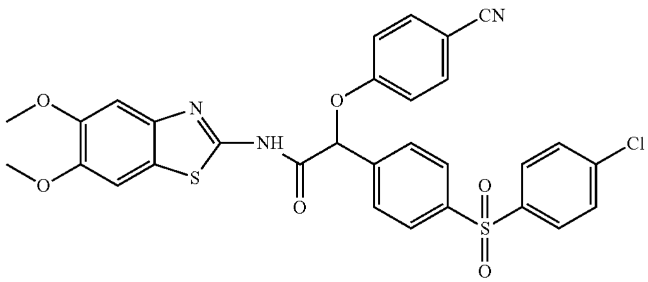 [SMILES: COc1cc2nc(NC(=O)C(Oc3ccc(C#N)cc3)c3ccc(S(=O)(=O)c4ccc(Cl)cc4)cc3)sc2cc1OC] | 2-[4-(4-Chloro-benzenesulfonyl)-phenyl]-2-(4-cyano-phenoxy)-N-(5,6-dimethoxy-benzothiazol-2-yl)-acetamide |
| 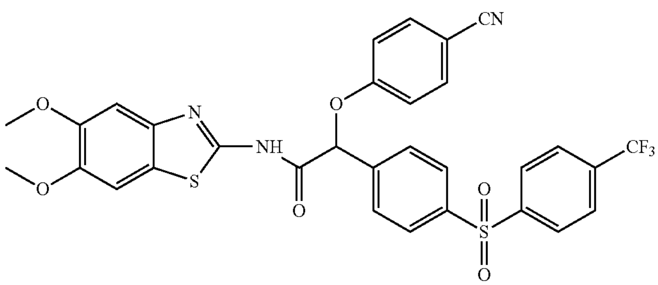 [SMILES: COc1cc2nc(NC(=O)C(Oc3ccc(C#N)cc3)c3ccc(S(=O)(=O)c4ccc(C(F)(F)F)cc4)cc3)sc2cc1OC] | 2-(4-Cyano-phenoxy)-N-(5,6-dimethoxy-benzothiazol-2-yl)-2-[4-(4-trifluoromethyl-benzenesulfonyl)-phenyl]-acetamide |
| 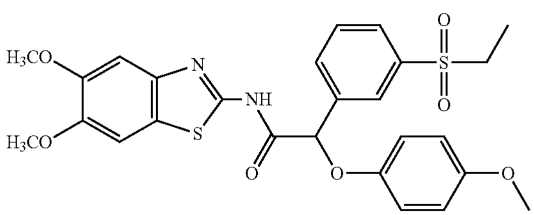 [SMILES: CCS(=O)(=O)c1cccc(C(Oc2ccc(OC)cc2)C(=O)Nc2nc3cc(OC)c(OC)cc3s2)c1] | N-(5,6-Dimethoxy-benzothiazol-2-yl)-2-(3-ethanesulfonyl-phenyl)-2-(4-methoxy-phenoxy)-acetamide |
| 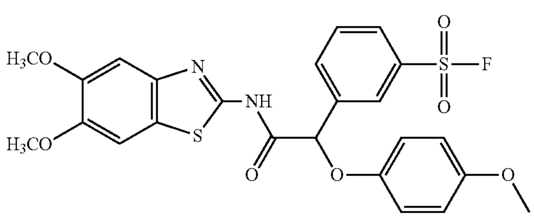 [SMILES: COc1ccc(OC(C(=O)Nc2nc3cc(OC)c(OC)cc3s2)c2cccc(S(=O)(=O)F)c2)cc1] | N-(5,6-Dimethoxy-benzothiazol-2-yl)-2-[3-(4-fluoro-benzenesulfonyl)-phenyl]-2-(4-methoxy-phenoxy)-acetamide |
| 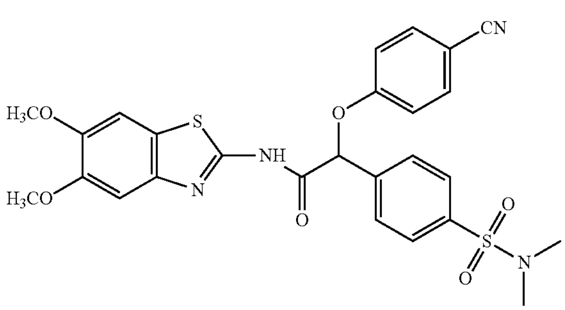 [SMILES: COc1cc2nc(NC(=O)C(Oc3ccc(C#N)cc3)c3ccc(S(=O)(=O)N(C)C)cc3)sc2cc1OC] | 2-(4-Cyano-phenoxy)-N-(5,6-dimethoxy-benzothiazol-2-yl)-2-(4-dimethylsulfamoyl-phenyl)-acetamide |

TABLE 1-continued

| Structure | Name |
|---|---|
| 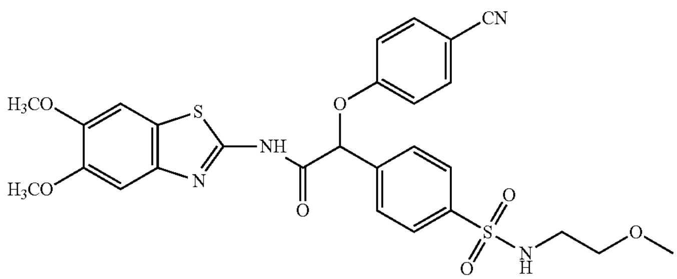 [SMILES: COCCNS(=O)(=O)c1ccc(C(Oc2ccc(C#N)cc2)C(=O)Nc2nc3cc(OC)c(OC)cc3s2)cc1] | 2-(4-Cyano-phenoxy)-N-(5,6-dimethoxy-benzothiazol-2-yl)-2-[4-(2-methoxy-ethylsulfamoyl)-phenyl]-acetamide |
| 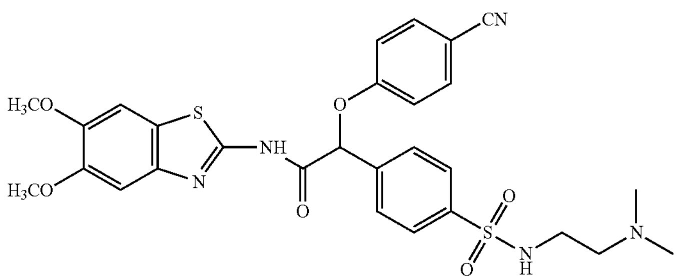 [SMILES: COc1cc2nc(NC(=O)C(Oc3ccc(C#N)cc3)c3ccc(S(=O)(=O)NCCN(C)C)cc3)sc2cc1OC] | 2-(4-Cyano-phenoxy)-N-(5,6-dimethoxy-benzothiazol-2-yl)-2-[4-(2-dimethylamino-ethylsulfamoyl)-phenyl]-acetamide |
| 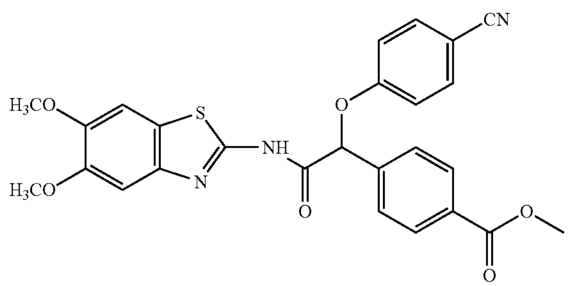 [SMILES: COC(=O)c1ccc(C(Oc2ccc(C#N)cc2)C(=O)Nc2nc3cc(OC)c(OC)cc3s2)cc1] | 4-[(4-Cyano-phenoxy)-(5,6-dimethoxy-benzothiazol-2-ylcarbamoyl)-methyl]-benzoic acid methyl ester |
| 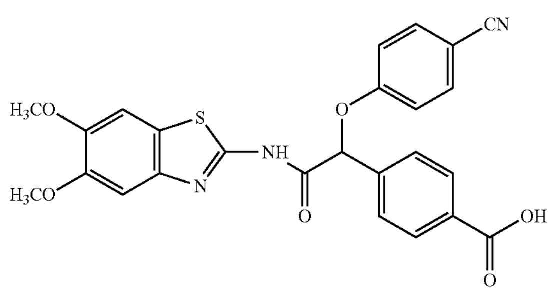 [SMILES: COc1cc2nc(NC(=O)C(Oc3ccc(C#N)cc3)c3ccc(C(=O)O)cc3)sc2cc1OC] | 4-[(4-Cyano-phenoxy)-(5,6-dimethoxy-benzothiazol-2-ylcarbamoyl)-methyl]-benzoic acid |
| 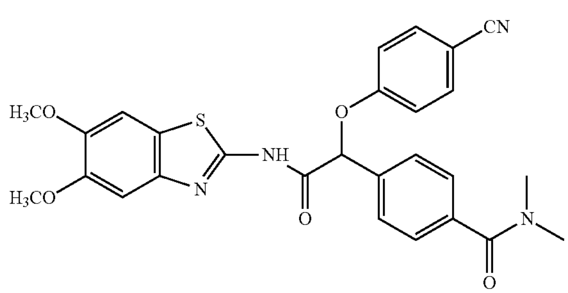 [SMILES: COc1cc2nc(NC(=O)C(Oc3ccc(C#N)cc3)c3ccc(C(=O)N(C)C)cc3)sc2cc1OC] | 4-[(4-Cyano-phenoxy)-(5,6-dimethoxy-benzothiazol-2-ylcarbamoyl)-methyl]-N,N-dimethyl-benzamide |

TABLE 1-continued

| Structure | Name |
|---|---|
| 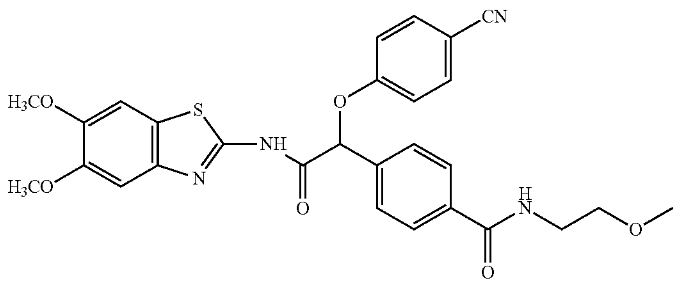 | 4-[(4-Cyano-phenoxy)-(5,6-dimethoxy-benzothiazol-2-ylcarbamoyl)-methyl]-N-(2-methoxy-ethyl)-benzamide |
| 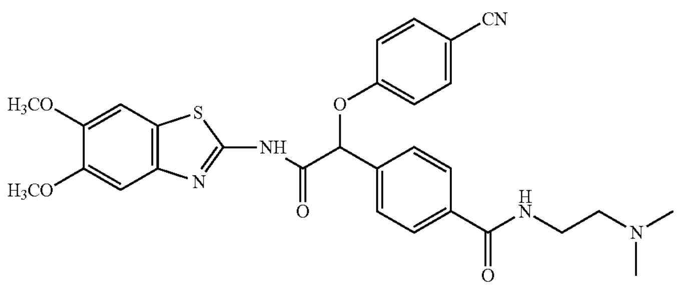 [SMILES: COCCNC(=O)c1ccc(C(Oc2ccc(C#N)cc2)C(=O)Nc2nc3cc(OC)c(OC)cc3s2)cc1] | 4-[(4-Cyano-phenoxy)-(5,6-dimethoxy-benzothiazol-2-ylcarbamoyl)-methyl]-N-(2-dimethylamino-ethyl)-benzamide |
| 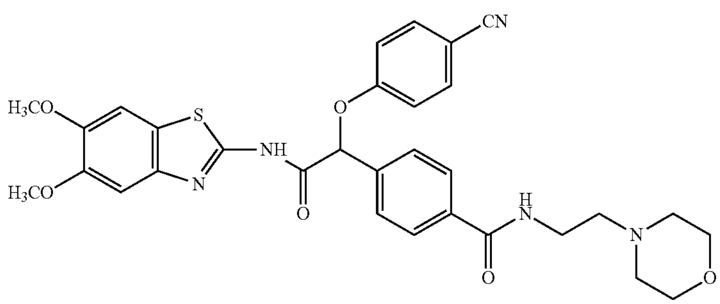 [SMILES: COc1cc2nc(NC(=O)C(Oc3ccc(C#N)cc3)c3ccc(C(=O)NCCN4CCOCC4)cc3)sc2cc1OC] | 4-[(4-Cyano-phenoxy)-(5,6-dimethoxy-benzothiazol-2-ylcarbamoyl)-methyl]-N-(2-morpholin-4-yl-ethyl)-benzamide |
| 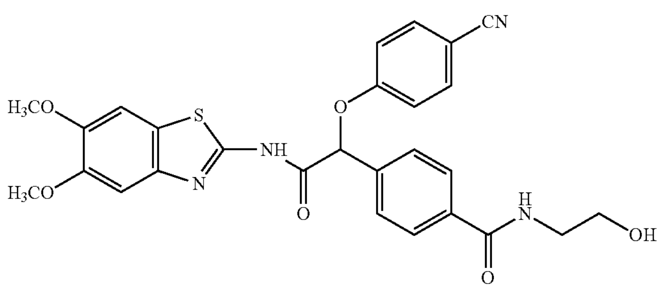 [SMILES: COc1cc2nc(NC(=O)C(Oc3ccc(C#N)cc3)c3ccc(C(=O)NCCO)cc3)sc2cc1OC] | 4-[(4-Cyano-phenoxy)-(5,6-dimethoxy-benzothiazol-2-ylcarbamoyl)-methyl]-N-(2-hydroxy-ethyl)-benzamide |
| 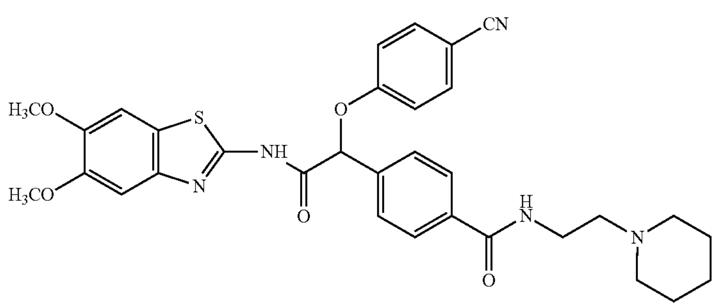 | 4-[(4-Cyano-phenoxy)-(5,6-dimethoxy-benzothiazol-2-ylcarbamoyl)-methyl]-N-(2-piperidin-1-yl-ethyl)-benzamide |

TABLE 1-continued

| Structure | Name |
|---|---|
| 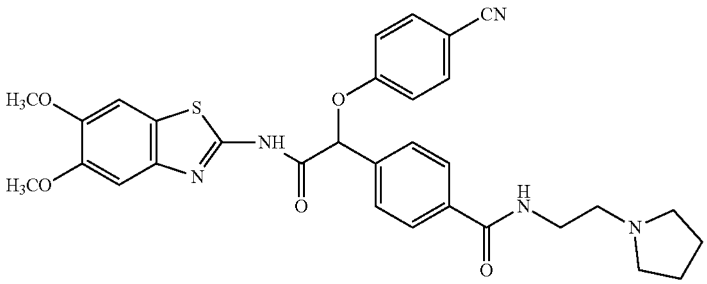 [SMILES: COc1cc2nc(NC(=O)C(Oc3ccc(C#N)cc3)c3ccc(C(=O)NCCN4CCCC4)cc3)sc2cc1OC] | 4-[(4-Cyano-phenoxy)-(5,6-dimethoxy-benzothiazol-2-ylcarbamoyl)-methyl]-N-(2-pyrrolidin-1-yl-ethyl)-benzamide |
| 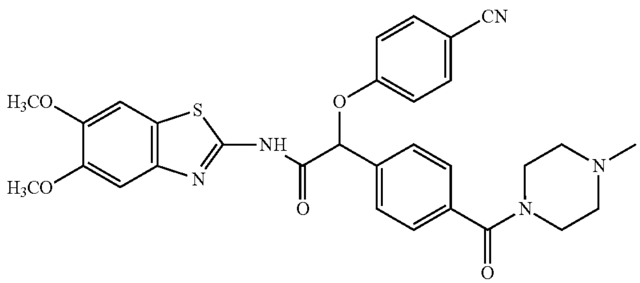 [SMILES: COc1cc2nc(NC(=O)C(Oc3ccc(C#N)cc3)c3ccc(C(=O)N4CCN(C)CC4)cc3)sc2cc1OC] | 2-(4-Cyano-phenoxy)-N-(5,6-dimethoxy-benzothiazol-2-yl)-2-[4-(4-methyl-piperazine-1-carbonyl)-phenyl]-acetamide |
| 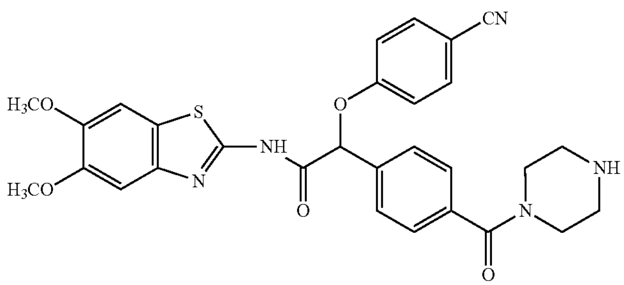 [SMILES: COc1cc2nc(NC(=O)C(Oc3ccc(C#N)cc3)c3ccc(C(=O)N4CCNCC4)cc3)sc2cc1OC] | 2-(4-Cyano-phenoxy)-N-(5,6-dimethoxy-benzothiazol-2-yl)-2-[4-(piperazine-1-carbonyl)-phenyl]-acetamide |
| 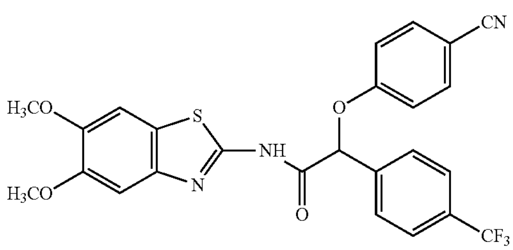 [SMILES: COc1cc2nc(NC(=O)C(Oc3ccc(C#N)cc3)c3ccc(C(F)(F)F)cc3)sc2cc1OC] | 2-(4-Cyano-phenoxy)-N-(5,6-dimethoxy-benzothiazol-2-yl)-2-(4-trifluoromethyl-phenyl)-acetamide |
| 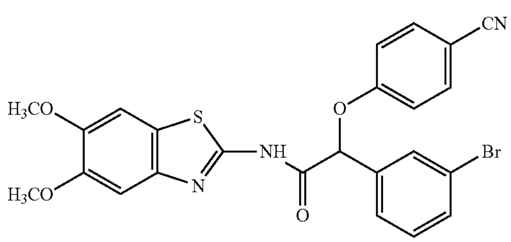 [SMILES: COc1cc2nc(NC(=O)C(Oc3ccc(C#N)cc3)c3cccc(Br)c3)sc2cc1OC] | 2-(3-Bromo-phenyl)-2-(4-cyano-phenoxy)-N-(5,6-dimethoxy-benzothiazol-2-yl)-acetamide |
| 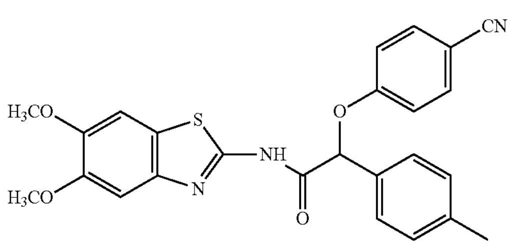 [SMILES: COc1cc2nc(NC(=O)C(Oc3ccc(C#N)cc3)c3ccc(C)cc3)sc2cc1OC] | 2-(4-Cyano-phenoxy)-N-(5,6-dimethoxy-benzothiazol-2-yl)-2-p-tolyl-acetamide |

TABLE 1-continued

| Structure | Name |
|---|---|
| 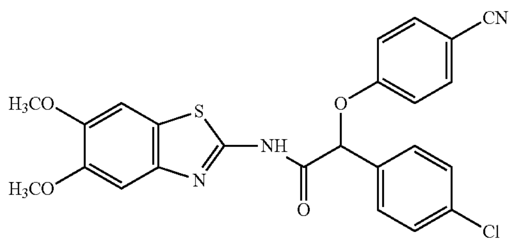 [SMILES: COc1cc2nc(NC(=O)C(Oc3ccc(C#N)cc3)c3ccc(Cl)cc3)sc2cc1OC] | 2-(4-Chloro-phenyl)-2-(4-cyano-phenoxy)-N-(5,6-dimethoxy-benzothiazol-2-yl)-acetamide |
| 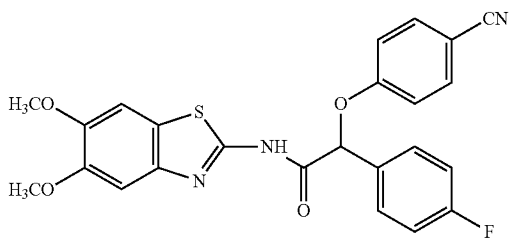 [SMILES: COc1cc2nc(NC(=O)C(Oc3ccc(C#N)cc3)c3ccc(F)cc3)sc2cc1OC] | 2-(4-Cyano-phenoxy)-N-(5,6-dimethoxy-benzothiazol-2-yl)-2-(4-fluoro-phenyl)-acetamide |
| 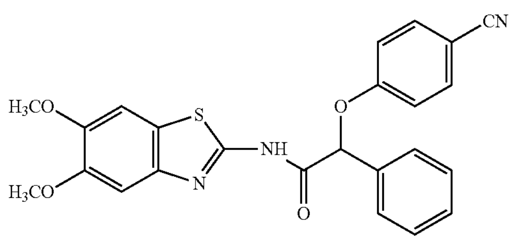 [SMILES: COc1cc2nc(NC(=O)C(Oc3ccc(C#N)cc3)c3ccccc3)sc2cc1OC] | 2-(4-Cyano-phenoxy)-N-(5,6-dimethoxy-benzothiazol-2-yl)-2-phenyl-acetamide |
| 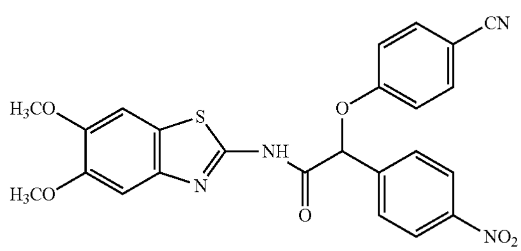 [SMILES: COc1cc2nc(NC(=O)C(Oc3ccc(C#N)cc3)c3ccc([N+](=O)[O-])cc3)sc2cc1OC] | 2-(4-Cyano-phenoxy)-N-(5,6-dimethoxy-benzothiazol-2-yl)-2-(4-nitro-phenyl)-acetamide |
| 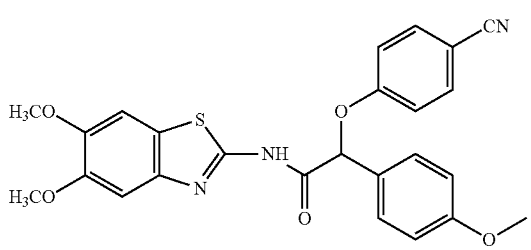 [SMILES: COc1ccc(C(Oc2ccc(C#N)cc2)C(=O)Nc2nc3cc(OC)c(OC)cc3s2)cc1] | 2-(4-Cyano-phenoxy)-N-(5,6-dimethoxy-benzothiazol-2-yl)-2-(4-methoxy-phenyl)-acetamide |
| 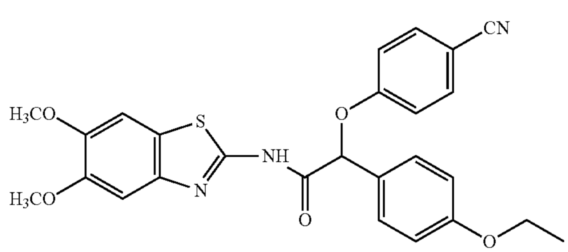 [SMILES: CCOc1ccc(C(Oc2ccc(C#N)cc2)C(=O)Nc2nc3cc(OC)c(OC)cc3s2)cc1] | 2-(4-Cyano-phenoxy)-N-(5,6-dimethoxy-benzothiazol-2-yl)-2-(4-ethoxy-phenyl)-acetamide |

TABLE 1-continued

| Structure | Name |
|---|---|
| 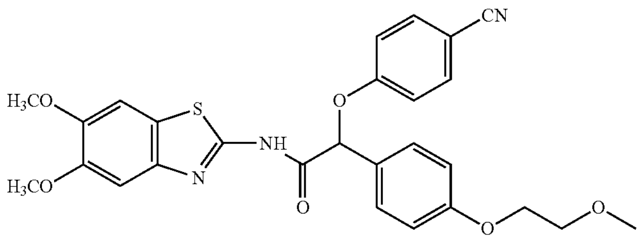 [SMILES: COCCOc1ccc(C(Oc2ccc(C#N)cc2)C(=O)Nc2nc3cc(OC)c(OC)cc3s2)cc1] | 2-(4-Cyano-phenoxy)-N-(5,6-dimethoxy-benzothiazol-2-yl)-2-[4-(2-methoxy-ethoxy)-phenyl]-acetamide |
| 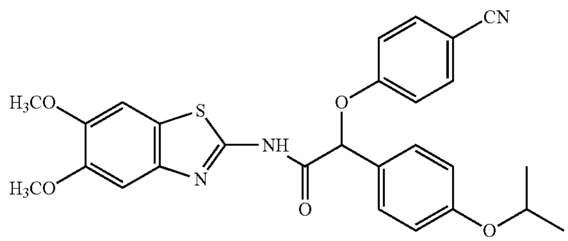 | 2-(4-Cyano-phenoxy)-N-(5,6-dimethoxy-benzothiazol-2-yl)-2-(4-isopropoxy-phenyl)-acetamide |
| 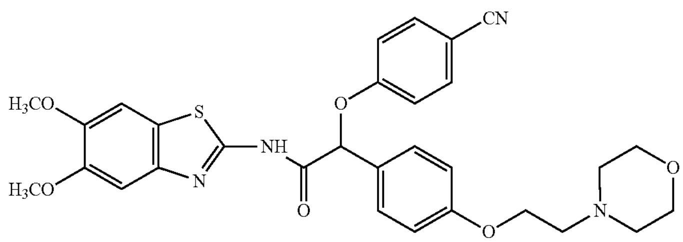 [SMILES: COc1cc2nc(NC(=O)C(Oc3ccc(C#N)cc3)c3ccc(OCCN4CCOCC4)cc3)sc2cc1OC] | 2-(4-cyano-phenoxy)-N-(5,6-dimethoxy-benzothiazol-2-yl)-2-[4-(2-morpholin-4-yl-ethoxy)-phenyl]-acetamide |
| 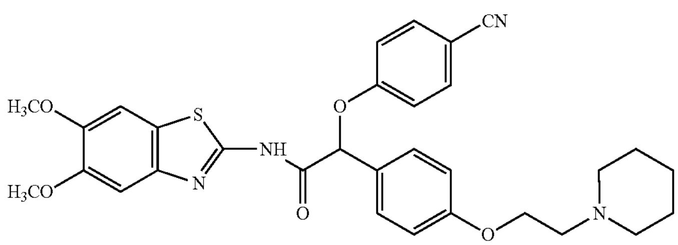 [SMILES: COc1cc2nc(NC(=O)C(Oc3ccc(C#N)cc3)c3ccc(OCCN4CCCCC4)cc3)sc2cc1OC] | 2-(4-cyano-phenoxy)-N-(5,6-dimethoxy-benzothiazol-2-yl)-2-[4-(2-piperidin-1-yl-ethoxy)-phenyl]-acetamide |
| 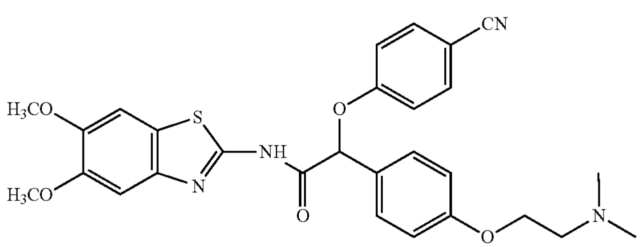 [SMILES: COc1cc2nc(NC(=O)C(Oc3ccc(C#N)cc3)c3ccc(OCCN(C)C)cc3)sc2cc1OC] | 2-(4-Cyano-phenoxy)-N-(5,6-dimethoxy-benzothiazol-2-yl)-2-[4-(2-dimethylamino-ethoxy)-phenyl]-acetamide |
| 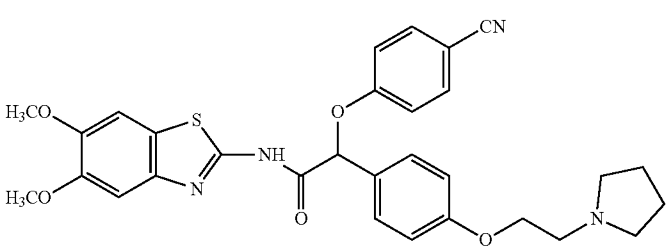 [SMILES: COc1cc2nc(NC(=O)C(Oc3ccc(C#N)cc3)c3ccc(OCCN4CCCC4)cc3)sc2cc1OC] | 2-(4-Cyano-phenoxy)-N-(5,6-dimethoxy-benzothiazol-2-yl)-2-[4-(2-pyrrolidin-1-yl-ethoxy)-phenyl]-acetamide |

TABLE 1-continued

| Structure | Name |
|---|---|
| 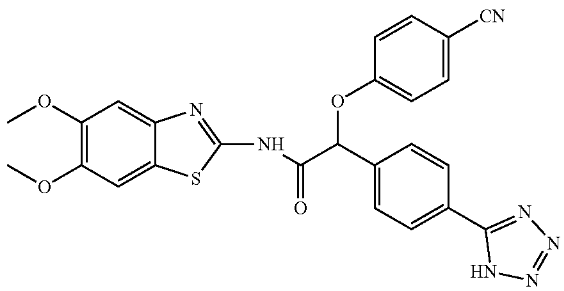 [SMILES: COc1cc2nc(NC(=O)C(Oc3ccc(C#N)cc3)c3ccc(-c4nnn[nH]4)cc3)sc2cc1OC] | 2-(4-Cyano-phenoxy)-N-(5,6-dimethoxy-benzothiazol-2-yl)-2-[4-(1H-tetrazol-5-yl)-phenyl]-acetamide |
| 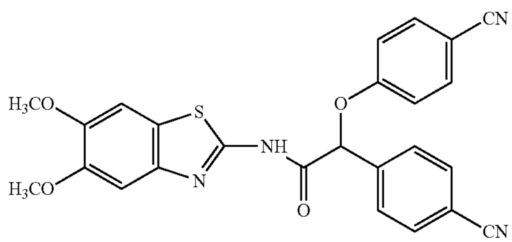 [SMILES: COc1cc2nc(NC(=O)C(Oc3ccc(C#N)cc3)c3ccc(C#N)cc3)sc2cc1OC] | 2-(4-Cyano-phenoxy)-2-(4-cyano-phenyl)-N-(5,6-dimethoxy-benzothiazol-2-yl)-acetamide |
| 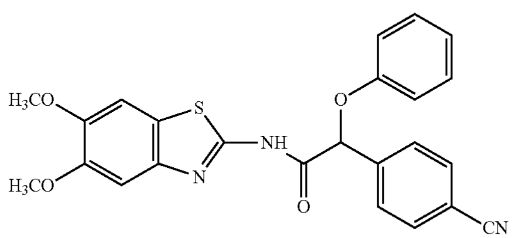 [SMILES: COc1cc2nc(NC(=O)C(Oc3ccccc3)c3ccc(C#N)cc3)sc2cc1OC] | 2-(4-Cyano-phenyl)-N-(5,6-dimethoxy-benzothiazol-2-yl)-2-phenoxy-acetamide |
| 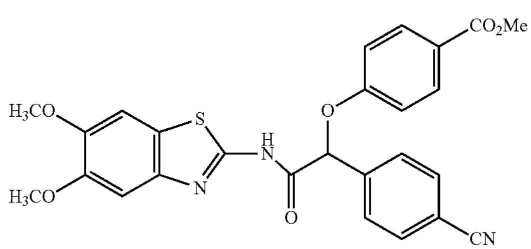 [SMILES: COC(=O)c1ccc(OC(C(=O)Nc2nc3cc(OC)c(OC)cc3s2)c2ccc(C#N)cc2)cc1] | 4-[(4-Cyano-phenyl)-(5,6-dimethoxy-benzothiazol-2-ylcarbamoyl)-methoxy]-benzoic acid methyl ester |
| 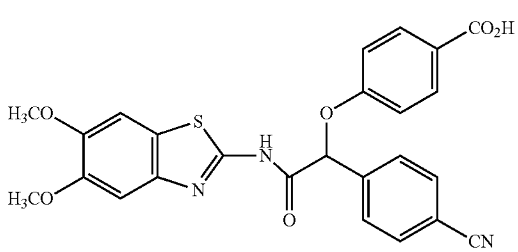 [SMILES: COc1cc2nc(NC(=O)C(Oc3ccc(C(=O)O)cc3)c3ccc(C#N)cc3)sc2cc1OC] | 4-[(4-Cyano-phenyl)-(5,6-dimethoxy-benzothiazol-2-ylcarbamoyl)-methoxy]-benzoic acid |
| 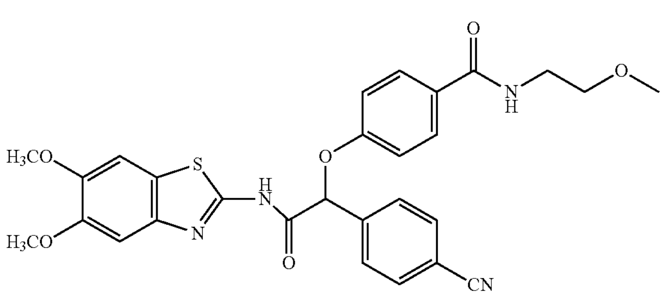 [SMILES: COCCNC(=O)c1ccc(OC(C(=O)Nc2nc3cc(OC)c(OC)cc3s2)c2ccc(C#N)cc2)cc1] | 4-[(4-Cyano-phenyl)-(5,6-dimethoxy-benzothiazol-2-ylcarbamoyl)-methoxy]-N-(2-methoxy-ethyl)-benzamide |

TABLE 1-continued

| Structure | Name |
|---|---|
| 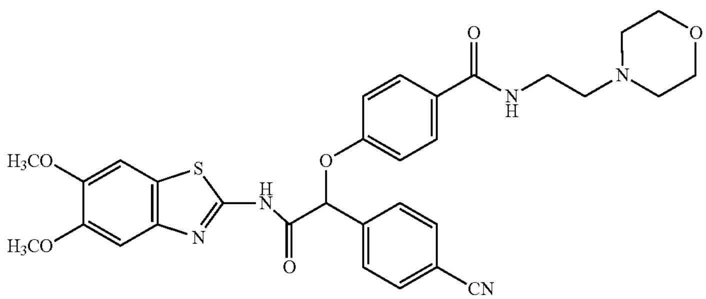 [SMILES: COc1cc2nc(NC(=O)C(Oc3ccc(C(=O)NCCN4CCOCC4)cc3)c3ccc(C#N)cc3)sc2cc1OC] | 4-[(4-Cyano-phenyl)-(5,6-dimethoxy-benzothiazol-2-ylcarbamoyl)-methoxy]-N-(2-morpholin-4-yl-ethyl)-benzamide |
| 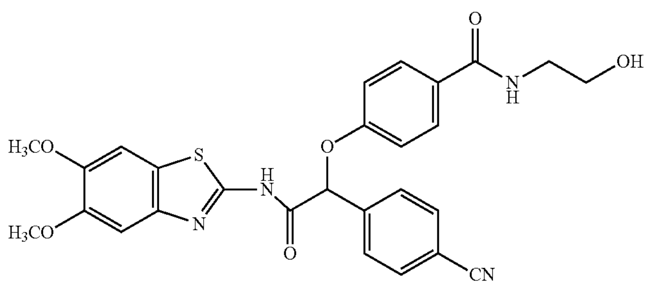 [SMILES: COc1cc2nc(NC(=O)C(Oc3ccc(C(=O)NCCO)cc3)c3ccc(C#N)cc3)sc2cc1OC] | 4-[(4-Cyano-phenyl)-(5,6-dimethoxy-benzothiazol-2-ylcarbamoyl)-methoxy]-N-(2-methoxy-ethyl)-benzamide |
| 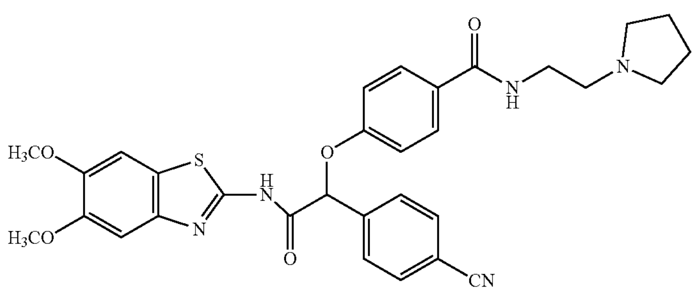 [SMILES: COc1cc2nc(NC(=O)C(Oc3ccc(C(=O)NCCN4CCCC4)cc3)c3ccc(C#N)cc3)sc2cc1OC] | 4-[(4-Cyano-phenyl)-(5,6-dimethoxy-benzothiazol-2-ylcarbamoyl)-methoxy]-N-(2-pyrrolidin-1-yl-ethyl)-benzamide |
|  | 2-(4-Cyano-phenyl)-N-(5,6-dimethoxy-benzothiazol-2-yl)-2-[4-(4-methyl-piperazine-1-carbonyl)-phenoxy]-acetamide |
| 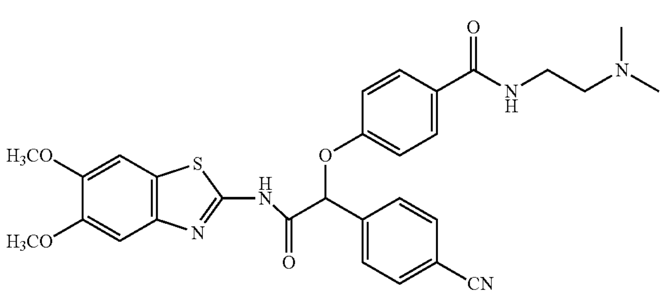 [SMILES: COc1cc2nc(NC(=O)C(Oc3ccc(C(=O)NCCN(C)C)cc3)c3ccc(C#N)cc3)sc2cc1OC] | 4-[(4-Cyano-phenyl)-(5,6-dimethoxy-benzothiazol-2-ylcarbamoyl)-methoxy]-N-(2-dimethylamino-ethyl)-benzamide |

TABLE 1-continued

| Structure | Name |
|---|---|
| 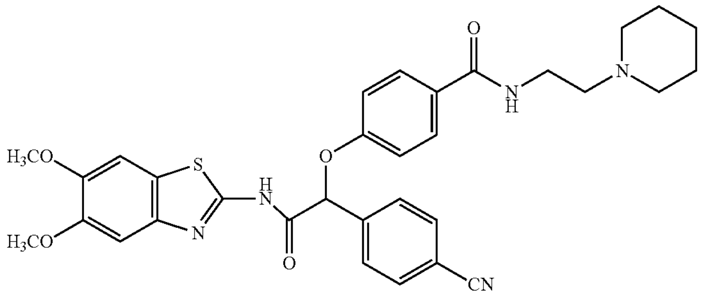 [SMILES: COc1cc2nc(NC(=O)C(Oc3ccc(C(=O)NCCN4CCCCC4)cc3)c3ccc(C#N)cc3)sc2cc1OC] | 4-[(4-Cyano-phenyl)-(5,6-dimethoxy-benzothiazol-2-ylcarbamoyl)-methoxy]-N-(2-piperidin-1-yl-ethyl)-benzamide |
| 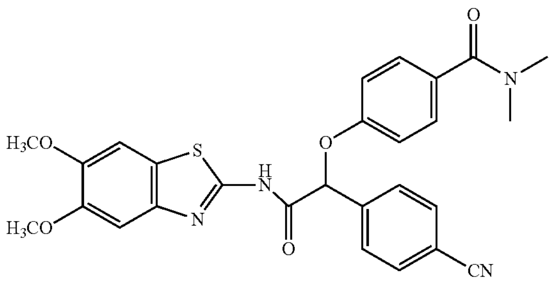 [SMILES: COc1cc2nc(NC(=O)C(Oc3ccc(C(=O)N(C)C)cc3)c3ccc(C#N)cc3)sc2cc1OC] | 4-[(4-Cyano-phenyl)-(5,6-dimethoxy-benzothiazol-2-ylcarbamoyl)-methoxy]-N,N-dimethyl-benzamide |
| 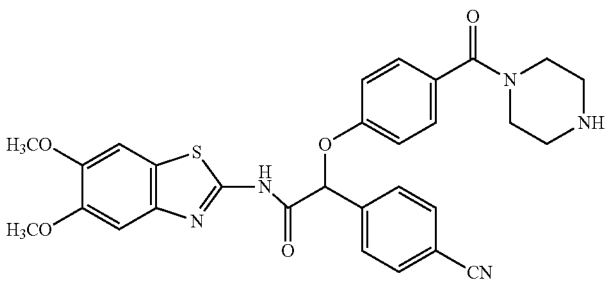 [SMILES: COc1cc2nc(NC(=O)C(Oc3ccc(C(=O)N4CCNCC4)cc3)c3ccc(C#N)cc3)sc2cc1OC] | 2-(4-Cyano-phenyl)-N-(5,6-dimethoxy-benzothiazol-2-yl)-2-[4-(piperazine-1-carbonyl)-phenoxy]-acetamide |
| 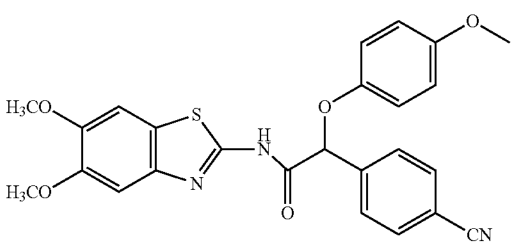 [SMILES: COc1ccc(OC(C(=O)Nc2nc3cc(OC)c(OC)cc3s2)c2ccc(C#N)cc2)cc1] | 2-(4-Cyano-phenyl)-N-(5,6-dimethoxy-benzothiazol-2-yl)-2-(4-methoxy-phenoxy)-acetamide |
| 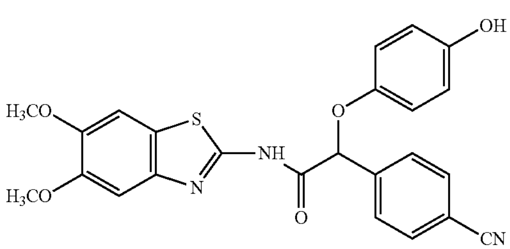 | 2-(4-Cyano-phenyl)-N-(5,6-dimethoxy-benzothiazol-2-yl)-2-(4-hydroxy-phenoxy)-acetamide |
| 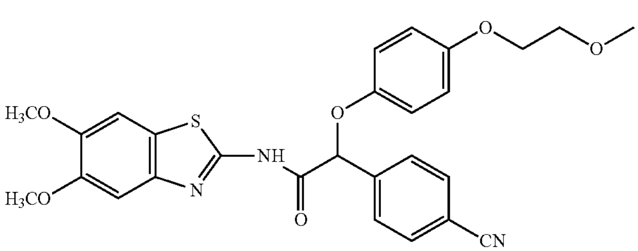 [SMILES: COCCOc1ccc(OC(C(=O)Nc2nc3cc(OC)c(OC)cc3s2)c2ccc(C#N)cc2)cc1] | 2-(4-Cyano-phenyl)-N-(5,6-dimethoxy-benzothiazol-2-yl)-2-[4-(2-methoxy-ethoxy)-phenoxy]-acetamide |

TABLE 1-continued

| Structure | Name |
| --- | --- |
| 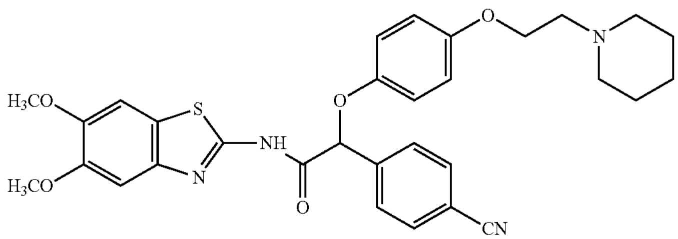 [SMILES: COc1cc2nc(NC(=O)C(Oc3ccc(OCCN4CCCCC4)cc3)c3ccc(C#N)cc3)sc2cc1OC] | 2-(4-Cyano-phenyl)-N-(5,6-dimethoxy-benzothiazol-2-yl)-2-[4-(2-piperidin-1-yl-ethoxy)-phenoxy]-acetamide |
| 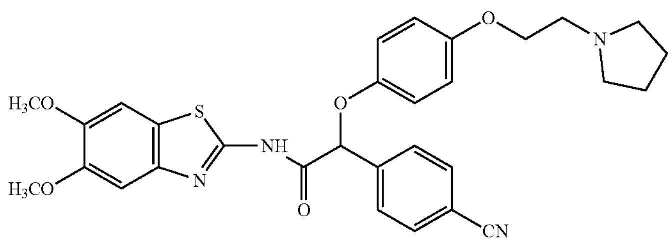 [SMILES: COc1cc2nc(NC(=O)C(Oc3ccc(OCCN4CCCC4)cc3)c3ccc(C#N)cc3)sc2cc1OC] | 2-(4-Cyano-phenyl)-N-(5,6-dimethoxy-benzothiazol-2-yl)-2-[4-(2-pyrrolidin-1-yl-ethoxy)-phenoxy]-acetamide |
| 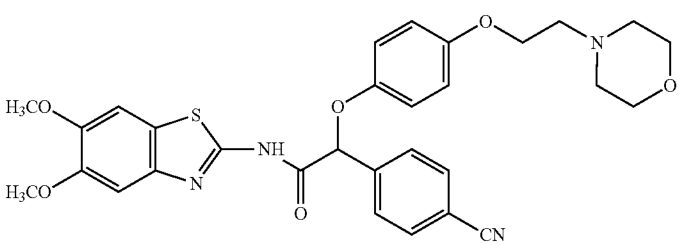 [SMILES: COc1cc2nc(NC(=O)C(Oc3ccc(OCCN4CCOCC4)cc3)c3ccc(C#N)cc3)sc2cc1OC] | 2-(4-Cyano-phenyl)-N-(5,6-dimethoxy-benzothiazol-2-yl)-2-[4-(2-morpholin-4-yl-ethoxy)-phenoxy]-acetamide |
| 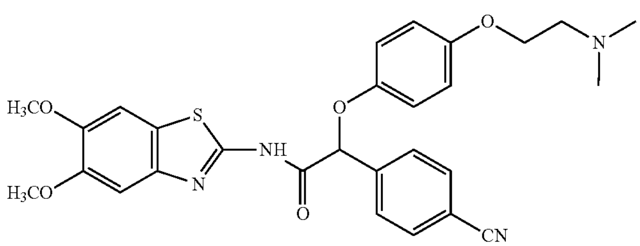 [SMILES: COc1cc2nc(NC(=O)C(Oc3ccc(OCCN(C)C)cc3)c3ccc(C#N)cc3)sc2cc1OC] | 2-(4-Cyano-phenyl)-N-(5,6-dimethoxy-benzothiazol-2-yl)-2-[4-(2-dimethylamino-ethoxy)-phenoxy]-acetamide |
| 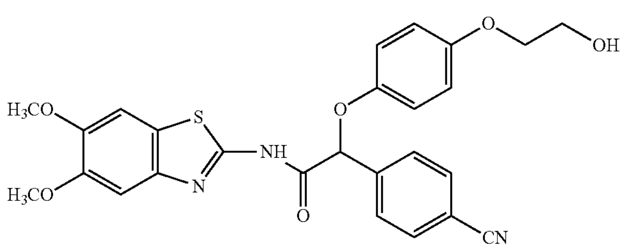 [SMILES: COc1cc2nc(NC(=O)C(Oc3ccc(OCCO)cc3)c3ccc(C#N)cc3)sc2cc1OC] | 2-(4-Cyano-phenyl)-N-(5,6-dimethoxy-benzothiazol-2-yl)-2-[4-(2-hydroxy-ethoxy)-phenoxy]-acetamide |
| 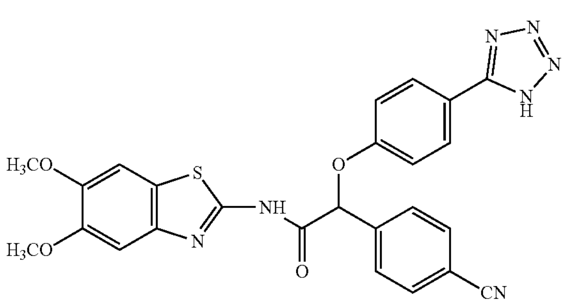 [SMILES: COc1cc2nc(NC(=O)C(Oc3ccc(-c4nnn[nH]4)cc3)c3ccc(C#N)cc3)sc2cc1OC] | 2-(4-Cyano-phenyl)-N-(5,6-dimethoxy-benzothiazol-2-yl)-2-[4-(1H-tetrazol-5-yl)-phenoxy]-acetamide |

TABLE 1-continued

| Structure | Name |
|---|---|
| 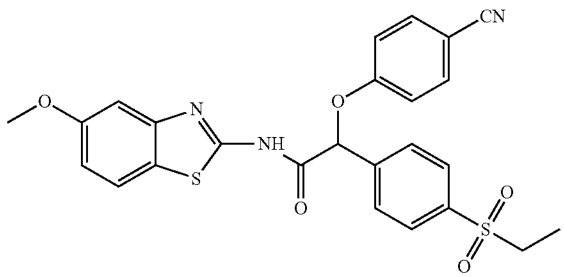 [SMILES: CCS(=O)(=O)c1ccc(C(Oc2ccc(C#N)cc2)C(=O)Nc2nc3cc(OC)ccc3s2)cc1] | 2-(4-Cyano-phenoxy)-2-(4-ethanesulfonyl-phenyl)-N-(5-methoxy-benzothiazol-2-yl)-acetamide |
| 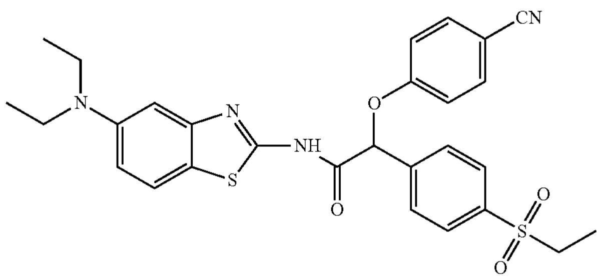 [SMILES: CCN(CC)c1ccc2sc(NC(=O)C(Oc3ccc(C#N)cc3)c3ccc(S(=O)(=O)CC)cc3)nc2c1] | 2-(4-Cyano-phenoxy)-N-(5-diethylamino-benzothiazol-2-yl)-2-(4-ethanesulfonyl-phenyl)-acetamide |
| 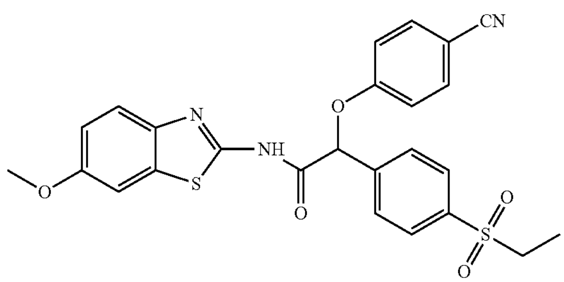 [SMILES: CCS(=O)(=O)c1ccc(C(Oc2ccc(C#N)cc2)C(=O)Nc2nc3ccc(OC)cc3s2)cc1] | 2-(4-Cyano-phenoxy)-2-(4-ethanesulfonyl-phenyl)-N-(6-methoxy-benzothiazol-2-yl)-acetamide |
| 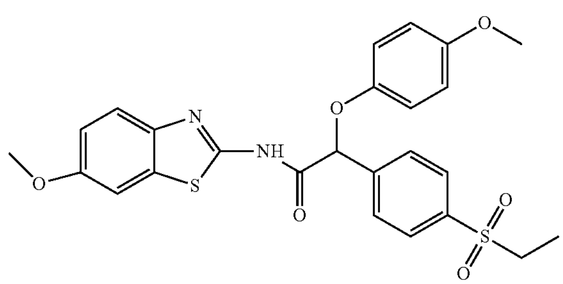 [SMILES: CCS(=O)(=O)c1ccc(C(Oc2ccc(OC)cc2)C(=O)Nc2nc3ccc(OC)cc3s2)cc1] | 2-(4-Ethanesulfonyl-phenyl)-N-(6-methoxy-benzothiazol-2-yl)-2-(4-methoxy-phenoxy)-acetamide |
| 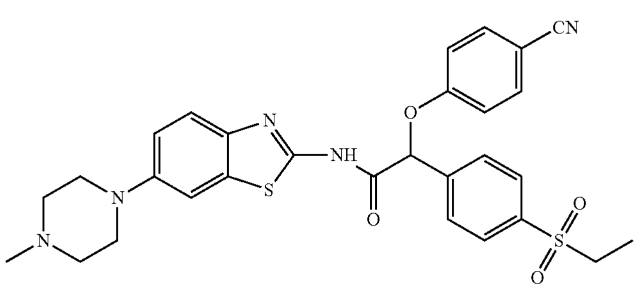 [SMILES: CCS(=O)(=O)c1ccc(C(Oc2ccc(C#N)cc2)C(=O)Nc2nc3ccc(N4CCN(C)CC4)cc3s2)cc1] | 2-(4-Cyano-phenoxy)-2-(4-ethanesulfonyl-phenyl)-N-[6-(4-methyl-piperazin-1-yl)-benzothiazol-2-yl]-acetamide |

TABLE 1-continued

| Structure | Name |
|---|---|
| 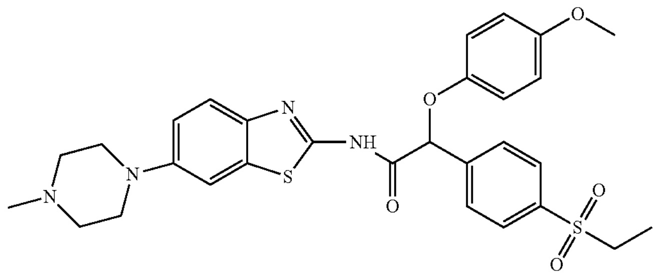 [SMILES: CCS(=O)(=O)c1ccc(C(Oc2ccc(OC)cc2)C(=O)Nc2nc3ccc(N4CCN(C)CC4)cc3s2)cc1] | 2-(4-Ethanesulfonyl-phenyl)-2-(4-methoxy-phenoxy)-N-[6-(4-methyl-piperazin-1-yl)-benzothiazol-2-yl]-acetamide |
| 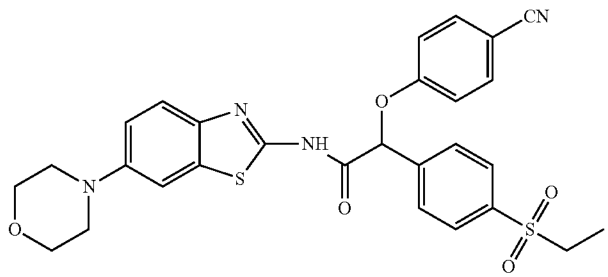 [SMILES: CCS(=O)(=O)c1ccc(C(Oc2ccc(C#N)cc2)C(=O)Nc2nc3ccc(N4CCOCC4)cc3s2)cc1] | 2-(4-Cyano-phenoxy)-2-(4-ethanesulfonyl-phenyl)-N-(6-morpholin-4-yl-benzothiazol-2-yl)-acetamide |
| 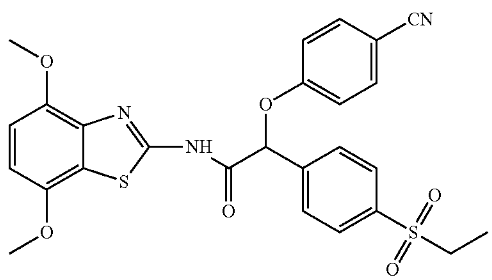 [SMILES: CCS(=O)(=O)c1ccc(C(Oc2ccc(C#N)cc2)C(=O)Nc2nc3c(OC)ccc(OC)c3s2)cc1] | 2-(4-Cyano-phenoxy)-N-(4,7-dimethoxy-benzothiazol-2-yl)-2-(4-ethanesulfonyl-phenyl)-acetamide |
| 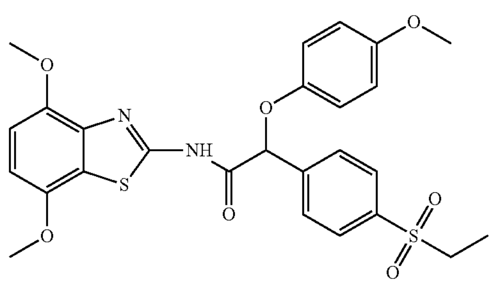 [SMILES: CCS(=O)(=O)c1ccc(C(Oc2ccc(OC)cc2)C(=O)Nc2nc3c(OC)ccc(OC)c3s2)cc1] | N-(4,7-Dimethoxy-benzothiazol-2-yl)-2-(4-ethanesulfonyl-phenyl)-2-(4-methoxy-phenoxy)-acetamide |
| 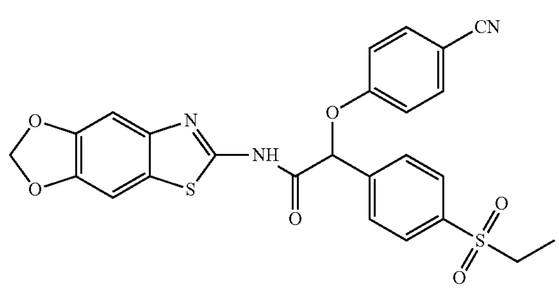 [SMILES: CCS(=O)(=O)c1ccc(C(Oc2ccc(C#N)cc2)C(=O)Nc2nc3cc4c(cc3s2)OCO4)cc1] | 2-(4-Cyano-phenoxy)-N-[1,3]dioxolo[4',5':4,5]benzo[1,2-d]thiazol-6-yl-2-(4-ethanesulfonyl-phenyl)-acetamide |

TABLE 1-continued

| Structure | Name |
|---|---|
| 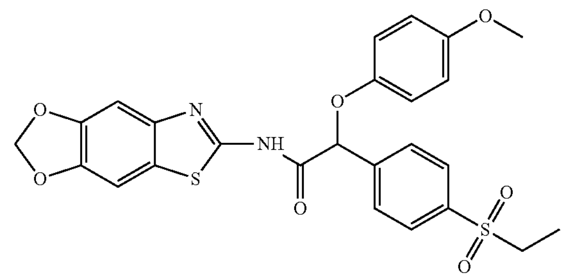 [SMILES: CCS(=O)(=O)c1ccc(C(Oc2ccc(OC)cc2)C(=O)Nc2nc3cc4c(cc3s2)OCO4)cc1] | N-[1,3]Dioxolo[4',5':4,5]benzo[1,2-d]thiazol-6-yl-2-(4-ethanesulfonyl-phenyl)-2-(4-methoxy-phenoxy)-acetamide |
| 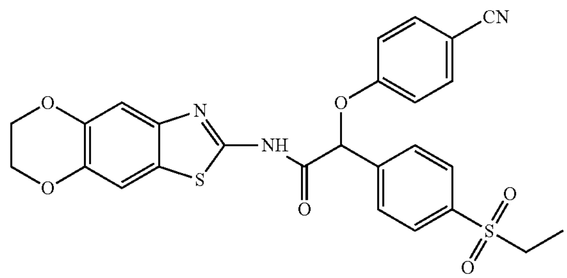 [SMILES: CCS(=O)(=O)c1ccc(C(Oc2ccc(C#N)cc2)C(=O)Nc2nc3cc4c(cc3s2)OCCO4)cc1] | 2-(4-cyano-phenoxy)-N-(6,7-dihydro-5,8-dioxa-1-thia-3-aza-cyclopenta[b]naphthalen-2-yl)-2-(4-ethanesulfonyl-phenyl)-acetamide |
| 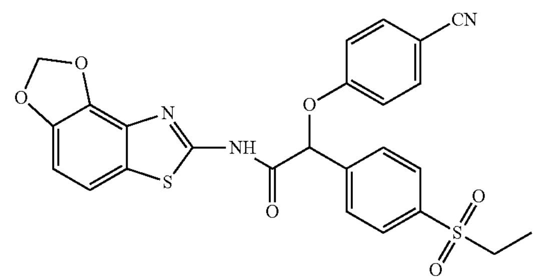 [SMILES: CCS(=O)(=O)c1ccc(C(Oc2ccc(C#N)cc2)C(=O)Nc2nc3c4c(ccc3s2)OCO4)cc1] | 2-(4-Cyano-phenoxy)-N-[1,3]dioxolo[4',5':3,4]benzo[2,1-d]thiazol-7-yl-2-(4-ethanesulfonyl-phenyl)-acetamide |
| 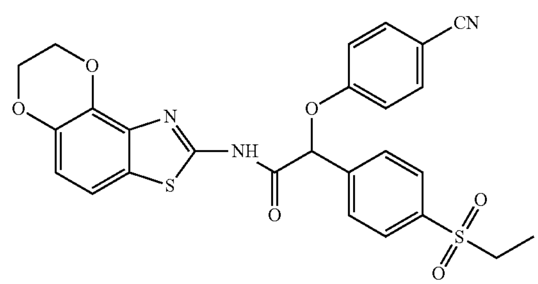 [SMILES: CCS(=O)(=O)c1ccc(C(Oc2ccc(C#N)cc2)C(=O)Nc2nc3c4c(ccc3s2)OCCO4)cc1] | 2-(4-Cyano-phenoxy)-N-(7,8-dihydro-6,9-dioxa-3-thia-1-aza-cyclopenta[a]naphthalen-2-yl)-2-(4-ethanesulfonyl-phenyl)-acetamide |
| 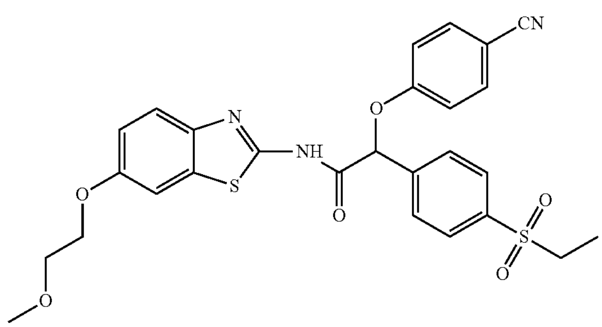 [SMILES: CCS(=O)(=O)c1ccc(C(Oc2ccc(C#N)cc2)C(=O)Nc2nc3ccc(OCCOC)cc3s2)cc1] | 2-(4-Cyano-phenoxy)-2-(4-ethanesulfonyl-phenyl)-N-[6-(2-methoxy-ethoxy)-benzothiazol-2-yl]-acetamide |

TABLE 1-continued

| Structure | Name |
|---|---|
| 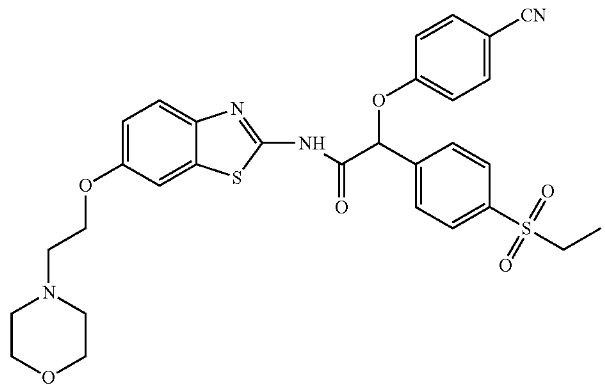 [SMILES: CCS(=O)(=O)c1ccc(C(Oc2ccc(C#N)cc2)C(=O)Nc2nc3ccc(OCCN4CCOCC4)cc3s2)cc1] | 2-(4-Cyano-phenoxy)-2-(4-ethanesulfonyl-phenyl)-N-[6-(2-morpholin-4-yl-ethoxy)-benzothiazol-2-yl]-acetamide |
| 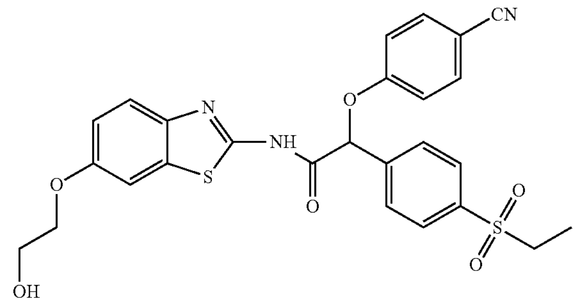 [SMILES: CCS(=O)(=O)c1ccc(C(Oc2ccc(C#N)cc2)C(=O)Nc2nc3ccc(OCCO)cc3s2)cc1] | 2-(4-Cyano-phenoxy)-2-(4-ethanesulfonyl-phenyl)-N-[6-(2-hydroxy-ethoxy)-benzothiazol-2-yl]-acetamide |
| 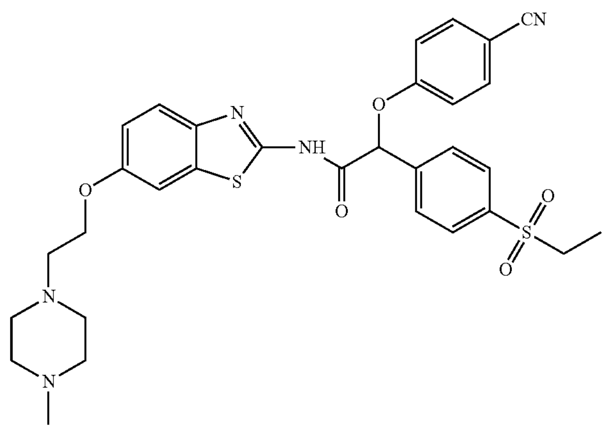 [SMILES: CCS(=O)(=O)c1ccc(C(Oc2ccc(C#N)cc2)C(=O)Nc2nc3ccc(OCCN4CCN(C)CC4)cc3s2)cc1] | 2-(4-Cyano-phenoxy)-2-(4-ethanesulfonyl-phenyl)-N-{6-[2-(4-methyl-piperazin-1-yl)-ethoxy]-benzothiazol-2-yl}-acetamide |
| 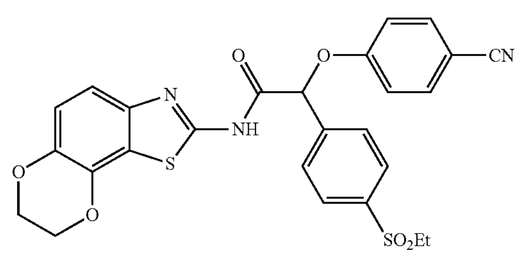 | 2-(4-Cyano-phenoxy)-N-(7,8-dihydro-6,9-dioxa-1-thia-3-aza-cyclopenta[a]naphthalen-2-yl)-2-(4-ethanesulfonyl-phenyl)-acetamide |
| 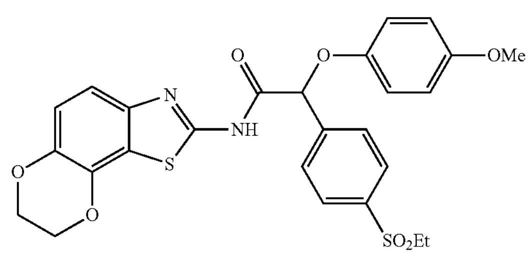 | N-(7,8-Dihydro-6,9-dioxa-1-thia-3-aza-cyclopenta[a]naphthalen-2-yl)-2-(4-ethanesulfonyl-phenyl)-2-(4-methoxy-phenoxy)-acetamide |

TABLE 1-continued

| Structure | Name |
|---|---|
| 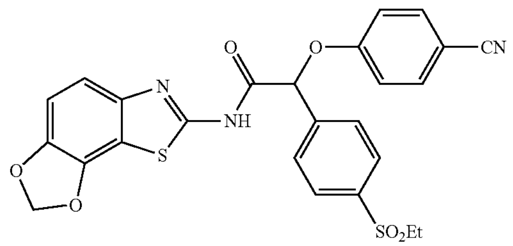 | 2-(4-Cyano-phenoxy)-N-(1,3-dioxa-8-thia-6-aza-as-indacen-7-yl)-2-(4-ethanesulfonyl-phenyl)-acetamide |
| 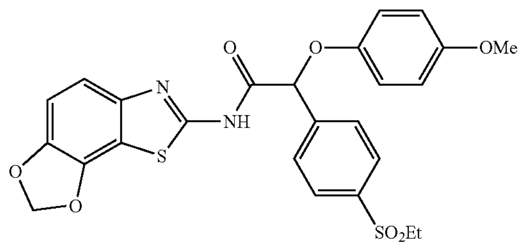 | N-(1,3-Dioxa-8-thia-6-aza-as-indacen-7-yl)-2-(4-ethanesulfonyl-phenyl)-2-(4-methoxy-phenoxy)-acetamide |
| 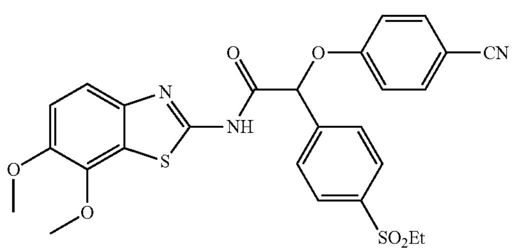 | 2-(4-Cyano-phenoxy)-N-(6,7-dimethoxy-benzothiazol-2-yl)-2-(4-ethanesulfonyl-phenyl)-acetamide |
| 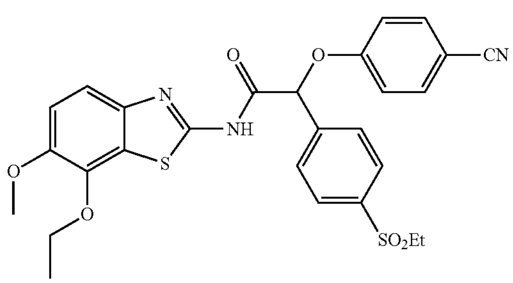 | 2-(4-Cyano-phenoxy)-2-(4-ethanesulfonyl-phenyl)-N-(7-ethoxy-6-methoxy-benzothiazol-2-yl)-acetamide |
| 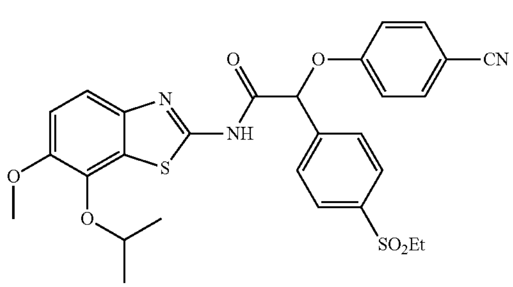 | 2-(4-Cyano-phenoxy)-2-(4-ethanesulfonyl-phenyl)-N-(7-isopropoxy-6-methoxy-benzothiazol-2-yl)-acetamide |
| 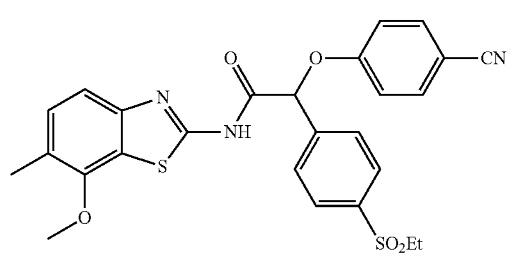 | 2-(4-Cyano-phenoxy)-2-(4-ethanesulfonyl-phenyl)-N-(7-methoxy-6-methyl-benzothiazol-2-yl)-acetamide |

TABLE 1-continued

| Structure | Name |
|---|---|
| 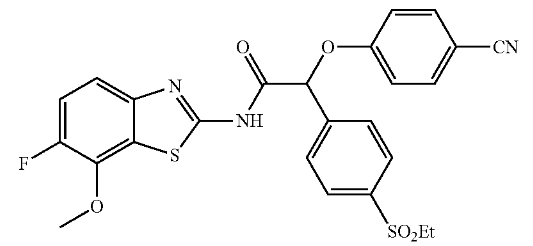 | 2-(4-Cyano-phenoxy)-2-(4-ethanesulfonyl-phenyl)-N-(6-fluoro-7-methoxy-benzothiazol-2-yl)-acetamide |
| 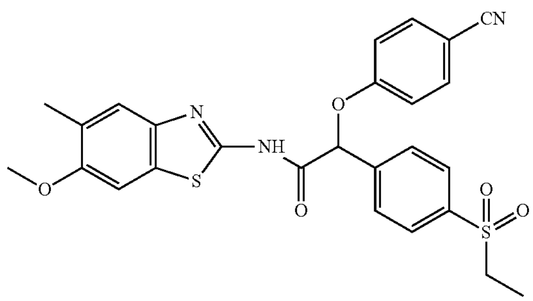 [SMILES: CCS(=O)(=O)c1ccc(C(Oc2ccc(C#N)cc2)C(=O)Nc2nc3cc(C)c(OC)cc3s2)cc1] | 2-(4-Cyano-phenoxy)-2-(4-ethanesulfonyl-phenyl)-N-(6-methoxy-5-methyl-benzothiazol-2-yl)-acetamide |
| 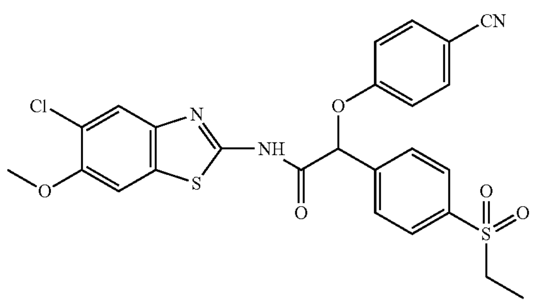 [SMILES: CCS(=O)(=O)c1ccc(C(Oc2ccc(C#N)cc2)C(=O)Nc2nc3cc(Cl)c(OC)cc3s2)cc1] | N-(5-Chloro-6-methoxy-benzothiazol-2-yl)-2-(4-cyano-phenoxy)-2-(4-ethanesulfonyl-phenyl)-acetamide |
| 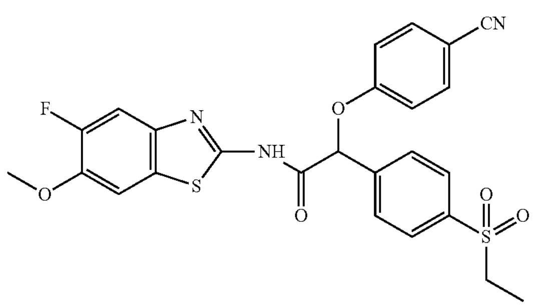 | 2-(4-Cyano-phenoxy)-2-(4-ethanesulfonyl-phenyl)-N-(6-fluoro-6-methoxy-benzothiazol-2-yl)-acetamide |
| 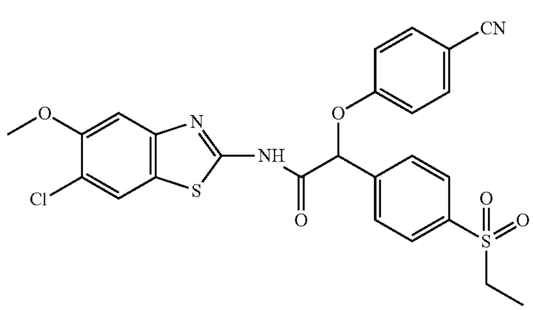 [SMILES: CCS(=O)(=O)c1ccc(C(Oc2ccc(C#N)cc2)C(=O)Nc2nc3cc(OC)c(Cl)cc3s2)cc1] | N-(6-Chloro-5-methoxy-benzothiazol-2-yl)-2-(4-cyano-phenoxy)-2-(4-ethanesulfonyl-phenyl)-acetamide |

TABLE 1-continued

| Structure | Name |
|---|---|
| 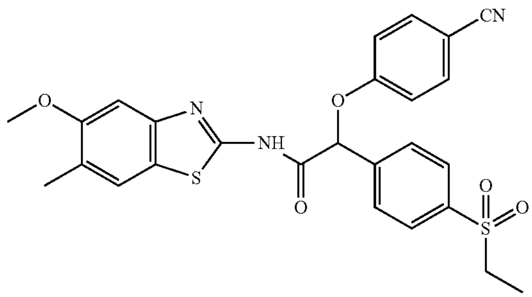 [SMILES: CCS(=O)(=O)c1ccc(C(Oc2ccc(C#N)cc2)C(=O)Nc2nc3cc(OC)c(C)cc3s2)cc1] | 2-(4-Cyano-phenoxy)-2-(4-ethanesulfonyl-phenyl)-N-(5-methoxy-6-methyl-benzothiazol-2-yl)-acetamide |
| 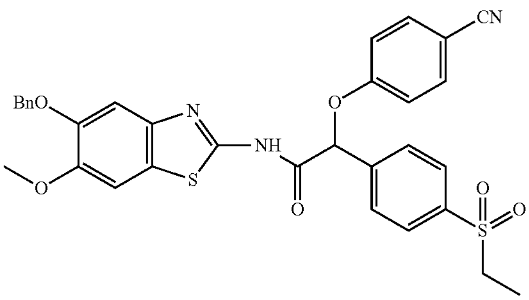 [SMILES: CCS(=O)(=O)c1ccc(C(Oc2ccc(C#N)cc2)C(=O)Nc2nc3cc(OCc4ccccc4)c(OC)cc3s2)cc1] | N-(5-Benzyloxy-6-methoxy-benzothiazol-2-yl)-2-(4-cyano-phenoxy)-2-(4-ethanesulfonyl-phenyl)-acetamide |
| 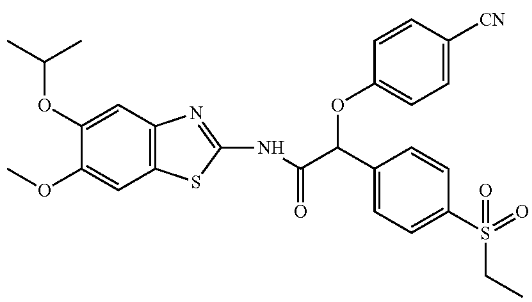 [SMILES: CCS(=O)(=O)c1ccc(C(Oc2ccc(C#N)cc2)C(=O)Nc2nc3cc(OC(C)C)c(OC)cc3s2)cc1] | 2-(4-Cyano-phenoxy)-2-(4-ethanesulfonyl-phenyl)-N-(5-isopropoxy-6-methoxy-benzothiazol-2-yl)-acetamide |
| 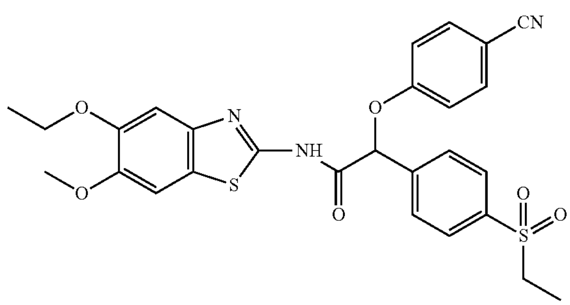 [SMILES: CCOc1cc2nc(NC(=O)C(Oc3ccc(C#N)cc3)c3ccc(S(=O)(=O)CC)cc3)sc2cc1OC] | 2-(4-Cyano-phenoxy)-2-(4-ethanesulfonyl-phenyl)-N-(5-ethoxy-6-methoxy-benzothiazol-2-yl)-acetamide |
| 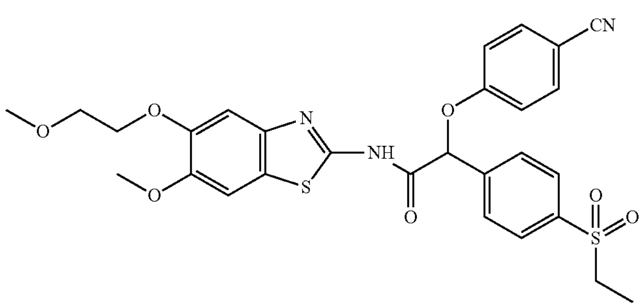 [SMILES: CCS(=O)(=O)c1ccc(C(Oc2ccc(C#N)cc2)C(=O)Nc2nc3cc(OCCOC)c(OC)cc3s2)cc1] | 2-(4-Cyano-phenoxy)-2-(4-ethanesulfonyl-phenyl)-N-[6-methoxy-5-(2-methoxy-ethoxy)-benzothiazol-2-yl]-acetamide |

TABLE 1-continued

| Structure | Name |
|---|---|
| 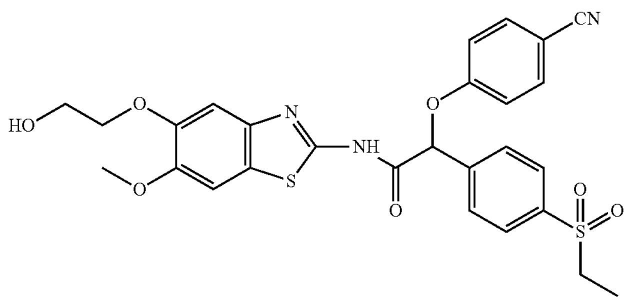 [SMILES: CCS(=O)(=O)c1ccc(C(Oc2ccc(C#N)cc2)C(=O)Nc2nc3cc(OCCO)c(OC)cc3s2)cc1] | 2-(4-Cyano-phenoxy)-2-(4-ethanesulfonyl-phenyl)-N-[5-(2-hydroxy-ethoxy)-6-methoxy-benzothiazol-2-yl]-acetamide |
| 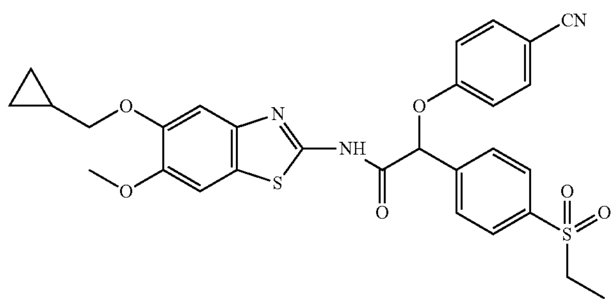 [SMILES: CCS(=O)(=O)c1ccc(C(Oc2ccc(C#N)cc2)C(=O)Nc2nc3cc(OCC4CC4)c(OC)cc3s2)cc1] | 2-(4-Cyano-phenoxy)-N-(5-cyclopropylmethoxy-6-methoxy-benzothiazol-2-yl)-2-(4-ethanesulfonyl-phenyl)-acetamide |
| 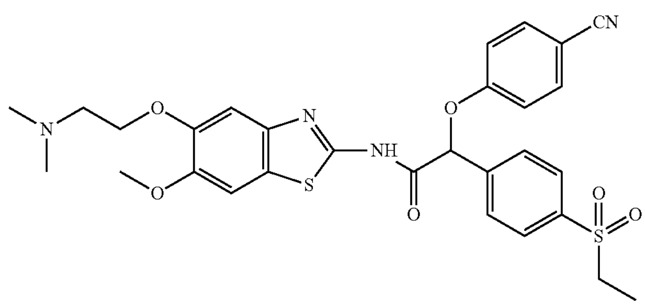 [SMILES: CCS(=O)(=O)c1ccc(C(Oc2ccc(C#N)cc2)C(=O)Nc2nc3cc(OCCN(C)C)c(OC)cc3s2)cc1] | 2-(4-Cyano-phenoxy)-N-[5-(2-dimethylamino-ethoxy)-6-methoxy-benzothiazol-2-yl]-2-(4-ethanesulfonyl-phenyl)-acetamide |
| 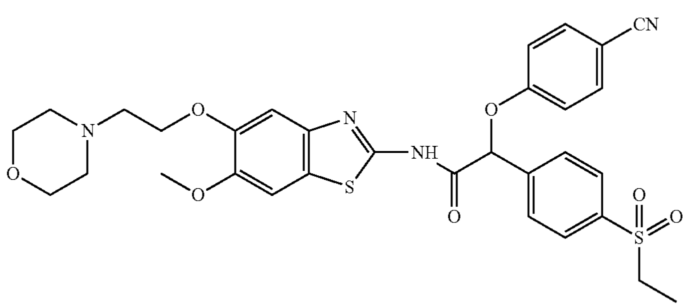 [SMILES: CCS(=O)(=O)c1ccc(C(Oc2ccc(C#N)cc2)C(=O)Nc2nc3cc(OCCN4CCOCC4)c(OC)cc3s2)cc1] | 2-(4-Cyano-phenoxy)-2-(4-ethanesulfonyl-phenyl)-N-[6-methoxy-5-(2-morpholin-4-yl-ethoxy)-benzothiazol-2-yl]-acetamide |
| 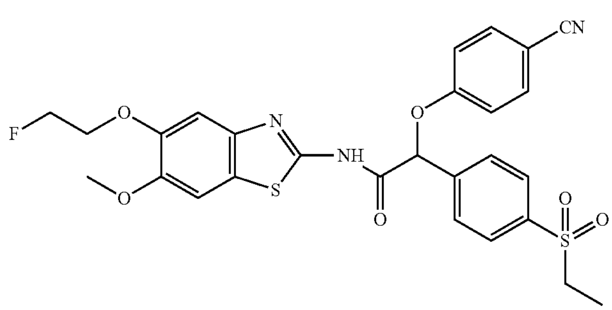 [SMILES: CCS(=O)(=O)c1ccc(C(Oc2ccc(C#N)cc2)C(=O)Nc2nc3cc(OCCF)c(OC)cc3s2)cc1] | 2-(4-Cyano-phenoxy)-2-(4-ethanesulfonyl-phenyl)-N-[5-(2-fluoro-ethoxy)-6-methoxy-benzothiazol-2-yl]-acetamide |

TABLE 1-continued

| Structure | Name |
|---|---|
| | 2-(4-Cyano-phenoxy)-2-(4-ethanesulfonyl-phenyl)-N-(6-methoxy-thiazolo[4,5-b]pyridin-2-yl)-acetamide |
| | 2-(4-Cyano-phenoxy)-2-(4-ethanesulfonyl-phenyl)-N-(6-methoxy-thiazolo[4,5-b]pyridin-2-yl)-acetamide |
| 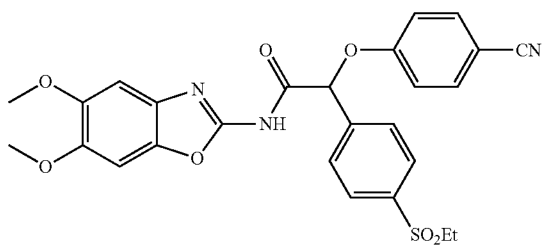 | 2-(4-Cyano-phenoxy)-N-(5,6-dimethoxy-benzooxazol-2-yl)-2-(4-ethanesulfonyl-phenyl)-acetamide |
| 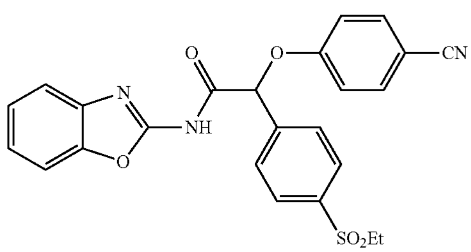 | N-Benzooxazol-2-yl-2-(4-cyano-phenoxy)-2-(4-ethanesulfonyl-phenyl)-acetamide |
| 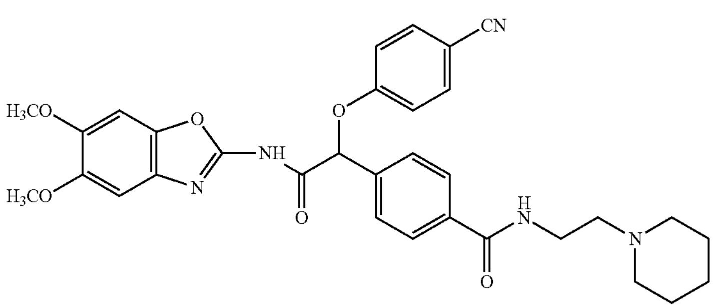 [SMILES: COc1cc2nc(NC(=O)C(Oc3ccc(C#N)cc3)c3ccc(C(=O)NCCN4CCCCC4)cc3)oc2cc1OC] | 4-[(4-Cyano-phenoxy)-(5,6-dimethoxy-benzooxazol-2-ylcarbamoyl)-methyl]-N-(2-piperidin-1-yl-ethyl)-benzamide |
| 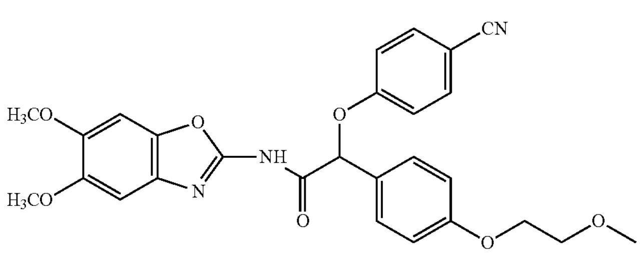 | 2-(4-Cyano-phenoxy)-N-(5,6-dimethoxy-benzooxazol-2-yl)-2-[4-(2-methoxy-ethoxy)-phenyl]-acetamide |

TABLE 1-continued

| Structure | Name |
|---|---|
| 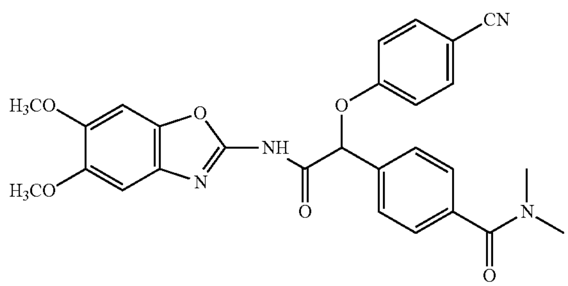 [SMILES: COc1cc2nc(NC(=O)C(Oc3ccc(C#N)cc3)c3ccc(C(=O)N(C)C)cc3)oc2cc1OC] | 4-[(4-Cyano-phenoxy)-(5,6-dimethoxy-benzooxazol-2-ylcarbamoyl)-methyl]-N,N-dimethyl-benzamide |
| 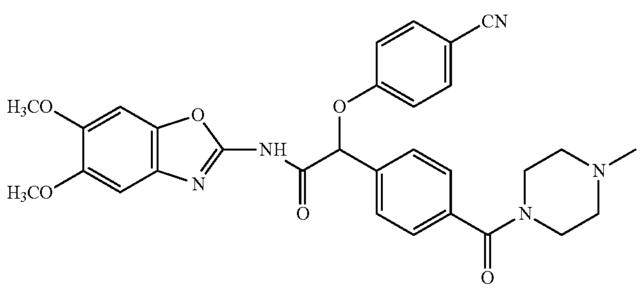 | 2-(4-Cyano-phenoxy)-N-(5,6-dimethoxy-benzooxazol-2-yl)-2-[4-(4-methyl-piperazine-1-carbonyl)-phenyl]-acetamide |
| 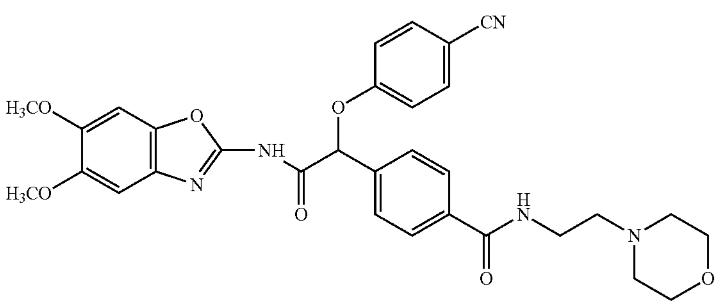 | 4-[(4-Cyano-phenoxy)-(5,6-dimethoxy-benzooxazol-2-ylcarbamoyl)-methyl]-N-(2-morpholin-4-yl-ethyl)-benzamide |
| 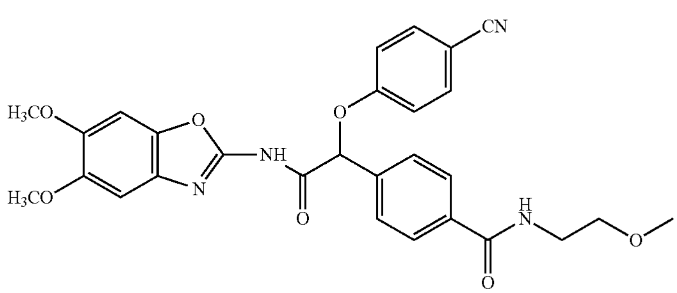 | 4-[(4-Cyano-phenoxy)-(5,6-dimethoxy-benzooxazol-2-ylcarbamoyl)-methyl]-N-(2-methoxy-ethyl)-benzamide |
| 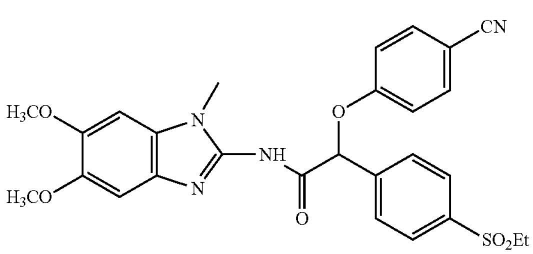 | 2-(4-Cyano-phenoxy)-N-(5,6-dimethoxy-1-methyl-1H-benzoimidazol-2-yl)-2-(4-ethanesulfonyl-phenyl)-acetamide |

TABLE 1-continued

| Structure | Name |
|---|---|
| 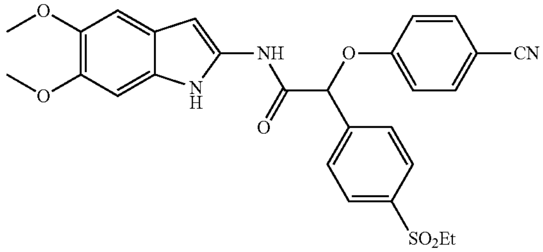 | 2-(4-Cyano-phenoxy)-N-(5,6-dimethoxy-1H-indol-2-yl)-2-(4-ethanesulfonyl-phenyl)-acetamide |
| 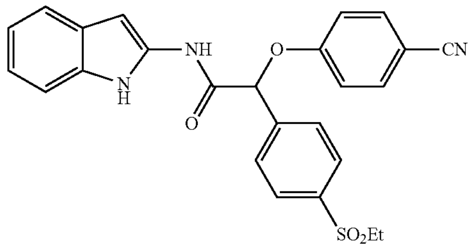 | 2-(4-Cyano-phenoxy)-2-(4-ethanesulfonyl-phenyl)-N-(1H-indol-2-yl)-acetamide |
| 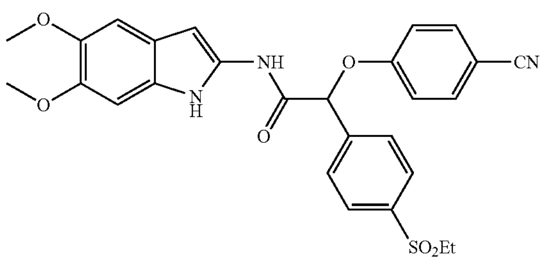 | 2-(4-Chloro-phenyl)-2-(4-cyano-phenoxy)-N-(5,6-dimethoxy-benzothiazol-2-yl)-acetamide |
| 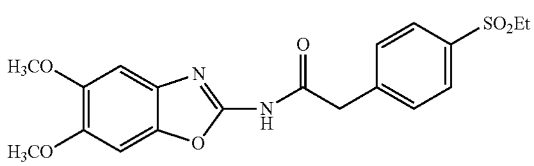 | N-(5,6-dimethoxy-benzooxazol-2-yl)-2-(4-ethanesulfonyl-phenyl)-acetamide |
| 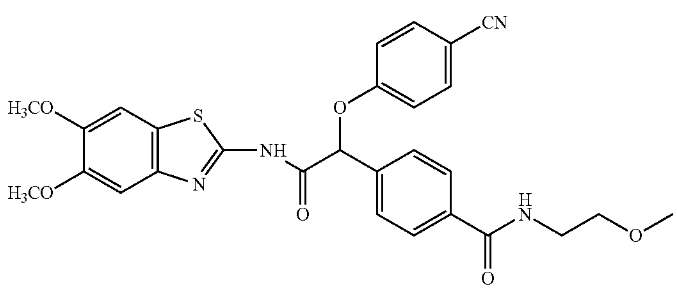 | 4-[(4-Cyano-phenoxy)-(5,6-dimethoxy-benzothiazol-2-ylcarbamoyl)-methyl]-N-(2-methoxy-ethyl)-benzamide |

Also provided herein is a pharmaceutical composition comprising a compound of structural Formulas I, II or III or a pharmaceutically acceptable salt thereof and a pharmaceutically acceptable excipient.

A method of preventing or treating in a subject an apelin-mediated disease or disorder, comprising administering to the subject a pharmaceutical a compound of structural Formulas I, II or III thereby preventing or treating the disease or disorder is also provided herein. In one embodiment, the subject is a human.

In certain aspects the disease or disorder is a cardiovascular disease or disorder, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery or valvular heart disease.

In other aspects the disease or disorder is a metabolic disease or disorder, metabolic syndrome, insulin resistance, diabetes mellitus, diabetic late complications, diabetic macro- and micro-vasculopathies, diabetic nephropathy, diabetic retinopathy, diabetic neuropathies or cardiac autonomic neuropathy.

In further aspects the disease or disorder is caused by CNS-dependent or CNS-independent disturbed fluid homeostasis, acute or chronic renal failure, hypertension, pulmonary hypertension, portal hypertension or systolic hypertension.

In other aspects, the disease or disorder is a vascular disease or disorder, vascular permeability, nonfunctional blood vessels, vascular hypertrophy, vascular remodeling, vascular stiffness, atherosclerosis, peripheral arterial occlusive disease (PAOD), restenosis, thrombosis, vascular permeability disorders, ischemia, reperfusion damage, ischemia or reperfusion damage of the heart, kidney or retina, or a combination thereof.

A method of treating an infectious disease, including administering to a subject in need thereof an effective amount of a compound of structural Formula I is also provided herein.

DETAILED DESCRIPTION OF THE INVENTION

The present invention is based on the seminal discovery of a series of potent small molecule apelin receptor agonists, which are useful for the treatment of diseases including heart failure, chronic kidney disease, hypertension, and metabolic disorders such as insulin resistance/diabetes and obesity. The compounds disclosed herein are highly specific for the apelin receptor versus the angiotensin II receptor (AT1).

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycloalkyl, or any other moiety were the atom attached to the carbonyl is carbon. An "acetyl" group, which is a type of acyl, refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—N(R)$_2$ group with R as defined herein. The term "N-amido" as used herein, alone or in combination, refers to a RC(=O)N(R')— group, with R and R' as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —N(R)(R') or —N$^+$(R)(R')(R"), wherein R, R' and R" are independently selected from the group consisting of hydrogen, alkyl, acyl, heteroalkyl, aryl, cycloalkyl, heteroaryl, and heterocycloalkyl, any of which may themselves be optionally substituted.

The term "amino acid," as used herein, alone or in combination, means a substituent of the form —NRCH(R')C(O)OH, wherein R is typically hydrogen, but may be cyclized with N (for example, as in the case of the amino acid proline), and R' is selected from the group consisting of hydrogen, alkyl, heteroalkyl, cycloalkyl, heterocycloalkyl, aryl, heteroaryl, amino, amido, cycloalkylalkyl, heterocycloalkylalkyl, arylalkyl, heteroarylalkyl, aminoalkyl, amidoalkyl, hydroxyalkyl, thiol, thioalkyl, alkylthioalkyl, and alkylthio, any of which may be optionally substituted. The term "amino acid" includes all naturally occurring amino acids as well as synthetic analogues.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH, O-carboxy, C-carboxy, or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxyl group bridging two moieties linked at carbon atoms.

The term "ether," as used herein, alone or in combination, typically refers to an oxy group bridging two moieties linked at carbon atoms. "Ether" may also include polyethers, such as, for example, —RO(CH2)2O(CH2)2O(CH2)2OR', —RO(CH2)2O(CH2)2OR', —RO(CH2)2OR', and —RO(CH2)2OH.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF2-), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3. The term heteroalkyl may include ethers.

The term "heteroaryl," as used herein, alone or in combination, refers to 3 to 7 membered unsaturated heteromonocyclic rings, or fused polycyclic rings in which at least one of the fused rings is unsaturated, wherein at least one atom is selected from the group consisting of O, S, and N. In certain embodiments, said heteroaryl will comprise from 5 to 7 carbon atoms. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one heteroatom as ring members, wherein each said heteroatom may be independently selected from the group consisting of nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sugars, sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycloalkyl groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycloalkyl groups may be optionally substituted unless specifically prohibited.

The term "hydrazinyl" as used herein, alone or in combination, refers to two amino groups joined by a single bond, i.e., —N—N—.

The term "hydroxamic acid" as used herein, refers to —C(O)ON(R)O(R'), wherein R and R' are as defined herein, or the corresponding "hydroxamate" anion, including any corresponding hydroxamic acid salt.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —NO2.

The terms "oxy" or "oxa" as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphoamide" as used herein, alone or in combination, refers to a phosphate group [(OH)2P(O)O—] in which one or more of the hydroxyl groups has been replaced by nitrogen, amino, or amido.

The term "phosphonate" as used herein, alone or in combination, refers to a group of the form ROP(OR')(OR)O—wherein R and R' are selected from the group consisting of hydrogen, alkyl, acyl, heteroalkyl, aryl, cycloalkyl, heteroaryl, and heterocycloalkyl, any of which may themselves be optionally substituted. "Phosphonate" includes "phosphate [(OH) 2P(O)O—] and related phosphoric acid anions which may form salts.

The terms "sulfonate," "sulfonic acid," and "sulfonic," as used herein, alone or in combination, refers to the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2-.

The term "N-sulfonamido" refers to a RS(=O).sub.2NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. A "null" group occurring between two other groups may also be understood to be a collapsing of flanking groups. For example, if in —(CH$_2$)G$_1$G$_2$G$_3$, the element G$_2$ were null, said group would become —(CH$_2$)G$_1$G$_3$.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, hydroxyl, halogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R$_n$, where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers, including keto-enol tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the body or of one of its parts that impairs normal functioning and is typically manifested by distinguishing signs and symptoms.

The term "apelin mediated disease or disorder" as used herein includes any disease or disorder that is mediated by apelin. Examples of apelin mediated diseases or disorders include, but are not limited to, In certain aspects the disease or disorder is a cardiovascular disease or disorder, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, valvular heart disease; a metabolic disease or disorder, metabolic syndrome, insulin resistance, diabetes mellitus, diabetic late complications, diabetic macro- and microvasculopathies, diabetic nephropathy, diabetic retinopathy, diabetic neuropathies, cardiac autonomic neuropathy; a disease or disorder is caused by CNS-dependent or CNS-independent disturbed fluid homeostasis, acute or chronic renal failure, hypertension, pulmonary hypertension, portal hypertension, systolic hypertension; a vascular disease or disorder, vascular permeability, nonfunctional blood vessels, vascular hypertrophy, vascular remodeling, vascular stiffness, atherosclerosis, peripheral arterial occlusive disease (PAOD), restenosis, thrombosis, vascular permeability disorders, ischemia, reperfusion damage, ischemia, reperfusion damage of the heart, kidney or retina, or a combination thereof.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain of the present compounds can also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

The compounds of the present invention can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds of the present invention, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds of the present invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10%0/w/w (by weight) of the formulation. In certain embodiments, the active ingredient may comprise as much as 10%0/w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Administrations of apelins have been shown to cause vasodilatation in different pre-clinical models and accordingly, intravenous administration in rodents reduces mean arterial blood pressure, systemic venous tone and cardiac pre- and afterload. Vasodilatation to apelin in rodents is dependent on endothelium and mediated through nitric oxide and prostacyclin dependent pathways. Ishida and colleagues demonstrated in 2004, that a functional knockdown of the apelin receptor abolished blood pressure lowering effects of apelins, confirming that vascular effects of apelins are mediated by the apelin receptor specifically.

The vascular effects of apelin in preclinical studies translate into similar effects in humans. Infusions of apelins increased forearm and coronary blood flow and lowered mean arterial pressure and peripheral vascular resistance in heart failure patients and healthy control subjects in heart failure patients without raising heart rates. An increased cardiac index could be noted, which may be explained by either direct effects on the cardiac muscle (see below) and/or reduction of pre- and afterload in the peripheral circulation. In man, vasodilatation by apelins is reduced by two thirds during nitric oxide synthase inhibition but is unaffected by prostacyclin inhibition. The apelin receptor has been linked to direct cardiac actions. In vitro, exogenous apelin increases contractility at subnanomolar concentrations in atrial strips and whole rat hearts. In healthy rodents, acute apelin infusion increases myocardial contractility independently of its effects on loading conditions. Uniquely among current inotropic agents, chronic dosing causes a sustained increase in cardiac output without inducing left ventricular hypertrophy. While apelin-deficient mice display normal or only slightly impaired basal cardiac function at early life cycles, they demonstrate progressive cardiac dysfunction from 6 months of age and develop severe heart failure when subjected to chronic pressure overload.

Controversial results have been published regarding the involvement of intracellular calcium on the contractility effects of apelin in cardiomyocytes. Two groups described that intracellular calcium is not a signaling mechanism. However, others reported at least a modest increase in the amplitude of the intracellular calcium ion transients in failing rat trabeculae and isolated cardiomyocytes. Additionally, effects of apelins in pre-clinical models have been described. Apelins may have an important counter-regulatory role to vasopressin and hence fluid homoeostasis. Apelin and the APJ receptor are both expressed also in the kidney and many areas of the brain. Synthesis in certain brain regions involved in fluid homeostasis are regulated by vasopressin. To the contrary, intracerebral injection of apelin directly inhibits vasopressin release leading to a 40% reduction in plasma vasopressin concentrations.

A link of apelins to metabolic syndrome is suggested by pre-clinical data. Apelins are produced by adipose tissue and may influence glucose and lipid metabolism as adipocytokines. Acute intravenous administration of pyf-apelin-13 stimulates glucose utilization in normal and obese insulin-resistant mice. These acute effects were explained by a direct effect of $^1$pyr-apelin-13 on glucose uptake into skeletal muscle. Mice deficient for the apelins have reduced insulin sensitivity which can be corrected by sub-chronic supplementation with apelin via minipumps. Furthermore in insulin resistant homozygous leptin receptor mutant mice (db/db mice) a similar sub-chronic administration results in improved glucose utilization. Results with glucose utilization in apelin receptor knockout mice have not been published. Furthermore it is not reported yet, whether apelins significantly affect glucose handling in man.

The clinical and pre-clinical profile suggests applications of apelin receptor agonists in different patient populations and indications. In heart failure, apelins demonstrate a unique hemodynamic profile in enhancing myocardial contractility without inducing left ventricular hypertrophy. In parallel, ventricular pre- and afterload is reduced by reduced peripheral resistance. In pre-clinical models, apelin increases contractility at least to the same extent in the failing compared to normal myocardium. Irrespective of changes in receptor and ligand expression, these studies indicate agonism of the receptor is not diminished in situations of established heart failure. First data from clinical studies with acute apelin infusions are promising. In contrast to acetylcholine, another vaso-active principle, vascular and cardiac hemodynamic effects of apelins are preserved in chronic heart failure patients. These patients received optimal pharmacological treatment, suggesting that the effects of apelin were additive to established heart failure therapies like ACE-Inhibitors and/or β-blockers.

Regarding therapies targeting the diseased heart, acute beneficial effects of apelins after acute myocardial infarction may be envisaged. It was shown that in preclinical models of acute myocardial ischemia and reperfusion administration of apelins at reperfusion strongly reduces myocardial injury, however opposing results regarding the underlying signaling of this cardioprotective mechanism have been reported. One alternative is a mechanism based on activation of phosphatide-3-kinase, AKT kinase and P70S6 kinase. However, signaling pathways independent of PI-3-kinase, AKT-kinase and p70S6 kinase may also explain the beneficial effects of apelin receptor agonists in ischemia-reperfusion injury. Apelin increases both phosphorylation and activity of key components within reperfusion injury salvage kinase pathway. This pro-survival pathway is known to be associated with reduced ischemia-reperfusion-injury by preserving mitochondrial function. Despite the fact, preconditioning agents are difficult to implement in clinical practice, apelin receptor agonists may be administered with the reperfusion solution directly after acute myocardial infarction and thereby display potential benefits in both restoring cardiac survival and function. Another application, especially of oral bioavailable small molecule apelin receptor agonists, could be to start in a patient with an acute myocardial infarction with an intravenous formulation during reperfusion and continue later, e.g. outside the clinic, with an oral bioavailable formulation of the same drug component. Furthermore, intravenous or oral administration of apelin receptor agonists could be envisaged in patients with acute heart failure. Very often acute heart failure develops in the progression of chronic heart failure spontaneously as acute episodes of disease worsening but without signs of myocardial infarction. Patients are then hospitalized and stabilized during hospitalization by agents increasing the contractility of the disease heart muscle. Apelin receptor agonists display a unique hemodynamic profile suggesting a safe and efficient use in such patients.

Agonists of the apelin receptor may also represent a novel class of anti-hypertensive agents. In preclinical models, administration of apelin peptides lowers blood pressure, greatly enhanced in hypertensive animals compared with normotensive controls. In first clinical studies modest but significant effects on blood pressure lowering could be demonstrated in normotensive middle-aged subjects. Whether intravenously applied apelin peptides lower blood pressure stronger in hypertensive patient populations, similar to the situation in normotensive vs. hypertensive rats, needs to be evaluated. Application of apelin peptides in hypertensive patients is strongly limited by the need of intravenous administration route. However, small molecule apelin receptor agonists as claimed in this patent application may have a much wider application in these patients due to better oral bioavailability.

Apelin receptor agonists appear to have beneficial effects on additional vascular based diseases. In atherosclerotic mice deficient for the Apolipoprotein-E, apelin infusion inhibits atherosclerosis progress and completely abrogates angiotensin II-accelerated detrimental effects independent of blood pressure. And in double knockout mice, deficient in for the apelin receptor ligand and Apolipoprotein-E, accelerated atherosclerosis could be observed compared versus single Apolipoprotein-E-knockout. Pro-atherosclerotic effects of the apelin receptor have also been described in a combined mice knockout-model of the apelin receptor and apolipoprotein-E ApoE. Overall these results are difficult to reconcile: Most probably very different fat feeding regimens or different genetic backgrounds and so called off-target genetic effects best explain the observed differences. Independent of effects on atherosclerosis progression, apelin treatment resulted in reduced aneurysm by 50% in a mouse model of abdominal aortic aneurysms, an effect explained by the authors by a direct anti-inflammatory effect within the vessel wall.

Furthermore, apelin receptor agonists may play an important role in maturation of newly formed blood vessels. It was described in a model of vascular remodeling after hind limb ischemia in mice, that apelins induce the maturation into enlarged and non-leaky blood vessels for functional recovery. Especially pathologically increased vascular permeability induced by VEGF under hypoxic conditions seems to be corrected by apelins.

In humans, apelins cause nitric oxide-mediated vasodilatation in forearm resistance vessels of healthy subjects. Based on promising preclinical data, the role of apelin receptor agonists in preventing human vascular disease merits further investigations. These investigations will be strongly facilitated by small molecule apelin receptor agonists, as claimed in this patent application, because the oral bioavailability allows for much easier chronic administration routes.

In patients with metabolic syndrome and diabetes, apelin receptor agonists may provide additional benefits. Apelins are produced also by adipose tissue and influence glucose and lipid metabolism as adipocytokines. Mice with no apelin receptor ligands have reduced insulin sensitivity which can be corrected by the administration of exogenous apelin. Acute and sub-chronic positive effects of apelins on glucose utilizations following a glucose load have been described in insulin-resistant animal strains. Although the translation of these effects to man needs to be performed, apelin receptor agonists may offer additional therapeutic options especially in insulin-resistant patients, insufficiently dealing with increased plasma glucose load in metabolic syndrome and diabetes. The simultaneous beneficial effects on blood glucose lowering and vascular and cardiac homeostasis are a unique advantage to therapeutic principles affecting blood glucose alone and open an avenue to macro- and microvascular diabetic late complications, like diabetic cardiomyopathies, diabetic retinopathy, diabetic macular edema, diabetic nephropathy and diabetic neuropathy. Oral bioavailable small molecule apelin receptor agonist would strongly boost these areas of applications because they would be not restricted to intravenous or subcutaneous administration routes.

There continues to be a need for further effective low molecular weight APJ modulators, in particular in view of safety and selectivity. The compounds disclosed herein are selective for the apelin receptor, and have been shown to be highly specific for the apelin receptor versus the angiotensin II receptor (AT1), the most closely related receptor. Broad selectivity profiling experiments revealed no significant off target binding. The compounds disclosed herein show favorable in vitro absorption, distribution, metabolism, and excretion (ADME) properties and excellent in vivo pharmacokinetics. The compounds of the present disclosure are contemplated to be useful as novel therapies for the treatment for a range of cardiovascular, renal and metabolic conditions.

The following examples are intended to illustrate but not limit the invention.

EXAMPLE 1

Biological Data

This example illustrates the biological activity of various compounds tested against the APJ receptor.

Commercially available cell lines were used to screen chemical libraries to identify compounds that potently and selectively activated the human apelin receptor. The assays disclosed herein were performed using cell lines from DiscoveX, Inc.

Biological activity was determined to the cell—based assay. This assay detects activation of the receptor by reporting on intracellular cyclic adenosine monophosphate (cAMP) level. Chinese hamster ovary cells engineered to express the stably integrated human apelin receptor (APJ, AGTRL—one, APLNR), pleaded into the wells of the microtiter plate. Cells were stimulated with source: to increase intracellular cyclic AMP. Immediately following, compounds were added to the range of final concentrations 0.0-100 µM, in DMSO (not to exceed a final DMSO concentration greater than 1% v/v), and allowed to incubate with the cells for 0.5 h. At the end of the incubation, cells were lysed to stop APJ signaling and cAMP was quantified using a commercially available competitive immunoassay kit that applies homogenous time—resolved florescence energy transfer (TR-FRET). The assay is based on the competition between a europium (Eu) chelate—labeled cAMP donor tracer and cellular cAMP for binding sites on a cAMP—specific monoclonal antibody labeled with an acceptor fluorophore. When antibodies are bound to the cAMP tracer light emissions at 320 nm stimulate the energy transfer from the donor to the acceptor, which in turn emits light at 665 nm. In the presence of competitive unlabeled cAMP (derived from the activity of the receptor or forskolin-stimulated production of cAMP), the labelled cAMP tracer is dissociated from the cAMP antibody, resulting in a loss of FRET signal. The amount of light emitted by the FRET is inversely proportional to the cAMP generated by the cell/receptor system. Potency and efficacy at APJ are reported in reference to the canonical APJ receptor agonist apelin-13 when tested at 1 nM.

Compound potency is reported as the effective concentration required to effect 50% (EC 50) of the control (apelin-13, 1 nM) response in nanomole are (nM) units. Compound efficacy (% response) is reported as a percentage of the maximal apein-13 response at InM (control). Potencies were calculated by fitting a four-point logistic curve to concentration response consisting of at least 10 discrete data points spanning effective range of the compounds in the cell-based assay that measures cAMP. Results are shown in Table 2 below. The potencies are expressed in categories where Category A is >500 nM; Category B is 200-500 nM; Category C is 100-200 nM; Category D is 50-100 nM; and Category E is <50 nM.

TABLE 2

| Structure | Potency Category |
|---|---|
| 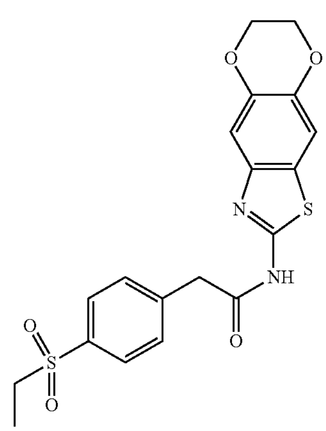 [SMILES: CCS(=O)(=O)c1ccc(CC(=O)Nc2nc3cc4c(cc3s2)OCCO4)cc1] | A |

TABLE 2-continued

| Structure | Potency Category |
|---|---|
| | A |
| | A |
| | A |
| | A |
| | A |
| | A |
| | A |

TABLE 2-continued

| Structure | Potency Category |
|---|---|
| | A |
| | A |
| | A |
| | A |
| | A |
| | A |

TABLE 2-continued

| Structure | Potency Category |
|---|---|
| | A |
| | A |
| | A |
| | A |
| | A |
| | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |
| | A |
| | A |
| | A |

TABLE 2-continued

| Structure | Potency Category |
|---|---|
| | A |
| | A |
| | A |
| | A |
| | A |
| | A |

TABLE 2-continued

| Structure | Potency Category |
|---|---|
| (5,6-dimethoxybenzothiazol-2-yl)-NH-C(=O)-CH2-(3-(cyclopentylsulfonyl)phenyl) | A |
| (5,6-dimethoxybenzothiazol-2-yl)-NH-C(=O)-CH(O-(2-methoxyphenyl))-(4-(ethylsulfonyl)phenyl) | A |
| (5,6-dimethoxybenzothiazol-2-yl)-NH-C(=O)-CH(O-(3-methoxyphenyl))-(4-(ethylsulfonyl)phenyl) | A |
| (5,6-dimethoxybenzothiazol-2-yl)-NH-C(=O)-CH(O-isopropyl)-(4-(ethylsulfonyl)phenyl) | A |
| (5,6-dimethoxybenzothiazol-2-yl)-NH-C(=O)-CH(O-propyl)-(4-(ethylsulfonyl)phenyl) | A |

TABLE 2-continued
| Structure | Potency Category |
|---|---|
| 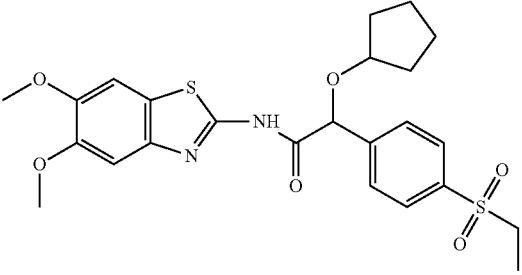 [SMILES: CCS(=O)(=O)c1ccc(C(OC2CCCC2)C(=O)Nc2nc3cc(OC)c(OC)cc3s2)cc1] | A |
| 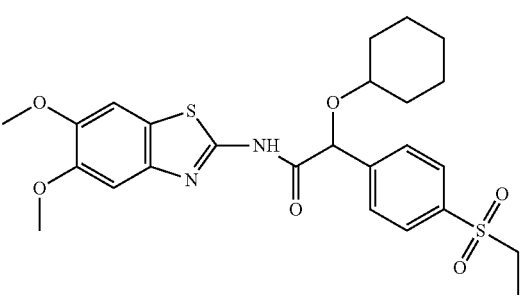 [SMILES: CCS(=O)(=O)c1ccc(C(OC2CCCCC2)C(=O)Nc2nc3cc(OC)c(OC)cc3s2)cc1] | A |
| 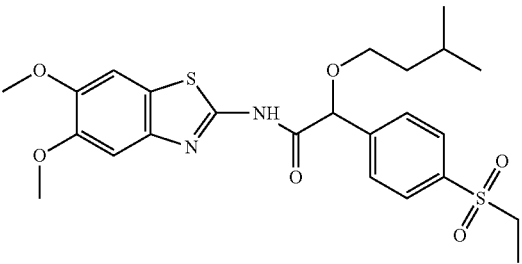 [SMILES: CCS(=O)(=O)c1ccc(C(OCCC(C)C)C(=O)Nc2nc3cc(OC)c(OC)cc3s2)cc1] | A |
| 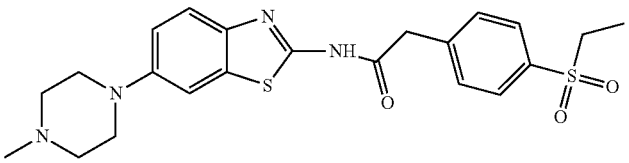 [SMILES: CCS(=O)(=O)c1ccc(CC(=O)Nc2nc3ccc(N4CCN(C)CC4)cc3s2)cc1] | A |
| 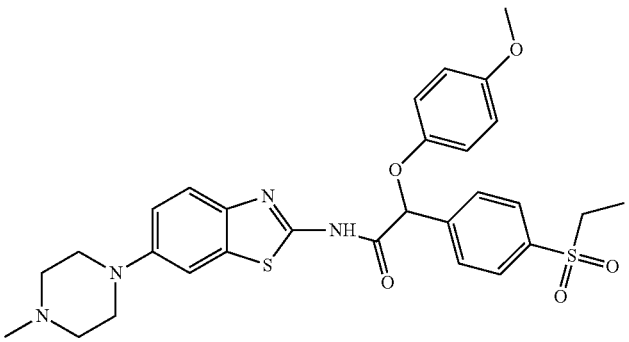 [SMILES: CCS(=O)(=O)c1ccc(C(Oc2ccc(OC)cc2)C(=O)Nc2nc3ccc(N4CCN(C)CC4)cc3s2)cc1] | A |
| 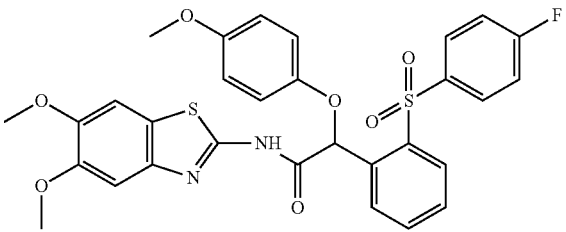 [SMILES: COc1ccc(OC(C(=O)Nc2nc3cc(OC)c(OC)cc3s2)c2ccccc2S(=O)(=O)c2ccc(F)cc2)cc1] | A |

TABLE 2-continued

| Structure | Potency Category |
|---|---|
| (structure) | A |
| (structure) | A |
| (structure) | A |
| (structure) | A |
| (structure) | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |
| | A |
| | A |

TABLE 2-continued

| Structure | Potency Category |
|---|---|
| | A |
| | A |
| | A |
| | A |
| | A |

TABLE 2-continued
| Structure | Potency Category |
|---|---|
| 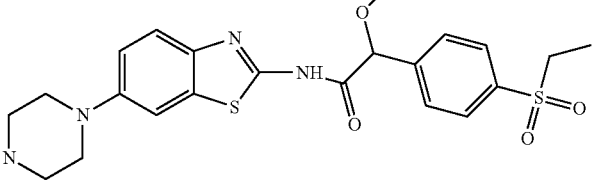 | A |
| 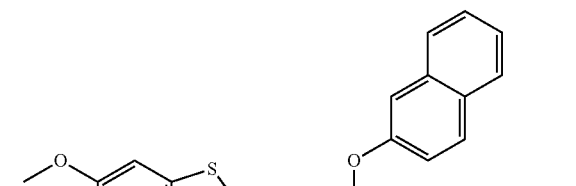 | A |
| 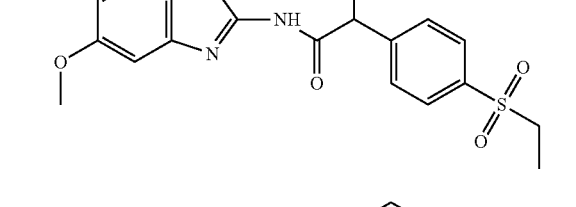 | A |
| 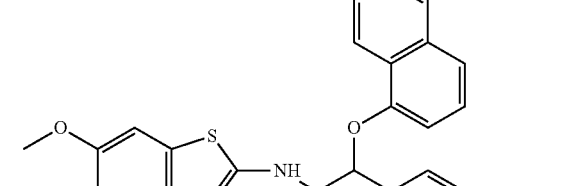 | A |
| 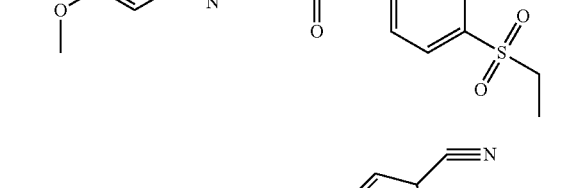 | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |
| | A |

TABLE 2-continued
| Structure | Potency Category |
|---|---|
| 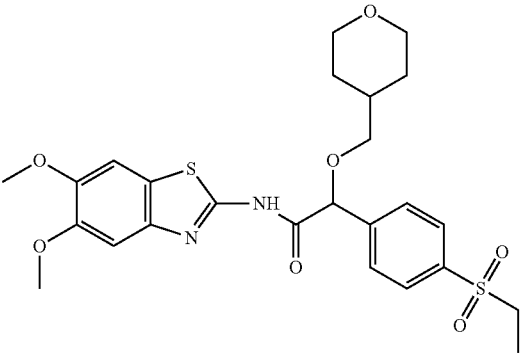 [SMILES: CCS(=O)(=O)c1ccc(C(OCC2CCOCC2)C(=O)Nc2nc3cc(OC)c(OC)cc3s2)cc1] | A |
| 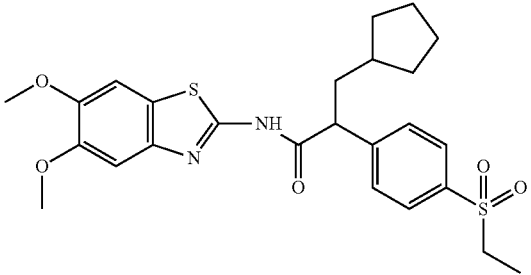 [SMILES: CCS(=O)(=O)c1ccc(C(CC2CCCC2)C(=O)Nc2nc3cc(OC)c(OC)cc3s2)cc1] | A |
| 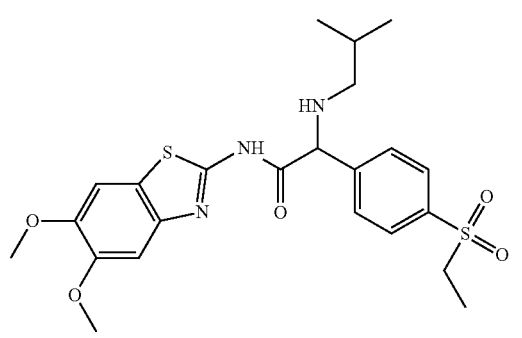 [SMILES: CCS(=O)(=O)c1ccc(C(NCC(C)C)C(=O)Nc2nc3cc(OC)c(OC)cc3s2)cc1] | A |
| 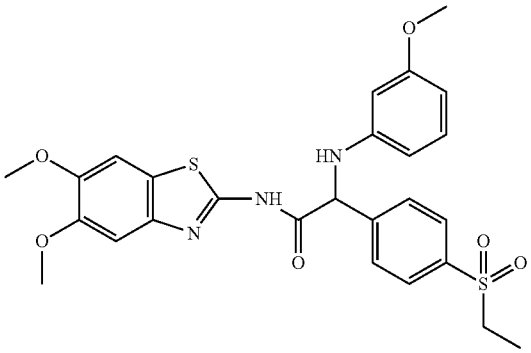 [SMILES: CCS(=O)(=O)c1ccc(C(Nc2cccc(OC)c2)C(=O)Nc2nc3cc(OC)c(OC)cc3s2)cc1] | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |

TABLE 2-continued

| Structure | Potency Category |
|---|---|
| | A |
| | A |
| | A |
| | A |

TABLE 2-continued
| Structure | Potency Category |
|---|---|
| 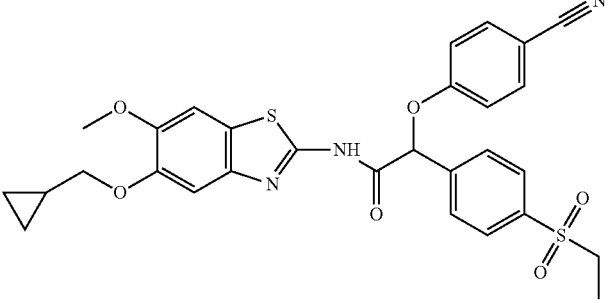 | A |
| 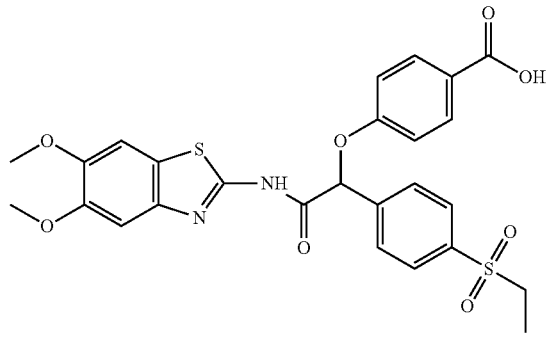 [SMILES: CCS(=O)(=O)c1ccc(C(Oc2ccc(C(=O)O)cc2)C(=O)Nc2nc3cc(OC)c(OC)cc3s2)cc1] | A |
| 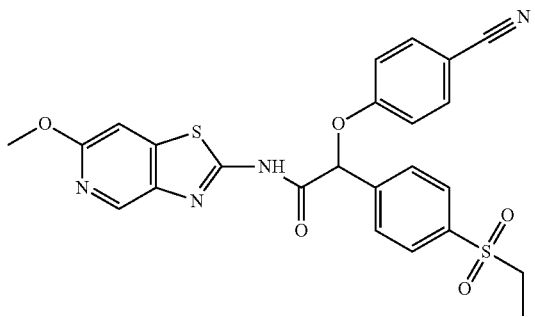 [SMILES: CCS(=O)(=O)c1ccc(C(Oc2ccc(C#N)cc2)C(=O)Nc2nc3cnc(OC)cc3s2)cc1] | A |
| 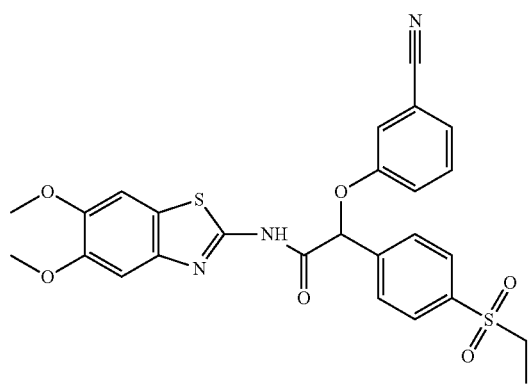 [SMILES: CCS(=O)(=O)c1ccc(C(Oc2cccc(C#N)c2)C(=O)Nc2nc3cc(OC)c(OC)cc3s2)cc1] | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |
| | A |

TABLE 2-continued

| Structure | Potency Category |
|---|---|
| | A |
| | A |
| | A |
| | A |

TABLE 2-continued

| Structure | Potency Category |
|---|---|
| | B |
| | B |
| | B |
| | B |
| | B |

TABLE 2-continued
| Structure | Potency Category |
|---|---|
| 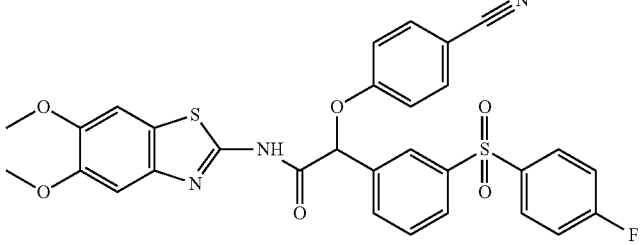 | B |
| 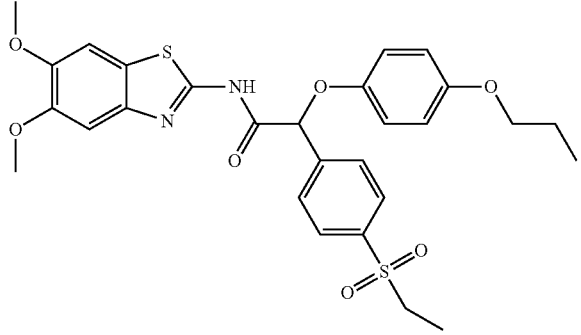 [SMILES: CCCOc1ccc(OC(C(=O)Nc2nc3cc(OC)c(OC)cc3s2)c2ccc(S(=O)(=O)CC)cc2)cc1] | B |
| 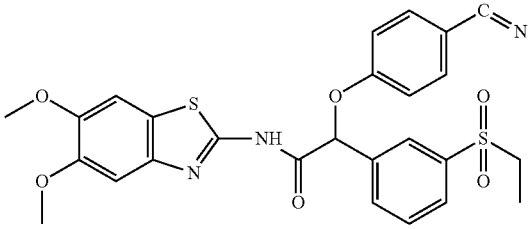 [SMILES: CCS(=O)(=O)c1cccc(C(Oc2ccc(C=N)cc2)C(=O)Nc2nc3cc(OC)c(OC)cc3s2)c1] | B |
| 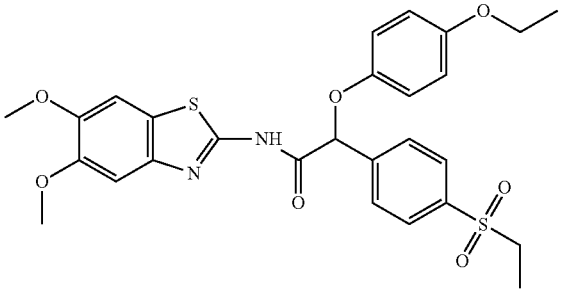 [SMILES: CCOc1ccc(OC(C(=O)Nc2nc3cc(OC)c(OC)cc3s2)c2ccc(S(=O)(=O)CC)cc2)cc1] | B |
| 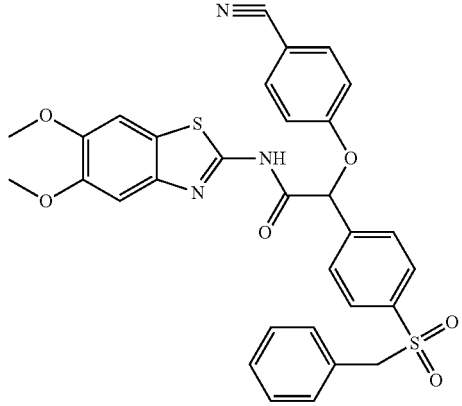 [SMILES: COc1cc2nc(NC(=O)C(Oc3ccc(C#N)cc3)c3ccc(S(=O)(=O)Cc4ccccc4)cc3)sc2cc1OC] | B |

TABLE 2-continued

| Structure | Potency Category |
|---|---|
| | B |
| | B |
| | B |
| | B |
| | B |

TABLE 2-continued

| Structure | Potency Category |
|---|---|
| | B |
| | B |
| | B |
| | B |
| | B |

TABLE 2-continued

| Structure | Potency Category |
|---|---|
| | B |
| | B |
| | B |
| | B |
| | B |

TABLE 2-continued

| Structure | Potency Category |
|---|---|
| | B |
| | B |
| | B |
| | B |
| | B |

TABLE 2-continued

| Structure | Potency Category |
|---|---|
| | B |
| | B |
| | B |
| | B |
| | B |

TABLE 2-continued
| Structure | Potency Category |
|---|---|
| 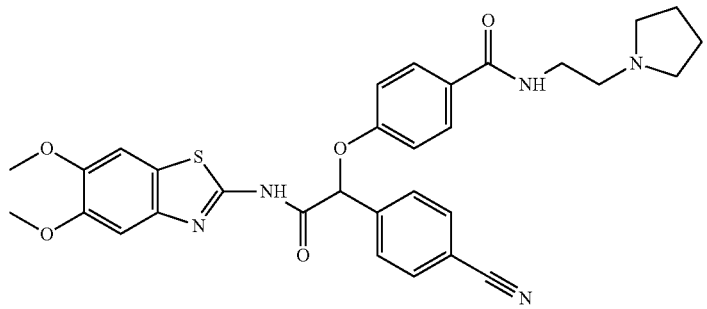 [SMILES: COc1cc2nc(NC(=O)C(Oc3ccc(C(=O)NCCN4CCCC4)cc3)c3ccc(C#N)cc3)sc2cc1OC] | B |
| 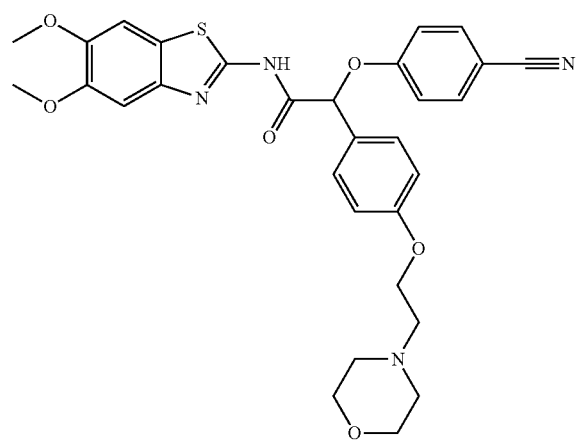 [SMILES: COc1cc2nc(NC(=O)C(Oc3ccc(C#N)cc3)c3ccc(OCCN4CCOCC4)cc3)sc2cc1OC] | B |
| 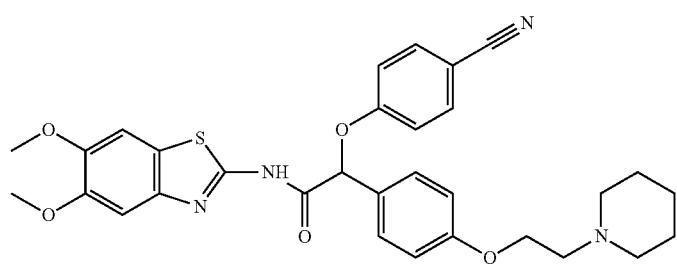 [SMILES: COc1cc2nc(NC(=O)C(Oc3ccc(C#N)cc3)c3ccc(OCCN4CCCCC4)cc3)sc2cc1OC] | B |
| 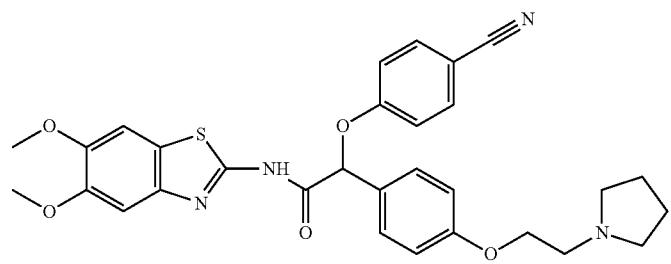 [SMILES: COc1cc2nc(NC(=O)C(Oc3ccc(C#N)cc3)c3ccc(OCCN4CCCC4)cc3)sc2cc1OC] | B |

TABLE 2-continued

| Structure | Potency Category |
|---|---|
| 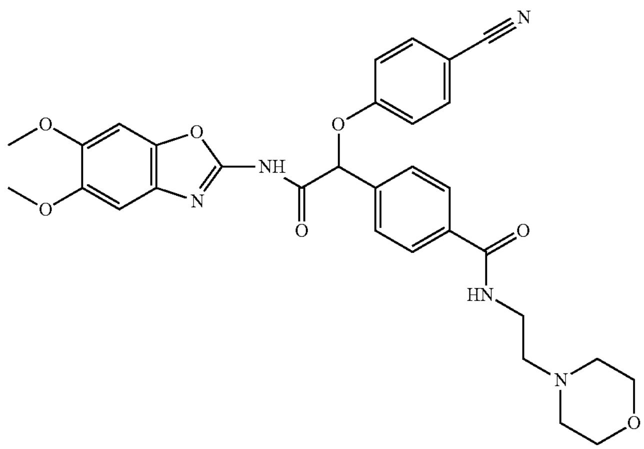 [SMILES: COc1cc2nc(NC(=O)C(Oc3ccc(C#N)cc3)c3ccc(C(=O)NCCN4CCOCC4)cc3)oc2cc1OC] | B |
| | C |
| | C |
| | C |

TABLE 2-continued

| Structure | Potency Category |
|---|---|
| | C |
| | C |
| | C |
| | C |
| | C |

TABLE 2-continued

| Structure | Potency Category |
|---|---|
| (structure) | C |
| (structure) | C |
| (structure) | C |
| (structure) | C |
| (structure) | C |

TABLE 2-continued

| Structure | Potency Category |
|---|---|
| | D |
| | D |
| | D |
| | D |
| | D |

TABLE 2-continued

| Structure | Potency Category |
|---|---|
| | D |
| | D |
| | D |
| | D |
| | D |

TABLE 2-continued

| Structure | Potency Category |
|---|---|
| (structure) | D |
| (structure) | D |
| (structure) | D |
| (structure) | D |
| (structure) | D |

TABLE 2-continued
| Structure | Potency Category |
|---|---|
| 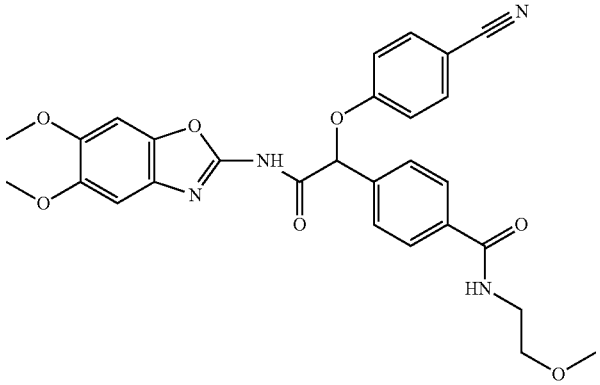 | D |
| 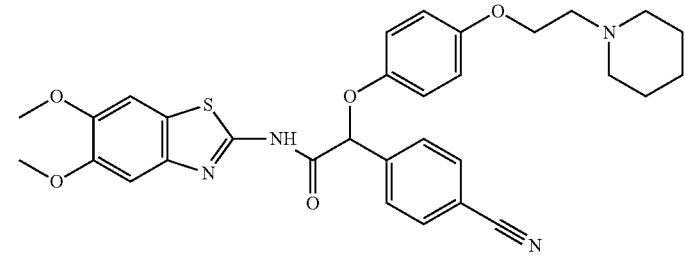 [SMILES: COc1cc2nc(NC(=O)C(Oc3ccc(OCCN4CCCCC4)cc3)c3ccc(C#N)cc3)sc2cc1OC] | D |
| 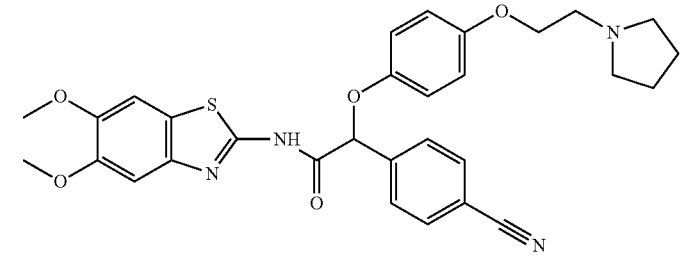 [SMILES: COc1cc2nc(NC(=O)C(Oc3ccc(OCCN4CCCC4)cc3)c3ccc(C#N)cc3)sc2cc1OC] | D |
| 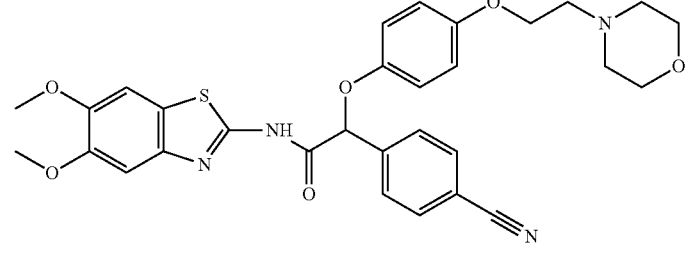 | D |
| 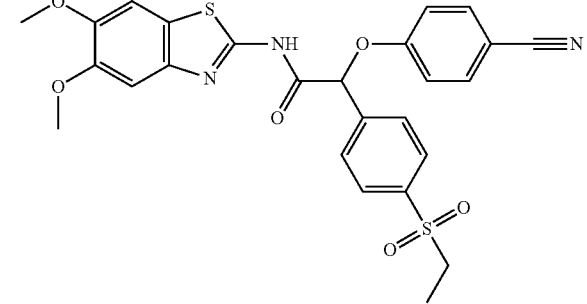 | E |

TABLE 2-continued

| Structure | Potency Category |
|---|---|
| | E |
| | E |
| | E |
| | E |
| | E |

TABLE 2-continued

| Structure | Potency Category |
|---|---|
| | E |
| | E |
| | E |
| | E |
| | E |

TABLE 2-continued

| Structure | Potency Category |
|---|---|
| (structure) | E |
| (structure) | E |
| (structure) | E |
| (structure) | E |
| (structure) | E |

TABLE 2-continued

| Structure | Potency Category |
|---|---|
| | E |
| | E |
| | E |
| | E |

TABLE 2-continued

| Structure | Potency Category |
|---|---|
| | E |
| | E |
| | E |
| | E |
| | E |

TABLE 2-continued

| Structure | Potency Category |
|---|---|
| | E |
| | E |
| | E |
| | E |

TABLE 2-continued

| Structure | Potency Category |
|---|---|
| | E |
| | E |
| | E |
| | E |
| | E |

TABLE 2-continued
| Structure | Potency Category |
|---|---|
| 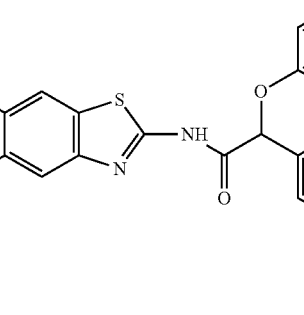 | E |
| 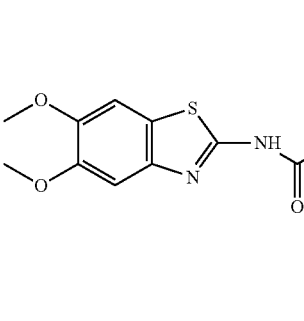 | E |
| 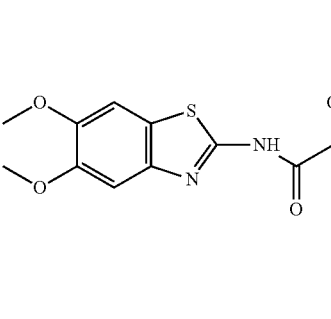 | E |
| 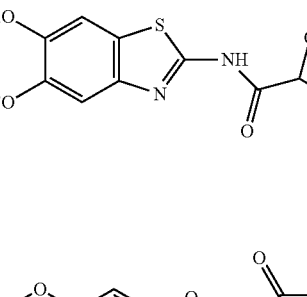 | E |
| 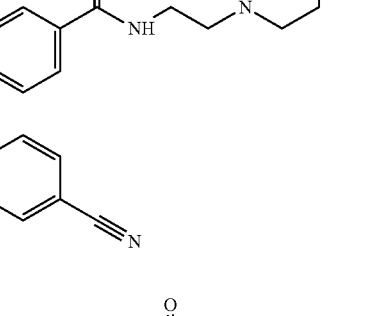 | E |

TABLE 2-continued

| Structure | Potency Category |
|---|---|
| (structure) | E |
| (structure) | E |
| (structure) | E |

Although the invention has been described with reference to the above example, it will be understood that modifications and variations are encompassed within the spirit and scope of the invention. Accordingly, the invention is limited only by the following claims.

What is claimed is:

1. A compound of structural Formula I, or a pharmaceutically acceptable salt, polymorph, solvate, tautomer, or N-oxide thereof:

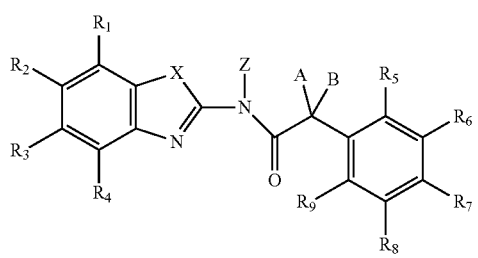

(I)

wherein:

X is selected from the group consisting of S, O, and $NR^9$;

A is selected from the group consisting of substituted phenoxy, optionally substituted aniline, and substituted 5- or 6-membered heteroaryl or heteroaryl-oxy;

B is selected from the group consisting of H, optionally substituted aryl, optionally substituted alkoxy, optionally substituted phenoxy, optionally substituted amino, optionally substituted aniline, and optionally substituted 5- or 6-membered heteroaryl or heteroaryl-oxy;

wherein the optionally substituted aniline of A or B is attached to the parent molecule through a nitrogen atom;

each $R^1$-$R^9$ is independently selected from the group consisting of hydrogen, halogen, —CN, —C(O)—N($R^{10}$)—$R^{11}$, —C(O)—O—$R^{12}$, —$SO_2R^{13}$ optionally substituted alkyl, optionally substituted cycloalkyl, optionally substituted heterocycloalkyl, optionally substituted alkoxy, haloalkyl, haloalkoxy, optionally substituted phenyl, optionally substituted amino, and optionally substituted 5- or 6-membered heteroaryl;

each $R^{10}$-$R^{13}$ is independently selected from the group consisting of hydrogen, optionally substituted alkyl, optionally substituted cycloalkyl, optionally substituted heterocycloalkyl, optionally substituted alkoxy, haloalkyl, haloalkoxy, optionally substituted phenyl, optionally substituted amino, and optionally substituted 5- or 6-membered heteroaryl; and Z is selected from the group consisting of hydrogen, optionally substituted alkyl, optionally substituted cycloalkyl, and optionally substituted heterocycloalkyl.

2. A compound of structural Formula II, or a pharmaceutically acceptable salt, polymorph, solvate, tautomer, or N-oxide thereof:

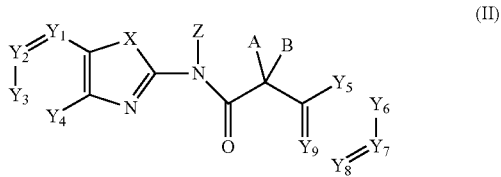

(II)

wherein:

X is selected from the group consisting of S, O and $NR^9$;

A is selected from the group consisting of substituted phenoxy, optionally substituted aniline, and substituted 5- or 6-membered heteroaryl or heteroaryl-oxy;

B is selected from the group consisting of H, optionally substituted aryl, optionally substituted alkoxy, optionally substituted phenoxy, optionally substituted amino, optionally substituted aniline, and optionally substituted 5- or 6-membered heteroaryl or heteroaryl-oxy; wherein the optionally substituted aniline of A or B is attached to the parent molecule through a nitrogen atom;

$Y^1$ is $CR^{14}$;

each $Y^2$-$Y^9$ are independently selected from the group consisting of N and $CR^{14}$;

each $R^{14}$ is independently selected from the group consisting of hydrogen, halogen, —CN, —C(O)—N($R^{15}$)—$R^{16}$, —C(O)—O—$R^{17}$, —$SO_2R^{18}$ optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

each $R^{15}$-$R^{18}$ is independently selected from the group consisting of optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl; and Z is selected from the group consisting of hydrogen, optionally substituted alkyl, optionally substituted cycloalkyl, and optionally substituted heterocycloalkyl.

3. A compound selected from the group consisting of: methyl 4-{[N-(5,6-dimethoxybenzothiazol-2-yl)carbamoyl]methyl}benzoate, methyl 3-{[N-(5,6-dimethoxybenzothiazol-2-yl)carbamoyl]methyl}benzoate, 3-{[N-(5,6-dimethoxybenzothiazol-2-yl)carbamoyl]methyl}benzoic acid, 4-{[N-(5,6-dimethoxybenzothiazol-2-yl)carbamoyl]methyl}benzoic acid, 2-{[N-(5,6-dimethoxybenzothiazol-2-yl)carbamoyl]methyl}benzoic acid, N-(5,6-dimethoxybenzothiazol-2-yl)-2-[4-(ethylsulfonyl)phenyl]propanamide, N-(5,6-dimethoxybenzothiazol-2-yl)-2-[4-(ethylsulfonyl)phenyl]butanamide, N-(5,6-dimethoxybenzothiazol-2-yl)-2-[4-(ethylsulfonyl)phenyl]-3-methylbutanamide, N-(5,6-dimethoxybenzothiazol-2-yl)-2-[4-(ethylsulfonyl)phenyl]-2-(4-methoxyphenoxy)acetamide, N-(5,6-dimethoxybenzothiazol-2-yl)-2-[3-(N,N-dimethylcarbamoyl)phenyl]acetamide, N-(5,6-dimethoxybenzothiazol-2-yl)-2-[4-(N,N-dimethylcarbamoyl)phenyl]acetamide, N-(5,6-dimethoxybenzothiazol-2-yl)-2-{4-[(dimethylamino)sulfonyl]phenyl}acetamide, N-(5,6-dimethoxybenzothiazol-2-yl)-2-[4-(ethylsulfonyl)phenyl]-4-methoxybutanamide, N-(5,6-dimethoxybenzothiazol-2-yl)-3-cyclopropyl-2-[4-(ethylsulfonyl)phenyl]propanamide, N-(5,6-dimethoxybenzothiazol-2-yl)-2-[4-(ethylsulfonyl)phenyl]-3-phenylpropanamide, N-(5,6-dimethoxybenzothiazol-2-yl)-2-[2-(N,N-dimethylcarbamoyl)phenyl]acetamide, N-(5,6-dimethoxybenzothiazol-2-yl)-2-[3-(ethylsulfonyl)phenyl]acetamide, N-(2H-1,3-dioxolano[4,5-e]benzothiazol-7-yl)-2-[4-(ethylsulfonyl)phenyl]acetamide, N-(5,6-dimethoxybenzothiazol-2-yl){[4-(ethylsulfonyl)phenyl]cyclopropyl}carboxamide, N-(5,6-dimethoxybenzothiazol-2-yl)-2-cyclopentyl-2-[4-(ethylsulfonyl)phenyl]acetamide, N-(7H,8H-1,4-dioxano[5,6-e]benzothiazol-2-yl)-2-[4-(ethylsulfonyl)phenyl]acetamide, N-[5-(diethylamino)benzothiazol-2-yl]-2-[4-(ethylsulfonyl)phenyl]acetamide, N-(5,6-dimethoxybenzothiazol-2-yl)-2-{3-[(4-fluorophenyl)sulfonyl]phenyl}acetamide, N-(5,6-dimethoxybenzothiazol-2-yl)-2-{4-[(cyclopropylmethyl)sulfonyl]phenyl}acetamide, N-(5,6-dimethoxybenzothiazol-2-yl)-2-[4-(cyclopentylsulfonyl)phenyl]acetamide, N-(5,6-dimethoxybenzothiazol-2-yl)-2-[4-(ethylsulfonyl)phenyl]-2-methoxyacetamide, N-(5,6-dimethoxybenzimidazol-2-yl)-2-[4-(ethylsulfonyl)phenyl]acetamide, N-(5,6-dimethoxybenzothiazol-2-yl)-2-(dimethylamino)-2-[4-(ethylsulfonyl)phenyl]acetamide, N-(5,6-dimethoxybenzothiazol-2-yl)-2-[4-(ethylsulfonyl)phenyl]-2-piperidylacetamide, N-(5,6-dimethoxybenzothiazol-2-yl)-2-[4-(ethylsulfonyl)phenyl]-2-morpholin-4-ylacetamide, N-(5,6-dimethoxybenzoxazol-2-yl)-2-[4-(ethylsulfonyl)phenyl]acetamide, N-(5,6-dimethoxybenzothiazol-2-yl)-2-{4-[(2-methoxyethyl)sulfonyl]phenyl}acetamide, N-(5,6-dimethoxybenzothiazol-2-yl)-2-{3-[(methylethyl)sulfonyl]phenyl}acetamide, N-(5,6-dimethoxybenzothiazol-2-yl)-2-{3-[(cyclopropylmethyl)sulfonyl]phenyl}acetamide, N-(5,6-dimethoxybenzothiazol-2-yl)-2-[3-(cyclopentylsulfonyl)phenyl]acetamide, N-(5,6-dimethoxybenzothiazol-2-yl)-2-[4-(ethylsulfonyl)phenyl]-2-(2-methoxyphenoxy)acetamide, N-(5,6-dimethoxybenzothiazol-2-yl)-2-[4-(ethylsulfonyl)phenyl]-2-(3-methoxyphenoxy)acetamide, N-(5,6-dimethoxybenzothiazol-2-yl)-2-[4-(ethylsulfonyl)phenyl]-2-[4-(trifluoromethyl)phenoxy]acetamide, N-(5,6-dimethoxybenzothiazol-2-yl)-2-(4-cyanophenoxy)-2-[4-(ethylsulfonyl)phenyl]acetamide, N-(5,6-dimethoxybenzothiazol-2-yl)-2-[4-(ethylsulfonyl)phenyl]-2-(methylethoxy)acetamide, N-(5,6-dimethoxybenzothiazol-2-yl)-2-[4-(ethylsulfonyl)phenyl]-2-propoxyacetamide, N-(5,6-dimethoxybenzothiazol-2-yl)-2-cyclopentyloxy-2-[4-(ethylsulfonyl)phenyl]acetamide, N-(5,6-dimethoxybenzothiazol-2-yl)-2-cyclohexyloxy-2-[4-(ethylsulfonyl)phenyl]acetamide, N-(5,6-dimethoxybenzothiazol-2-yl)-2-[4-(ethylsulfonyl)phenyl]-2-(3-methylbutoxy)acetamide, 2-[4-(ethylsulfonyl)phenyl]-N-[6-(4-methylpiperazinyl)benzothiazol-2-yl]acetamide, 2-[4-(ethylsulfonyl)phenyl]-2-(4-methoxyphenoxy)-N-[6-(4-methylpiperazinyl)benzothiazol-2-yl]acetamide, N-(5,6-dimethoxybenzothiazol-2-yl)-2-{2-[(4-fluorophenyl)sulfonyl]phenyl}-2-(4-methoxyphenoxy)acetamide, N-(5,6-dimethoxybenzothiazol-2-yl)-2-[3-(ethylsulfonyl)phenyl]-2-(4-methoxyphenoxy)acetamide, N-(5,6-dimethoxybenzothiazol-2-yl)-2-[4-(ethylsulfonyl)phenyl]-2-(4-methylphenoxy)acetamide, N-(5,6-dimethoxybenzothiazol-2-yl)-2-(4-chlorophenoxy)-2-[4-

(ethylsulfonyl)phenyl]acetamide, N-(5,6-dimethoxybenzothiazol-2-yl)-2-[4-(ethylsulfonyl)phenyl]-2-(2-methylphenoxy)acetamide, N-(5,6-dimethoxybenzothiazol-2-yl)-2-(2-chlorophenoxy)-2-[4-(ethylsulfonyl)phenyl]acetamide, N-(5,6-dimethoxybenzothiazol-2-yl)-2-[4-(ethylsulfonyl)phenyl]-2-(phenylmethoxy)acetamide, N-(5,6-dimethoxybenzothiazol-2-yl)-2-[4-(ethylsulfonyl)phenyl]-2-(2-methylpropoxy)acetamide, N-(5,6-dimethoxybenzothiazol-2-yl)-2-[4-(ethylsulfonyl)phenyl]-2-(3-methylbut-2-enyloxy)acetamide, 2-(2H-3,4,5,6-tetrahydropyran-4-yloxy)-N-(5,6-dimethoxybenzothiazol-2-yl)-2-[4-(ethylsulfonyl)phenyl]acetamide, N-(7H,8H-1,4-dioxano[5,6-g]benzothiazol-2-yl)-2-[4-(ethylsulfonyl)phenyl]-2-(4-methoxyphenoxy)acetamide, N-(7H,8H-1,4-dioxano[5,6-g]benzothiazol-2-yl)-2-(4-cyanophenoxy)-2-[4-(ethylsulfonyl)phenyl]acetamide, 2-[4-(ethylsulfonyl)phenyl]-N-(6-methoxybenzothiazol-2-yl)-2-(4-methoxyphenoxy)acetamide, 2-(4-cyanophenoxy)-2-[4-(ethylsulfonyl)phenyl]-N-(6-methoxybenzothiazol-2-yl)acetamide, N-(5,6-dimethoxybenzothiazol-2-yl)-2-(4-cyanophenoxy)-2-{2-[(4-fluorophenyl)sulfonyl]phenyl}acetamide, N-(5,6-dimethoxybenzothiazol-2-yl)-2-(4-methoxyphenoxy)-2-{2-[(4-methoxyphenyl)sulfonyl]phenyl}acetamide, N-(5,6-dimethoxybenzothiazol-2-yl)-2-(4-cyanophenoxy)-2-{2-[(4-methoxyphenyl)sulfonyl]phenyl}acetamide, N-(5,6-dimethoxybenzothiazol-2-yl)-2-{3-[(4-fluorophenyl)sulfonyl]phenyl}-2-(4-methoxyphenoxy)acetamide, N-(5,6-dimethoxybenzothiazol-2-yl)-2-(3-chlorophenoxy)-2-[4-(ethylsulfonyl)phenyl]acetamide, N-(5,6-dimethoxybenzothiazol-2-yl)-2-[4-(ethylsulfonyl)phenyl]-2-(3-methylphenoxy)acetamide, N-(5,6-dimethoxybenzothiazol-2-yl)-2-[4-(ethylsulfonyl)phenyl]-2-phenoxyacetamide, N-(5,6-dimethoxybenzothiazol-2-yl)-2-(4-cyano-3-fluorophenoxy)-2-[4-(ethylsulfonyl)phenyl]acetamide, N-(5,6-dimethoxybenzothiazol-2-yl)-2-[4-(ethylsulfonyl)phenyl]-2-(2-methoxyethoxy)acetamide, N-(2H-1,3-dioxolano[4,5-g]benzothiazol-7-yl)-2-[4-(ethylsulfonyl)phenyl]-2-(4-methoxyphenoxy)acetamide, N-(2H-1,3-dioxolano[4,5-g]benzothiazol-7-yl)-2-(4-cyanophenoxy)-2-[4-(ethylsulfonyl)phenyl]acetamide, 2-(4-cyanophenoxy)-2-[4-(ethylsulfonyl)phenyl]-N-(5-methoxybenzothiazol-2-yl)acetamide, N-(4,7-dimethoxybenzothiazol-2-yl)-2-(4-cyanophenoxy)-2-[4-(ethylsulfonyl)phenyl]acetamide, N-(2H-1,3-dioxoleno[4,5-f]benzothiazol-6-yl)-2-[4-(ethylsulfonyl)phenyl]-2-(4-methoxyphenoxy)acetamide, N-(4,7-dimethoxybenzothiazol-2-yl)-2-[4-(ethylsulfonyl)phenyl]-2-(4-methoxyphenoxy)acetamide, 2-(4-cyanophenoxy)-2-[4-(ethylsulfonyl)phenyl]-N-[6-(4-methylpiperazinyl)benzothiazol-2-yl]acetamide, N-(5,6-dimethoxybenzothiazol-2-yl)-2-(4-cyanophenoxy)-2-{2-[benzylsulfonyl]phenyl}acetamide, N-(5,6-dimethoxybenzothiazol-2-yl)-2-(4-cyanophenoxy)-2-[2-(ethylsulfonyl)phenyl]acetamide, N-(5,6-dimethoxybenzothiazol-2-yl)-2-(4-cyanophenoxy)-2-{3-[(4-fluorophenyl)sulfonyl]phenyl}acetamide, N-(5,6-dimethoxybenzothiazol-2-yl)-2-(4-cyanophenoxy)-2-{3-[benzylsulfonyl]phenyl}acetamide, N-[4-(3,4-dimethoxyphenyl)(1,3-thiazol-2-yl)]-2-(4-cyanophenoxy)-2-[4-(ethylsulfonyl)phenyl]acetamide, 2-(4-cyanophenoxy)-2-[4-(ethylsulfonyl)phenyl]-N-[4-(3-methoxyphenyl)(1,3-thiazol-2-yl)]acetamide, 2-(4-cyanophenoxy)-2-[4-(ethylsulfonyl)phenyl]-N-(4-phenyl(1,3-thiazol-2-yl))acetamide, methyl 2-(2-{2-(4-cyanophenoxy)-2-[4-(ethylsulfonyl)phenyl]acetylamino}-1,3-thiazol-4-yl) acetate, 4-{1-[4-(ethylsulfonyl)phenyl]-2-(4-hydroxypiperidyl)-2-oxoethoxy}benzenecarbonitrile, 4-{1-[4-(ethylsulfonyl)phenyl]-2-oxo-2-(4-oxopiperidyl)ethoxy}benzenecarbonitrile, 2-(4-cyanophenoxy)-2-[4-(ethylsulfonyl)phenyl]-N-(4-hydroxycyclohexyl)acetamide, 2-(4-cyanophenoxy)-2-[4-(ethylsulfonyl)phenyl]-N-(3-methoxypropyl)acetamide and 2-(4-cyanophenoxy)-2-[4-(ethylsulfonyl)phenyl]-N-(2-morpholin-4-ylethyl)acetamide.

4. A compound selected from the group consisting of: N-[1,3]Dioxolo[4',5':3,4]benzo[2,1-d]thiazol-7-yl-2-(4-ethanesulfonyl-phenyl)-acetamide, N-(7,8-Dihydro-6,9-dioxa-3-thia-1-aza-cyclopenta[a]naphthalen-2-yl)-2-(4-ethanesulfonyl-phenyl)-acetamide, N-(5-Dimethylamino-benzothiazol-2-yl)-2-(4-ethanesulfonyl-phenyl)-acetamide, N-(5-Diethylamino-benzothiazol-2-yl)-2-(4-ethanesulfonyl-phenyl)-acetamide, 2-(4-Ethanesulfonyl-phenyl)-N-[6-(4-methyl-piperazin-1-yl)-benzothiazol-2-yl]-acetamide, N-(5,6-Dimethoxy-1H-benzoimidazol-2-yl)-2-(4-ethanesulfonyl-phenyl)-acetamide, N-(5,6-dimethoxy-benzooxazol-2-yl)-2-(4-ethanesulfonyl-phenyl)-acetamide, 2-(4-Cyclopropylmethanesulfonyl-phenyl)-N-(5,6-dimethoxy-benzothiazol-2-yl)-acetamide, N-(5,6-Dimethoxy-benzothiazol-2-yl)-2-[4-(propane-2-sulfonyl)-phenyl]-acetamide, 2-(4-Cyclopentanesulfonyl-phenyl)-N-(5,6-dimethoxy-benzothiazol-2-yl)-acetamide, N-(5,6-Dimethoxy-benzothiazol-2-yl)-2-[4-(2-methoxy-ethanesulfonyl)-phenyl]-acetamide, N-(5,6-Dimethoxy-benzothiazol-2-yl)-2-(3-ethanesulfonyl-phenyl)-acetamide, 2-(3-Cyclopropylmethanesulfonyl-phenyl)-N-(5,6-dimethoxy-benzothiazol-2-yl)-acetamide, N-(5,6-Dimethoxy-benzothiazol-2-yl)-2-[3-(propane-2-sulfonyl)-phenyl]-acetamide, 2-(3-Cyclopentanesulfonyl-phenyl)-N-(5,6-dimethoxy-benzothiazol-2-yl)-acetamide, N-(5,6-Dimethoxy-benzothiazol-2-yl)-2-(3-ethanesulfonyl-phenyl)-acetamide, N-(5,6-Dimethoxy-benzothiazol-2-yl)-2-(4-dimethylsulfamoyl-phenyl)-acetamide, 2-[(5,6-Dimethoxy-benzothiazol-2-ylcarbamoyl)-methyl]-benzoic acid, 3-[(5,6-Dimethoxy-benzothiazol-2-ylcarbamoyl)-methyl]-benzoic acid, 4-[(5,6-Dimethoxy-benzothiazol-2-ylcarbamoyl)-methyl]-benzoic acid, 3-[(5,6-Dimethoxy-benzothiazol-2-ylcarbamoyl)-methyl]-benzoic acid methyl ester, 4-[(5,6-Dimethoxy-benzothiazol-2-ylcarbamoyl)-methyl]-benzoic acid methyl ester, 2-[(5,6-Dimethoxy-benzothiazol-2-ylcarbamoyl)-methyl]-N,N-dimethyl-benzamide, 3-[(5,6-Dimethoxy-benzothiazol-2-ylcarbamoyl)-methyl]-N,N-dimethyl-benzamide, 4-[(5,6-Dimethoxy-benzothiazol-2-ylcarbamoyl)-methyl]-N,N-dimethyl-benzamide, N-(5,6-Dimethoxy-benzothiazol-2-yl)-2-(4-ethanesulfonyl-phenyl)-propionamide, N-(5,6-Dimethoxy-benzothiazol-2-yl)-2-(4-ethanesulfonyl-phenyl)-butyramide, N-(5,6-Dimethoxy-benzothiazol-2-yl)-2-(4-ethanesulfonyl-phenyl)-3-methyl-butyramide, N-(5,6-Dimethoxy-benzothiazol-2-yl)-2-(4-ethanesulfonyl-phenyl)-4-methoxy-butyramide, 3-Cyclopropyl-N-(5,6-dimethoxy-benzothiazol-2-yl)-2-(4-ethanesulfonyl-phenyl)-propionamide, N-(5,6-Dimethoxy-benzothiazol-2-yl)-2-(4-ethanesulfonyl-phenyl)-3-phenyl-propionamide, 2-Cyclopentyl-N-(5,6-dimethoxy-benzothiazol-2-yl)-2-(4-ethanesulfonyl-phenyl)-acetamide, 1-(4-Ethanesulfonyl-phenyl)-cyclopropanecarboxylic acid (5,6-dimethoxy-benzothiazol-2-yl)-amide, N-(5,6-Dimethoxy-benzothiazol-2-yl)-2-(4-ethanesulfonyl-phenyl)-2-isopropoxy-acetamide, N-(5,6-Dimethoxy-benzothiazol-2-yl)-2-(4-ethanesulfonyl-phenyl)-2-methoxy-acetamide, N-(5,6-Dimethoxy-benzothiazol-2-yl)-2-(4-ethanesulfonyl-phenyl)-2-propoxy-acetamide, 2-Cyclopentyloxy-N-(5,6-dimethoxy-benzothiazol- 2-yl)-2-(4-ethanesulfonyl-phenyl)-acetamide, 2-Cyclohexyloxy-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(3-methyl-butoxy)-acetamide, 2-Benzyloxy-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-isobutoxy-acetamide, N-(5,6-Dimethoxy-benzothiazol-2-yl)-2-(4-ethanesulfonyl-phenyl)-2-(3-methyl-but-2-enyloxy)-acetamide, N-(5,6-Dimethoxy-benzothiazol-2-yl)-2-(4-ethanesulfonyl-phenyl)-2-(tetrahydro-pyran-4-yloxy)-acetamide, N-(5,6-Dimethoxy-benzothiazol-2-yl)-2-(4-ethanesulfonyl-phenyl)-2-(2-methoxy-ethoxy)-acetamide, 2-Cyclohexylmethoxy-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(tetrahydro-pyran-4-ylmethoxy)-acetamide, N-(5,6-Dimethoxy-benzothiazol-2-yl)-2-(4-ethanesulfonyl-phenyl)-2-(3-methoxy-propoxy)-acetamide, N-(5,6-Dimethoxy-benzothiazol-2-yl)-2-(4-ethanesulfonyl-phenyl)-2-phenethyloxy-acetamide, 2-(4-Cyano-benzyloxy)-N-(5,6-dimethoxy-benzothiazol-2-yl)-2-(4-ethanesulfonyl-phenyl)-acetamide, 2-(4-Cyano-phenoxy)-N-(5,6-dimethoxy-benzothiazol-2-yl)-2-(4-ethanesulfonyl-phenyl)-acetamide (SBI-0662457), 2-(4-Cyano-phenoxy)-N-(5,6-dimethoxy-benzothiazol-2-yl)-2-(4-ethanesulfonyl-phenyl)-acetamide, 2-(4-Cyano-phenoxy)-N-(5,6-dimethoxy-benzothiazol-2-yl)-2-(4-ethanesulfonyl-phenyl)-acetamide, 2-(4-Cyano-phenoxy)-N-(5,6-dimethoxy-benzothiazol-2-yl)-2-(4-ethanesulfonyl-phenyl)-N-methyl-acetamide, 2-(3-Cyano-phenoxy)-N-(5,6-dimethoxy-benzothiazol-2-yl)-2-(4-ethanesulfonyl-phenyl)-acetamide, 2-(4-Cyano-2-trifluoromethyl-phenoxy)-N-(5,6-dimethoxy-benzothiazol-2-yl)-2-(4-ethanesulfonyl-phenyl)-acetamide, 2-(2-Chloro-4-cyano-phenoxy)-N-(5,6-dimethoxy-benzothiazol-2-yl)-2-(4-ethanesulfonyl-phenyl)-acetamide, 2-(3-Chloro-4-cyano-phenoxy)-N-(5,6-dimethoxy-benzothiazol-2-yl)-2-(4-ethanesulfonyl-phenyl)-acetamide, 2-(4-Cyano-2-fluoro-phenoxy)-N-(5,6-dimethoxy-benzothiazol-2-yl)-2-(4-ethanesulfonyl-phenyl)-acetamide, 2-(4-Cyano-3-fluoro-phenoxy)-N-(5,6-dimethoxy-benzothiazol-2-yl)-2-(4-ethanesulfonyl-phenyl)-acetamide, 2-(4-Cyano-2-methyl-phenoxy)-N-(5,6-dimethoxy-benzothiazol-2-yl)-2-(4-ethanesulfonyl-phenyl)-acetamide, 2-(4-Cyano-3-methyl-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(naphthalen-1-yloxy)-acetamide, N-(5,6-Dimethoxy-benzothiazol-2-yl)-2-(4-ethanesulfonyl-phenyl)-2-(naphthalen-2-yloxy)-acetamide, N-(5,6-Dimethoxy-benzothiazol-2-yl)-2-(4-ethanesulfonyl-phenyl)-2-phenoxy-acetamide, 2-(4-Chloro-phenoxy)-N-(5,6-dimethoxy-benzothiazol-2-yl)-2-(4-ethanesulfonyl-phenyl)-acetamide, 2-(2-Chloro-phenoxy)-N-(5,6-dimethoxy-benzothiazol-2-yl)-2-(4-ethanesulfonyl-phenyl)-acetamide, 2-(3-Chloro-phenoxy)-N-(5,6-dimethoxy-benzothiazol-2-yl)-2-(4-ethanesulfonyl-phenyl)-acetamide, 2-(4-Bromo-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(4-iodo-phenoxy)-acetamide, N-(5,6-Dimethoxy-benzothiazol-2-yl)-2-(4-ethanesulfonyl-phenyl)-2-(4-ethynyl-phenoxy)-acetamide, N-(5,6-Dimethoxy-benzothiazol-2-yl)-2-(4-ethanesulfonyl-phenyl)-2-(iodo-phenoxy)-acetamide, N-(5,6-Dimethoxy-benzothiazol-2-yl)-2-(4-ethanesulfonyl-phenyl)-2-(4-fluoro-phenoxy)-acetamide, N-(5,6-Dimethoxy-benzothiazol-2-yl)-2-(4-ethanesulfonyl-phenyl)-2-(4-trifluoromethyl-phenoxy)-acetamide, N-(5,6-Dimethoxy-benzothiazol-2-yl)-2-(4-ethanesulfonyl-phenyl)-2-p-tolyloxy-acetamide, N-(5,6-Dimethoxy-benzothiazol-2-yl)-2-(4-ethanesulfonyl-phenyl)-2-o-tolyloxy-acetamide, N-(5,6-Dimethoxy-benzothiazol-2-yl)-2-(4-ethanesulfonyl-phenyl)-2-m-tolyloxy-acetamide, N-(5,6-Dimethoxy-benzothiazol-2-yl)-2-(4-ethanesulfonyl-phenyl)-2-(4-ethyl-phenoxy)-acetamide, N-(5,6-Dimethoxy-benzothiazol-2-yl)-2-(4-ethanesulfonyl-phenyl)-2-(4-propyl-phenoxy)-acetamide, N-(5,6-Dimethoxy-benzothiazol-2-yl)-2-(4-ethanesulfonyl-phenyl)-2-(4-isopropyl-phenoxy)-acetamide, 2-(4-Butyl-phenoxy)-N-(5,6-dimethoxy-benzothiazol-2-yl)-2-(4-ethanesulfonyl-phenyl)-acetamide, 2-(4-Cyclopentyl-phenoxy)-N-(5,6-dimethoxy-benzothiazol-2-yl)-2-(4-ethanesulfonyl-phenyl)-acetamide, 2-(4-Cyclohexyl-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(4-trifluoromethoxy-phenoxy)-acetamide, N-(5,6-Dimethoxy-benzothiazol-2-yl)-2-(4-ethanesulfonyl-phenyl)-2-(4-methoxy-phenoxy)-acetamide, N-(5,6-Dimethoxy-benzothiazol-2-yl)-2-(4-ethanesulfonyl-phenyl)-2-(2-methoxy-phenoxy)-acetamide, N-(5,6-Dimethoxy-benzothiazol-2-yl)-2-(4-ethanesulfonyl-phenyl)-2-(3-methoxy-phenoxy)-acetamide, N-(5,6-Dimethoxy-benzothiazol-2-yl)-2-(4-ethanesulfonyl-phenyl)-2-(4-ethoxy-phenoxy)-acetamide, N-(5,6-Dimethoxy-benzothiazol-2-yl)-2-(4-ethanesulfonyl-phenyl)-2-(4-propoxy-phenoxy)-acetamide, 2-(4-Butoxy-phenoxy)-N-(5,6-dimethoxy-benzothiazol-2-yl)-2-(4-ethanesulfonyl-phenyl)-acetamide, 2-(4-Benzyloxy-phenoxy)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-(4-nitro-phenoxy)-acetamide, N-(5,6-Dimethoxy-benzothiazol-2-yl)-2-(4-dimethylamino-phenoxy)-2-(4-ethanesulfonyl-phenyl)-acetamide, 4-[(5,6-Dimethoxy-benzothiazol-2-ylcarbamoyl)-(4-ethanesulfonyl-phenyl)-methoxy]-benzoic acid methyl ester, 4-[(5,6-Dimethoxy-benzothiazol-2-ylcarbamoyl)-(4-ethanesulfonyl-phenyl)-methoxy]-benzoic acid, 4-[(5,6-Dimethoxy-benzothiazol-2-ylcarbamoyl)-(4-ethanesulfonyl-phenyl)-methoxy]-N,N-dimethyl-benzamide, N-(5,6-Dimethoxy-benzothiazol-2-yl)-2-(4-ethanesulfonyl-phenyl)-2-(4-methoxy-phenylamino)-acetamide, N-(5,6-Dimethoxy-benzothiazol-2-yl)-2-(4-ethanesulfonyl-phenyl)-2-(3-methoxy-phenylamino)-acetamide, N-(5,6-Dimethoxy-benzothiazol-2-yl)-2-(4-ethanesulfonyl-phenyl)-2-(2-methoxy-phenylamino)-acetamide, N-(5,6-Dimethoxy-benzothiazol-2-yl)-2-(4-ethanesulfonyl-phenyl)-2-p-tolylamino-acetamide, N-(5,6-Dimethoxy-benzothiazol-2-yl)-2-(4-ethanesulfonyl-phenyl)-2-m-tolylamino-acetamide, N-(5,6-Dimethoxy-benzothiazol-2-yl)-2-(4-ethanesulfonyl-phenyl)-2-o-tolylamino-acetamide, 2-(4-Cyano-phenylamino)-N-(5,6-dimethoxy-benzothiazol-2-yl)-2-(4-ethanesulfonyl-phenyl)-acetamide, N-(5,6-Dimethoxy-benzothiazol-2-yl)-2-(4-ethanesulfonyl-phenyl)-2-isobutylamino-acetamide, 2-Cyclopentylamino-N-(5,6-dimethoxy-benzothiazol-2-yl)-2-(4-ethanesulfonyl-phenyl)-acetamide, N-(5,6-Dimethoxy-benzothiazol-2-yl)-2-dimethylamino-2-(4-ethanesulfonyl-phenyl)-acetamide, N-(5,6-Dimethoxy-benzothiazol-2-yl)-2-(4-ethanesulfonyl-phenyl)-2-piperidin-1-yl-acetamide, N-(5,6-Dimethoxy-benzothiazol-2-yl)-2-(4-ethanesulfonyl-phenyl)-2-morpholin-4-yl-acetamide, 2-(4-Cyano-phenoxy)-N-(5,6-dimethoxy-benzothiazol-2-yl)-2-(4-phenyl-methanesulfonyl-phenyl)-acetamide, 2-(4-Cyano-phenoxy)-

N-(5,6-dimethoxy-benzothiazol-2-yl)-2-[4-(propane-2-sulfonyl)-phenyl]-acetamide, 2-[4-(Butane-1-sulfonyl)-phenyl]-2-(4-cyano-phenoxy)-N-(5,6-dimethoxy-benzothiazol-2-yl)-acetamide, 2-(4-Cyano-phenoxy)-2-(4-cyclopropylmethanesulfonyl-phenyl)-N-(5,6-dimethoxy-benzothiazol-2-yl)-acetamide, 2-(4-Cyano-phenoxy)-N-(5,6-dimethoxy-benzothiazol-2-yl)-2-[4-(2-methoxy-ethanesulfonyl)-phenyl]-acetamide, 2-(4-Cyano-phenoxy)-N-(5,6-dimethoxy-benzothiazol-2-yl)-2-(2-phenylmethanesulfonyl-phenyl)-acetamide, 2-(4-Cyano-phenoxy)-N-(5,6-dimethoxy-benzothiazol-2-yl)-2-(2-ethanesulfonyl-phenyl)-acetamide, 2-(4-Cyano-phenoxy)-N-(5,6-dimethoxy-benzothiazol-2-yl)-2-[2-(propane-2-sulfonyl)-phenyl]-acetamide, 2-[2-(Butane-1-sulfonyl)-phenyl]-2-(4-cyano-phenoxy)-N-(5,6-dimethoxy-benzothiazol-2-yl)-acetamide, N-(5,6-Dimethoxy-benzothiazol-2-yl)-2-[2-(4-fluoro-benzenesulfonyl)-phenyl]-2-(4-methoxy-phenoxy)-acetamide, 2-(4-Cyano-phenoxy)-N-(5,6-dimethoxy-benzothiazol-2-yl)-2-[2-(4-fluoro-benzenesulfonyl)-phenyl]-acetamide, N-(5,6-Dimethoxy-benzothiazol-2-yl)-2-[2-(4-methoxy-benzenesulfonyl)-phenyl]-2-(4-methoxy-phenoxy)-acetamide, 2-(4-Cyano-phenoxy)-N-(5,6-dimethoxy-benzothiazol-2-yl)-2-[2-(4-methoxy-benzenesulfonyl)-phenyl]-acetamide, 2-(4-Cyano-phenoxy)-N-(5,6-dimethoxy-benzothiazol-2-yl)-2-(3-phenylmethanesulfonyl-phenyl)-acetamide, 2-(4-Cyano-phenoxy)-N-(5,6-dimethoxy-benzothiazol-2-yl)-2-(3-ethanesulfonyl-phenyl)-acetamide, 2-(4-Cyano-phenoxy)-N-(5,6-dimethoxy-benzothiazol-2-yl)-2-[3-(propane-2-sulfonyl)-phenyl]-acetamide, 2-[3-(Butane-1-sulfonyl)-phenyl]-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-[3-(2-methyl-propane-2-sulfonyl)-phenyl]-acetamide, 2-(4-Cyano-phenoxy)-N-(5,6-dimethoxy-benzothiazol-2-yl)-2-[3-(4-fluoro-benzenesulfonyl)-phenyl]-acetamide, 2-(4-Cyano-phenoxy)-N-(5,6-dimethoxy-benzothiazol-2-yl)-2-[3-(4-methoxy-benzenesulfonyl)-phenyl]-acetamide, 2-(4-Cyano-phenoxy)-N-(5,6-dimethoxy-benzothiazol-2-yl)-2-[4-(4-fluoro-benzenesulfonyl)-phenyl]-acetamide, 2-(4-Cyano-phenoxy)-N-(5,6-dimethoxy-benzothiazol-2-yl)-2-[4-(4-methoxy-benzenesulfonyl)-phenyl]-acetamide, 2-[3-(4-Chloro-benzenesulfonyl)-phenyl]-2-(4-cyano-phenoxy)-N-(5,6-dimethoxy-benzothiazol-2-yl)-acetamide, 2-[4-(4-Chloro-benzenesulfonyl)-phenyl]-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-[4-(4-trifluoromethyl-benzenesulfonyl)-phenyl]-acetamide, N-(5,6-Dimethoxy-benzothiazol-2-yl)-2-(3-ethanesulfonyl-phenyl)-2-(4-methoxy-phenoxy)-acetamide, N-(5,6-Dimethoxy-benzothiazol-2-yl)-2-[3-(4-fluoro-benzenesulfonyl)-phenyl]-2-(4-methoxy-phenoxy)-acetamide, 2-(4-Cyano-phenoxy)-N-(5,6-dimethoxy-benzothiazol-2-yl)-2-(4-dimethylsulfamoyl-phenyl)-acetamide, 2-(4-Cyano-phenoxy)-N-(5,6-dimethoxy-benzothiazol-2-yl)-2-[4-(2-methoxy-ethylsulfamoyl)-phenyl]-acetamide, 2-(4-Cyano-phenoxy)-N-(5,6-dimethoxy-benzothiazol-2-yl)-2-[4-(2-dimethylamino-ethylsulfamoyl)-phenyl]-acetamide, 4-[(4-Cyano-phenoxy)-(5,6-dimethoxy-benzothiazol-2-ylcarbamoyl)-methyl]-benzoic acid methyl ester, 4-[(4-Cyano-phenoxy)-(5,6-dimethoxy-benzothiazol-2-ylcarbamoyl)-methyl]-benzoic acid, 4-[(4-Cyano-phenoxy)-(5,6-dimethoxy-benzothiazol-2-ylcarbamoyl)-methyl]-N,N-dimethyl-benzamide, 4-[(4-Cyano-phenoxy)-(5,6-dimethoxy-benzothiazol-2-ylcarbamoyl)-methyl]-N-(2-methoxy-ethyl)-benzamide, 4-[(4-Cyano-phenoxy)-(5,6-dimethoxy-benzothiazol-2-ylcarbamoyl)-methyl]-N-(2-dimethylamino-ethyl)-benzamide, 4-[(4-Cyano-phenoxy)-(5,6-dimethoxy-benzothiazol-2-ylcarbamoyl)-methyl]-N-(2-morpholin-4-yl-ethyl)-benzamide, 4-[(4-Cyano-phenoxy)-(5,6-dimethoxy-benzothiazol-2-ylcarbamoyl)-methyl]-N-(2-hydroxy-ethyl)-benzamide, 4-[(4-Cyano-phenoxy)-(5,6-dimethoxy-benzothiazol-2-ylcarbamoyl)-methyl]-N-(2-piperidin-1-yl-ethyl)-benzamide, 4-[(4-Cyano-phenoxy)-(5,6-dimethoxy-benzothiazol-2-ylcarbamoyl)-methyl]-N-(2-pyrrolidin-1-yl-ethyl)-benzamide, 2-(4-Cyano-phenoxy)-N-(5,6-dimethoxy-benzothiazol-2-yl)-2-[4-(4-methyl-piperazine-1-carbonyl)-phenyl]-acetamide, 2-(4-Cyano-phenoxy)-N-(5,6-dimethoxy-benzothiazol-2-yl)-2-[4-(piperazine-1-carbonyl)-phenyl]-acetamide, 2-(4-Cyano-phenoxy)-N-(5,6-dimethoxy-benzothiazol-2-yl)-2-(4-trifluoromethyl-phenyl)-acetamide, 2-(3-Bromo-phenyl)-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-p-tolyl-acetamide, 2-(4-Chloro-phenyl)-2-(4-cyano-phenoxy)-N-(5,6-dimethoxy-benzothiazol-2-yl)-acetamide, 2-(4-Cyano-phenoxy)-N-(5,6-dimethoxy-benzothiazol-2-yl)-2-(4-fluoro-phenyl)-acetamide, 2-(4-Cyano-phenoxy)-N-(5,6-dimethoxy-benzothiazol-2-yl)-2-phenyl-acetamide, 2-(4-Cyano-phenoxy)-N-(5,6-dimethoxy-benzothiazol-2-yl)-2-(4-nitro-phenyl)-acetamide, 2-(4-Cyano-phenoxy)-N-(5,6-dimethoxy-benzothiazol-2-yl)-2-(4-methoxy-phenyl)-acetamide, 2-(4-Cyano-phenoxy)-N-(5,6-dimethoxy-benzothiazol-2-yl)-2-(4-ethoxy-phenyl)-acetamide, 2-(4-Cyano-phenoxy)-N-(5,6-dimethoxy-benzothiazol-2-yl)-2-[4-(2-methoxy-ethoxy)-phenyl]-acetamide, 2-(4-Cyano-phenoxy)-N-(5,6-dimethoxy-benzothiazol-2-yl)-2-(4-isopropoxy-phenyl)-acetamide, 2-(4-cyano-phenoxy)-N-(5,6-dimethoxy-benzothiazol-2-yl)-2-[4-(2-morpholin-4-yl-ethoxy)-phenyl]-acetamide, 2-(4-cyano-phenoxy)-N-(5,6-dimethoxy-benzothiazol-2-yl)-2-[4-(2-piperidin-1-yl-ethoxy)-phenyl]-acetamide, 2-(4-Cyano-phenoxy)-N-(5,6-dimethoxy-benzothiazol-2-yl)-2-[4-(2-dimethylamino-ethoxy)-phenyl]-acetamide, 2-(4-Cyano-phenoxy)-N-(5,6-dimethoxy-benzothiazol-2-yl)-2-[4-(2-pyrrolidin-1-yl-ethoxy)-phenyl]-acetamide, 2-(4-Cyano-phenoxy)-N-(5,6-dimethoxy-benzothiazol-2-yl)-2-[4-(1H-tetrazol-5-yl)-phenyl]-acetamide, 2-(4-Cyano-phenoxy)-2-(4-cyano-phenyl)-N-(5,6-dimethoxy-benzothiazol-2-yl)-acetamide, 2-(4-Cyano-phenyl)-N-(5,6-dimethoxy-benzothiazol-2-yl)-2-phenoxy-acetamide, 4-[(4-Cyano-phenyl)-(5,6-dimethoxy-benzothiazol-2-ylcarbamoyl)-methoxy]-benzoic acid methyl ester, 4-[(4-Cyano-phenyl)-(5,6-dimethoxy-benzothiazol-2-ylcarbamoyl)-methoxy]-benzoic acid, 4-[(4-Cyano-phenyl)-(5,6-dimethoxy-benzothiazol-2-ylcarbamoyl)-methoxy]-N-(2-methoxy-ethyl)-benzamide, 4-[(4-Cyano-phenyl)-(5,6-dimethoxy-benzothiazol-2-ylcarbamoyl)-methoxy]-N-(2-morpholin-4-yl-ethyl)-benzamide, 4-[(4-Cyano-phenyl)-(5,6-dimethoxy-benzothiazol-2-ylcarbamoyl)-methoxy]-N-(2-hydroxy-ethyl)-benzamide, 4-[(4-Cyano-phenyl)-(5,6-dimethoxy-benzothiazol-2-ylcarbamoyl)-methoxy]-N-(2-pyrrolidin-1-yl-ethyl)-benzamide, 2-(4-Cyano-phenyl)-N-(5,6-dimethoxy-benzothiazol-2-yl)-2-[4-(4-methyl-piperazine-1-carbonyl)-phenoxy]-acetamide, 4-[(4-Cyano-phenyl)-(5,6-dimethoxy-benzothiazol-2-ylcarbamoyl)-methoxy]-N-(2-dimethylamino-ethyl)-benzamide, 4-[(4-Cyano-phenyl)-(5,6-dimethoxy-benzothiazol-2-ylcarbamoyl)-methoxy]-N-(2-piperidin-1-yl-ethyl)-benzamide, 4-[(4-Cyano-phenyl)-(5,6-dimethoxy-benzothiazol-2-ylcarbamoyl)-methoxy]-N,N-dimethyl-benzamide, 2-(4-Cyano-phenyl)-N-(5,6- dimethoxy-benzothiazol-2-yl)-2-[4-(piperazine-1-carbonyl)-phenoxy]-acetamide, 2-(4-Cyano-phenyl)-N-(5,6-dimethoxy-benzothiazol-2-yl)-2-(4-methoxy-phenoxy)-acetamide, 2-(4-Cyano-phenyl)-N-(5,6-dimethoxy-benzothiazol-2-yl)-2-(4-hydroxy-phenoxy)-acetamide, 2-(4-Cyano-phenyl)-N-(5,6-dimethoxy-benzothiazol-2-yl)-2-[4-(2-methoxy-ethoxy)-phenoxy]-acetamide, 2-(4-Cyano-phenyl)-N-(5,6-dimethoxy-benzothiazol-2-yl)-2-[4-(2-piperidin-1-yl-ethoxy)-phenoxy]-acetamide, 2-(4-Cyano-phenyl)-N-(5,6-dimethoxy-benzothiazol-2-yl)-2-[4-(2-pyrrolidin-1-yl-ethoxy)-phenoxy]-acetamide, 2-(4-Cyano-phenyl)-N-(5,6-dimethoxy-benzothiazol-2-yl)-2-[4-(2-morpholin-4-yl-ethoxy)-phenoxy]-acetamide, 2-(4-Cyano-phenyl)-N-(5,6-dimethoxy-benzothiazol-2-yl)-2-[4-(2-dimethylamino-ethoxy)-phenoxy]-acetamide, 2-(4-Cyano-phenyl)-N-(5,6-dimethoxy-benzothiazol-2-yl)-2-[4-(2-hydroxy-ethoxy)-phenoxy]-acetamide, 2-(4-Cyano-phenyl)-N-(5,6-dimethoxy-benzothiazol-2-yl)-2-[4-(1H-tetrazol-5-yl)-phenoxy]-acetamide, 2-(4-Cyano-phenoxy)-2-(4-ethanesulfonyl-phenyl)-N-(5-methoxy-benzothiazol-2-yl)-acetamide, 2-(4-Cyano-phenoxy)-N-(5-diethylamino-benzothiazol-2-yl)-2-(4-ethanesulfonyl-phenyl)-acetamide, 2-(4-Cyano-phenoxy)-2-(4-ethanesulfonyl-phenyl)-N-(6-methoxy-benzothiazol-2-yl)-acetamide, 2-(4-Ethanesulfonyl-phenyl)-N-(6-methoxy-benzothiazol-2-yl)-2-(4-methoxy-phenoxy)-acetamide, 2-(4-Cyano-phenoxy)-2-(4-ethanesulfonyl-phenyl)-N-[6-(4-methyl-piperazin-1-yl)-benzothiazol-2-yl]-acetamide, 2-(4-Ethanesulfonyl-phenyl)-2-(4-methoxy-phenoxy)-N-[6-(4-methyl-piperazin-1-yl)-benzothiazol-2-yl]-acetamide, 2-(4-Cyano-phenoxy)-2-(4-ethanesulfonyl-phenyl)-N-(6-morpholin-4-yl-benzothiazol-2-yl)-acetamide, 2-(4-Cyano-phenoxy)-N-(4,7-dimethoxy-benzothiazol-2-yl)-2-(4-ethanesulfonyl-phenyl)-acetamide, N-(4,7-Dimethoxy-benzothiazol-2-yl)-2-(4-ethanesulfonyl-phenyl)-2-(4-methoxy-phenoxy)-acetamide, 2-(4-Cyano-phenoxy)-N-[1,3]dioxolo[4',5':4,5]benzo[1,2-d]thiazol-6-yl-2-(4-ethanesulfonyl-phenyl)-acetamide, N-[1,3]Dioxolo[4',5':4,5]benzo[1,2-d]thiazol-6-yl-2-(4-ethanesulfonyl-phenyl)-2-(4-methoxy-phenoxy)-acetamide, 2-(4-cyano-phenoxy)-N-(6,7-dihydro-5,8-dioxa-1-thia-3-aza-cyclopenta[b]naphthalen-2-yl)-2-(4-ethanesulfonyl-phenyl)-acetamide, 2-(4-Cyano-phenoxy)-N-[1,3]dioxolo[4',5':3,4]benzo[2,1-d]thiazol-7-yl-2-(4-ethanesulfonyl-phenyl)-acetamide, 2-(4-Cyano-phenoxy)-N-(7,8-dihydro-6,9-dioxa-3-thia-1-aza-cyclopenta[a]naphthalen-2-yl)-2-(4-ethanesulfonyl-phenyl)-acetamide, 2-(4-Cyano-phenoxy)-2-(4-ethanesulfonyl-phenyl)-N-[6-(2-methoxy-ethoxy)-benzothiazol-2-yl]-acetamide, 2-(4-Cyano-phenoxy)-2-(4-ethanesulfonyl-phenyl)-N-[6-(2-morpholin-4-yl-ethoxy)-benzothiazol-2-yl]-acetamide, 2-(4-Cyano-phenoxy)-2-(4-ethanesulfonyl-phenyl)-N-[6-(2-hydroxy-ethoxy)-benzothiazol-2-yl]-acetamide, 2-(4-Cyano-phenoxy)-2-(4-ethanesulfonyl-phenyl)-N-{6-[2-(4-methyl-piperazin-1-yl)-ethoxy]-benzothiazol-2-yl}-acetamide, 2-(4-Cyano-phenoxy)-N-(7,8-dihydro-6,9-dioxa-1-thia-3-aza-cyclopenta[a]naphthalen-2-yl)-2-(4-ethanesulfonyl-phenyl)-acetamide, N-(7,8-Dihydro-6,9-dioxa-1-thia-3-aza-cyclopenta[a]naphthalen-2-yl)-2-(4-ethanesulfonyl-phenyl)-2-(4-methoxy-phenoxy)-acetamide, 2-(4-Cyano-phenoxy)-N-(1,3-dioxa-8-thia-6-aza-as-indacen-7-yl)-2-(4-ethanesulfonyl-phenyl)-acetamide, N-(1,3-Dioxa-8-thia-6-aza-as-indacen-7-yl)-2-(4-ethanesulfonyl-phenyl)-2-(4-methoxy-phenoxy)-acetamide 2-(4-Cyano-phenoxy)-N-(6,7-dimethoxy-benzothiazol-2-yl)-2-(4-ethanesulfonyl-phenyl)-acetamide, 2-(4-Cyano-phenoxy)-2-(4-ethanesulfonyl-phenyl)-N-(7-ethoxy-6-methoxy-benzothiazol-2-yl)-acetamide, 2-(4-Cyano-phenoxy)-2-(4-ethanesulfonyl-phenyl)-N-(7-isopropoxy-6-methoxy-benzothiazol-2-yl)-acetamide, 2-(4-Cyano-phenoxy)-2-(4-ethanesulfonyl-phenyl)-N-(7-methoxy-6-methyl-benzothiazol-2-yl)-acetamide, 2-(4-Cyano-phenoxy)-2-(4-ethanesulfonyl-phenyl)-N-(6-fluoro-7-methoxy-benzothiazol-2-yl)-acetamide, 2-(4-Cyano-phenoxy)-2-(4-ethanesulfonyl-phenyl)-N-(6-methoxy-5-methyl-benzothiazol-2-yl)-acetamide, N-(5-Chloro-6-methoxy-benzothiazol-2-yl)-2-(4-cyano-phenoxy)-2-(4-ethanesulfonyl-phenyl)-acetamide, 2-(4-Cyano-phenoxy)-2-(4-ethanesulfonyl-phenyl)-N-(5-fluoro-6-methoxy-benzothiazol-2-yl)-acetamide, N-(6-Chloro-5-methoxy-benzothiazol-2-yl)-2-(4-cyano-phenoxy)-2-(4-ethanesulfonyl-phenyl)-acetamide, 2-(4-Cyano-phenoxy)-2-(4-ethanesulfonyl-phenyl)-N-(5-methoxy-6-methyl-benzothiazol-2-yl)-acetamide, N-(5-Benzyloxy-6-methoxy-benzothiazol-2-yl)-2-(4-cyano-phenoxy)-2-(4-ethanesulfonyl-phenyl)-acetamide, 2-(4-Cyano-phenoxy)-2-(4-ethanesulfonyl-phenyl)-N-(5-isopropoxy-6-methoxy-benzothiazol-2-yl)-acetamide, 2-(4-Cyano-phenoxy)-2-(4-ethanesulfonyl-phenyl)-N-(5-ethoxy-6-methoxy-benzothiazol-2-yl)-acetamide, 2-(4-Cyano-phenoxy)-2-(4-ethanesulfonyl-phenyl)-N-[6-methoxy-5-(2-methoxy-ethoxy)-benzothiazol-2-yl]-acetamide, 2-(4-Cyano-phenoxy)-2-(4-ethanesulfonyl-phenyl)-N-[5-(2-hydroxy-ethoxy)-6-methoxy-benzothiazol-2-yl]-acetamide, 2-(4-Cyano-phenoxy)-N-(5-cyclopropylmethoxy-6-methoxy-benzothiazol-2-yl)-2-(4-ethanesulfonyl-phenyl)-acetamide, 2-(4-Cyano-phenoxy)-N-[5-(2-dimethylamino-ethoxy)-6-methoxy-benzothiazol-2-yl]-2-(4-ethanesulfonyl-phenyl)-acetamide, 2-(4-Cyano-phenoxy)-2-(4-ethanesulfonyl-phenyl)-N-[6-methoxy-5-(2-morpholin-4-yl-ethoxy)-benzothiazol-2-yl]-acetamide, 2-(4-Cyano-phenoxy)-2-(4-ethanesulfonyl-phenyl)-N-[5-(2-fluoro-ethoxy)-6-methoxy-benzothiazol-2-yl]-acetamide, 2-(4-Cyano-phenoxy)-2-(4-ethanesulfonyl-phenyl)-N-(6-methoxy-thiazolo[4,5-b]pyridin-2-yl)-acetamide, 2-(4-Cyano-phenoxy)-2-(4-ethanesulfonyl-phenyl)-N-(6-methoxy-thiazolo[4,5-b]pyridin-2-yl)-acetamide, 2-(4-Cyano-phenoxy)-N-(5,6-dimethoxy-benzooxazol-2-yl)-2-(4-ethanesulfonyl-phenyl)-acetamide, N-Benzooxazol-2-yl-2-(4-cyano-phenoxy)-2-(4-ethanesulfonyl-phenyl)-acetamide, 4-[(4-Cyano-phenoxy)-(5,6-dimethoxy-benzooxazol-2-ylcarbamoyl)-methyl]-N-(2-piperidin-1-yl-ethyl)-benzamide, 2-(4-Cyano-phenoxy)-N-(5,6-dimethoxy-benzooxazol-2-yl)-2-[4-(2-methoxy-ethoxy)-phenyl]-acetamide, 4-[(4-Cyano-phenoxy)-(5,6-dimethoxy-benzooxazol-2-ylcarbamoyl)-methyl]-N,N-dimethyl-benzamide, 2-(4-Cyano-phenoxy)-N-(5,6-dimethoxy-benzooxazol-2-yl)-2-[4-(4-methyl-piperazine-1-carbonyl)-phenyl]-acetamide, 4-[(4-Cyano-phenoxy)-(5,6-dimethoxy-benzooxazol-2-ylcarbamoyl)-methyl]-N-(2-morpholin-4-yl-ethyl)-benzamide, 4-[(4-Cyano-phenoxy)-(5,6-dimethoxy-benzooxazol-2-ylcarbamoyl)-methyl]-N-(2-methoxy-ethyl)-benzamide, 2-(4-Cyano-phenoxy)-N-(5,6-dimethoxy-1-methyl-1H-benzoimidazol-2-yl)-2-(4-ethanesulfonyl-phenyl)-acetamide, 2-(4-Cyano-phenoxy)-N-(5,6-dimethoxy-1H-indol-2-yl)-2-(4-ethanesulfonyl-phenyl)-acetamide, 2-(4-Cyano-phenoxy)-2-(4-ethanesulfonyl-phenyl)-N-(1H-indol-2-yl)-acetamide, 2-(4-Chloro-phenyl)-2-(4-cyano-phenoxy)-N-(5,6-dimethoxy-benzothiazol-2-yl)-acetamide, 2-(4-Cyano-phenyl)-N-(5,6-dimethoxy-benzothiazol-2-yl)-2-[4-(2-dimethylamino-ethoxy)-phenoxy]-acetamide, N-(5,6-dimethoxy-benzooxazol-2-yl)-2-(4-ethanesulfonyl-phenyl)-acetamide, and 4-[(4-Cyano-phenoxy)-(5,6-dimethoxy-benzothiazol-2-ylcarbamoyl)-methyl]-N-(2-methoxy-ethyl)-benzamide.

5. A pharmaceutical composition comprising a compound of structural Formula (I) according to claim 1 or a pharmaceutically acceptable salt thereof and a pharmaceutically acceptable excipient.

6. A method of treating in a subject an apelin-mediated disease or disorder, comprising administering to the subject a pharmaceutical a compound of structural Formula I of claim 1 thereby treating the disease or disorder, wherein the disease or disorder is heart failure, myocardial infarction, hypertension, atherosclerosis, reperfusion damage, ischemia, insulin resistance, diabetic macro- and micro-vasculopathies, diabetic retinopathy, or any combination thereof.

7. The method of claim 6, wherein the disease or disorder is heart failure or myocardial infarction.

8. A pharmaceutical composition comprising a compound of structural Formula (II) according to claim 2 or a pharmaceutically acceptable salt thereof and a pharmaceutically acceptable excipient.

9. A method of treating in a subject an apelin-mediated disease or disorder, comprising administering to the subject a pharmaceutical a compound of structural Formula II of claim 2 thereby treating the disease or disorder, wherein the disease or disorder is heart failure, myocardial infarction, hypertension, atherosclerosis, reperfusion damage, ischemia, insulin resistance, diabetic macro- and micro-vasculopathies, diabetic retinopathy, or any combination thereof.

10. The method of claim 9, wherein the disease or disorder is heart failure or myocardial infarction.

* * * * *